(12) United States Patent
Nakai et al.

(10) Patent No.: US 7,459,459 B2
(45) Date of Patent: *Dec. 2, 2008

(54) TRI-HETEROCYCLIC COMPOUNDS AND A PHARMACEUTICAL COMPRISING THEM AS AN ACTIVE INGREDIENT

(75) Inventors: Hisao Nakai, Mishima-gun (JP);
Yoshifumi Kagamiishi, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 157 days.

This patent is subject to a terminal disclaimer.

(21) Appl. No.: 11/219,736

(22) Filed: Sep. 7, 2005

(65) Prior Publication Data

US 2006/0122392 A1    Jun. 8, 2006

Related U.S. Application Data

(63) Continuation of application No. 10/250,328, filed as application No. PCT/JP01/11581 on Dec. 27, 2001, now Pat. No. 7,034,153.

(30) Foreign Application Priority Data

Dec. 28, 2000   (JP)  ............. P. 2000-402517

(51) Int. Cl.
| | |
|---|---|
| A01N 43/54 | (2006.01) |
| A61K 31/505 | (2006.01) |
| C07D 239/00 | (2006.01) |
| C07D 239/70 | (2006.01) |
| C07D 471/00 | (2006.01) |
| C07D 487/00 | (2006.01) |
| C07D 491/00 | (2006.01) |

(52) U.S. Cl. ............... 514/267; 544/249; 544/250; 544/252

(58) Field of Classification Search ............... 514/267; 544/249, 250, 252
See application file for complete search history.

(56) References Cited

U.S. PATENT DOCUMENTS

| | | | |
|---|---|---|---|
| 5,420,128 A | 5/1995 | Kiyokawa et al. | |
| 5,843,951 A | 12/1998 | Inoue et al. | |
| 7,034,153 B2 * | 4/2006 | Nakai et al. ............ | 544/249 |

FOREIGN PATENT DOCUMENTS

| | | |
|---|---|---|
| WO | WO 92/06096 A1 | 4/1992 |
| WO | WO 97/11946 A1 | 4/1997 |
| WO | 99/64422 A | 12/1999 |
| WO | 00/27846 A | 5/2000 |
| WO | 00/27850 A | 5/2000 |

OTHER PUBLICATIONS

Sivakamasundari, et al., Pyrroloquinolines: Part IV—Synthesis of 1-Aryl-1H-pyrrolo[2,3-b]quinolines, Indian J. of Chem., vol. 26B, 744-47 (1987).*
Tominaga, et al., Synthesis of Methylthiomaleimides for the Preparation of Pyridazines and Related Compounds, Journal of Heterocyclic Chemistry, 39(3), 571-591 (2002).*
Leach, Colin A., et al., "Reversible Inhibitors of the Gastric (H+/K+) - ATPase, 2. 1-Arylpyrrolo [3,2-c] quinolines: Effect of the 4-Substituent", J. Med. Chem., vol. 35, No. 10, 1992, pp. 1845 to 1852.
Sivakamasundari, S., et al/. "Pyrrologuinolines, Part IV, Synthesis of 1-aryl-1h-pyrrolo[2,3-b] quinolines" Indian J. Chem., Sect.B, vol. 26, No. 8, 1987, pp. 744 to 747.
Smith, Leon, et al., "Novel and highly efficient synthesis of the aza analogs of tacrine" Tetranedron Lett., vol. 40, No. 31, 1999, pp. 5643 to 5446.
Hirbert, Gerhard, et al., "(Aminoethinyl) metallierungen, 14, Cyclisierung von $n^1$, $n^2$-Diaryl-$N^1$-Phenacyl-3-aminopropiolamidinen", Liebigs Ann. Chem., (1985), (7) pp. 1389 t 1397.

* cited by examiner

*Primary Examiner*—James O. Wilson
*Assistant Examiner*—Erich A Leeser
(74) *Attorney, Agent, or Firm*—Sughrue Mion, PLLC

(57) ABSTRACT

Tri-heterocyclic compound of formula (I)

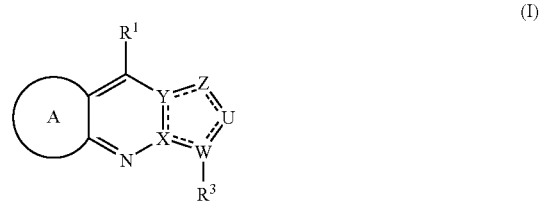

wherein each of W, X and Y is carbon or nitrogen; each of U and Z is $CR^2$, $NR^{13}$, nitrogen, oxygen, sulfur etc.; A ring is carbocyclic ring, heterocyclic ring; $R^1$ is alkyl, alkenyl, alkynyl, $NR^4R^5$, $OR^6$ etc.; $R^3$ is carbocyclic ring, heterocyclic ring;
and a pharmaceutically acceptable salt thereof, a process for the preparation thereof, a pharmaceutical comprising them as an active ingredient.

A compound of formula (I) is useful, in order to possess corticotropin releasing factor receptor antagonistic activity, for the prevention and/or treatment of depression, anxiety, eating disorder, posttraumatic stress disorder, peptic ulcer, irritable bowl syndrome, Alzheimer's disease, drug addiction or alcohol dependence syndrome etc.

12 Claims, 1 Drawing Sheet

TRI-HETEROCYCLIC COMPOUNDS AND A PHARMACEUTICAL COMPRISING THEM AS AN ACTIVE INGREDIENT

This is a continuation of application Ser. No. 10/250,328 filed Jun. 30, 2003, now U.S. Pat. No. 7,034,153 which is U.S. national stage entry of PCT/JP01/11581, filed Dec. 27, 2001. The entire disclosures of the prior applications, application Ser. No. 10/250,328 and PCT/JP01/11581 are hereby incorporated by reference.

TECHNICAL FIELD

The present invention relates to tri-heterocyclic compounds of formula (I)

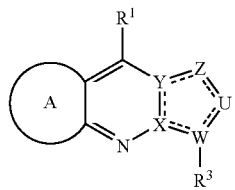

wherein all symbols are as hereinafter defined; which is useful as a pharmaceutical, and a pharmaceutical comprising them as an active ingredient.

BACKGROUND

Corticotropin Releasing Factor (CRF) was a peptide comprising 41 amino acid residues and isolated from ovine hypothalamic in 1981. It was suggested that CRF was released from hypothalamic and controlled a secretion of adrenocorticotropic hormone (ACTH) from hypophysis [Science, 218, 377-379 (1982)].

A biological effect is begun from CRF binds to CRF receptor, which exists on membranous surface of ACTH producing cell in anterior pituitary. Two subtypes of CRF receptors have been identified, and each one of these is distributed in a different area of brain. For example, a lot of receptor 1 is distributed in hypophysis, hypothalamic, cerebral cortex and a lot of receptor 2 is distributed in septal of brain, hypothalamus nucleus paraventricularis. Besides, receptors are also distributed in peripheral organ, for example, heart, gastrointestinal, lung, adrenal medulla, spleen, liver, renal, glandula prostatica. Concretely, receptor 1 is existed in bowel or spleen, receptor 2 is existed in stomach and especially receptor 2β is existed in heart and skeletal muscle.

ACTH, which is released by a stimulation of CRF, stimulates a secretion of cortisol from adrenal cortex, and relates to a systemic action for reproduction, growth, gastrointestinal function, inflammation, immune system, nervous system etc. Consequently, CRF is believed to plays a role as a regulator of these functions.

It was reported that excess CRF was secreted in brain of patient with depression and anxiety disorders [Science, 226, 1342-1343 (1984); Neuroscience and Behavioral Reviews, 22, 635-651 (1998); J. Endocrinol, 160, 1-12 (1999)].

Besides, a relation of CRF and various disorders was reported, for example, eating disorder [Science, 273, 1561-1564 (1996)], inflammation [Endocrinology, 137, 5747-5750 (1996)], irritable bowel syndrome [Am. J. Physiol, 253, G582-G586 (1987)], drug dependence [Psychopharmacology 137, 184-190 (1998)] and ischemia [Soc Neurosci Abstr (November 4-9, New Orleans), 807.5 (2000)].

On the other hand, CRF has an intimate involvement in stress. For example, administration of CRF to the brain elicited same behavior and endocrine response as an animal under stressful conditions [Nature, 297, 331 (1982)].

As above, a relationship of CRF and a disorder of central nerve system, neuropsychiatric disorder or a disorder of peripheral organ has been attracted attention.

Accordingly, an antagonism of CRF receptor is considered to be useful for a disease by abnormal secretion of CRF, for example, various diseases comprising stress-related disorders. For examples, it is believed to be useful for a prevention and/or treatment of depression, single episode depression, recurrent depression, postpartum depression, child abuse induced depression, anxiety, anxiety related disorders (e.g. panic disorder, particular phobia, fear of falling, social phobia, obsessive compulsive disorder), emotional disorder, bipolar disorder, posttraumatic stress disorder, peptic ulcer, diarrhea, constipation, irritable bowel syndrome, inflammatory bowel disease (ulcerative colitis, Crohn's disease), stress-induced gastrointestinal disturbance, nervous emesis, eating disorder (e.g. anorexia nervosa, bulimia nervosa), obesity, stress-induced sleep disorder, pain of muscular fiber induced sleep disorder, stress-induced immune suppression, stress-induced headache, stress-induced fever, stress-induced pain, post operative stress, rheumatoid arthritis, osteoarthritis, osteoporosis, psoriasis, thyroid dysfunction, uveitis, asthma, inappropriate anti-diarrhea hormone induced disorder, pain, inflammation, allergic disease, head injury, spinal cord injury, ischemic neuron injury, toxicity neuron injury, Cushing's disease, seizure, spasm, muscular spasm, epilepsy, ischemic disease, Parkinson's disease, Huntington disease, urinary incontinence, Alzheimer's disease, senile dementia of Alzheimer type, multi-infarct dementia, amyotrophic lateral sclerosis, hypoglycemia, cardiovascular or heart-related disease (hypertension, tachycardia, congestive heart failure), drug addiction or alcohol dependence syndrome.

On the other hand, following compounds having an antagonism activity of CRF were known.

(1) In a specification of WO 97/29109, a compound of formula (A)

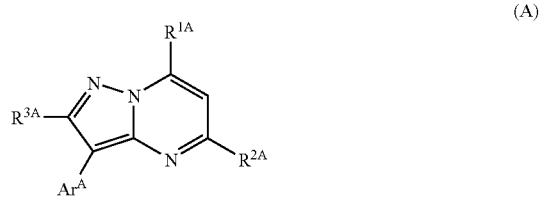

wherein
$R^{1A}$ is $NR^{4A}R^{5A}$ or $OR^{5A}$;
$R^{2A}$ is alkyl, alkyloxy, alkylthio:
$R^{3A}$ is H, alkyl, alkylsulfonyl, alkylsufoxy or alkylthio;
$R^{4A}$ is H, alkyl, mono- or di(cycloalkyl)methyl, cycloalkyl, alkenyl, hydroxyalkyl, alkylcarbonyloxyalkyl or alkyloxyalkyl;
$R^{5A}$ is alkyl, mono- or di(cycloalkyl)methyl, $Ar^{1A}$—$CH_2$, alkenyl, alkyloxyalkyl, hydroxyalkyl, thienylmethyl, furanylmethyl, alkylthioalkyl, morpholinyl etc.;

or R$^{4A}$ and R$^{5A}$ taken together with the nitrogen atom to which they are attached may form a pyrrolidinyl, piperidinyl, homopiperidinyl or morpholinyl, optionally substituted with alkyl, alkyloxyalkyl;

Ar$^4$ is phenyl, phenyl substituted with 1, 2 or 3 substitutes independently selected from halo, alkyl, trifluoromethyl, hydroxy, etc.; pyridinyl, pyridinyl substituted with 1, 2 or 3 substitutes independently selected from halo, alkyl, trifluoromethyl, hydroxy; was described as CRF receptor antagonist.

(2) In a specification of WO 98/03510, a compound of formula (B)

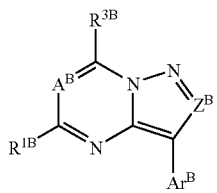

(B)

wherein
A$^B$ is N or CR$^B$;
Z$^B$ is N or CR$^{2B}$;
Ar$^B$ is selected from phenyl, naphthyl, pyridyl, pyrimidinyl, triazinyl, furanyl, thienyl, benzothienyl, benzofuranyl, etc., each Ar$^B$ optionally substituted with 1 to 5 R$^{4B}$;
R$^B$ is H, alkyl, alkenyl, alkynyl, cycloalkyl, cycloalkylalkyl, halo, cyano or haloalkyl;
R$^{1B}$ is H, alkyl, alkenyl, alkynyl, halo, cyano or haloalkyl, hydroxyalkyl, etc.;
R$^{2B}$ is H, alkyl, alkenyl, alkynyl, cycloalkyl, cycloalkylalkyl, hydroxyalkyl, etc.;
R$^{3B}$ is H, OR$^{7B}$, SH, S(O)$_n$R$^{13B}$, COR$^{7B}$, CO$_2$R$^{7B}$, OC(O)R$^{13B}$, NR$^{8B}$COR$^{7B}$, N(COR$^{7B}$)$_2$, NR$^{8B}$CONR$^{6B}$R$^{7B}$, NR$^{8B}$CO$_2$R$^{13B}$, NR$^{6B}$R$^{7B}$, alkyl, alkenyl, alkynyl, cycloalkyl, cycloalkylalkyl, etc.;
R$^{4B}$ is alkyl, alkenyl, alkynyl, cycloalkyl, cycloalkylalkyl, NO$_2$, halo, cyano, haloalkyl, NR$^{6B}$R$^{7B}$, NR$^{8B}$COR$^{7B}$, etc.;

was described as CRF receptor antagonist.

(3) In a specification of WO 98/08847, a compound of formula (C)

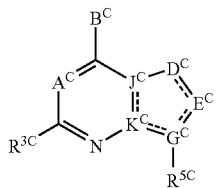

(C)

wherein the dashed lines is optional double bonds;
A$^C$ is nitrogen or CR$^{7C}$;
B$^C$ is NR$^{1C}$R$^{2C}$, CR$^{1C}$R$^{2C}$R$^{10C}$, C(=CR$^{2C}$R$^{11C}$)R$^{1C}$, NHCR$^{1C}$R$^{2C}$R$^{10C}$, OCR$^{1C}$R$^{2C}$R$^{10C}$, SCR$^{1C}$R$^{2C}$R$^{10C}$, CR$^{2C}$R$^{10C}$NHR$^{1C}$, CR$^{2C}$R$^{10C}$OR$^{1C}$, CR$^{2C}$R$^{10C}$SR$^{1C}$ or COR$^{2C}$;
J$^C$ and K$^C$ are each independently nitrogen or carbon and both are not nitrogens;

D$^C$ and E$^C$ are each selected, independently, from nitrogen, CR$^{4C}$, C=O, C=S, sulfur, oxygen, CR$^{4C}$R$^{6C}$ and NR$^{8C}$;
G$^C$ is nitrogen or carbon;
The ring containing D$^C$, E$^C$, G$^C$, K$^C$ and J$^C$ may be a saturated or unsaturated 5-membered ring and optionally substituted with one or two double bonds and may optionally contain from one to three heteroatoms in the ring and may optionally have one or two C=O or C=S;
R$^{1C}$ is alkyl optionally substituted with one or two substitutes independently selected from hydroxy, fluoro, chloro, bromo, iodo, O-alkyl, CF$_3$, C(=O)O-alkyl, OC(=O)alkyl, etc.;
R$^{2C}$ is alkyl, which may optionally contain from one to three double or triple bonds, aryl or arylalkyl, cycloalkyl, cycloalkylalkyl, etc.;
R$^{3C}$ is H, alkyl, O-alkyl, chloro, fluoro, bromo, iodo, alkylene-O-alkyl, alkylene-OH or S-alkyl;
R$^{4C}$ is H, alkyl, fluoro, chloro, bromo, iodo, hydroxy, cyano, amino, alkylene-OH, CF$_3$, etc;
R$^{5C}$ is phenyl, pyridyl, pyrazinyl, pyrimidinyl, pyridazinyl and each group is substituted with from one to four substitutes R$^{13C}$, wherein one to three of said substitutes may be selected, independently, from fluoro, chloro, alkyl and O-alkyl, and one of said substitutes may be selected from bromo, iodo, formyl, OH, alkylene-OH, alkylene-O-alkyl, cyano, CF$_3$, nitro, amino, alkylamino, dialkylamino, etc.;

was described as CRF receptor antagonist.

DISCLOSURE OF INVENTION

The present invention relates to tri-heterocyclic compounds. More particularly, this invention is related to compounds of formula (I)

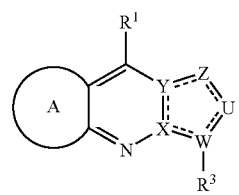

(I)

wherein X and Y each independently, is carbon or nitrogen and both are not nitrogens at the same time;
W is carbon or nitrogen;
U and Z each independently, is CR$^2$, NR$^{13}$, nitrogen, oxygen, sulfur, C=O or C=S;
R$^2$ is
(i) hydrogen,
(ii) C1-8 alkyl,
(iii) C2-8 alkenyl,
(iv) C2-8 alkynyl,
(v) halogen atom,
(vi) CF$_3$,
(vii) cyano,
(viii) nitro,
(ix) NR$^9$R$^{10}$ in which R$^9$ and R$^{10}$ each independently,
  (i) hydrogen,
  (ii) C1-4 alkyl,
  (iii) C3-10 mono- or bi-carbocyclic ring,
  (iv) 3-10 membered mono- or bi-heterocyclic ring containing 1-4 of nitrogen(s), 1-2 of oxygen(s) and/or 1-2 of sulfur(s) or (v) C1-4 alkyl substituted by C3-10 mono- or bi-carbocyclic ring or 3-10 membered mono- or bi-heterocyclic ring containing 1-4 of nitrogen(s), 1-2 of oxygen(s) and/or 1-2 of sulfur(s), (x) $OR^{11}$ in which $R^{11}$ is
  (i) hydrogen,
  (ii) C1-4 alkyl,
  (iii) C5-6 carbocyclic ring,
  (iv) 5 or 6 membered heterocyclic ring containing 1-2 of nitrogen(s), 1 of oxygen and/or 1 of sulfur or
  (v) C1-4 alkyl substituted by C5-6 carbocyclic ring or 5 or 6 membered heterocyclic ring containing 1-2 of nitrogen(s), 1 of oxygen and/or 1 of sulfur, (xi) SH, (xii) $S(O)_n R^{12}$ in which n is 0, 1 or 2, $R^{12}$ is
  (i) C1-4 alkyl,
  (ii) C5-6 carbocyclic ring,
  (iii) 5 or 6 membered heterocyclic ring containing 1-2 of nitrogen(s), 1 of oxygen and/or 1 of sulfur or
  (iv) C1-4 alkyl substituted by C5-6 carbocyclic ring or 5 or 6 membered heterocyclic ring containing 1-2 of nitrogen(s), 1 of oxygen and/or 1 of sulfur, (xiii) $COR^{11}$, (xiv) $COOR^{11}$, (xv) $CONR^9 R^{10}$, (xvi) C3-10 mono-or bi-carbocyclic ring, (xvii) 3-10 membered mono- or bi-heterocyclic ring containing 1-4 of nitrogen(s), 1-2 of oxygen(s) and/or 1-2 of sulfur(s) or (xviii) C1-4 alkyl substituted by 1-2 of substitutes selected from halogen atom, $CF_3$, $OCF_3$, cyano, nitro, $NR^9 R^{10}$, $OR^{11}$, $=N-OR^{11}$, SH, $S(O)_n R^{12}$, $COR^{11}$, $COOR^{11}$, $CONR^9 R^{10}$, C3-10 mono- or bi-carbocyclic ring and 3-10 membered mono- or bi-heterocyclic ring containing 1-4 of nitrogen(s), 1-2 of oxygen(s) and/or 1-2 of sulfur(s), $R^{13}$ is
(i) hydrogen,
(ii) C1-4 alkyl,
(iii) C2-4 alkenyl,
(iv) C2-4 alkynyl,
(v) C3-10 mono- or bi-carbocyclic ring,
(vi) 3-10 membered mono- or bi-heterocyclic ring containing 1-4 of nitrogen(s), 1-2 of oxygen(s) and/or 1-2 of sulfur(s) or
(vii) C1-4 alkyl substituted by C3-10 mono- or bi-carbocyclic ring or 3-10 membered mono- or bi-heterocyclic ring containing 1-4 of nitrogen(s), 1-2 of oxygen(s) and/or 1-2 of sulfur(s), ══ is a single bond or a double bond,

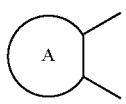

is C4-6 carbocyclic ring or 4-6 membered heterocyclic ring containing at least one of nitrogen, oxygen and sulfur and these rings are unsubstituted or substituted by 1-3 of substitutes selected from C1-4 alkyl, C1-4 alkoxy, halogen atom and $CF_3$, $R^1$ is
(i) C1-8 alkyl which is unsubstituted or substituted by 1-5 of $R^{14}$,
(ii) C2-8 alkenyl which is unsubstituted or substituted by 1-5 of $R^{14}$,
(iii) C2-8 alkynyl which is unsubstituted or substituted by 1-5 of $R^{14}$,
(iv) $NR^4 R^5$ in which $R^4$ and $R^5$ each independently,
  (i) hydrogen,
  (ii) C1-15 alkyl which is unsubstituted or substituted by 1-5 of $R^{17}$,
  (iii) C2-15 alkenyl which is unsubstituted or substituted by 1-5 of $R^{17}$,
  (iv) C2-15 alkynyl which is unsubstituted or substituted by 1-5 of $R^{17}$,
  (v) C3-15 mono- or bi-carbocyclic ring which is unsubstituted or substituted by 1-5 of $R^{18}$,
  (vi) 3-15 membered mono- or bi-heterocyclic ring containing 1-4 of nitrogen(s), 1-2 of oxygen(s) and/or 1-2 of sulfur(s) which is unsubstituted or substituted by 1-5 of $R^{18}$,
(v) $OR^6$ in which $R^6$ is
  (i) hydrogen,
  (ii) C1-10 alkyl,
  (iii) C2-10 alkenyl,
  (iv) C2-10 alkynyl,
  (v) C3-15 mono- or bi-carbocyclic ring which is unsubstituted or substituted by 1-5 of $R^{18}$,
  (vi) 3-15 membered mono- or bi-heterocyclic ring containing 1-4 of nitrogen(s), 1-2 of oxygen(s) and/or 1-2 of sulfur(s) which is unsubstituted or substituted by 1-5 of $R^{18}$,
  (vii) C1-4 alkyl substituted by 1-2 of substitutes selected from halogen atom, $CF_3$, $OCF_3$, cyano, nitro, $NR^9 R^{10}$, $OR^{11}$, $=N-OR^{11}$, SH, $S(O)nR^{12}$, $COR^{11}$, $COOR^{11}$, $CONR^9 R^{10}$, C3-10 mono- or bi-carbocyclic ring which is unsubstituted or substituted by 1-5 of $R^{18}$, and 3-10 membered mono- or bi-heterocyclic ring containing 1-4 of nitrogen(s), 1-2 of oxygen(s) and/or 1-2 of sulfur(s) which is unsubstituted or substituted by 1-5 of $R^{18}$,
(vi) SH,
(vii) $S(O)nR^7$ in which n is as hereinbefore defined, $R^7$ is
  (i) C1-8 alkyl,
  (ii) C3-10 mono- or bi-carbocyclic ring which is unsubstituted or substituted by 1-5 of $R^{18}$,
  (iii) 3-10 membered mono- or bi-heterocyclic ring containing 1-4 of nitrogen(s), 1-2 of oxygen(s) and/or 1-2 of sulfur(s) which is unsubstituted or substituted by 1-5 of $R^{18}$,
  (iv) C1-4 alkyl substituted by C3-10 mono- or bi-carbocyclic ring, which is is unsubstituted or substituted by 1-5 of $R^{18}$ or 3-10 membered mono- or bi-heterocyclic ring containing 1-4 of nitrogen(s), 1-2 of oxygen(s) and/or 1-2 of sulfur(s) which is unsubstituted or substituted by 1-5 of $R^{18}$,
(viii) $COR^6$,
(ix) $COOR^6$,
(x) $CONR^4 R^6$,
(xi) $NR^8 COR^{6a}$ in which $R^{6a}$ is
  (i) hydrogen,
  (ii) C1-10 alkyl,
  (iii) C2-10 alkenyl,
  (iv) C2-10 alkynyl or (v) C1-4 alkyl substituted by 1-2 of substitutes selected from halogen atom, $CF_3$, $OCF_3$, cyano, nitro, $N^9R^{10}$, $OR^{11a}$, $=N-OR^{11}$, SH, $S(O)_nR^{12}$, $COR^{11}$, $COOR^{11}$ and $CONR^9R^{10}$, (xii) $NR^8COOR^6$ in which $R^6$ is as hereinbefore defined, $R^8$ is
  (i) hydrogen,
  (ii) C1-8 alkyl,
  (iii) C2-8 alkenyl,
  (iv) C2-8 alkynyl,
  (v) C3-10 mono- or bi-carbocyclic ring which is unsubstituted or substituted by 1-5 of $R^{18}$,
  (vi) 3-10 membered mono- or bi-heterocyclic ring containing 1-4 of nitrogen(s), 1-2 of oxygen(s) and/or 1-2 of sulfur(s) which is unsubstituted or substituted by 1-5 of $R^{18}$ or
  (vii) C1-4 alkyl substituted by 1-2 of substitutes selected from halogen atom, $CF_3$, $OCF_3$, cyano, nitro, $NR^9R^{10}$, $OR^{11}$, $=N-OR^{11}$, SH, $S(O)nR^{12}$, $COR^{11}$, $COOR^{11}$, $CONR^9R^{10}$, C3-10 mono- or bi-carbocyclic ring which is unsubstituted or substituted by 1-5 of $R^{18}$, and 3-10 membered mono- or bi-heterocyclic ring containing 1-4 of nitrogen(s), 1-2 of oxygen(s) and/or 1-2 of sulfur(s) which is unsubstituted or substituted by 1-5 of $R^{18}$, (xiii) $NR^8CONR^4R^5$, (xiv) C3-15 mono- or bi-carbocyclic ring which is unsubstituted or substituted by 1-5 of $R^{15}$ or (xv) 3-15 membered mono- or bi-heterocyclic ring containing 1-4 of nitrogen(s), 1-2 of oxygen(s) and/or 1-2 of sulfur(s) which is unsubstituted or substituted by 1-5 of $R^{15}$, $R^{11a}$ is (i) hydrogen, (ii) C1-4 alkyl or (iii) C1-4 alkyl substituted by C5-6 carbocyclic ring or 5 or 6 membered heterocyclic ring containing 1-2 of nitrogen(s), 1 of oxygen and/or 1 of sulfur, $R^{14}$ is (a) halogen atom, (b) $CF_3$, (c) $OCF_3$, (d) cyano, (e) nitro, (f) $NR^4R^5$, (g) $OR^6$, (h) $=N-OR^6$, (j) SH, (k) $S(O)_nR^7$, (l) $COR^6$, (m) $COOR^6$, (n) $CONR^4R^5$, (o) $NR^8COR^6$, (p) $NR^8COOR^6$, (q) $NR^8CONR^4R^5$, (r) C3-15 mono- or bi-carbocyclic ring which is unsubstituted or substituted by 1-5 of $R^{15}$ or (s) 3-15 membered mono- or bi-heterocyclic ring containing 1-4 of nitrogen(s), 1-2 of oxygen(s) and/or 1-2 of sulfur(s) which is unsubstituted or substituted by 1-5 of $R^{15}$, $R^{15}$ is (a) C1-8 alkyl, (b) C2-8 alkenyl, (c) C2-8 alkynyl, (d) C1-4 alkoxy(C1-4)alkyl, (e) halogen atom, (f) $CF_3$, (g) $OCF_3$, (h) cyano, (j) nitro, (k) $NR^4R^5$, (l) $OR^6$, (m) SH, (n) $S(O)_nR^7$, (o) $COR^6$, (p) $COOR^6$, (q) $CONR^4R^5$, (r) $NR^8COR^6$, (s) $NR^8COOR^6$, (t) $NR^8CONR^4R^5$, (u) C3-10 mono- or bi-carbocyclic ring which is unsubstituted or substituted by 1-5 of $R^{20}$, (v) 3-10 membered mono- or bi-heterocyclic ring containing 1-4 of nitrogen(s), 1-2 of oxygen(s) and/or 1-2 of sulfur(s) which is unsubstituted or substituted by 1-5 of $R^{20}$ or (w) C1-4 alkyl substituted by 1-2 of substitutes selected from halogen atom, $CF_3$, $OCF_3$, cyano, nitro, $NR^4R^5$, $OR^6$, $=N-OR^6$, SH, $S(O)_nR^7$, $COR^6$, $COOR^6$, $CONR^4R^5$, $NR^8COR^6$, $NR^8COOR^6$, $NR^8CONR^4R^5$, C3-10 mono- or bi-carbocyclic ring which is unsubstituted or substituted by 1-5 of $R^{20}$, and 3-10 membered mono- or bi-heterocyclic ring containing 1-4 of nitrogen(s), 1-2 of oxygen(s) and/or 1-2 of sulfur(s) which is unsubstituted or substituted by 1-5 of $R^{20}$, $R^{17}$ is (a) halogen atom, (b) $CF_3$, (c) $OCF_3$, (d) cyano, (e) nitro, (f) $NR^9R^{10}$, (g) $OR^{11a}$, (h) $=N-OR^{11a}$, (j) SH, (k) $S(O)_nR^{12}$, (l) $COR^{11}$, (m) $COOR^{11}$, (n) $CONR^9R^{10}$, (o) $NR^8COR^{11}$, (p) $NR^8COOR^{11}$, (q) $NR^8CONR^9R^{10}$, (r) C3-15 mono- or bi-carbocyclic ring which is unsubstituted or substituted by 1-5 of $R^{18a}$ or (s) 3-15 membered mono- or bi-heterocyclic ring containing 1-4 of nitrogen(s), 1-2 of oxygen(s) and/or 1-2 of sulfur(s) which is unsubstituted or substituted by 1-5 of $R^{18a}$, $R^{18}$ is (a) C1-4 alkyl, (b) C2-4 alkenyl, (c) C2-4 alkynyl, (d) halogen atom, (e) $CF_3$, (f) $OCF_3$, (g) cyano, (h) nitro, (j) SH, (k) $S(O)_nR^{12}$, (l) $NR^9R^{10}$, (m) $OR^{11}$, (n) $COR^{11}$, (o) $COOR^{11}$, (p) $CONR^9R^{10}$, (q) C5-6 carbocyclic ring, (r) 5 or 6 membered heterocyclic ring containing 1-2 of nitrogen(s), 1 of oxygen and/or 1 of sulfur or (s) C1-4 alkyl substituted by C5-6 carbocyclic ring or 5 or 6 membered heterocyclic ring containing 1-2 of nitrogen(s), 1 of oxygen and/or 1 of sulfur, $R^{18a}$ is (a) C1-4 alkyl, (b) C2-4 alkenyl, (c) C2-4 alkynyl, (d) halogen atom, (e) $CF_3$, (f) $OCF_3$, (g) cyano, (h) nitro, (j) SH, (k) $S(O)_nR^{12}$, (l) $NR^9R^{10}$, (m) $OR^{11}$, (n) $COR^{11}$, (o) $COOR^{11}$ or (p) $CONR^9R^{10}$, $R^{19}$ is C1-4 alkyl, C1-4 alkoxy, halogen atom, $CF_3$, $OCF_3$, cyano, nitro, amino, NH(C1-4 alkyl) or N(C1-4 alkyl)$_2$, $R^3$ is (i) C5-10 mono- or bi-carbocyclic ring substituted by 1-5 of $R^{16}$ or (ii) 5-10 membered mono- or bi-heterocyclic ring containing 1-4 of nitrogen(s), 1-2 of oxygen(s) and/or 1-2 of sulfur(s) substituted by 1-5 of $R^{16}$, $R^{16}$ is (a) C1-8 alkyl,
  (b) C2-8 alkenyl,
  (c) C2-8 alkynyl,
  (d) halogen atom,
  (e) $CF_3$,
  (f) $OCF_3$,
  (g) cyano,
  (h) nitro,
  (j) $NR^9R^{10}$,
  (k) $OR^{11}$,
  (l) SH,
  (m) $S(O)_nR^{12}$, which is excepted phenylthio,
  (n) $COR^{11}$,
  (O) $COOR^{11}$,
  (p) $CONR^9R^{10}$,
  (q) $NR^8COR^{11}$,
  (r) $NR^8COOR^{11}$,
  (s) $NR^8CONR^9R^{10}$,
  (t) C3-10 mono- or bi-carbocyclic ring,
  (u) 3-10 membered mono- or bi-heterocyclic ring containing 1-4 of nitrogen(s), 1-2 of oxygen(s) and/or 1-2 of sulfur(s)
  (v) C1-4 alkyl substituted by 1-2 of substitutes selected from halogen atom, $CF_3$, $OCF_3$, cyano, nitro, $NR^9R^{10}$, $OR^{11}$, $=N-OR^{11}$, SH, $S(O)_nR^{12}$, $COR^{11}$, $COOR^{11}$, $CONR^9R^{10}$, $NR^8COR^{11}$, $NR^8COOR^{11}$, $NR^8CONR^9R^{10}$, C3-10 mono- or bi-carbocyclic ring, and 3-10 membered mono- or bi-heterocyclic ring containing 1-4 of nitrogen(s), 1-2 of oxygen(s) and/or 1-2 of sulfur(s), with the proviso that (1) when X and W are carbons, Y and Z are nitrogens, U is $CR^4$ and $R^1$ is $OR^6$, then $R^3$ is not phenyl substituted by 1 of halogen atom, phenyl substituted by 1 of trifluoromethyl and phenyl substituted by trifluoromethyl and nitro, (2) when X, Y and Z are carbons and U and W are nitrogens, then $R^3$ is C5-10 mono- or bi-carbocyclic ring substituted by 1-5 of $R^{16}$;

a pharmaceutically acceptable salt thereof or a hydrate thereof, (2) a process for the preparation thereof and (3) a pharmaceutical composition comprising them as CRF receptor antagonist.

In the specification, C1-4 alkyl means methyl, ethyl, propyl, butyl and isomeric groups thereof.

In the specification, C1-8 alkyl means methyl, ethyl, propyl, butyl, pentyl, hexyl, heptyl, octyl and isomeric groups thereof.

In the specification, C1-15 alkyl means methyl, ethyl, propyl, butyl, pentyl, hexyl, heptyl, octyl, nonyl, decyl, undecyl, dodecyl, tridecyl, tetradecyl, pentadecyl and isomeric groups thereof.

In the specification, C1-4 alkoxy means methoxy, ethoxy, propoxy, butoxy and isomeric groups thereof.

In the specification, C2-4 alkenyl means vinyl, propenyl, butenyl and isomeric groups thereof.

In the specification, C2-8 alkenyl means ethyl, propyl, butyl, pentyl, hexyl, heptyl, octyl having 1-3 of double bond(s) and isomeric groups thereof. For example, vinyl, propenyl, butenyl, pentenyl, hexenyl, hexadienyl, heptenyl, heptadienyl, octenyl, octadienyl.

In the specification, C2-15 alkenyl means ethyl, propyl, butyl, pentyl, hexyl, heptyl, octyl, nonyl, decyl, undecyl, dodecyl, tridecyl, tetradecyl, pentadecyl having 1-3 of double bond(s) and isomeric groups thereof. For example, vinyl, propenyl, butenyl, pentenyl, hexenyl, hexadienyl, heptenyl, heptadienyl, octenyl, octadienyl, nonenyl, nonadienyl, decenyl, decadienyl, undecenyl, dodecenyl, tridecenyl, tetradecenyl, pentadecenyl.

In the specification, C2-4 alkynyl means ethynyl, propynyl, butynyl and isomeric groups thereof.

In the specification, C2-8 alkynyl means ethyl, propyl, butyl, pentyl, hexyl, heptyl, octyl having 1-3 of triple bond(s) and isomeric groups thereof. For example, ethynyl, propynyl, butynyl, pentynyl, hexynyl, hexadiynyl, heptynyl, heptadiynyl, octynyl, octadiynyl.

In the specification, C2-15 alkynyl means ethyl, propyl, butyl, pentyl, hexyl, heptyl, octyl, nonyl, decyl, undecyl, dodecyl, tridecyl, tetradecyl, pentadecyl having 1-3 of triple bond(s) and isomeric groups thereof. For example, ethynyl, propynyl, butynyl, pentynyl, hexynyl, hexadiynyl, heptynyl, heptadiynyl, octynyl, octadiynyl, nonynyl, decynyl, undecynyl, dodecynyl, tridecynyl, tetradecynyl, pentadecynyl.

In the specification, halogen atom is fluorine, chlorine, bromine and iodine.

In the specification, C1-4 alkoxy(C1-4)alkyl means methyl, ethyl, propyl, butyl, and isomeric groups thereof substituted by one of methoxy, ethoxy, propoxy, butoxy and isomeric groups thereof.

In the specification, C4-6 carbocyclic ring is C4-6 carbocyclic aryl or partially or fully saturated thereof. For example, cyclobutane, cyclopentane, cyclohexane, cyclopentene, cyclohexene, cyclopentadiene, cyclohexadiene, benzene.

In the specification, C5-6 carbocyclic ring is C5-6 carbocyclic aryl or partially or fully saturated thereof. For example, cyclopentane, cyclohexane, cyclopentene, cyclohexene, cyclopentadiene, cyclohexadiene, benzene.

In the specification, C3-10 mono- or bi-carbocyclic ring is C3-10 c mono- or bi-carbocyclic aryl or partially or fully saturated thereof. For example, cyclopropane, cyclobutane, cyclopentane, cyclohexane, cycloheptane, cyclopentene, cyclohexene, cyclopentadiene, cyclohexadiene, benzene, pentalene, indene, naphthalene, azulene, perhydropentalene, indan, perhydroindene, teterahydronaphthalene, perhydronaphthalene, perhydroazulene.

In the specification, C3-15 mono- or bi-carbocyclic ring is C3-15 mono- or bi-carbocyclic aryl or partially or fully saturated thereof or bridged bi-carbocyclic ring. For example, cyclopropane, cyclobutane, cyclopentane, cyclohexane, cycloheptane, cyclopentene, cyclohexene, cyclopentadiene, cyclohexadiene, benzene, pentalene, indene, naphthalene, azulene, heptalene, perhydropentalene, indan, perhydroindene, teterahydronaphthalene, perhydronaphlithalene, perhydroazulene, perhydroheptalene, bicyclo[3.1.1]heptane.

In the specification, C5-10 mono- or bi-carbocyclic ring is C5-10 mono- or bi-carbocyclic aryl or partially or fully saturated thereof. For example, cyclopentane, cyclohexane, cycloheptane, cyclopentene, cyclohexene, cycloheptene, cyclopentadiene, cyclohexadiene, cycloheptadiene, benzene, pentalene, indene, naphthalene, azulene, perhydropentalene, indan, perhydroindene, teterahydronaphthalene, perhydronaphthalene, perhydroazulene.

In the specification, 4-6 membered heterocyclic ring containing at least one of nitrogen, oxygen and sulfur is 4-6 membered heterocyclic aryl containing at least one of nitrogen, oxygen and sulfur or partially or fully saturated thereof. For example, azetidine, pyrrolidine, pyrroline, pyrrole, tetrahydrofuran, dihydrofuran, furan, tetrahydrothiophene, dihydrothiophene, thiophene, piperidine, dihydropyridine, pyridine, tetrahydropyran, dihydropyran, pyran, tetrahydrothiopyran, dihydrothiopyran, thiopyran.

In the specification, 5 or 6 membered heterocyclic ring containing 1-2 of nitrogen(s), 1 of oxygen and/or 1 of sulfur is 5 or 6 membered heterocyclic aryl containing 1-2 of nitrogen(s), 1 of oxygen and/or 1 of sulfur or partially or fully saturated thereof. For example, pyrrole, imidazole, pyrazole, pyridine, pyrazine, pyrimidine, pyridazine, furan, pyran, thiophene, thiain (thiopyran), oxazole, isoxazole, thiazole, isothiazole, pyrroline, pyrrolidine, piperidine, imidazoline, imidazolidine, pyrazoline, pyrazolidine, piperazine, perhydropyrimidine, perhydropyridazine, dihydrofuran, tetrahydrofuran, tetrahydropyran, dihydrothiophene, tetrahydrothiophene, tetrahydrothiain, morpholine, thiomorpholine.

In the specification, 3-10 membered mono- or bi-heterocyclic ring containing 1-4 of nitrogen(s), 1-2 of oxygen(s) and/or 1-2 of sulfur(s) is 3-10 membered mono- or bi-heterocyclic aryl containing 1-4 of nitrogen(s), 1-2 of oxygen(s) and/or 1-2 of sulfur(s) or partially or fully saturated thereof. 3-10 membered mono- or bi-heterocyclic aryl containing 1-4 of nitrogen(s), 1-2 of oxygen(s) and/or 1-2 of sulfur(s) is, for example, pyrrole, imidazole, pyrazole, triazole, tetrazole, pyridine, pyrazine, pyrimidine, pyridazine, azepine, diazepine, furan, pyran, oxepine, thiophene, thiain (thiopyran), thiepine, oxazole, isoxazole, oxadiazole, oxazine, oxadiazine, oxazepine, oxadiazepine, thiazole, isothiazole, thiadiazole, thiazine, thiadiazine, thiazepine, thiadiazepine, indole, isoindole, indolizine, benzofuran, isobenzofuran, benzothiophene, isobenzothiophene, indazole, quinoline, isoquinoline, quinolizine, phthalazine, naphthyridine, quinoxaline, quinazoline, cinnoline, benzoxazole, benzoxadiazole, benzothiazole, benzimidazole, benzofurazan, benzothiadiazole, benzotriazole.

The above partially or fully saturated 3-10 membered mono- or bi-heterocyclic aryl containing 1-4 of nitrogen(s), 1-2 of oxygen(s) and/or 1-2 of sulfur(s) is, for example, aziridine, azetine, azetidine, pyrroline, pyrrolidine, imidazoline, imidazolidine, pyrazoline, pyrazolidine, triazoline, triazolidine, tetrazoline, tetrazolidine, piperidine, piperazine, dihydropyridine, tetrahydropyridine, dihydropyrazine, tetrahydropyrazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiain (dihyrdothiopyran), tetrahydrothiain (tetrahydrothiopyran), dihydrothiepine, tetrahydrothiepine, perhydrothiepine, oxazoline (dihydrooxazole), oxazolidine (tetrahydrooxazole), dihydroisoxazole, tetrahydroisoxazole, oxadiazoline (dihydrooxadiazole), oxadiazolidine (tetrahydrooxadiazole), thiazoline (dihydrothiazole), thiazolidine (tetrahydrothiazole), dihydroisothiazole, tetrahydroisothiazole, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzimidazole, perhydrobenzimidazole, dioxolane, dioxane, dioxazine, dioxaindan, chroman, isochroman.

In the specification, 3-15 membered mono- or bi-heterocyclic ring containing 1-4 of nitrogen(s), 1-2 of oxygen(s) and/or 1-2 of sulfur(s) is 3-15 membered mono- or bi-heterocyclic aryl containing 1-4 of nitrogen(s), 1-2 of oxygen(s) and/or 1-2 of sulfur(s) or partially or fully saturated thereof. 3-15 membered mono- or bi-heterocyclic aryl containing 1-4 of nitrogen(s), 1-2 of oxygen(s) and/or 1-2 of sulfur(s) is, for example, pyrrole, imidazole, pyrazole, triazole, tetrazole, pyridine, pyrazine, pyrimidine, pyridazine, azepine, diazepine, furan, pyran, oxepine, thiophene, thiain (thiopyran), thiepine, oxazole, isoxazole, oxadiazole, oxazine, oxadiazine, oxazepine, oxadiazepine, thiazole, isothiazole, thiadiazole, thiazine, thiadiazine, thiazepine, thiadiazepine, indole, isoindole, indolizine, benzofuran, isobenzofuran, benzothiophene, isobenzothiophene, indazole, quinoline, isoquinoline, quinolizine, phthalazine, naphthyridine, quinoxaline, quinazoline, cinnoline, benzoxazole, benzoxadiazole, benzothiazole, benzimidazole, benzazepine, benzodiazepine, benzotriazole, benzoxazepine, benzoxadiazepine, benzothiazepine, benzothiadiazole, benzothiadiazepine, benzofurazan.

The above partially or fully saturated 3-15 membered mono- or bi-heterocyclic aryl containing 1-4 of nitrogen(s), 1-2 of oxygen(s) and/or 1-2 of sulfur(s) is, for example, aziridine, azetine, azetidine, pyrroline, pyrrolidine, imidazoline, imidazolidine, pyrazoline, pyrazolidine, triazoline, triazolidine, tetrazoline, tetrazolidine, piperidine, piperazine, dihydropyridine, tetrahydropyridine, dihydropyrazine, tetrahydropyrazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiain (dihyrdothiopyran), tetrahydrothiain (tetrahydrothiopyran), dihydrothiepine, tetrahydrothiepine, perhydrothiepine, oxazoline (dihydrooxazole), oxazolidine (tetrahydrooxazole), dihydroisoxazole, tetrahydroisoxazole, oxadiazoline (dihydrooxadiazole), oxadiazolidine (tetrahydrooxadiazole), thiazoline (dihydrothiazole), thiazolidine (tetrahydrothiazole), dihydroisothiazole, tetrahydroisothiazole, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, dihydrobenzoxazepine, tetrahydrobenzoxazepine, dioxolane, dioxane, dioxazine, dioxaindan, chroman, isochroman.

In the specification, 5-10 membered mono- or bi-heterocyclic ring containing 1-4 of nitrogen(s), 1-2 of oxygen(s) and/or 1-2 of sulfur(s) is 5-10 membered mono- or bi-heterocyclic aryl containing 1-4 of nitrogen(s), 1-2 of oxygen(s) and/or 1-2 of sulfur(s) or partially or fully saturated thereof 5-10 membered mono- or bi-heterocyclic aryl containing 1-4 of nitrogen(s), 1-2 of oxygen(s) and/or 1-2 of sulfur(s) is, for example, pyrrole, imidazole, pyrazole, triazole, tetrazole, pyridine, pyrazine, pyrimidine, pyridazine, azepine, diazepine, furan, pyran, oxepine, thiophene, thiain (thiopyran), thiepine, oxazole, isoxazole, oxadiazole, oxazine, oxadiazine, oxazepine, oxadiazepine, thiazole, isothiazole, thiadiazole, thiazine, thiadiazine, thiazepine, thiadiazepine, indole, isoindole, indolizine, benzofuran, isobenzofuran, benzothiophene, isobenzothiophene, indazole, quinoline, isoquinoline, quinolizine, phthalazine, naphthyridine, quinoxaline, quinazoline, cinnoline, benzoxazole, benzoxadiazole, benzothiazole, benzimidazole, benzofurazan, benzothiadiazole, benzotriazole.

The above partially or fully saturated 5-10 membered mono- or bi-heterocyclic aryl containing 1-4 of nitrogen(s), 1-2 of oxygen(s) and/or 1-2 of sulfur(s) is, for example, pyrroline, pyrrolidine, imidazoline, imidazolidine, pyrazoline, pyrazolidine, triazoline, triazolidine, tetrazoline, tetrazolidine, piperidine, piperazine, dihydropyridine, tetrahydropyridine, dihydropyrazine, tetrahydropyrazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiain (dihyrdothiopyran), tetrahydrothiain (tetrahydrothiopyran), dihydrothiepine, tetrahydrothiepine, perhydrothiepine, oxazoline (dihydrooxazole), oxazolidine (tetrahydrooxazole), dihydroisoxazole, tetrahydroisoxazole, oxadiazoline (dihydrooxadiazole), oxadiazolidine (tetrahydrooxadiazole), thiazoline (dihycirothiazole), thiazolidine (tetrahydrothiazole), dihydroisothiazole, tetrahydroisothiazole, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzimidazole, perhydrobenzimidazole, dioxolane, dioxane, dioxazine, dioxaindan, chroman, isochroman.

In the compound of formula (I) of the present invention,

is saturated, partially saturated or unsaturated 5 membered carbocyclic ring or heterocyclic ring. X and Y in the ring may be all combinations that X is carbon and Y is nitrogen, X is nitrogen and Y is carbon and both of X and Y are carbons. Concretely, following combinations are preferable.

(i) X is carbon, Y is nitrogen, each of U and Z is carbon or nitrogen and W is carbon,
(ii) X is nitrogen, Y is carbon, each of U and Z is carbon or nitrogen and W is carbon,
(iii) each of X and Y is carbon, each of U and W is carbon or nitrogen and Z is carbon,
(iv) each of X and Y are carbon, U is nitrogen and Z is oxygen or sulfur, U is oxygen or sulfur, Z is nitrogen and W is carbon, or
(v) each of X and Y is carbon, each of Z and W is nitrogen and U is C=O or C=S.

More preferable combination is
(i-1) each of X, U and W is carbon, and each of Y and Z is nitrogen,
(i-2) each of X, Z and W is carbon, and each of Y and U is nitrogen,
(i-3) each of X, Z, U and W is carbon and Y is nitrogen,
(ii-1) each of X, Z and U is nitrogen, and each of Y and W is carbon,
(ii-2) each of X and Z is nitrogen, and each of Y, U and W is carbon,
(ii-3) each of X and U is nitrogen, and each of Y, Z and W is carbon,
(ii-4) X is nitrogen, and each of Y, Z, U and W is carbon,
(iii-1) each of X, Y and Z is carbon, and each of U and W is nitrogen,
(iii-2) each of X, Y, Z and U is carbon and W is nitrogen,
(iv-1) each of X, Y and W is carbon, Z is oxygen and U is nitrogen,
(iv-2) each of X, Y and W is carbon, Z is sulfur and U is nitrogen,
(iv-3) each of X, Y and W is carbon, Z is nitrogen and U is oxygen,
(iv-4) each of X, Y and W is carbon, Z is nitrogen and U is sulfur,
(v-1) each of X and Y is carbon, each of Z and W is nitrogen and U is C=O, or
(v-2) each of X and Y is carbon, each of Z and W is nitrogen and U is C=S.

In the compound of formula (I) of the present invention, following compounds of formula (I-i)-(I-xxvi) are showed as concretely compounds.

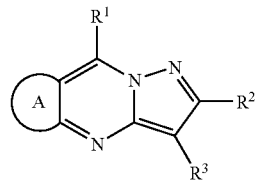 (I-i)

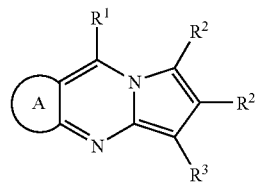 (I-ii)

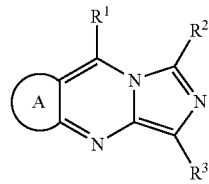 (I-iii)

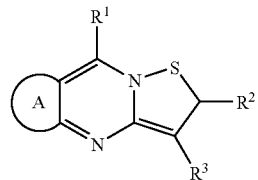 (I-iv)

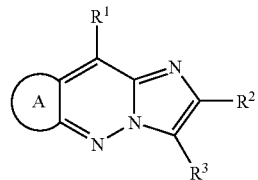 (I-v)

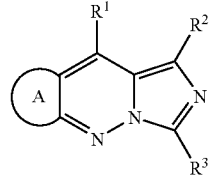 (I-vi)

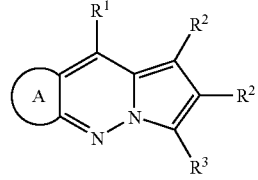 (I-vii)

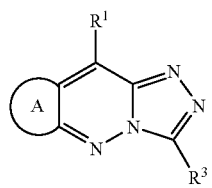 (I-viii)
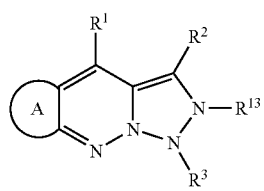 (I-iv)
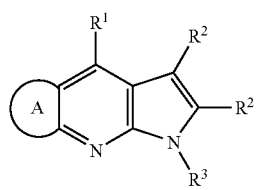 (I-x)
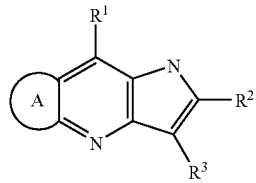 (I-xi)
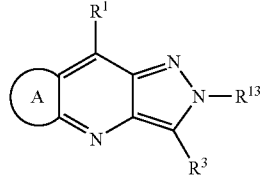 (I-xii)
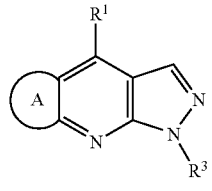 (I-xiii)
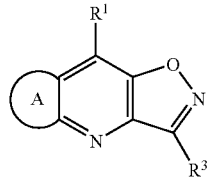 (I-xiv)
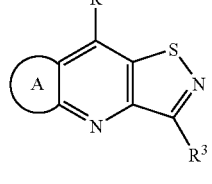 (I-xv)
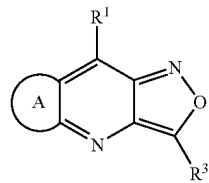 (I-xvi)
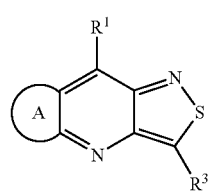 (I-xvii)
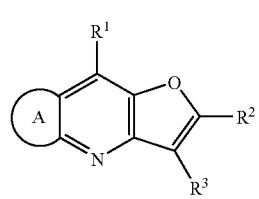 (I-xviii)
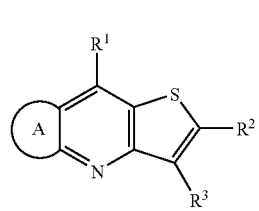 (I-xix)
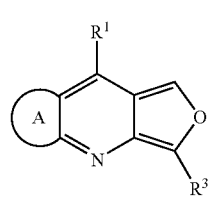 (I-xx)
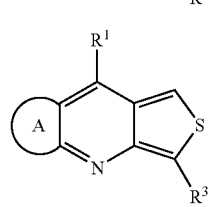 (I-xxi)
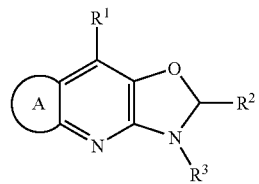 (I-xxii)
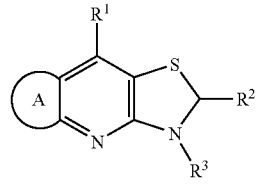 (I-xxiii)

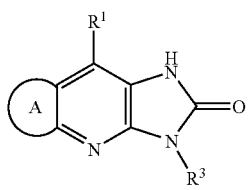
(I-xxiv)
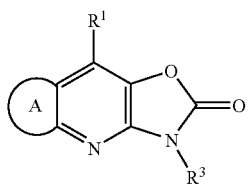
(I-xxv)
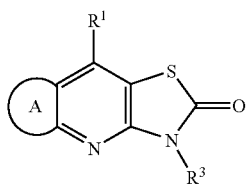
(I-xxvi)
In the compound of formula (I-i)-(I-xxvi), following compounds are preferable.
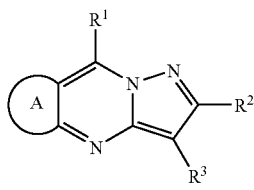
(I-i)
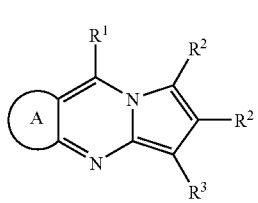
(I-ii)
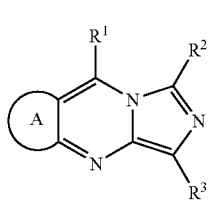
(I-iii)
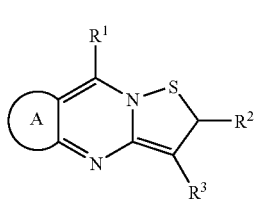
(I-iv)
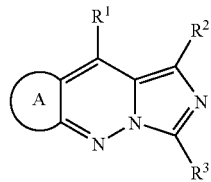
(I-vi)
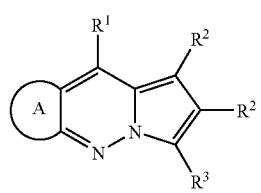
(I-vii)
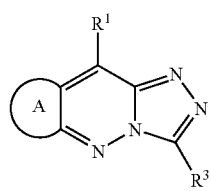
(I-viii)
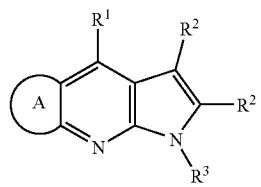
(I-x)
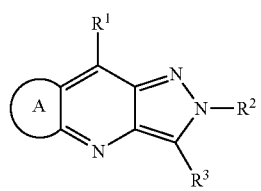
(I-xiii)
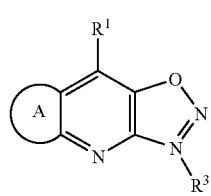
(I-xiv)
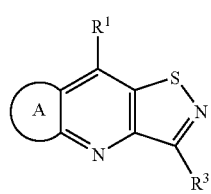
(I-xv)

-continued

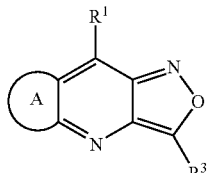
(I-xvi)

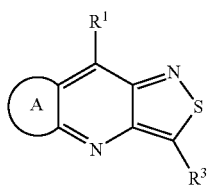
(I-xvii)

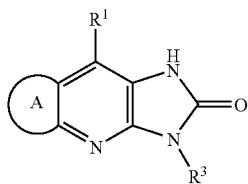
(I-xxiv)

In the compound of formula (I) of the present invention, C4-6 carbocyclic ring or 4-6 membered heterocyclic ring containing at least one of nitrogen, oxygen and sulfur presented by

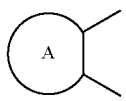

is C4-6 carbocyclic aryl or partially or fully saturated thereof, or 4-6 membered heterocyclic aryl containing at least one of nitrogen, oxygen and sulfur or partially or fully saturated thereof.

The following are preferable as A ring:

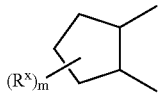
(A-1)

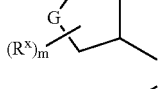
(A-2)

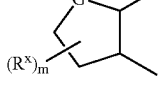
(A-3)

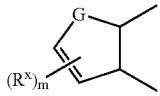
(A-4)

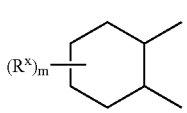
(A-5)

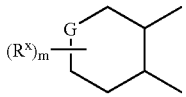
(A-6)

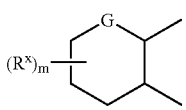
(A-7)

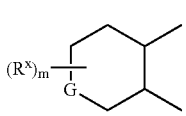
(A-8)

wherein G is O, S or NH; RX is C1-4 alkyl, C1-4 alkoxy, halogen atom or $CF_3$; m is 0-3.

In the compound of formula (I) of the present invention, preferable $R^1$ is (i) C1-8 alkyl which is unsubstituted or substituted by 1-5 of $R^{14}$, (ii) C2-8 alkenyl which is unsubstituted or substituted by 1-5 of $R^{14}$, (iii) C2-8 alkynyl which is unsubstituted or substituted by 1-5 of $R^{14}$, (iv) $NR^4R^5$, (v) $OR^6$, (vi) C3-15 mono- or bi-carbocyclic ring which is unsubstituted or substituted by 1-5 of $R^5$ or (vii) 3-15 membered mono- or bi-heterocyclic ring containing 1-4 of nitrogen(s), 1-2 of oxygen(s) and/or 1-2 of sulfur(s) which is unsubstituted or substituted by 1-5 of $R^{15}$.

A preferable combination of $R^4$ and $R^5$ in $NR^4R^5$ of the above preferable $R^1$ is (a) $R^4$ is (i) hydrogen and $R^5$ is (ii) C1-15 alkyl which is unsubstituted or substituted by 1-5 of $R^{17}$, (iii) C2-15 alkenyl which is unsubstituted or substituted by 1-5 of $R^{17}$, (iv) C2-15 alkynyl which is unsubstituted or substituted by 1-5 of $R^{17}$, (v) C3-15 mono- or bi-carbocyclic ring which is unsubstituted or substituted by 1-5 of $R^8$ or (vi) 3-15 membered mono- or bi-heterocyclic ring containing 1-4 of nitrogen(s), 1-2 of oxygen(s) and/or 1-2 of sulfur(s) which is unsubstituted or substituted by 1-5 of $R^{18}$ or (b) $R^4$ is (ii) C1-15 alkyl which is unsubstituted or substituted by 1-5 of $R^7$, (iii) C2-15 alkenyl which is unsubstituted or substituted by 1-5 of $R^{17}$, (iv) C2-15 alkynyl which is unsubstituted or substituted by 1-5 of $R^{17}$ or (v-1) C3-6 mono-carbocyclic ring and $R^5$ is (ii) C1-15 alkyl which is unsubstituted or substituted by 1-5 of $R^7$, (iii) C2-15 alkenyl which is unsubstituted or substituted by 1-5 of $R^{17}$, (iv) C2-15 alkynyl which is unsubstituted or substituted by 1-5 of $R^7$, (v) C3-15 mono- or bi-carbocyclic ring which is unsubstituted or substituted by 1-5 of $R^{18}$ or (vi) 3-15 membered mono- or bi-heterocyclic ring containing 1-4 of nitrogen(s), 1-2 of oxygen(s) and/or 1-2 of sulfur(s) which is unsubstituted or substituted by 1-5 of $R^{18}$.

It is preferable that 3-15 membered mono- or bi-heterocyclic ring containing 1-4 of nitrogen(s), 1-2 of oxygen(s) and/or 1-2 of sulfur(s) which is unsubstituted or substituted by 1-5 of $R^{15}$ of the above preferable $R^1$, bonds through nitrogen atom in the ring. That is group:

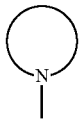

which is unsubstituted or substituted by 1-5 of $R^{15}$, and this group is 3-15 membered mono- or bi-heterocyclic ring containing one of nitrogen necessarily, and furthermore optionally containing one of nitrogen, oxygen or sulfur. Concretely, there are following heterocyclic rings which is unsubstituted or substituted by 1-5 of $R^{15}$.

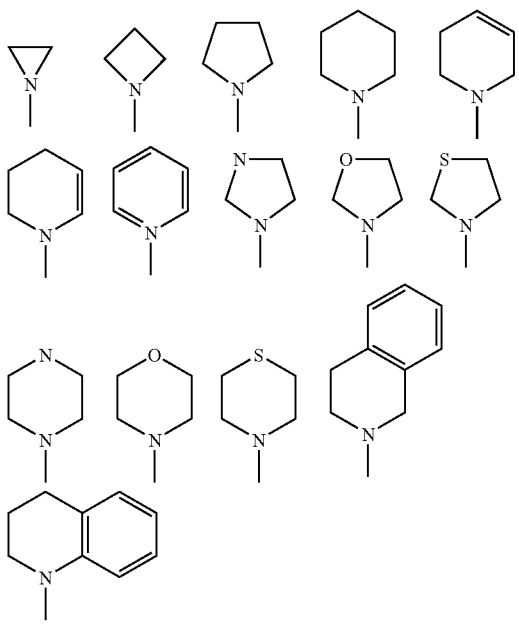

As specific compounds of the present invention, there are compounds described in Examples hereinafter and a pharmaceutically acceptable salt thereof.

Unless otherwise specified, all isomers are included in the present invention. For example, alkyl, alkoxy, alkylene and alkynyl include straight and branched isomers. Isomers based on double bond, ring, fused ring (E, Z, cis, trans), isomers resulting from the presence of asymmetric carbon(s) (R-configuration, S-configuration, α-configuration, β-configuration, enantiomers, diastereoisomers), optically active compounds having optical rotation (D, L, d, l-configuration), polar compounds obtained by chromatographic separations (highly polar compound, less polar compound), equilibrium compounds, the mixtures are existed by free ratio, racemic mixtures are included in the present invention.

[Salt]

The compound of the present invention of formula (I) may be converted into a corresponding pharmaceutically acceptable salt by known methods. In the present invention, pharmaceutically acceptable salts are salts of alkali metals, salts of alkaline-earth metals, ammonium salts, amine salts, acid addition salts.

Non-toxic and water-soluble salts are preferable. Appropriate salts are, salts of alkali metals, such as potassium, sodium; salts of alkaline-earth metals, such as calcium, magnesium; ammonium salts, pharmaceutically acceptable organic amines, such as tetramethylammonium, triethylamine, methylamine, dimethylamine, cyclopentylamine, benzylamine, phenethylamine, piperidine, monoethanolamine, diethanolamine, tris(hydroxymethyl)methylaminomethane, lysine, arginine, N-methyl-D-glucamine. A salt of alkali metal is preferable.

Non-toxic and water-soluble acid addition salts are preferable. Appropriate acid addition salts are, salts of inorganic acids, such as hydrochloride, hydrobromide, sulfate, phosphate, nitrate; salts of organic acid, such as acetate, trifluoroacetate, lactate, tartrate, oxalate, fumarate, maleate, citrate, benzoate, methanesulphonate, ethanesulphonate, benzenesulphonate, toluenesulphonate, isethionate, glucuronate, gluconate.

The compound of formula (I) of the present invention and salts thereof may be converted into the corresponding hydrates by conventional means.

Preparation of the Compound of the Present Invention

The present compound of formula (I) may be prepared, for example, by the following method.

(A) In the compound of formula (I), the compound in which $R^1$ is OH, and $R^2$ and $R^3$ is not OH, cyano, =N—$OR^{11}$ or a group containing OH, cyano or =N—$OR^{11}$, that is the compound of formula (I-A)

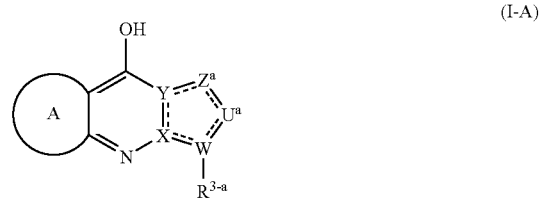

(I-A)

wherein each of $Z^a$, $U^a$ and $R^{3-a}$ is same meaning as Z, U and $R^3$, with the proviso that they are not OH, cyano, =N—$OR^{11}$ or a group containing OH, cyano or =N—$OR^{11}$; the other symbols are as hereinbefore defined;

may be prepared by reacting the compound of formula (II-1)

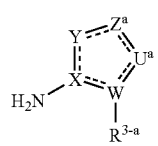

(II-1)

wherein all symbols are as hereinbefore defined;

with the compound of formula (III-1)

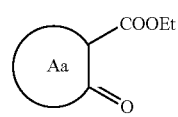

(III-1)

wherein $A^a$ ring is saturated or partially saturated C4-6 carbocyclic ring or 4-6 membered heterocyclic ring, Et is ethyl, the other symbols are as hereinbefore defined;

or successively, subjecting to oxidative reaction.

The above reaction of the compound of formula (II) and the compound of formula (III) is known, for example, it is carried out in an organic solvent (e.g. acetic acid) at from room temperature to reflux temperature.

Oxidative reaction is known, for example, it is carried out in an organic solvent (e.g. diphenyl ether), using a metal catalyst (e.g. palladium carbon, palladium, palladium hydroxide, palladium acetate, palladium black), at 0° C.~250° C.

(B) In the compound of formula (I), the compound in which $R^1$ is not OH, and cyano, =N—$OR^6$ or a group containing cyano or =N—$OR^{11}$, and C3-10 mono-, or bi-carbocyclic ring, 3-10 membered mono-, or bi-heterocyclic ring containing 1-4 of nitrogen(S), 1-2 of oxygen(s) and/or 1-2 of sulfur(s), $R^2$ and $R^1$ is not OH, cyano, =N—$OR^{11}$ or a group containing OH, cyano or =N—$OR^{11}$, that is the compound of formula (I-B)

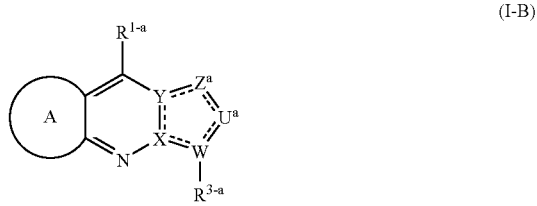

(I-B)

wherein $R^{1-a}$ is same meaning as $R^1$, with the proviso that it is not OH, and cyano, =N—$OR^6$ or a group containing cyano or =N—$OR^{11}$, and C3-10 mono-, or bi-carbocyclic ring, 3-10 membered mono-, or bi-heterocyclic ring containing 1-4 of nitrogen(S), 1-2 of oxygen(s) and/or 1-2 of sulfur(s); the other symbols are as hereinbefore defined; may be prepared by reacting the compound of formula (IV)

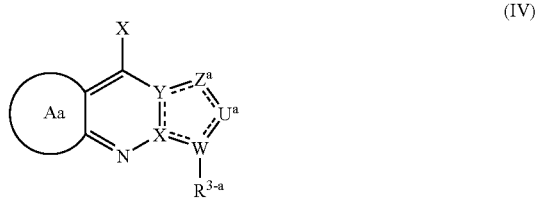

(IV)

wherein X is halogen atom, the other symbols are as hereinbefore defined;

with the compound of formula (V-1)

H—$R^{1-ab}$ (V-1)

wherein $R^{1-ab}$ is same meaning as $R^1$, with the proviso that it is not OH, and cyano, =N—$OR^6$ or a group containing cyano or =N—$OR^6$, and C3-10 mono-, or bi-carbocyclic ring, 3-10 membered mono-, or bi-heterocyclic ring containing 1-4 of nitrogen(S), 1-2 of oxygen(s) and/or 1-2 of sulfur(s);

or successively, subjecting to oxidative reaction, or with the compound of formula (V-2)

$R^{1-ac}$ (V-2)

wherein $R^{1-ac}$ is C3-10 mono-, or bi-carbocyclic ring, 3-10 membered mono-, or bi-heterocyclic ring containing 1-4 of nitrogen(S), 1-2 of oxygen(s) and/or 1-2 of sulfur(s);

or successively, subjecting to oxidative reaction.

The above reaction of the compound of formula (IV) and the compound of formula (V-1) is known, for example, it is carried out in an organic solvent (e.g. isopropyl alcohol, toluene, ethanol, tetrahydrofuran) or without a solvent, optionally in the presence of a base (e.g. sodium hydroxide, sodium ethoxide) at 0~200° C.

The above reaction of the compound of formula (IV) and the compound of formula (V-2) is known, for example, it is carried out in an organic solvent (e.g. dimethoxyethane, dimethylformaide), in the presence of a catalyst (e.g. palladium acetate) using a phosphine compound (e.g. triphenylphosphine) at 20° C.~reflux temperature.

Oxidative reaction is carried out by the above method.

On the other hand, in the compound of formula (I-B), the compound in which $R^{1-a}$ is C1-4 alkyl substituted by 1-2 of $OR^6$ or $CONR^4R^5$, that is the compound (I-B-1)

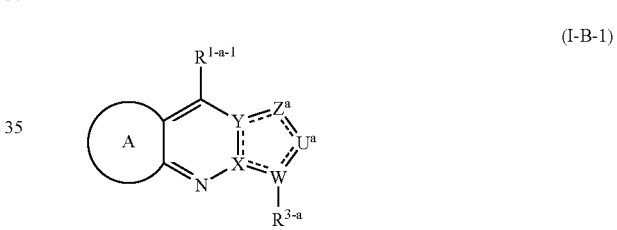

(I-B-1)

wherein $R^{1-a-1}$ is C1-4 alkyl substituted by 1-2 of $OR^6$ or $CONR^4R^5$ and the other symbols are as hereinbefore defined;

may be also prepared by subjecting to reductive reaction the compound of formula (I-B-2)

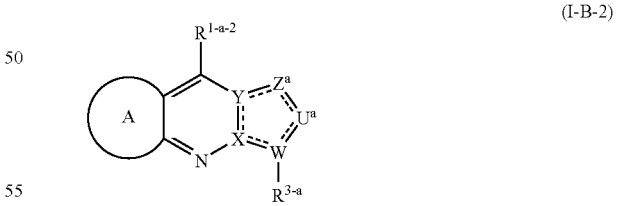

(I-B-2)

wherein $R^{1-a-2}$ is C1-4 alkyl substituted 1-2 of $COOR^6$ and the other symbols are as hereinbefore defined;

or after reductive reaction, by reacting with the compound formula (VI)

X—$R^{6-a-2}$ (VI)

wherein $R^{6-a-2}$ is (i) C1-10 alkyl, (ii) C2-10 alkenyl, (iii) C2-10 alkynyl, (iv) C3-15 mono-, or bi-carbocyclic ring which is substituted by 1-5 of $R^{18}$ or unsubstituted, (v) 3-15 membered mono-, or bi-heterocyclic ring containing 1-4 of nitrogen(S), 1-2 of oxygen(s) and/or 1-2 of sulfur(s) which is substituted by 1-5 of $R^{18}$ or unsubstituted, or (vi) C1-4 alkyl substituted by 1-2 of the group(s) selected from C3-10 mono-, or bi-carbocyclic ring which is substituted by 1-5 of $R^{18}$ or unsubstituted and 3-10 membered mono-, or bi-heterocyclic ring containing 1-4 of nitrogen(S), 1-2 of oxygen(s) and/or 1-2 of sulfur(s) which is substituted by 1-5 of $R^{18}$ or unsubstituted;

or with the compound formula (VI)

$$HNR^9R^{10} \qquad\qquad (VII)$$

wherein all symbols are as hereinbefore defined.

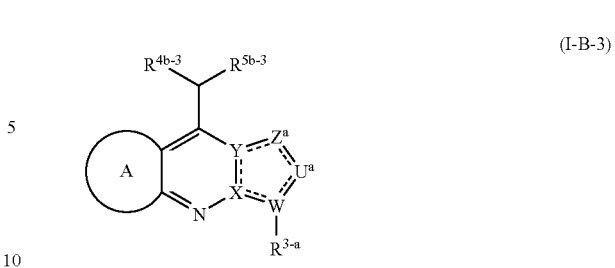

wherein $R^{4b-3}$ and $R^{5b-3}$ each independently, is C1-15 alkyl which is substituted by 1-5 of $R^{17}$ or unsubstituted and the other symbols are as hereinbefore defined;

may be also prepared according to following Scheme (1).

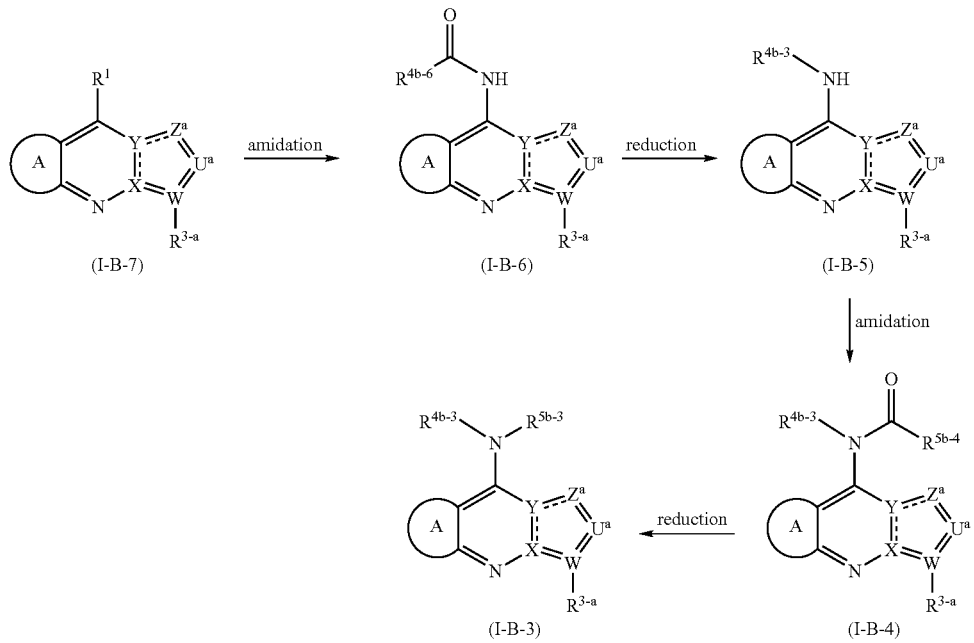

Reductive reaction is known, for example, it is carried out in an organic solvent (e.g. diethyl ether, methylene chloride, toluene), using a reducing agent (e.g. diisopropyl aluminum hydride) at −78° C.~50° C.

The reaction of the compound (VI) and the compound after reductive reaction of the compound of formula (I-B-2) is known, for example, it is carried out in an organic solvent (e.g. dimethylformamide), using a base (e.g. sodium hydride) at 0° C.~50° C.

The reaction of the compound (VII) and the compound after reductive reaction of the compound of formula (I-B-2) is known, for example, it is carried out in an organic solvent (e.g. methanol, ethanol, isopropanol) at 0° C.~100° C.

On the other hand, in the compound of formula (I-B), the compound in which $R^1$ is $NR^4R^5$ and $R^4$ and $R^5$ each independently, is C1-15 alkyl which is substituted by 1-5 of $R^{17}$ or unsubstituted, and $R^2$ and $R^3$ are not OH, cyano, =N—$OR^{11}$ or a group containing OH, cyano or =N—$OR^{11}$, that is the compound (I-B-3)

In Scheme (1), $R^{4b-6}$ is C1-14 alkyl which is substituted by 1-5 of $R^{17}$ or unsubstituted, $R^{5b-4}$ is C1-14 alkyl which is substituted by 1-5 of $R^{17}$ or unsubstituted and the other symbols are as hereinbefore defined.

Amidation reaction is known, for example, it is carried out in an organic solvent (e.g. chloroform, methylene chloride, diethyl ether, tetrahydrofuran) or without a solvent, using an acyl halide (e.g. oxalyl chloride or thionyl chloride etc.) at −20° C.~reflux temperature, and then the obtained acyl halide derivative may be reacted with amine, in an organic solvent (e.g. chloroform, methylene chloride, diethyl ether, tetrahydrofuran), in the presence of a tertiary amine (e.g. pyridine, triethyl amine, dimethyl aniline, dimethylaminopyridine) at 0-40° C. The reaction may be carried out under an inert gas (e.g. argon, nitrogen) to avoid water in order to obtain a preferable result.

Reductive reaction is known, for example, it is carried out in an organic solvent (e.g. tetrahydrofuran), using a reducing agent (e.g. borane dimethylsulfide complex, lithium aluminum hydride) at 0° C.~reflux temperature.

The compound of formula (I-B-7) may be prepared by reacting the compound of formula (II-2)

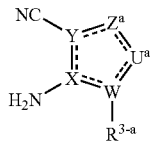
(II-2)

wherein all symbols are as hereinafter defined;

with a compound of formula (III-2)

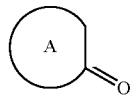
(III-2)

wherein all symbols are as hereinafter defined;

or successively, subjecting to oxidative reaction.

The above reaction of the compound of formula (II-2) and the compound of formula (III-2) is known, for example, it is carried out in an organic solvent (e.g. benzene, toluene) using an acid (e.g. p-toluenesulfonic acid or hydrate thereof) at from room temperature to reflux temperature, and successively, in an organic solvent (e.g. tetrahydrofuran), using base (e.g. lithium isopropylamide) at −10~50° C.

(C) In the compound of formula (I), the compound in which at least one of $R^2$ and $R^3$ is OH or a group containing OH, that is the compound of formula (I-C)

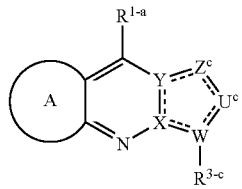
(I-C)

wherein each $Z^C$, $U^C$ and $R^{3-C}$ is same meaning as Z, U and $R^3$, with the proviso that at least one of them is OH or a group containing OH and the other symbols are as hereinbefore defined;

may be also prepared by subjecting to demethylation of the compound in which at least one of $R^2$ and $R^3$ is methoxy or a group containing methoxy in the compound of formula (I-B), that is the compound of formula (I-B-8)

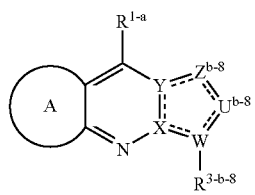
(I-B-8)

wherein each $Z^{b-8}$, $U^{b-8}$ and $R^{3-b-8}$ is same meaning as Z, U and $R^3$, with the proviso that at least one of them is methoxy or a group containing methoxy and the other symbols are as hereinbefore defined.

Demethylation reaction is known, for example, it is carried out in an organic solvent (e.g. methylene chloride, ethyl acetate, chloroform), using Lewis acid (e.g. boron tribomide), at −80° C.~80° C.

(D) In the compound of formula (I), the compound in which at least one of $R^1$, $R^2$ and $R^3$ is a group containing =N—$OR^6$ or =N—$OR^{11}$, that is the compound of formula (I-D)

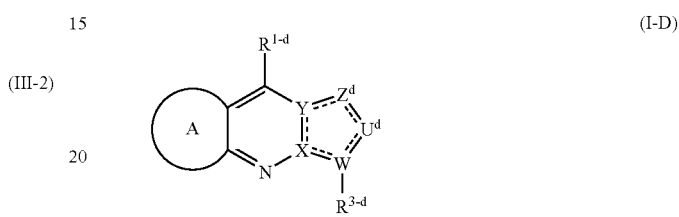
(I-D)

wherein each $R^{1-d}$, $Z^d$, $U^d$ and $R^{3-d}$ is same meaning as $R^1$, Z, U and $R^3$, with the proviso that at least one of them is a group containing =N—$OR^6$ or =N—$OR^{11}$ and the other symbols are as may be prepared (1) by subjecting to deacetalization the compound in which at least one of $R^1$, $R^2$ and $R^3$ is a group containing —CH(O—C1-4 alkyl)$_2$ in the compound of formula (I-B), that is the compound of formula (I-B-9)

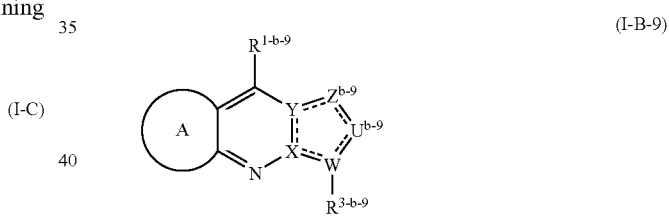
(I-B-9)

wherein each $R^{1-b-9}$, $Z^{b-9}$, $U^{b-9}$ and $R^{3-b-9}$ is same meaning as $R^1$, Z, U and $R^3$, with the proviso that at least one of them is a group containing —CH(O—C1-4 alkyl)$_2$ and the other symbols are as hereinbefore defined:

successively, to oxime formation reaction, or (2) by subjecting to oxidative reaction the compound in which $R^{1-a}$ is a group containing OH in the compound of formula (I-B), or the compound of formula (I-C). that is the compound of formula (I-B-10)

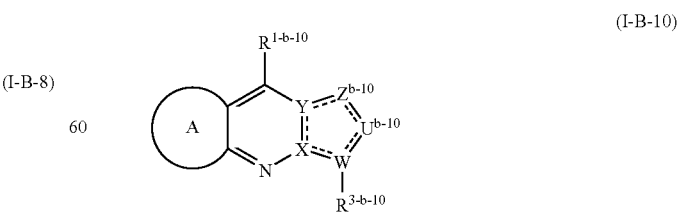
(I-B-10)

wherein each $R^{1-b-10}$, $Z^{b-10}$, $U^{b-10}$ and $R^{3-b-10}$ is same meaning as $R^1$, Z, U and $R^3$, with the proviso that $R^{1-b-10}$ is OH or at least one of $Z^{b-10}$, $U^{b-10}$ and $R^{3-b-10}$ is a group containing OH and the other symbols are as hereinbefore defined;

successively, to oxime formation reaction.

Deacetalization reaction is known, for example, it is carried out in an organic solvent (e.g. acetic acid, dioxane), using an acid (e.g. hydrochloric acid, sulfuric acid) at 0~100° C.

Oxidative reaction is known, for example, it is carried out in an organic solvent (e.g. methylene chloride) or without a solvent, in the presence of a base (e.g. triethylamine, diisopropylethylamine), using dimethylsulfoxide and sulfur trioxide pyridine complex, dicyclohexylcarbodiimide or oxalyl chloride at 0~50° C.

Oxime formation reaction is known, for example, it is carried out in an organic solvent (e.g. pyridine), using $H_2N$—O—$R^6$ or $H_2N$—O—$R^{11}$, at 0~50° C.

(E) In the compound of formula (I), the compound in which at least one of $R^1$, $R^2$ and $R^3$ is cyano or a group containing cyano, that is the compound of formula (I-E)

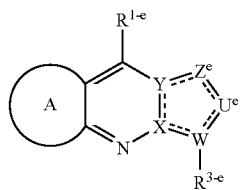

(I-E)

wherein each $R^{1-e}$, $Z^e$, $U^e$ and $R^{3-e}$ is same meaning as $R^1$, Z, U and $R^3$, with the proviso that at least one of $R^{1-e}$, $Z^e$, $U^e$ and $R^{3-e}$ is cyano or a group containing cyano and the other symbols are as hereinbefore defined;

may be prepared by subjecting to dehydration reaction the compound in which at least one of $R^1$, $R^2$ and $R^3$ is a group containing =N—OH in the compound of formula (I-D), that is the compound of (I-D-1)

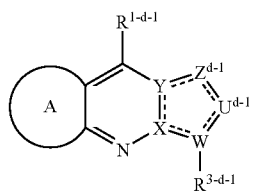

(I-D-1)

wherein each $R^{1-d-1}$, $Z^{d-1}$, $U^{d-1}$ and $R^{3-d-1}$ is same meaning as $R^1$, Z, U and $R^3$, with the proviso that at least one of $R^{1-d-1}$, $Z^{d-1}$, $U^{d-1}$ and $R^{3-d-1}$ is a group containing =N—OH and the other symbols are as hereinbefore defined.

Dehydration reaction is known, for example, it is carried out in an organic solvent (e.g. methylene chloride), in the presence of a base (e.g. triethylamine, diisopropylethylamine), using trifluoromethansulforic acid anhydrous or trichloromethyl chlorocarbonate at 0~50° C.

The compound of formula (IV) may be prepared by subjecting to halogenation reaction the compound of formula (I-A).

The compounds of formula (II), (III), (V), (VI) and (VII) may be known per se, or may be prepared by known methods. For example, among the compound of formula (II)

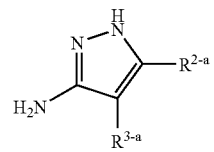

wherein $R^{2-a}$ is same meaning as $R^2$, with the proviso that it is not OH, cyano, =N—$OR^{11}$ or a group containing OH, cyano or =N—$OR^{11}$, and $R^{3-a}$ is as hereinbefore defined;

may be prepared by reacting the compound of formula (VIII)

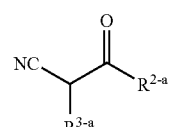

(VIII)

wherein all symbols are as hereinbefore defined;

with hydradine. Besides, in the compound of formula (III), cyclopentanon-2-carboxylic acid ethyl ester is commercially available. In the compound of formula (VI), 1-cyano-1-(2-methyl-4-methoxyphenyl)propane-2-one is described in the document of Bioorganic & Med. Chem., 8, 181-189 (2000).

And the starting materials and reagents in the present invention may be known per se or may be prepared by known methods.

In each reaction in the present specification, reaction products may be purified by conventional purification techniques, e.g. by distillation under atmospheric or reduced pressure, by high performance liquid chromatography, by thin layer chromatography or by column chromatography using silica gel or magnesium silicate; or by washing or by recrystallization. Purification may be carried out after each reaction or after a series of reactions.

PHARMACOLOGICAL ACTIVITIES

Figure 1:
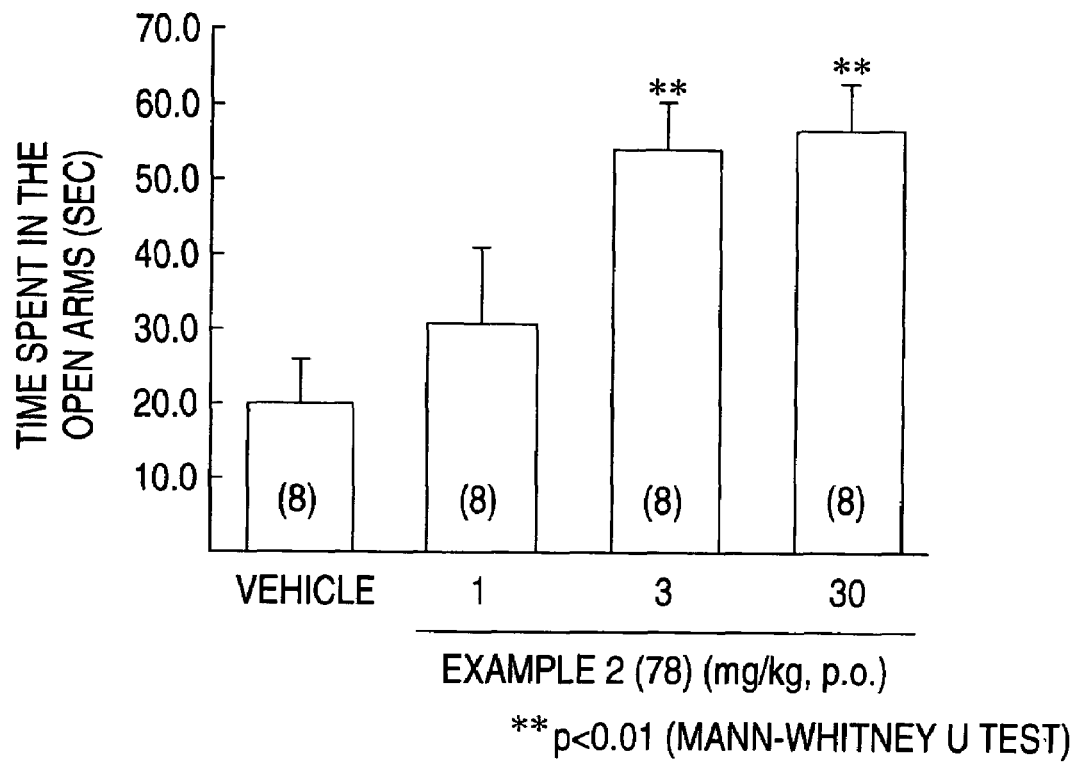
FIG. 1 shows a graph of the time spent in the open arms of rats that were administered 1, 3, 10 and 30 mg/kg of the present compound.

The compound of the present invention of formula (I) possesses CRF receptor antagonistic activity, for example, such an effect of the compound of the present invention was confirmed by following tests.

(1) Binding Assay

[Cell Membrane Preparation]

After the cell line expressing human CRF1 receptor (expressed cell line: CHO-K1 cells) was cultured to reached confluence, the cells were harvested with a scraper. Harvested cells were washed twice with PBS before being suspended in binding assay buffer (Tris-HCl (50 mM, pH 7.0), EDTA (2 mM, pH8.0), MgCl$_2$ (10 mM)) cooled by ice. Suspended cells were homogenized with a Downs-type homogenizer and subjected to centrifugation at 10,000 g to collect the membrane fraction. The harvested cell membrane fraction was resuspended with a small quantity of the binding assay buffer, and further diluted with said buffer to 1 mg/mL. The membrane fraction thus obtained was used for binding assay.

[Binding Assay]

Fifty μL of [$^{125}$I] h/r CRF prepared to 0.5 nM with binding assay buffer was added to siliconized 1.5 mL tubes. 1 μL of compounds diluted in appropriate multiples, DMSO (for total binding use), or h/r CRF solution (100 μM, for the non-specific binding use), respectively, added to the tubes. Samples of 50 μl each of the membrane fraction preparation were added to the tubes to initiate the reaction (final concentration of [$^{125}$I] h/r CRF: 0.25 nM), then the mixtures were incubated for 2 hours at room temperature. After termination of the reaction, tubes were subjected to centrifugation at 15,000 g to collect the membrane fraction. The supernatant was discarded, and the pellet was rinsed twice with cooled PBS (−) containing 0.01% Triton X-100. Radioactivity values of the respective tubes were measured with a γ-counter.

The specific binding was derived by subtracting the non-specific binding value from the each binding value.

The results indicated that these invented compounds exhibited potent affinity on CRF1 receptor (IC$_{50}$: <1 μM).

(2) A Measurement of an Antianxiety Activity Using the Elevated Plus-Maze

Two arms (open and closed) of equal width and length (50 cm×10 cm), which crossed at a right angle to form a plus maze, were elevated to a height 50 cm above the ground level. The closed arm had a wall of 40 cm. Lighting on both ends of the open arm was maintained at constant illumination. Thirty minutes after administration of various doses of test-compounds (5 mL/kg), male SD rats were placed in the center of the plus maze. The time spent(s) in the open arms and the number of entries into the respective arms were measured within a 5 minutes period. The investigation personnel for measuring the indexes positioned at a fixed location during the course of the experiment.

Figure 2:
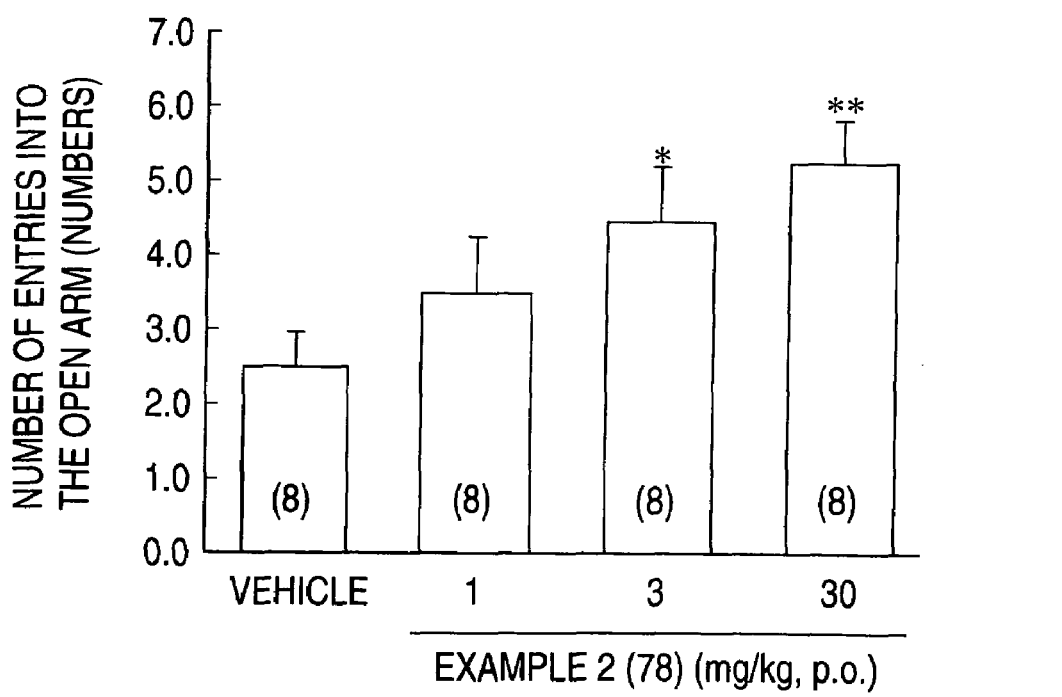
FIG. 2 shows a graph of the number of entries into the open arms of rats that were administered 1, 3, 10 and 30 mg/kg of the present compound.

The result was shown in FIGS. 1 and 2. These figures indicated that the time spent in the open arms was extend significantly and the number of entries into the open arms was increased significantly by an administration of 3 and 10 mg/kg of the compound of Example 2(78) of the present invention, that is it was shown an antianxiety effect.

[Toxicity]

The toxicity of the compounds of the present invention is very low and therefore, it is confirmed that these compounds are safe for use as medicine.

INDUSTRIAL APPLICABILITY

[Application to Pharmaceuticals]

The compounds of the present invention of the formula (I) are useful, in order to possess CRF receptor antagonistic activity, for the prevention and/or treatment of diseases induced by extraordinary secretion of CRF, for example, depression, single episode depression, recurrent depression, postpartum depression, child abuse induced depression, anxiety, anxiety related disorders (e.g. panic disorder, particular phobia, fear of falling, social phobia, obsessive compulsive disorder), emotional disorder, bipolar disorder, posttraumatic stress disorder, peptic ulcer, diarrhea, constipation, irritable bowl syndrome, inflammatory bowel disease (ulcerative colitis, Crohn's disease), stress-induced gastrointestinal disturbance, nervous emesis, eating disorder (e.g. anorexia nervosa, bulimia nervosa), obesity, stress-induced sleep disorder, pain of muscular fiber induced sleep disorder, stress-induced immune suppression, stress-induced headache, stress-induced fever, stress-induced pain, post operative stress, rheumatoid arthritis, osteoarthritis, osteoporosis, psoriasis, thyroid dysfunction, uveitis, asthma, inappropriate anti-diarrhea hormone induced disorder, pain, inflammation, allergic disease, head injury, spinal cord injury, ischemic neuron injury, toxicity neuron injury, Cushing's disease, seizure, spasm, muscular spasm, epilepsy, ischemic disease, Parkinson's disease, Huntington disease, urinary incontinence, Alzheimer's disease, senile dementia of Alzheimer type, multi-infarct dementia, amyotrophic lateral sclerosis, hypoglycemia, cardiovascular or heart-related disease (hypertension, tachycardia, congestive heart failure), drug addiction or alcohol dependence syndrome.

For the purpose described above, the compounds of formula (I) of the present invention, non-toxic salts thereof, an acid addition salts thereof or hydrates thereof may be normally administered systemically or topically, usually by oral or parenteral administration.

The doses to be administered are determined depending upon, for example, age, body weight, symptom, the desired therapeutic effect, the route of administration, and the duration of the treatment, etc. In the human adult, the doses per person at a time are generally from 1 mg to 1000 mg, by oral administration, up to several times per day, and from 0.1 mg to 100 mg, by parenteral administration, preferably intravenous administration, up to several times per day, or continuous administration between 1 and 24 hours per day into vein.

As mentioned above, the doses to be used depend upon various conditions. Therefore, there are cases wherein doses lower than or greater than the ranges specified above may be used.

The compounds of the present invention may be administered in the form of, for example, solid compositions, liquid compositions or other compositions for oral administration, injections, liniments or suppositories for parenteral administration.

Solid compositions for oral administration include compressed tablets, pills, capsules, dispersible powders and granules. Capsules include hard capsules and soft capsules.

In such solid forms, one or more of the active compound(s) may be admixed with vehicles, such as lactose, mannitol, glucose, microcrystalline cellulose, starch; binders, such as hydroxypropyl cellulose, polyvinylpyrrolidone or magnesium metasilicate aluminate; disintegrants, such as cellulose calcium glycolate; lubricants, such as magnesium stearate; stabilizing agents, and solution adjuvants, such as glutamic acid or aspartic acid; and prepared according to methods well known in normal pharmaceutical practice. The solid forms may, if desired, be coated with coating agents, such as sugar, gelatin, hydroxypropyl cellulose or hydroxypropylmethyl cellulose phthalate; or be coated with two or more films. And further, coating may include containment within capsules of absorbable materials such as gelatin.

Liquid forms for oral administration include pharmaceutically acceptable solutions, suspensions and emulsions, syrups and elixirs. In such forms, one or more of the active compound(s) may be dissolved, suspended or emulsified into diluent(s) commonly used in the art, such as purified water, ethanol or a mixture thereof. Besides such liquid forms may also comprise some additives, such as wetting agents, suspending agents, emulsifying agents, sweetening agents, flavoring agents, aroma, preservative or buffering agent.

Injections for parenteral administration include sterile aqueous, suspensions, emulsions and solid forms that are dissolved or suspended into solvent(s) for injection immediately before use. In injections, one or more of the active compound(s) may be dissolved, suspended or emulsified into solvent(s). The solvents may include distilled water for injection, physiological salt solution, vegetable oil, propylene glycol, polyethylene glycol, alcohol, e.g. ethanol, or a mixture thereof. Injections may comprise some additives, such as stabilizing agents, solution adjuvants, such as glutamic acid, aspartic acid or POLYSORBATE80 (registered trade mark); suspending agents, emulsifying agents, soothing agent, buffering agents, preservative. They may be sterilized at a final step, or may be prepared and compensated according to sterile methods. They may also be manufactured in the form of sterile solid forms, for example, freeze-dried products, which may be dissolved in sterile water or some other sterile diluent(s) for injection immediately before use.

Other forms for parenteral administration include liquids for external use, ointments and endermic liniments, inhalations, sprays, suppositories and pessaries for vaginal administration which comprise one or more of the active compound(s) and may be prepared by methods known per se. Sprays may comprise additional substances other than diluents, such as stabilizing agents, such as sodium sulfate; isotonic buffers, such as sodium chloride, sodium citrate or citric acid. For preparation of such sprays, for example, the method described in the U.S. Pat. No. 2,868,691 or 3,095,355 may be used.

BEST MODE FOR CARRYING OUT THE INVENTION

The following reference examples and examples illustrate, but do not limit the present invention.

The solvents in parenthesis show the developing or eluting solvents and the ratios of the solvents used are by volume in chromatographic separations and TLC.

The NMR data are shown with the solvent used in the measurements, in parentheses.

REFERENCE EXAMPLE 1

2-methyl-4-methoxyphenylacetonitrile

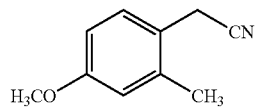

Under argon atmosphere, a mixture of N-bromosuccinimide (17.8 g) and 2,2'-azobisisobutyronitrile (492 mg) was added to a solution of 1,2-dimethyl-4-methoxybenzene (13.6 g) in carbon tetrachloride (200 ml). The mixture was refluxed for 6.5 hours. The reaction mixture was cooled with ice-bath. An insoluble matter was removed by filtration, and washed with carbon tetrachloride. A combined filtrate was concentrated. The residue was dissolved into N,N-dimethylformamide (100 ml) and sodium cyanide (9.86 g) was added to the mixture. The mixture was stirred over night at room temperature. The reaction mixture was poured into water, and the mixture was extracted with diethyl ether. The organic layer was washed with a saturated aqueous solution of sodium chloride, dried over anhydrous magnesium sulfate and concentrated. The residue was purified by column chromatography on silica gel (ethyl acetate:n-hexane=1:6→1:4) to give the title compound (11.78 g) having the following physical data.

TLC: Rf 0.20 (n-hexane:ethyl acetate=9:1);

NMR (300 MHz, CDCl$_3$): δ 7.24 (d, J=8.0 Hz, 1H), 6.78-6.72 (m, 2H), 3.79 (s, 3H), 3.60 (s, 2H), 2.32 (s, 3H).

REFERENCE EXAMPLE 2

1-cyano-1-(2-methyl-4-methoxyphenyl)propan-2-one

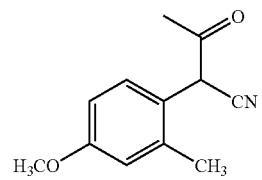

Under argon atmosphere, to a solution of the compound prepared in reference example 1 (11.7 g) in ethyl acetate (60 ml), metallic sodium (2.3 g) was added in numbers. The mixture was stirred for 2 hours at 50° C. Ethyl acetate (40 ml) was added to the reaction mixture, and the mixture was refluxed for 2.5 hours and then it was stirred overnight at room temperature. A precipitation matter was collected by filtration, and it was washed with diethyl ether. The obtained crystal was dissolved into water (300 ml). The solution was adjusted pH 4 by adding 2N hydrochloric acid, and extracted with ethyl acetate. The organic layer was dried over anhydrous sodium sulfate and concentrated to give the title compound (12.06 g) having the following physical data.

TLC: Rf 0.45 (n-hexane:ethyl acetate=1:1).

REFERENCE EXAMPLE 3

2-chloro-4-methoxyboronic acid

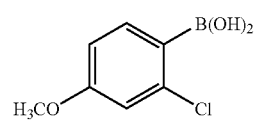

A solution of 3-chloro-4-bromoanisole (2.14 g) in anhydrous tetrahydrofuran (10 ml) was cooled at −78° C. 1.56 M n-butyl lithium/hexane (6.5 ml) was dropped into the solution, and the mixture was stirred for 30 minutes. Triisopropyl borate (2.3 ml) was dropped into the reaction mixture, and the mixture was stirred for 2 hours at −78° C. A saturated aqueous solution of ammonium chloride was added to the reaction mixture, and the mixture was extracted with ethyl acetate. The organic layer was washed with a saturated aqueous solution of sodium chloride, dried over anhydrous sodium sulfate and concentrated. A obtained solid was washed with t-butyl methyl ether (4 ml), filtered and dried over to give the title compound (681 mg) having the following physical data.

TLC: Rf 0.55 (methylene chloride:methanol=19:1);

NMR (300 MHz, CDCl$_3$): δ 7.22 (d, J=8.4 Hz, 1H), 6.93 (d, J=2.4 Hz, 1H), 6.86 (dd, J=8.4, 2.4 Hz, 1H), 3.79 (s, 3H).

REFERENCE EXAMPLE 4

4-(2-chloro-4-methoxyphenyl)-5-methylisoxazole

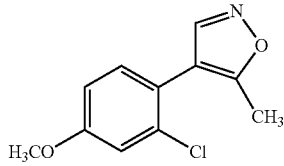

To a suspension of the compound prepared in reference example 3 (644 mg), 4-iodo-5-methylisoxazole (658 mg) and sodium bicarbonate (791 mg) in dimethoxyethane (2.5 ml)/water (2.5 ml), tetrakis (triphenylphosphine) palladium (36 mg) was added. The mixture was stirred for 16 hours at 80° C. To the reaction mixture that was cooled to room temperature, water and ethyl acetate were added. An insoluble matter was removed by filtration. An organic layer was separated from filtrate, it was washed with a saturated aqueous solution of sodium chloride, dried over anhydrous sodium sulfate and concentrated. The residue was purified by column chromatography on silica gel (n-hexane:ethyl acetate=19:1→15:1) to give the title compound (637 mg) having the following physical data.

TLC: Rf 0.44 (n-hexane:ethyl acetate=3:1);

NMR (300 MHz, CDCl$_3$): δ 8.29 (brs, 1H), 7.16 (d, J=8.4 Hz, 1H), 7.04 (d, J=2.4 Hz, 1H), 6.87 (dd, J=8.4, 2.4 Hz, 1H), 3.84 (s, 3H), 2.41 (brs, 3H).

REFERENCE EXAMPLE 5

1-cyano-1-(2-chloro-4-methoxyphenyl)propan-2-one

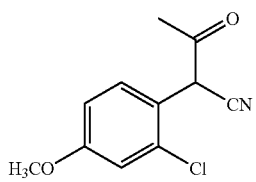

To a solution of the compound prepared in reference example 4 (623 mg) in methanol (2.8 ml), 1.5M sodium methoxide/methanol (2.8 ml) was added, and the mixture was stirred for 4 hours. The reaction mixture was diluted with water, and washed with hexane/t-butyl methyl ether (10 ml; 1:1). A water layer was adjusted pH 5 by adding 4N Hydrochloric acid (1 ml), and extracted with ethyl acetate. The organic layer was washed with a saturated aqueous solution of sodium bicarbonate and a saturated aqueous solution of sodium chloride, dried over anhydrous magnesium sulfate and concentrated to give the title compound (497 mg) having the following physical data.

TLC: Rf 0.13 (n-hexane:ethyl acetate=3:1);

NMR (300 MHz, CDCl$_3$): δ 7.38 (d, J=8.4 Hz, 1H), 7.00 (d, J=2.4 Hz, 1H), 6.89 (dd, J=8.4, 2.4 Hz, 1H), 5.11 (s, 1H), 3.83 (s, 3H), 2.29 (s, 3H).

REFERENCE EXAMPLE 6

5-amino-3-methyl-4-(2-methyl-4-methoxyphenyl)pyrazole

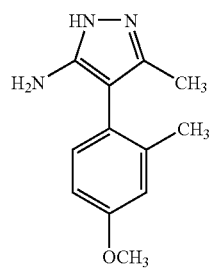

To a solution of the compound prepared in reference example 2 (8.63 g) in toluene (200 ml), acetic acid (8.0 ml) and hydrazine one hydrate (4.5 ml) were added. The mixture was refluxed for 5.5 hours and stirred overnight at room temperature. The reaction mixture was concentrated. 6N Hydrochloric acid was added to a residue, and the solution was extracted with ethyl acetate/n-hexane (30 ml/30 ml). A water layer was basified by adding concentrated aqueous ammonia, and extracted with ethyl acetate. The organic layer was dried over anhydrous sodium sulfate and concentrated to give the title compound (8.38 g) having the following physical data.

TLC: Rf 0.30 (chloroform:methanol=9:1);

NMR (300 MHz, CDCl$_3$): δ7.08 (d, J=8.0 Hz, 1H), 6.84 (d, J=2.5 Hz, 1H), 6.77 (dd, J=8.0, 2.5 Hz, 1H), 4.10 (brs, 3H), 3.83 (s, 3H), 2.18 (s, 3H), 2.07 (s, 3H).

EXAMPLE 1

8-hydroxy-2-methyl-3-(2-methyl-4-methoxyphenyl)-6,7-dihydro-5H-cyclopenta[d]pyrazolo[1,5-a]pyrimidine

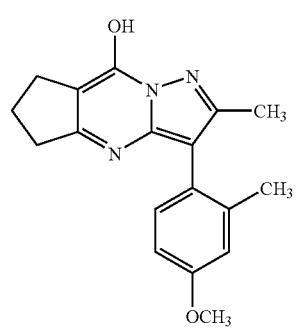

To a solution of the compound prepared in reference example 6 (500 mg) in acetic acid (3 ml), ethyl cyclopentanone-2-carboxylate (0.40 ml) was added. And the mixture was refluxed for 3 hours. After the reaction mixture was cooled to room temperature, diethyl ether/n-hexane (10 ml; 2:1) was added to the mixture. A precipitated crystal was collected by filtration, and the crystal was washed with diethyl ether/n-hexane (10 ml; 2:1), dried over to give the title compound (480 mg) having the following physical data.

TLC: Rf 0.47 (chloroform:methanol=9:1);

NMR (300 MHz, DMSO-d$_6$): δ 11.90 (brs, 1H), 7.10 (d, J=8.0 Hz, 1H), 6.93 (d, J=3.0 Hz, 1H), 6.83 (dd, J=8.0, 3.0 Hz, 1H), 3.78 (s, 3H), 2.81 (t, J=7.5 Hz, 2H), 2.66 (t, J=7.5 Hz, 2H), 2.07 (s, 3H), 2.05 (s, 3H), 2.03 (m, 2H).

REFERENCE EXAMPLE 7

8-chloro-2-methyl-3-(2-methyl-4-methoxyphenyl)-6,7-dihydro-5H-cyclopenta[d]pyrazolo[1,5-a]pyrimidine

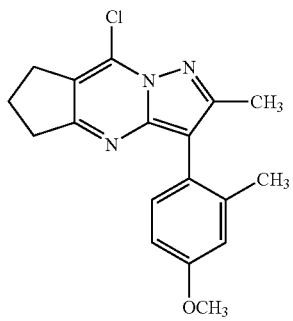

To a suspension of the compound prepared in Example 1 (400 mg) in toluene (4 ml), phosphorus oxychloride (0.60 ml) and diethylaniline (0.25 ml) were added. The mixture was refluxed for 1 hour. The reaction mixture was cooled, and it was poured into a cooled aqueous solution of sodium bicarbonate. The mixture was stirred for 10 minutes to degrade excess of phosphorus oxychloride. The reaction mixture was extracted with ethyl acetate. The organic layer was washed with a saturated aqueous solution of sodium chloride, dried over anhydrous sodium sulfate and concentrated. The residue was purified by column chromatography on silica gel (ethyl acetate:n-hexane=1:3→1:2) to give the title compound (411 mg) having the following physical data.

TLC: Rf 0.52 (n-hexane:ethyl acetate=1:1);

NMR (300 MHz, CDCl$_3$): δ 7.15 (d, J=8.5 Hz, 1H), 6.88 (d, J=2.5 Hz, 1H), 6.81 (dd, J=8.5, 2.5 Hz, 1H), 3.83 (s, 3H), 3.09-3.00 (m, 4H), 2.40 (s, 3H), 2.23 (m, 2H), 2.15 (s, 3H).

EXAMPLE 2

8-(3-pentylamino)-2-methyl-3-(2-methyl-4-methoxyphenyl)-6,7-dihydro-5H-cyclopenta[d]pyrazolo[1,5-a]pyrimidine

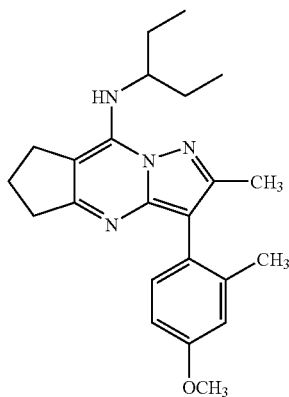

A mixture of the compound prepared in reference example 7 (150 mg) and 3-pentylamine (0.6 ml) was stirred for 1 hour at 140° C. The reaction mixture was cooled and purified by column chromatography on silica gel (ethyl acetate:n-hexane=1:3) to give the title compound (169 mg) having the following physical data.

TLC: Rf 0.57 (n-hexane:ethyl acetate=1:1);

NMR (300 MHz, CDCl$_3$): δ 7.15 (d, J=8.5 Hz, 1H), 6.85 (d, J=3.0 Hz, 1H), 6.78 (dd, J=8.5, 3.0 Hz, 1H), 6.21 (d, J=10.5 Hz, 1H), 3.82 (s, 3H), 3.81 (m, 1H), 3.08 (t, J=7.0 Hz, 2H), 2.89 (t, J=8.0 Hz, 2H), 2.30 (s, 3H), 2.19 (s, 3H), 2.14 (m, 2H), 1.69 (m 4H), 1.02 (m, 6H).

Example 2(1)-2(365)

The following compounds were obtained, using a corresponding compound in stead of 1,2-dimethyl-4-methoxybenzene, by the same procedure as a series of reactions of Reference example 1→Reference example 2→Reference example 6→Example 1 using a corresponding compound in stead of ethyl cyclopentanone-2-carboxylate→Reference example 7→Example 2 using a corresponding compound in stead of 3-pentylamine, or using the compound prepared in Reference example 5 or a corresponding compound, by the same procedure as a series of reactions of Reference example 6→Example 1→Reference example 7→Example 2, or successively by a known method to be a salt of compound.

EXAMPLE 2(1)

8-(N-ethyl-N-n-butylamino)-2-methoxymethyl-3-(2-methyl-4-methoxyphenyl)-6,7-dihydro-5H-cyclopenta[d]pyrazolo[1,5-a]pyrimidine

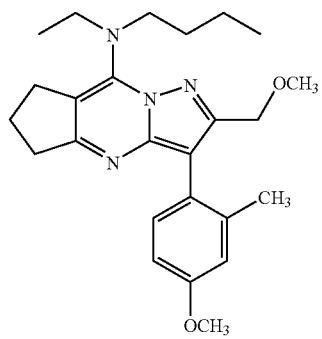

TLC: Rf 0.43 (n-hexane:ethyl acetate=2:1);

NMR (300 MHz, CDCl$_3$): δ 7.22 (d, J=8.7 Hz, 1 H), 6.84 (d, J=2.7 Hz, 1 H), 6.77 (dd, J=8.7, 2.7 Hz, 1 H), 4.49 (m, 2 H), 3.81 (s, 3 H), 3.67 (q, J=7.2 Hz, 2 H), 3.61 (t, J=7.2 Hz, 2 H), 3.33 (s, 3 H), 2.97 (t, J=7.2 Hz, 2 H), 2.91 (t, J=7.8 Hz, 2 H), 2.19 (s, 3 H), 2.13 (m, 2 H), 1.55 (m, 2 H), 1.35 (m, 2 H), 1.17 (t, J=7.2 Hz, 3 H), 0.89 (t, J=7.2 Hz, 3 H).

EXAMPLE 2(2)

8-(N-propyl-N-(2-hydroxyethyl)amino)-2-methyl-3-(2-methyl-4-methoxyphenyl)-6,7-dihydro-5H-cyclopenta[d]pyrazolo[1,5-a]pyrimidine

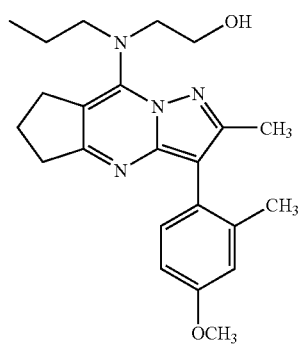

TLC: Rf 0.80 (n-hexane:ethyl acetate=1:1);
NMR (300 MHz, CDCl$_3$): δ 7.14 (d, J=8.4 Hz, 1 H), 6.86 (d, J=2.7 Hz, 1 H), 6.79 (dd, J=8.4, 2.7 Hz, 1 H), 3.90 (t, J=4.8 Hz, 2 H), 3.83 (s, 3 H), 3.64 (m, 2 H), 3.43 (m, 2H), 2.98 (t, J=7.2 Hz, 2 H), 2.92 (t, J=7.8 Hz, 2 H), 2.31 (s, 3 H), 2.17 (s, 3 H), 2.15 (m, 2 H), 1.58 (m, 2 H), 0.95 (t, J=7.2 Hz, 3 H).

EXAMPLE 2(3)

8-(3-pentylamino)-2-methyl-3-(2-methyl-4-methoxyphenyl)-5,7-dihydro-thieno[3,4-d]pyrazolo[1,5-a]pyrimidine

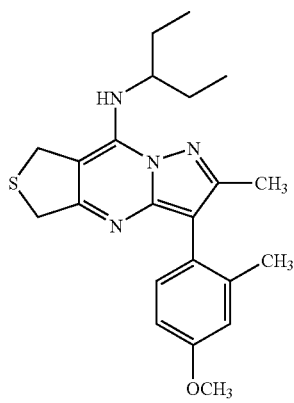

TLC: Rf 0.51 (n-hexane:ethyl acetate=2:1);
NMR (300 MHz, CDCl$_3$): δ 7.15 (d, J=8.5 Hz, 1H), 6.86 (d, J=2.5 Hz, 1H), 6.79 (dd, J=8.5, 2.5 Hz, 1H), 6.44 (d, J=10.0 Hz, 1H), 4.32 (brs, 2H), 4.14 (brs, 2H), 3.82 (s, 3H), 3.76 (m, 1H), 2.32 (s, 3H), 2.18 (s, 3H), 1.84-1.57 (m 4H), 1.03 (t, J=7.0 Hz, 6H).

EXAMPLE 2(4)

9-(3-pentylamino)-6-methyl-5-(2-methyl-4-methoxyphenyl)-2,3-dihydro-thieno[3,2-d]pyrazolo[1,5-a]pyrimidine

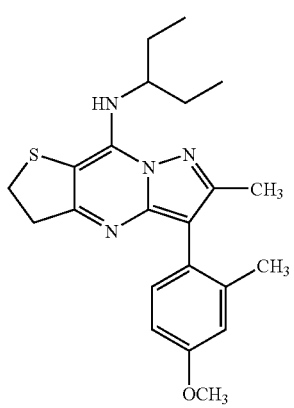

TLC: Rf 0.40 (n-hexane ethyl:acetate=2:1);
NMR (300 MHz, CDCl$_3$): δ 7.15 (d, J=8.5 Hz, 1H), 6.85 (d, J=3.0 Hz, 1H), 6.79 (dd, J=8.5, 3.0 Hz, 1H), 6.17 (d, J=10.0 Hz, 1H), 3.99 (m, 1H), 3.82 (s, 3H), 3.36-3.20 (m, 4H), 2.30 (s, 3H), 2.18 (s, 3H), 1.82-1.56 (m 4H), 1.03 (t, J=7.5 Hz, 6H).

EXAMPLE 2(5)

8-(3-pentylamino)-2-methyl-3-(2-methyl-4-methoxyphenyl)-5,7-dihydro-furo[3,4-d]pyrazolo[1,5-a]pyrimidine

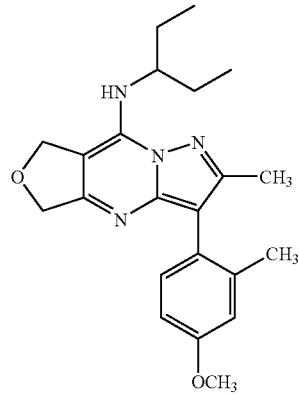

TLC: Rf 0.33 (n-hexane:ethyl acetate=2:1);
NMR (300 MHz, CDCl$_3$): δ 7.15 (d, J=8.5 Hz, 1H), 6.86 (d, J=2.5 Hz, 1H), 6.79 (dd, J=8.5, 2.5 Hz, 1H), 6.32 (d, J=10.0 Hz, 1H), 5.29 (s, 2H), 4.90 (brs, 2H), 3.82 (s, 3H), 3.24 (m, 1H), 2.33 (s, 3H), 2.18 (s, 3H), 1.84-1.56 (m 4H), 1.02 (t, J=7.5 Hz, 6H).

EXAMPLE 2(6)

9-(3-pentylamino)-6-methyl-5-(2-methyl-4-methoxyphenyl)-2,3-dihydro-furo[3,2-d]pyrazolo[1,5-a]pyrimidine

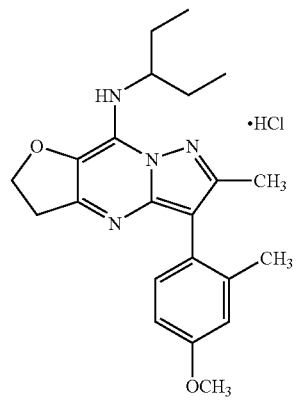

TLC: Rf 0.43 (n-hexane:ethyl acetate=2:1);
NMR (300 MHz, CDCl$_3$): δ 7.31 (brs, 1H), 7.12 (d, J=8.4 Hz, 1H), 6.89 (d, J=2.7 Hz, 1H), 6.82 (dd, J=8.4, 2.7 Hz, 1H), 4.76 (t, J=9.0 Hz, 2H), 4.30 (m, 1H), 3.83 (s, 3H), 3.74 (t, J=9.0 Hz, 2H), 2.34 (s, 3H), 2.19 (s, 3H), 1.90-1.70 (m, 4H), 1.04 (m, 6H).

EXAMPLE 2(7)

9-(3-pentylamino)-2-methyl-3-(2-methyl-4-methoxyphenyl)-5,6,7,8-tetrahydro-pyrazolo[3,2-b]quinazoline hydrochloride

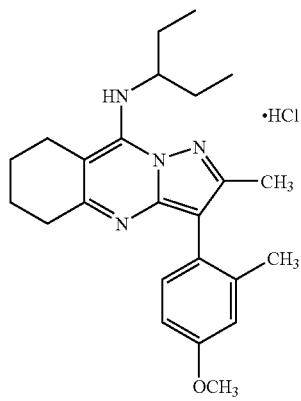

TLC: Rf 0.45 (n-hexane:ethyl acetate=2:1);

NMR (300 MHz, CDCl$_3$): δ 13.04 (brs, 1H), 7.91 (brs, 1H), 7.15 (d, J=8.5 Hz, 1H), 6.96 (d, J=2.5 Hz, 1H), 6.87 (dd, J=8.5, 2.5 Hz, 1H), 5.65 (brs, 1H), 3.79 (s, 3H), 2.75 (m, 2H), 2.58 (m, 2H), 2.19 (s, 3H), 2.05 (s, 3H), 1.88-1.64 (m, 8H), 0.91 (t, J=7.5 Hz, 6H).

EXAMPLE 2(8)

6-methyl-5-(2-methyl-4-methoxyphenyl)-9-[(2S,4R)-4-methoxy-2-methoxymethylpyrolidin-1-yl]-2,3-dihydro-furo[3,2-d]pyrazolo[1,5-a]pyrimidine

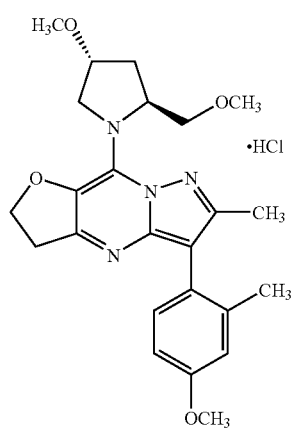

TLC: Rf 0.24 (n-hexane:ethyl acetate=1:1);

NMR (300 MHz, DMSO-d$_6$): δ 7.09 (d, J=7.5 Hz, 1H), 6.90 (d, J=2.4 Hz, 1H), 6.81 (dd, J=7.5, 2.4 Hz, 1H), 5.07 (brs, 1H), 4.66 (dt, J=9.0, 9.0 Hz, 1H), 4.56 (dt, J=9.0, 9.0 Hz, 1H), 4.24 (dd, J=12.6, 3.6 Hz, 1H), 4.05 (brs, 1H), 3.85 (d, J=12.6 Hz, 1H), 3.77 (s, 3H), 3.42 (dd, J=10.2, 3.9 Hz, 1H), 3.33 (dd, J=10.2, 5.1 Hz, 1H), 3.22 (dd, J=9.0, 9.0 Hz, 2H), 3.21 (s, 3H), 3.18 (s, 3H), 2.18 (s, 3H), 2.07 (s, 3H), 2.30-1.95 (m, 2H).

EXAMPLE 2(9)

9-(3-pentylamino)-6-methyl-5-(2-methyl-4-methoxyphenyl)-2,3-dihydro-pyrrolo[3,2-d]pyrazolo[1,5-a]pyrimidine

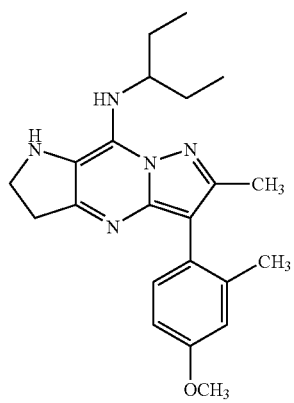

TLC: Rf 0.37 (n-hexane:ethyl acetate=1:1);

NMR (300 MHz, CDCl$_3$): δ 7.16 (d, J=8.4 Hz, 1H), 6.85 (d, J=2.7 Hz, 1H), 6.78 (dd, J=2.7, 8.4 Hz, 1H), 5.86 (d, J=10.5 Hz, 1H), 4.07 (m, 1H), 3.82 (s, 3H), 3.58 (t, J=8.1 Hz, 2H), 3.06 (t, J=8.1 Hz, 2H), 2.30 (s, 3H), 2.19 (s, 3H), 1.52-1.82 (m, 4H), 1.01 (m, 6H).

EXAMPLE 2(10)

2-methyl-3-(2-methyl-4-methoxyphenyl)-8-[(2S,4R)-4-methoxy-2-methoxymethylpyrrolidin-1-yl]-6,7-dihydro-5H-cyclopenta[d]pyrazolo[1,5-a]pyrimidine hydrochloride

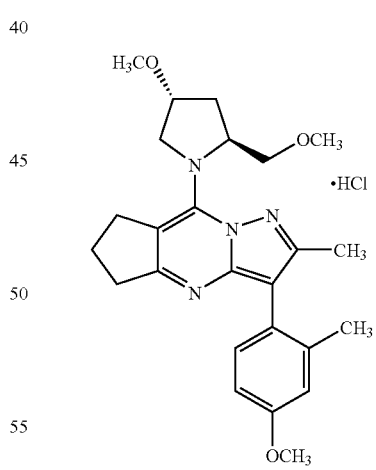

TLC: Rf 0.30 (n-hexane:ethyl acetate=1:1);

NMR (300 MHz, CDCl$_3$): δ 7.15 and 7.07 (d, J=8.4 Hz, two conformers, 1H), 6.89 and 6.87 (d, J=2.7 Hz, two conformers, 1H), 6.83 and 6.80 (dd, J=8.4, 2.7 Hz, two conformers, 1H), 5.65 (brs, 1H), 4.32-4.10 (m, 3H), 3.82 (s, 3H), 3.50-3.40 (m, 4H), 3.367 and 3.361 (s, two conformers, 3H), 3.29 and 3.28 (s, two conformers, 3H), 3.23-2.99 (m, 2H), 2.42 (m, 1H), 2.30-2.10 (m, 3H), 2.245 and 2.240 (s, two conformers, 3H), 2.22 and 2.14 (s, two conformers, 3H).

EXAMPLE 2(11)

2-methyl-3-(2-methyl-4-methoxyphenyl)-8-[(2S,4R)-4-methoxy-2-methoxymethylpyrolidin-1-yl]-5,7-dihydro-furo[3,4-d]pyrazolo[1,5-a]pyrimidine hydrochloride

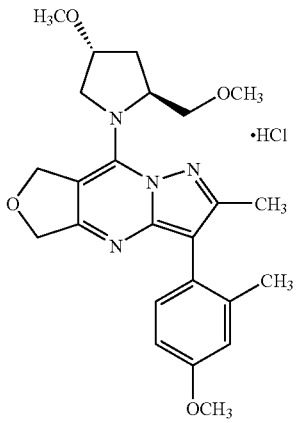

TLC: Rf 0.22 (n-hexane:ethyl acetate=1:1);

NMR (300 MHz, DMSO-$d_6$) 7.10 (brs, 1H), 6.89 (d, J=2.4 Hz, 1H), 6.81 (dd, J=8.1, 2.4 Hz, 1H), 5.33 (d, J=10.8 Hz, 1H), 5.25 (brs, 1H), 5.15 (d, J=10.8 Hz, 1H), 4.85 (d, J=14.4 Hz, 1H), 4.75 (d, J=14.4 Hz, 1H), 4.10-3.85 (m, 3H), 3.77 (s, 3H), 3.39 (dd, J=9.9, 4.5 Hz, 1H), 3.28 (dd, J=9.9, 5.1 Hz, 1H), 3.22 (s, 3H), 3.15 (s, 3H), 2.25 (m, 1H), 2.21 (s, 3H), 2.15-2.00 (m, 4H).

EXAMPLE 2(12)

6-methyl-5-(2-methyl-4-methoxyphenyl)-9-[(2S,4R)-4-methoxy-2-methoxymethylpyrolidin-1-yl]-2,3-dihydro-pyrrolo[3,2-d]pyrazolo[1,5-a]pyrimidine

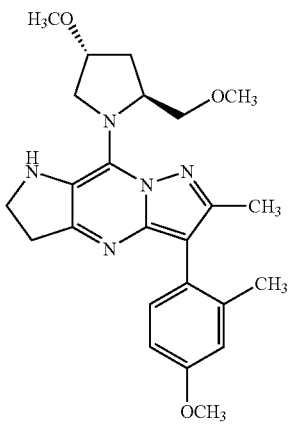

TLC: Rf 0.43 (chloroform:methanol=20:1);

NMR (300 MHz, CDCl$_3$): δ 7.16 (d, J=8.4 Hz, 1H), 6.86 (d, J=2.7 Hz, 1H), 6.79 (dd, J=2.7, 8.4 Hz, 1H), 4.71 (m, 1H), 4.20 (m, 1H), 4.06 (m, 1H), 3.82 (s, 3H), 3.60 (t, J=7.8 Hz, 2H), 3.54 (m, 1H), 3.48 (dd, J=4.5, 9.6 Hz, 1H), 3.39 (m, 1H), 3.34 (s, 3H), 3.28 (s, 3H), 3.09 (m, 2H), 2.24-2.40 (m, 4H), 2.18 (s, 3H), 2.01 (m, 1H).

EXAMPLE 2(13)

8-isopropylamino-2-methyl-3-(2-methyl-4-methoxyphenyl)-5,7-dihydro-furo[3,4-d]pyrazolo[1,5-a]pyrimidine

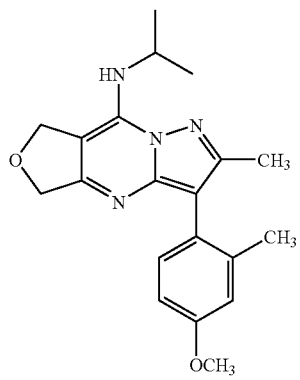

TLC: Rf 0.34 (n-hexane ethyl acetate=2:1);

NMR (300 MHz, CDCl$_3$): δ 7.15 (d, J=8.4 Hz, 1H), 6.86 (d, J=2.7 Hz, 1H), 6.79 (dd, J=8.4, 2.7 Hz, 1H), 6.39 (d, J=9.6 Hz, 1H), 5.32 (s, 2H), 4.90 (s, 2H), 3.82 (s, 3H), 3.74 (m, 1H), 2.32 (s, 3H), 2.16 (s, 3H), 1.41 (d, J=6.6 Hz, 6H).

EXAMPLE 2(14)

8-[(2S)-1,1-dimethoxybutan-2-yl]amino-2-methyl-3-(2-methyl-4-methoxyphenyl)-5,7-dihydro-furo[3,4-d]pyrazolo[1,5-a]pyrimidine

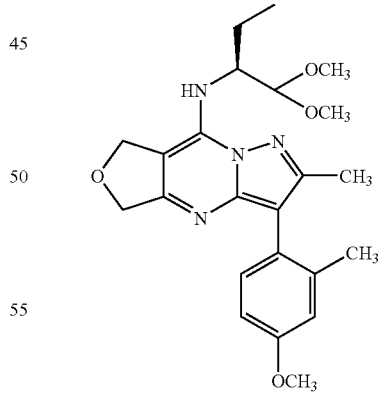

TLC: Rf 0.26 (n-hexane:ethyl acetate=2:1);

NMR (300 MHz, CDCl$_3$): δ 7.15 (d, J=8.1 Hz, 1H), 6.86 (d, J=2.4 Hz, 1H), 6.79 (dd, J=8.1, 2.4 Hz, 1H), 6.57 (brd, J=11.1 Hz, 1H), 5.36 (d, J=9.9 Hz, 1H), 5.26 (d, J=9.9 Hz, 1H), 4.90 (s, 2H), 4.33 (d, J=3.9 Hz, 1H), 3.82 (s, 3H), 3.50 (s, 3H), 3.48 (s, 3H), 3.39 (m, 1H), 2.32 (s, 3H), 2.17 (s, 3H), 1.88 (m, 1H), 1.68 (m, 1H), 1.04 (brs, 3H).

EXAMPLE 2(15)

8-[(2S)-1,1-dimethoxybutan-2-yl]amino-2-methyl-3-(2-methyl-4-methoxyphenyl)-6,7-dihydro-5H-cyclopenta[d]pyrazolo[1,5-a]pyrimidine

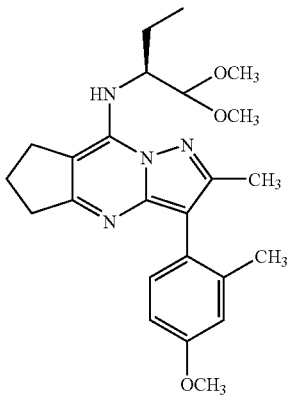

TLC: Rf 0.30 (n-hexane:ethyl acetate=2:1);

NMR (300 MHz, CDCl$_3$): δ 7.15 (d, J=8.1 Hz, 1H), 6.85 (d, J=3.0 Hz, 1H), 6.77 (dd, J=8.1, 3.0 Hz, 1H), 6.47 (brd, J=11.8 Hz, 1H), 4.34 (brs, 1H), 4.01 (m, 1H), 3.81 (s, 3H), 3.49 (s, 6H), 3.19-3.00 (m, 2H), 2.89 (t, J=7.8 Hz, 2H), 2.30 (s, 3H), 2.18 (s, 3H), 2.13 (m, 2H), 1.86 (m, 1H), 1.65 (m, 1H), 1.04 (brs, 3H).

EXAMPLE 2(16)

8-(1,3-dimethoxypropan-2-yl)amino-2-methyl-3-(2-methyl-4-methoxyphenyl)-5,7-dihydro-furo[3,4-d]pyrazolo[1,5-a]pyrimidine

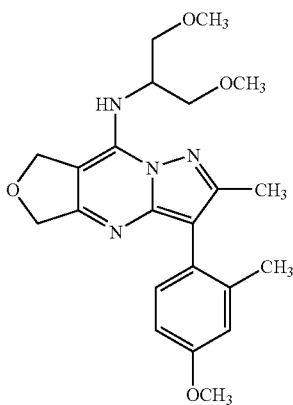

TLC: Rf 0.42 (n-hexane:ethyl acetate=1:1);

NMR (300 MHz, CDCl$_3$): δ 7.14 (d, J=8.1 Hz, 1H), 6.87 (brd, J=8.1 Hz, 1H), 6.85 (d, J=2.4 Hz, 1H), 6.79 (dd, J=8.1, 2.4 Hz, 1H), 5.33 (s, 2H), 4.89 (s, 2H), 3.81 (s, 3H), 3.75 (m, 1H), 3.62 (d, J=4.8 Hz, 4H), 3.42 (s, 6H), 2.33 (s, 3H), 2.16 (s, 3H).

EXAMPLE 2(17)

8-bis(2-methoxyethyl)amino-2-methyl-3-(2-methyl-4-methoxyphenyl)-5,7-dihydro-furo[3,4-d]pyrazolo[1,5-a]pyrimidine

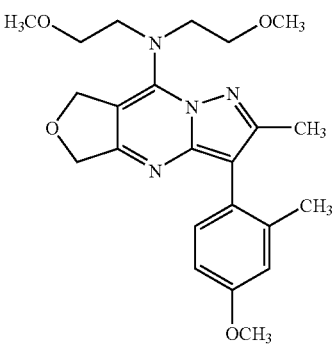

TLC: Rf 0.24 (n-hexane:ethyl acetate=1:1);

NMR (300 MHz, CDCl$_3$): δ 7.15 (d, J=8.1 Hz, 1H), 6.87 (d, J=2.7 Hz, 1H), 6.79 (dd, J=8.1, 2.7 Hz, 1H), 5.22 (s, 2H), 4.89 (s, 2H), 3.88 (t, J=6.0 Hz, 4H), 3.82 (s, 3H), 3.55 (t, J=6.0 Hz, 4H), 3.30 (s, 6H), 2.33 (s, 3H), 2.16 (s, 3H).

EXAMPLE 2(18)

8-(1,3-dimethoxypropan-2-yl)amino-2-methyl-3-(2-methyl-4-methoxyphenyl)-6,7-dihydro-5H-cyclopenta[d]pyrazolo[1,5-a]pyrimidine

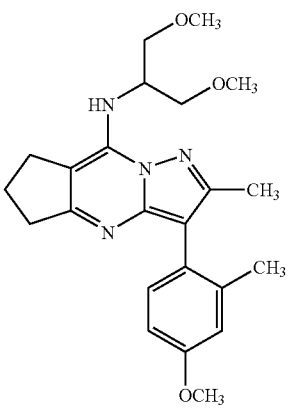

TLC: Rf 0.53 (n-hexane:ethyl acetate=1:1);

NMR (300 MHz, CDCl$_3$): δ 7.01 (d, J=8.4 Hz, 1H), 6.72 (d, J=2.7 Hz, 1H), 6.64 (dd, J=8.4, 2.7 Hz, 1H), 6.60 (d, J=9.9 Hz, 1H), 4.14 (m, 1H), 3.69 (s, 3H), 3.50 (d, J=5.4 Hz, 4H), 3.30 (s, 6H), 2.99 (t, J=7.2 Hz, 2H), 2.76 (t, J=7.8 Hz, 2H), 2.18 (s, 3H), 2.04 (s, 3H), 2.01 (m, 2H).

EXAMPLE 2(19)

8-bis(2-methoxyethyl)amino-2-methyl-3-(2-methyl-4-methoxyphenyl)-6,7-dihydro-5H-cyclopenta[d]pyrazolo[1,5-a]pyrimidine

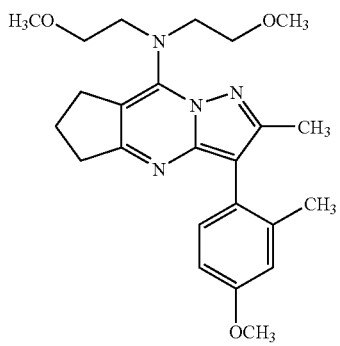

TLC: Rf 0.41 (n-hexane:ethyl acetate=1:1);

NMR (300 MHz, CDCl: δ 7.15 (d, J=8.4 Hz, 1H), 6.86 (d, J=2.7 Hz, 1H), 6.78 (dd, J=8.4, 2.7 Hz, 1H), 3.88 (t, J=5.7 Hz, 4H), 3.82 (s, 3H), 3.52 (t, J=5.7 Hz, 4H), 3.30 (s, 6H), 3.00 (t, J=6.9 Hz, 2H), 2.91 (t, J=7.8 Hz, 2H), 2.32 (s, 3H), 2.18 (s, 3H), 2.14 (m, 2H).

EXAMPLE 2(20)

(5RS)-8-(3-pentylamino)-2,5-dimethyl-3-(2-methyl-4-methoxyphenyl)-5,7-dihydro-furo[3,4-d]pyrazolo[1,5-a]pyrimidine hydrochloride

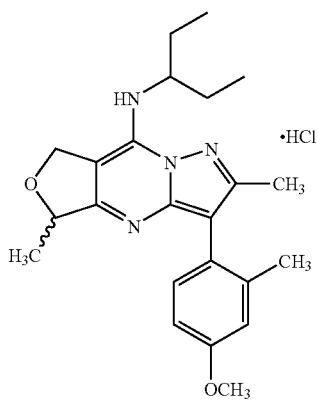

TLC: Rf 0.44 (n-hexane:ethyl acetate=2:1);

NMR (300 MHz, DMSO-$d_6$): δ 8.71 (brs, 1H), 7.15 (d, J=8.5 Hz, 1H), 6.93 (d, J=2.5 Hz, 1H), 6.85 (dd, J=8.5, 2.5 Hz, 1H), 5.70 (brs, 1H), 5.25 (dd, J=10.0, 2.0 Hz, 1H), 5.17 (d, J=10.0 Hz, 1H), 5.11 (m, 1H), 3.79 (s, 3H), 3.26 (m, 1H), 2.26 (s, 3H), 2.10 (s, 3H), 1.83-1.57 (m 4H), 1.41 (d, J=5.5 Hz, 3H), 0.93-0.83 (m, 6H).

EXAMPLE 2(21)

8-(3-pentylamino)-2-methyl-3-(2,4-dichlorophenyl)-6,7-dihydro-5H-cyclopenta[d]pyrazolo[1,5-a]pyrimidine

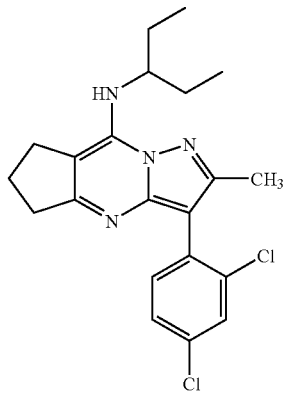

TLC: Rf 0.50 (n-hexane:ethyl acetate=2:1);

NMR (300 MHz, CDCl$_3$): δ 7.50 (d, J=2.0 Hz, 1H), 7.35 (d, J=8.5 Hz, 1H), 7.29 (dd, J=8.5, 2.0 Hz, 1H), 6.23 (d, J=10.5 Hz, 1H), 3.81 (m, 1H), 3.09 (t, J=7.5 Hz, 2H), 2.91 (t, J=7.5 Hz, 2H), 2.34 (s, 3H), 2.15 (m, 2H), 1.82-1.55 (m 4H), 1.01 (t, J=7.5 Hz, 6H).

EXAMPLE 2(22)

8-(3-pentylamino)-2-methyl-3-(2-methyl-4-methoxyphenyl)-5,7-dihydro-pyrrolo[3,4-d]pyrazolo[1,5-a]pyrimidine

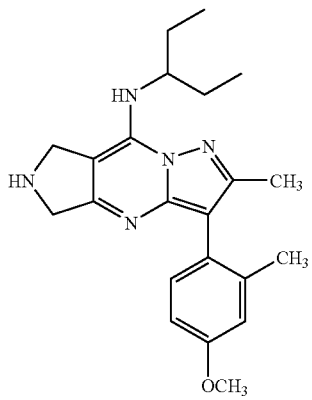

TLC: Rf 0.48 (chloroform:methanol=10:1);

NMR (300 MHz, CDCl$_3$): δ 7.16 (d, J=8.1H, 1H), 6.86 (d, J=2.7 Hz, 1H), 6.79 (dd, J=2.7, 8.1 Hz, 1H), 6.29 (d, J=10.2 Hz, 1H), 4.43 (s, 2H), 4.10 (s, 2H), 3.82 (s, 3H), 3.49 (m, 1H), 2.32 (s, 3H), 2.18 (s, 3H), 1.55-1.84 (m, 4H), 1.02 (m, 6H).

EXAMPLE 2(23)

8-diethylamino-2-methyl-3-(2-methyl-4-methoxyphenyl)-6,7-dihydro-5H-cyclopenta[d]pyrazolo[1,5-a]pyrimidine

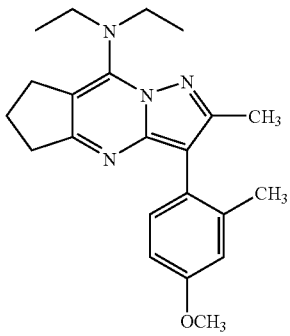

TLC: Rf 0.67 (n-hexane:ethyl acetate=1:1);

NMR (300 MHz, CDCl$_3$): δ 7.16 (d, J=8.4 Hz, 1H), 6.86 (d, J=2.7 Hz, 1H), 6.79 (dd, J=8.4, 2.7 Hz, 1H), 3.82 (s, 3H), 3.66 (q, J=7.2 Hz, 4H), 2.99 (t, J=7.5 Hz, 2H), 2.91 (t, J=7.5 Hz, 2H), 2.33 (s, 3H), 2.19 (s, 3H), 2.13 (m, 2H), 1.18 (t, J=7.2 Hz, 6H).

EXAMPLE 2(24)

8-(N-ethyl-N-n-butylamino)-2-methyl-3-(2,4-dichlorophenyl)-6,7-dihydro-5H-cyclopenta[d]pyrazolo[1,5-a]pyrimidine

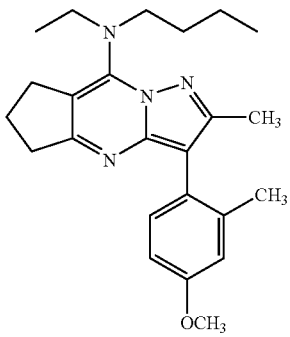

TLC: Rf 0.78 (n-hexane:ethyl acetate=1:1);

NMR (300 MHz, CDCl$_3$): δ 7.17 (d, J=8.4 Hz, 1H), 6.86 (d, J=3.0 Hz, 1H), 6.79 (dd, J=8.4, 3.0 Hz, 1H), 3.82 (s, 3H), 3.70-3.56 (m, 4H), 2.97 (t, J=6.9 Hz, 2H), 2.91 (t, J=7.7 Hz, 2H), 2.33 (s, 3H), 2.19 (s, 3H), 2.13 (m, 2H), 1.55 (m, 2H), 1.32 (m, 2H), 1.17 (t, J=7.2 Hz, 3H), 0.90 (t, J=7.2 Hz, 3H).

EXAMPLE 2(25)

8-dicyclopropylmethylamino-2-methyl-3-(2-methyl-4-methoxyphenyl)-6,7-dihydro-5H-cyclopenta[d]pyrazolo[1,5-a]pyrimidine

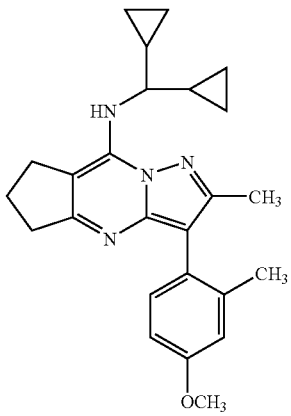

TLC: Rf 0.40 (n-hexane:ethyl acetate=3:1);

NMR (300 MHz, CDCl$_3$): δ 7.15 (d, J=8.1 Hz, 1H), 6.85 (d, J=2.7 Hz, 1H), 6.78 (dd, J=8.1, 2.7 Hz, 1H), 6.36 (d, J=10.2 Hz, 1H), 3.82 (s, 3H), 3.41 (m, 1H), 3.01 (t, J=7.2 Hz, 2H), 2.87 (t, J=8.1 Hz, 2H), 2.31 (s, 3H), 2.19 (s, 3H), 2.10 (m, 2H), 1.20-1.08 (m, 2H), 0.66-0.32 (m, 8H).

EXAMPLE 2(26)

8-(N-propyl-N-(2-hydroxyethyl)amino)-2-methyl-3-(2-methyl-4-methoxyphenyl)-5,7-dihydro-furo[3,4-d]pyrazolo[1,5-a]pyrimidine

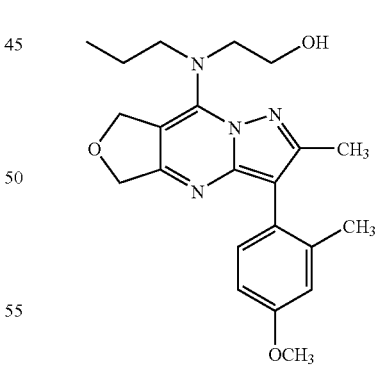

TLC: Rf 0.26 (n-hexane:ethyl acetate=1:2);

NMR (300 MHz, CDCl$_3$): δ 7.14 (d, J=8.4 Hz, 1 H), 6.87 (d, J=2.7 Hz, 1 H), 6.80 (dd, J=8.4, 2.7 Hz, 1 H), 6.54 (brs, 1 H), 5.21 (s, 2 H), 4.89 (s, 2 H), 3.96 (brt, J=4.8 Hz, 2 H), 3.83 (s, 3 H), 3.80 (m, 2 H), 3.29 (t, J=7.5 Hz, 2 H), 2.33 (s, 3 H), 2.17 (s, 3 H), 1.63 (m, 2 H), 1.00 (t, J=7.5 Hz, 3 H).

EXAMPLE 2(27)

8-(3-pentylamino)-2-methoxymethyl-3-(2-methyl-4-methoxyphenyl)-6,7-dihydro-5H-cyclopenta[d]pyrazolo[1,5-a]pyrimidine

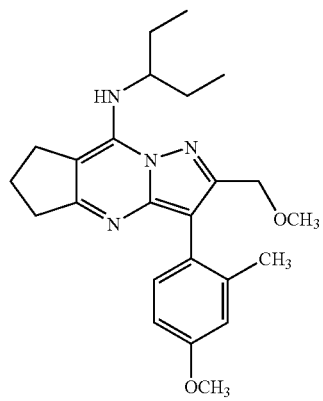

TLC: Rf 0.27 (n-hexane:ethyl acetate=2:1);

NMR (300 MHz, CDCl$_3$): δ 7.19 (d, J=8.5 Hz, 1H), 6.85 (d, J=2.5 Hz, 1H), 6.78 (dd, J=8.5, 2.5 Hz, 1H), 6.32 (d, J=10.5 Hz, 1H), 4.54-4.40 (m, 2H), 3.82 (s, 3H), 3.81 (m, 1H), 3.37 (s, 3H), 3.10 (t, J=7.0 Hz, 2H), 2.91 (t, J=8.0 Hz, 2H), 2.20 (s, 3H), 2.14 (m, 2H), 1.80-1.53 (m, 4H), 1.08-0.94 (m, 6H).

EXAMPLE 2(28)

8-(3-pentylamino)-2-methyl-3-(1,3-dioxaindan-5-yl)-6,7-dihydro-5H-cyclopenta[d]pyrazolo[1,5-a]pyrimidine

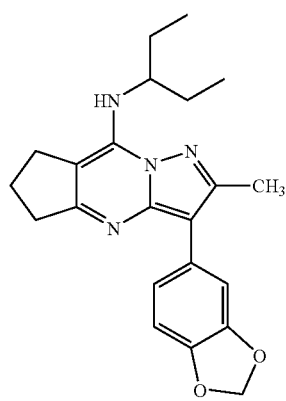

TLC: Rf 0.61 (n-hexane:ethyl acetate=2:1);

NMR (300 MHz, CDCl$_3$): δ 7.22 (d, J=1.5 Hz, 1H), 7.10 (dd, J=1.5, 8.1 Hz, 1H), 6.89 (d, J=8.1 Hz, 1H), 6.20 (br d, J=10.5 Hz, 1H), 5.96 (s, 2H), 3.80 (m, 1H), 3.08 (t, J=7.5 Hz, 2H), 2.94 (t, J=8.1 Hz, 2H), 2.52 (s, 3H), 2.15 (m, 2H), 1.51-1.80 (m, 4H), 1.00 (t, J=7.5 Hz, 6H).

EXAMPLE 2(29)

8-(3-pentylamino)-2-methyl-3-(3,4-dimethoxyphenyl)-6,7-dihydro-5H-cyclopenta[d]pyrazolo[1,5-a]pyrimidine

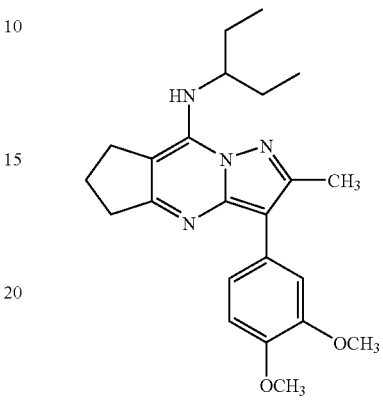

TLC: Rf 0.56 (n-hexane:ethyl acetate=1:1);

NMR (300 MHz, CDCl$_3$): δ 7.29 (d, J=2.1 Hz, 1H), 7.19 (dd, J=2.1, 8.1 Hz, 1H), 6.96 (d, J=8.1 Hz, 1H), 6.20 (br d, J=10.5 Hz, 1H), 3.93 (s, 3H), 3.91 (s, 3H), 3.80 (m, 1H), 3.09 (t, J=7.2 Hz, 2H), 2.94 (t, J=7.5 Hz, 2H), 2.55 (s, 3H), 2.16 (m, 2H), 1.53-1.81 (m, 4H), 1.00 (t, J=7.2 Hz, 6H).

EXAMPLE 2(30)

8-cyclopropylamino-2-methyl-3-(2-methyl-4-methoxyphenyl)-5,7-dihydro-furo[3,4-d]pyrazolo[1,5-a]pyrimidine

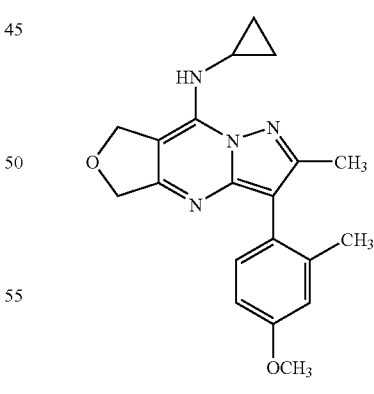

TLC: Rf 0.33 (n-hexane:ethyl acetate=3:2);

NMR (300 MHz, CDCl$_3$): δ 7.14 (d, J=8.1 Hz, 1H), 6.86 (d, J=2.7 Hz, 1H), 6.79 (dd, J=8.1, 2.7 Hz, 1H), 6.62 (brs, 1H), 5.54 (brs, 2H), 4.91 (brs, 2H), 3.82 (s, 3H), 2.89 (m, 1H), 2.30 (s, 3H), 2.15 (s, 3H), 0.98-0.84 (m, 4H).

EXAMPLE 2(31)

8-(3-pentylamino)-2-cyclobutyl-3-(2-methyl-4-methoxyphenyl)-6,7-dihydro-5H-cyclopenta[d]pyrazolo[1,5-a]pyrimidine

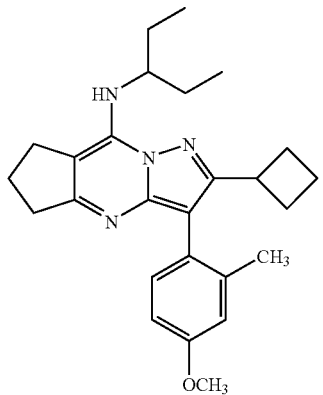

TLC: Rf 0.62 (benzene:ethyl acetate=5:1);

NMR (300 MHz, CDCl$_3$): δ 7.09 (d, J=8.1 Hz, 1H), 6.83 (d, J=2.7 Hz, 1H), 6.75 (dd, J=8.1, 2.7 Hz, 1H), 6.35 (d, J=10.5 Hz, 1H), 3.82 (s, 3H), 3.81 (m, 1H), 3.53 (m, 1H), 3.08 (t, J=7.5 Hz, 2H), 2.88 (t, J=7.8 Hz, 2H), 2.41 (m, 2H), 2.28-2.06 (m, 4H), 2.15 (s, 3H), 2.01-1.58 (m, 6H), 1.05 (t, J=7.5 Hz, 3H), 1.02 (t, J=7.8 Hz, 3H).

EXAMPLE 2(32)

8-(3-pentylamino)-2-ethyl-3-(2-methyl-4-methoxyphenyl)-6,7-dihydro-5H-cyclopenta[d]pyrazolo[1,5-a]pyrimidine

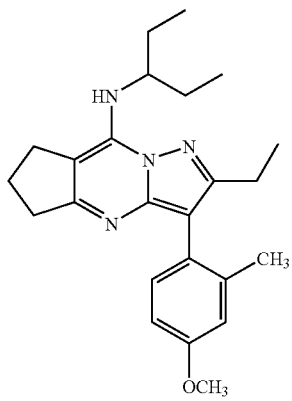

TLC: Rf 0.59 (benzene:ethyl acetate=5:1);

NMR (300 MHz, CDCl$_3$): δ 7.15 (d, J=8.1 Hz, 1H), 6.85 (d, J=2.7 Hz, 1H), 6.77 (dd, J=8.1, 2.7 Hz, 1H), 6.27 (d, J=10.5 Hz, 1H), 3.82 (s, 3H), 3.80 (m, 1H), 3.08 (t, J=7.5 Hz, 2H), 2.89 (t, J=7.8 Hz, 2H), 2.67 (m, 2H), 2.17 (s, 3H), 2.13 (m, 2H), 1.81-1.52 (m, 4H), 1.16 (t, J=7.2 Hz, 3H), 1.04 (t, J=7.5 Hz, 3H), 1.01 (t, J=7.8 Hz, 3H).

EXAMPLE 2(33)

8-(3-pentylamino)-2-isopropyl-3-(2-methyl-4-methoxyphenyl)-6,7-dihydro-5H-cyclopenta[d]pyrazolo[1,5-a]pyrimidine hydrochloride

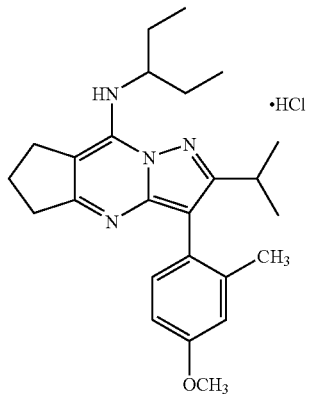

TLC: Rf 0.60 (n-hexane:ethyl acetate=3:1);

NMR (300 MHz, CDCl$_3$): δ 7.28 (m, 1H), 7.09 (d, J=8.4 Hz, 1H), 6.90 (d, J=2.4 Hz, 1H), 6.81 (dd, J=8.4, 2.4 Hz, 1H), 3.99 (m, 1H), 3.84 (s, 3H), 3.49 (m, 2H), 3.12 (t, J=7.2 Hz, 2H), 2.99 (m, 1H), 2.28 (m, 2H), 2.20 (s, 3H), 1.85 (m, 2H), 1.74 (m, 2H), 1.24 (d, J=6.9 Hz, 3H), 1.19 (d, J=7.2 Hz, 3H), 1.08 (t, J=7.5 Hz, 3H), 1.06 (t, J=7.5 Hz, 3H).

EXAMPLE 2(34)

8-(2-ethylbutylamino)-2-methyl-3-(2-methyl-4-methoxyphenyl)-6,7-dihydro-5H-cyclopenta[d]pyrazolo[1,5-a]pyrimidine hydrochloride

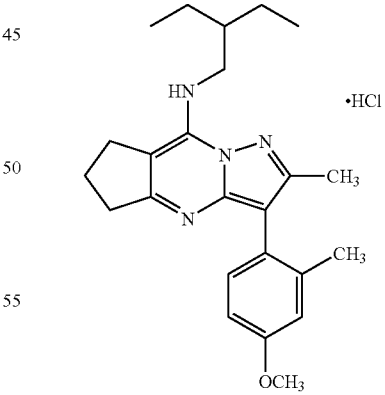

TLC: Rf 0.55 (n-hexane:ethyl acetate=3:1);

NMR (300 MHz, CDCl$_3$): δ 7.46 (m, 1H), 7.11 (d, J=8.4 Hz, 1H), 6.89 (d, J=2.4 Hz, 1H), 6.82 (dd, J=8.4, 2.4 Hz, 1H), 3.83 (s, 3H), 3.74 (t, J=6.0 Hz, 2H), 3.49 (t, J=7.8 Hz, 2H), 3.21 (t, J=7.5 Hz, 2H), 2.28 (s, 3H), 2.26 (m, 2H), 2.19 (s, 3H), 1.68 (m, 1H), 1.53 (m, 4H), 1.00 (t, J=7.5 Hz, 6H).

EXAMPLE 2(35)

8-(3-pentylamino)-2-methylthiomethyl-3-(2-methyl-4-methoxyphenyl)-6,7-dihydro-5H-cyclopenta[d]pyrazolo[1,5-a]pyrimidine hydrochloride

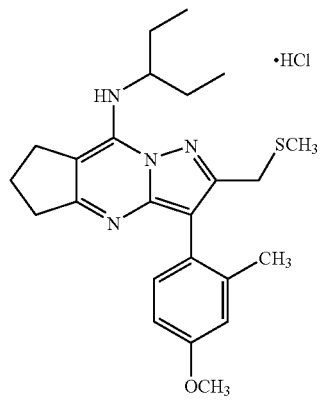

TLC: Rf 0.31 (n-hexane:ethyl acetate=3:1);

NMR (300 MHz, CDCl$_3$): δ 7.31 (brd, J=10.8 Hz, 1H), 7.16 (d, J=8.4 Hz, 1H), 6.89 (d, J=2.4 Hz, 1H), 6.80 (dd, J=8.4, 2.4 Hz, 1H), 4.00 (brs, 1H), 3.83 (s, 3H), 3.70 (d, J=13.5 Hz, 1H), 3.60 (d, J=13.5 Hz, 1H), 3.50 (m, 2H), 3.14 (t, J=7.2 Hz, 2H), 2.29 (m, 2H), 2.32 (s, 3H), 2.04 (s, 3H), 1.95-1.65 (m, 4H), 1.07 (t, J=7.2 Hz, 3H), 1.05 (t, J=7.5 Hz, 3H).

EXAMPLE 2(36)

8-(N-methyl-N-cyclopropylamino)-2-methyl-3-(2-methyl-4-methoxyphenyl)-5,7-dihydro-furo[3,4-d]pyrazolo[1,5-a]pyrimidine

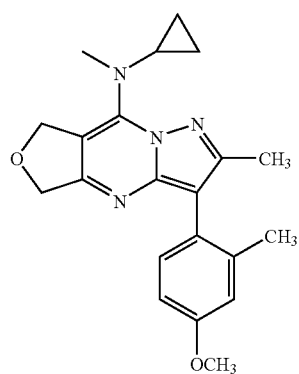

TLC: Rf 0.16 (n-hexane:ethyl acetate=3:1);

NMR (300 MHz, CDCl$_3$): δ 7.14 (d, J=8.1 Hz, 1H), 6.86 (d, J=2.7 Hz, 1H), 6.79 (dd, J=8.1, 2.7 Hz, 1H), 5.47 (brs, 2H), 4.90 (brs, 2H), 3.82 (s, 3H), 3.45 (s, 3H), 2.80 (m, 1H), 2.33 (s, 3H), 2.16 (s, 3H), 0.84 (d, J=6.0 Hz, 4H).

EXAMPLE 2(37)

8-(3-pentylamino)-2-methyl-3-(2,4-dimethylphenyl)-6,7-dihydro-5H-cyclopenta[d]pyrazolo[1,5-a]pyrimidine

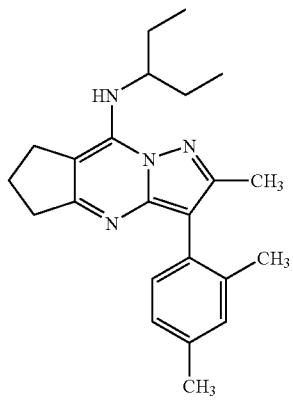

TLC: Rf 0.50 (benzene:ethyl acetate=10:1);

NMR (300 MHz, CDCl$_3$): δ 7.13 (d, J=7.5 Hz, 1H), 7.11 (brs, 1H), 7.03 (m, 1H), 6.21 (d, J=10.8 Hz, 1H), 3.80 (m, 1H), 3.08 (t, J=6.9 Hz, 2H), 2.89 (t, J=7.5 Hz, 2H), 2.34 (s, 3H), 2.31 (s, 3H), 2.18 (s, 3H), 2.13 (m, 2H), 1.56-1.82 (m, 4H), 1.02 (m, 6H).

EXAMPLE 2(38)

8-(3-pentylamino)-2-methyl-3-(2,5-dimethylphenyl)-6,7-dihydro-5H-cyclopenta[d]pyrazolo[1,5-a]pyrimidine hydrochloride

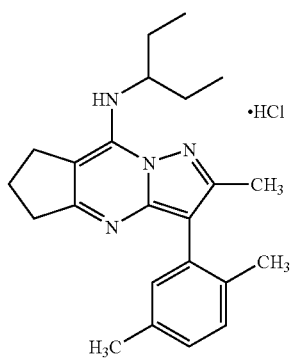

TLC: Rf 0.54 (n-hexane:ethyl acetate=3:1);

NMR (300 MHz, CDCl$_3$): δ 7.31 (br d, J=10.2 Hz, 1H), 7.24 (d, J=7.5 Hz, 1H), 7.15 (br dd, J=1.2, 7.5 Hz, 1H), 7.01 (brs, 1H), 3.99 (m, 1H), 3.49 (t, J=7.5 Hz, 2H), 3.14 (t, J=6.9 Hz, 2H), 2.35 (s, 3H), 2.32 (s, 3H), 2.29 (m, 2H), 2.18 (s, 3H), 1.64-1.94 (m, 4H), 1.07 (t, J=7.5 Hz, 3H), 1.06 (t, J=7.2 Hz, 3H).

EXAMPLE 2(39)

8-cyclobutylamino-2-methyl-3-(2-methyl-4-methoxyphenyl)-6,7-dihydro-5H-cyclopenta[d]pyrazolo[1,5-a]pyrimidine

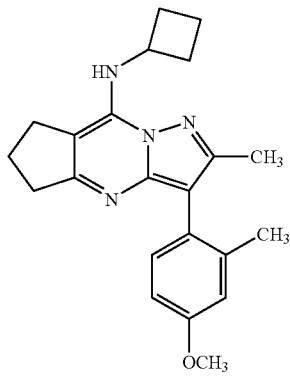

TLC: Rf 0.36 (n-hexane:ethyl acetate=3:1);

NMR (300 MHz, CDCl$_3$): δ 7.14 (d, J=8.7 Hz, 1H), 6.85 (d, J=2.7 Hz, 1H), 6.77 (dd, J=8.7, 2.7 Hz, 1H), 6.50 (brd, J=8.4 Hz, 1H), 4.46 (m, 1H), 3.81 (s, 3H), 3.12 (t, J=7.2 Hz, 2H), 2.88 (t, J=7.8 Hz, 2H), 2.43 (m, 2H), 2.30 (s, 3H), 2.23-2.08 (m, 4H), 2.16 (s, 3H), 1.90-1.70 (m, 2H).

EXAMPLE 2(40)

8-(N-ethyl-N-cyclobutylamino)-2-methyl-3-(2-methyl-4-methoxyphenyl)-6,7-dihydro-5H-cyclopenta[d]pyrazolo[1,5-a]pyrimidine hydrochloride

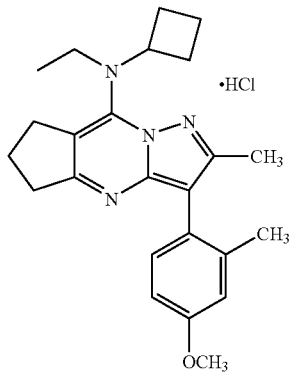

TLC: Rf 0.38 (n-hexane:ethyl acetate=3:1);

NMR (300 MHz, CDCl$_3$): δ 7.12 (d, J=8.7 Hz, 1H), 6.89 (d, J=2.7 Hz, 1H), 6.82 (dd, J=8.7, 2.7 Hz, 1H), 4.74 (m, 1H), 3.99 (m, 2H), 3.83 (s, 3H), 3.48 (t, J=7.5 Hz, 2H), 2.98 (t, J=7.5 Hz, 2H), 2.20-2.10 (m, 6H), 2.30 (s, 3H), 2.17 (s, 3H), 1.90-1.70 (m, 2H), 1.16 (t, J=7.2 Hz, 3H).

EXAMPLE 2(41)

8-(propan-1,3-diol-2-yl)amino-2-methyl-3-(2-methyl-4-methoxyphenyl)-6,7-dihydro-5H-cyclopenta[d]pyrazolo[1,5-a]pyrimidine

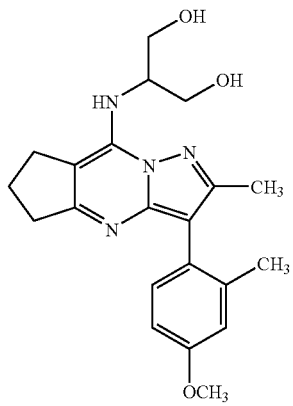

TLC: Rf 0.44 (chloroform:methanol=9:1);

NMR (300 MHz, CDCl$_3$): δ 7.17 (d, J=8.1 Hz, 1H), 6.86 (d, J=2.7 Hz, 1H), 6.79 (dd, J=8.1, 2.7 Hz, 1H), 6.73 (d, J=10.2 Hz, 1H), 4.12 (m, 1H), 3.98-3.83 (m, 4H), 3.82 (s, 3H), 3.05 (t, J=7.2 Hz, 2H), 2.87 (t, J=8.1 Hz, 2H), 2.30 (s, 3H), 2.16 (s, 3H), 2.11 (m, 2H).

EXAMPLE 2(42)

8-(3-pentylamino)-2-(2-furyl)-3-(2-methyl-4-methoxyphenyl)-6,7-dihydro-5H-cyclopenta[d]pyrazolo[1,5-a]pyrimidine

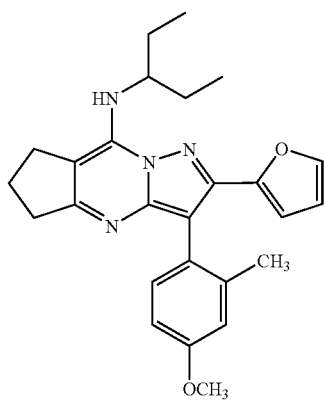

TLC: Rf 0.33 (n-hexane:ethyl acetate=4:1);

NMR (300 MHz, CDCl$_3$): δ 7.47 (m, 1H), 7.21 (d, J=8.1 Hz, 1H), 6.87 (d, J=2.7 Hz, 1H), 6.81 (dd, J=8.1, 2.7 Hz, 1H), 6.38-6.30 (m, 2H), 6.05 (m, 1H), 3.84 (s, 3H), 3.82 (m, 1H), 3.11 (t, J=7.2 Hz, 2H), 2.91 (t, J=7.8 Hz, 2H), 2.15 (m, 2H), 2.10 (s, 3H), 1.70 (m, 4H), 1.04 (t, J=7.2 Hz, 3H), 1.01 (t, J=7.2 Hz, 3H).

EXAMPLE 2(43)

8-(3-pentylamino)-2-phenyl-3-(2-methyl-4-methoxyphenyl)-6,7-dihydro-5H-cyclopenta[d]pyrazolo[1,5-a]pyrimidine hydrochloride

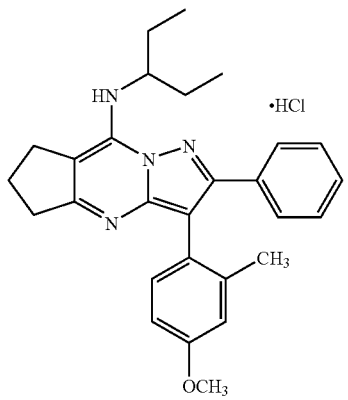

TLC: Rf 0.41 (n-hexane:ethyl acetate=4:1);

NMR (300 MHz, CDCl$_3$): δ 7.59-7.54 (m, 2H), 7.45-7.19 (m, 5H), 6.88-6.82 (m, 2H), 4.04 (m, 1H), 3.85 (s, 3H), 3.55 (t, J=7.8 Hz, 2H), 3.17 (t, J=7.8 Hz, 2H), 2.32 (m, 2H), 2.05 (s, 3H), 1.97-1.55 (m, 4H), 1.10 (t, J=6.9 Hz, 3H), 1.07 (t, J=7.2 Hz, 3H).

EXAMPLE 2(44)

8-(2-dimethylaminoethyl)amino-2-methyl-3-(2-methyl-4-methoxyphenyl)-6,7-dihydro-5H-cyclopenta[d]pyrazolo[1,5-a]pyrimidine

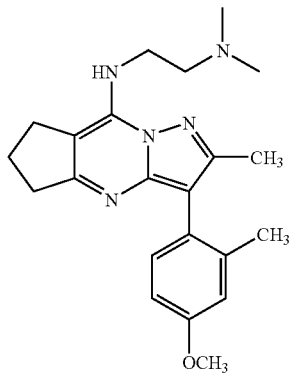

TLC: Rf 0.30 (methylene chloride:methanol=19:1);

NMR (300 MHz, CDCl$_3$): δ 7.15 (d, J=8.4 Hz, 1H), 6.85 (d, J=2.7 Hz, 1H), 6.77 (dd, J=8.4, 2.7 Hz, 1H), 6.71 (t, J=5.7 Hz, 1H), 3.82 (s, 3H), 3.75 (dt, J=5.7, 6.3 Hz, 2H), 3.19 (t, J=7.5 Hz, 2H), 2.88 (t, J=7.5 Hz, 2H), 2.63 (t, J=6.3 Hz, 2H), 2.33 (s, 6H), 2.31 (s, 3H), 2.17 (s, 3H), 2.12 (m, 2H).

EXAMPLE 2(45)

8-(N-methyl-N-(2-dimethylaminoethyl)amino)-2-methyl-3-(2-methyl-4-methoxyphenyl)-6,7-dihydro-5H-cyclopenta[d]pyrazolo[1,5-a]pyrimidine dihydrochloride

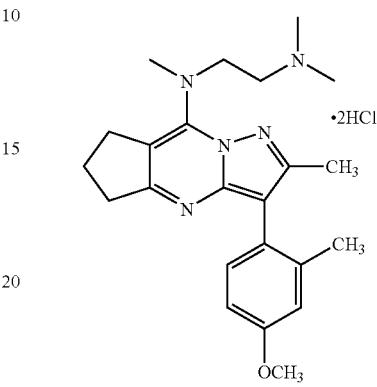

TLC: Rf 0.46 (methylene chloride:methanol=9:1);

NMR (300 MHz, pyridine-d$_6$ 0.5 ml+CDCl$_3$ 0.1 ml): δ 7.42 (d, J=8.4 Hz, 1H), 7.04 (d, J=2.7 Hz, 1H), 6.96 (dd, J=8.4, 2.7 Hz, 1H), 4.21 (t, J=7.5 Hz, 2H), 3.85 (t, J=7.5 Hz, 2H), 3.75 (s, 3H), 3.14 (s, 3H), 3.00 (s, 6H), 2.90 (t, J=7.5 Hz, 2H), 2.80 (t, J=7.5 HZ, 2H), 2.41 (s, 3H), 2.36 (s, 3H), 1.90 (m, 2H).

EXAMPLE 2(46)

8-(N-ethyl-N-(2-dimethylaminoethyl)amino)-2-methyl-3-(2-methyl-4-methoxyphenyl)-6,7-dihydro-5H-cyclopenta[d]pyrazolo[1,5-a]pyrimidine

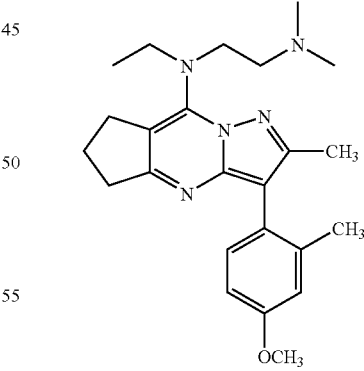

TLC: Rf 0.46 (methylene chloride:methanol=9:1);

NMR (300 MHz, CDCl$_3$): δ 7.15 (d, J=8.4 Hz, 1H), 6.85 (d, J=2.7 Hz, 1H), 6.78 (dd, J=8.4, 2.7 Hz, 1H), 3.82 (s, 3H), 3.80 (t, J=7.2 Hz, 2H), 3.64 (q, J=7.2 Hz, 2H), 2.99 (t, J=7.5 Hz, 2H), 2.90 (t, J=7.5 Hz, 2H), 2.56 (t, J=7.2 Hz, 2H), 2.31 (s, 3H), 2.25 (s, 6H), 2.17 (s, 3H), 2.12 (m, 2H), 1.17 (t, J=7.2 Hz, 3H).

EXAMPLE 2(47)

8-(4-heptylamino)-2-methyl-3-(2-methyl-4-methoxyphenyl)-6,7-dihydro-5H-cyclopenta[d]pyrazolo[1,5-a]pyrimidine hydrochloride

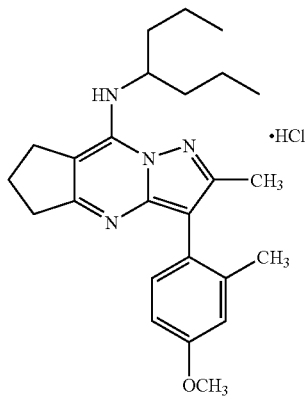

TLC: Rf 0.50 (n-hexane:ethyl acetate=3:1);

NMR (300 MHz, CDCl$_3$): δ 7.27 (brd, J=9.6 Hz, 1H), 7.11 (d, J=8.4 Hz, 1H), 6.88 (d, J=2.7 Hz, 1H), 6.81 (dd, J=8.4, 2.7 Hz, 1H), 4.12 (m, 1H), 3.82 (s, 3H), 3.49 (t, J=7.5 Hz, 2H), 3.11 (t, J=7.5 Hz, 2H), 2.32-2.20 (m, 2H), 2.28 (s, 3H), 2.20 (s, 3H), 1.82-1.60 (m, 4H), 1.60-1.36 (m, 4H), 0.99 (t, J=7.2 Hz, 3H), 0.98 (t, J=7.2 Hz, 3H).

EXAMPLE 2(48)

8-(2-butylamino)-2-methyl-3-(2-methyl-4-methoxyphenyl)-6,7-dihydro-5H-cyclopenta[d]pyrazolo[1,5-a]pyrimidine hydrochloride

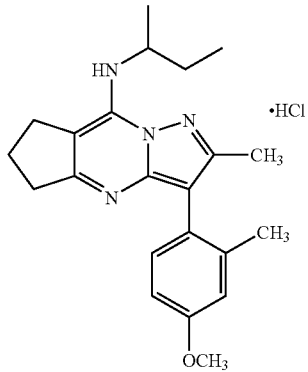

TLC: Rf 0.40 (n-hexane:ethyl acetate=3:1);

NMR (300 MHz, CDCl$_3$): δ 7.36 (brd, J=9.9 Hz, 1H), 7.12 and 7.11 (d, J=8.4 Hz, two conformers, 1H), 6.88 (d, J=2.7 Hz, 1H), 6.81 (dd, J=8.4, 2.7 Hz, 1H), 4.18 (m, 1H), 3.83 (s, 3H), 3.48 (t, J=7.5 Hz, 2H), 3.16 (t, J=7.5 Hz, 2H), 2.40-2.20 (m, 2H), 2.28 (s, 3H), 2.19 and 2.18 (s, two conformers, 3H), 1.80 (m, 2H), 1.48 and 1.47 (d, J=6.6 Hz, two conformers, 3H), 1.09 and 1.08 (t, J=7.2 Hz, two conformers, 3H).

EXAMPLE 2(49)

8-(N-propyl-N-cyclopropylmethylamino)-2-methyl-3-(2-methyl-4-methoxyphenyl)-6,7-dihydro-5H-cyclopenta[d]pyrazolo[1,5-a]pyrimidine hydrochloride

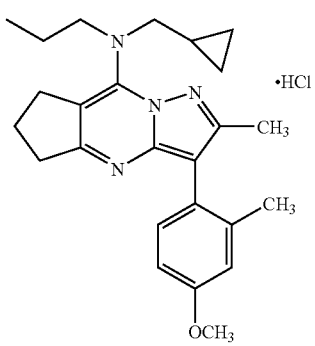

TLC: Rf 0.42 (n-hexane:ethyl acetate=3:1);

NMR (300 MHz, CDCl$_3$): δ 7.13 (m, 1H), 6.88 (brs, 1H), 6.82 (m, 1H), 3.88 (m, 2H), 3.83 (brs, 3H), 3.77 (brs, 2H), 3.37 (m, 2H), 3.06 (m, 2H), 2.29 (s, 3H), 2.24 (m, 2H), 2.19 (s, 3H), 1.73 (m, 2H), 1.12 (m, 1H), 0.96 (m, 3H), 0.62 (m, 2H), 0.26 (brs, 2H).

EXAMPLE 2(50)

8-(3-pentylamino)-3-(2-methyl-4-methoxyphenyl)-6,7-dihydro-5H-cyclopenta[d]pyrazolo[1,5-a]pyrimidine hydrochloride

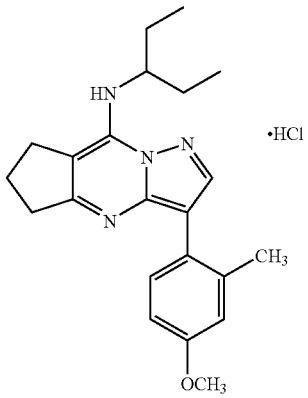

TLC: Rf 0.46 (n-hexane:ethyl acetate=3:1);

NMR (300 MHz, DMSO-d$_6$): δ 9.25 (m, 1H), 8.31 (s, 1H), 7.23 (d, J=8.1 Hz, 1H), 6.95 (d, J=2.4 Hz, 1H), 6.86 (dd, J=2.4, 8.1 Hz, 1H), 3.99 (m, 1H), 3.78 (s, 3H), 3.15 (m, 2H), 3.02 (t, J=7.8 Hz, 2H), 2.20 (s, 3H), 2.18 (m, 2H), 1.60-1.88 (m, 4H), 0.89 (t, J=7.5 Hz, 6H).

EXAMPLE 2(51)

8-[(2R)-1-methoxybutan-2-yl]amino-2-methyl-3-(2-methyl-4-methoxyphenyl)-6,7-dihydro-5H-cyclopenta[d]pyrazolo[1,5-a]pyrimidine hydrochloride

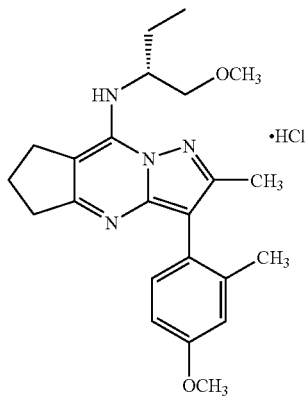

TLC: Rf 0.21 (n-hexane ethyl acetate=3:1);

NMR (300 MHz, CDCl₃): δ 7.63 (brd, J=8.4 Hz, 1H), 7.09 (d, J=8.7 Hz, 1H), 6.87 (d, J=2.7 Hz, 1H), 6.79 (dd, J=8.7, 2.7 Hz, 1H), 4.19 (m, 1H), 3.81 (s, 3H), 3.65-3.53 (m, 2H), 3.45 (t, J=8.1 Hz, 2H), 3.43 and 3.41 (s, two conformers, 3H), 3.26-3.01 (m, 2H), 2.30-2.20 (m, 2H), 2.28 (s, 3H), 2.18 (s, 3H), 1.96-1.58 (m, 2H), 1.08 and 1.07 (t, J=7.5 Hz, two conformers, 3H).

EXAMPLE 2(52)

8-[(2S)-1-methoxybutan-2-yl]amino-2-methyl-3-(2-methyl-4-methoxyphenyl)-6,7-dihydro-5H-cyclopenta[d]pyrazolo[1,5-a]pyrimidine hydrochloride

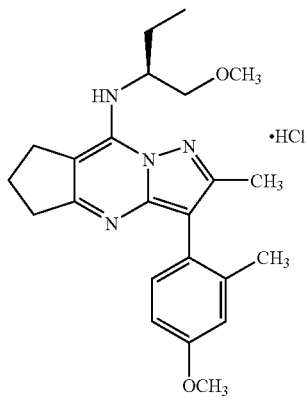

TLC: Rf 0.21 (n-hexane:ethyl acetate=3:1);

NMR (300 MHz, CDCl₃): δ 7.59 (brd, J=10.2 Hz, 1H), 7.11 (d, J=8.4 Hz, 1H), 6.88 (d, J=2.4 Hz, 1H), 6.81 (dd, J=8.4, 2.7 Hz, 1H), 4.19 (m, 1H), 3.83 (s, 3H), 3.66-3.53 (m, 2H), 3.48 (t, J=8.1 Hz, 2H), 3.44 and 3.42 (s, two conformers, 3H), 3.26-3.02 (m, 2H), 2.30-2.20 (m, 2H), 2.29 (s, 3H), 2.20 (s, 3H), 1.98-1.69 (m, 2H), 1.09 and 1.08 (t, J=7.5 Hz, two conformers, 3H).

EXAMPLE 2(53)

8-cyclopentylamino-2-methyl-3-(2-methyl-4-methoxyphenyl)-6,7-dihydro-5H-cyclopenta[d]pyrazolo[1,5-a]pyrimidine

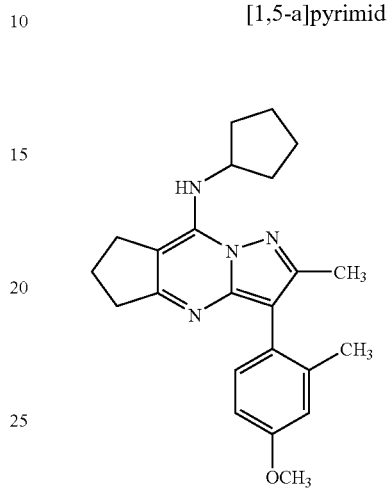

TLC: Rf 0.30 (n-hexane:ethyl acetate=3:1);

NMR (300 MHz, CDCl₃): δ 7.15 (d, J=8.7 Hz, 1H), 6.84 (d, J=2.7 Hz, 1H), 6.77 (dd, J=8.7, 2.7 Hz, 1H), 6.34 (brd, J=9.0 Hz, 1H), 4.38 (m, 1H), 3.82 (s, 3H), 3.15 (t, J=7.2 Hz, 2H), 2.89 (t, J=7.8 Hz, 2H), 2.30 (s, 3H), 2.17 (s, 3H), 2.18-2.00 (m, 4H), 1.95-1.65 (m, 6H).

EXAMPLE 2(54)

8-(3-pentylamino)-2-methyl-3-(2,4-difluorophenyl)-6,7-dihydro-5H-cyclopenta[d]pyrazolo[1,5-a]pyrimidine

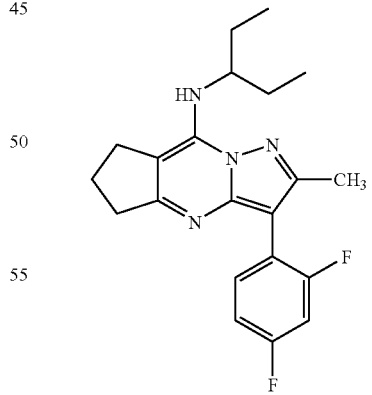

TLC: Rf 0.57 (n-hexane:ethyl acetate=3:1);

NMR (300 MHz, CDCl₃): δ 7.50 (ddd, J=6.6, 8.4, 8.4 Hz, 1H), 6.86-6.99 (m, 2H), 6.23 (d, J=10.8 Hz, 1H), 3.80 (m, 1H), 3.09 (t, J=7.2 Hz, 2H), 2.92 (t, J=8.1 Hz, 2H), 2.39 (d, J=1.5 Hz, 3H), 2.15 (m, 2H), 1.53-1.81 (m, 4H), 1.01 (t, J=7.2 Hz, 6H).

EXAMPLE 2(55)

8-(3-pentylamino)-2-trifluoromethyl-3-(2-methyl-4-methoxyphenyl)-6,7-dihydro-5H-cyclopenta[d]pyrazolo[1,5-a]pyrimidine hydrochloride

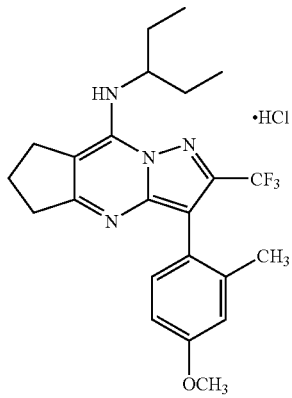

TLC: Rf 0.42 (n-hexane:ethyl acetate=3:1);

NMR (300 MHz, CDCl$_3$): δ 7.33 (br d, J=10.2 Hz, 1H), 7.13 (d, J=8.7 Hz, 1H), 6.89 (d, J=2.4 Hz, 1H), 6.81 (dd, J=2.4, 8.7 Hz, 1H), 4.04 (m, 1H), 3.83 (s, 3H), 3.56 (m, 2H), 3.20 (m, 2H), 2.33 (m, 2H), 2.19 (s, 3H), 1.70-2.22 (m, 4H), 1.08 (m, 6H).

EXAMPLE 2(56)

8-(N-ethyl-N-(2-methoxyethyl)amino)-2-methyl-3-(2-methyl-4-methoxyphenyl)-6,7-dihydro-5H-cyclopenta[d]pyrazolo[1,5-a]pyrimidine hydrochloride

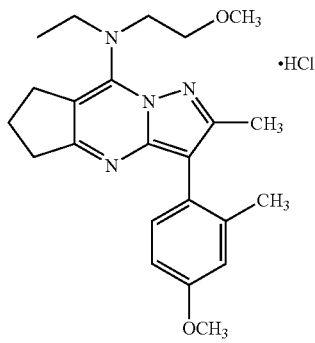

TLC: Rf 0.20 (n-hexane:ethyl acetate=3:1);

NMR (300 MHz, CDCl$_3$): δ 7.11 (d, J=8.4 Hz, 1H), 6.89 (d, J=2.7 Hz, 1H), 6.82 (dd, J=8.4, 2.7 Hz, 1H), 4.34-4.17 (m, 2H), 3.91 (q, J=7.2 Hz, 2H), 3.83 (s, 3H), 3.68 (t, J=5.1 Hz, 2H), 3.47 (t, J=7.8 Hz, 2H), 3.32 (s, 3H), 3.06 (t, J=7.2 Hz, 2H), 2.28 (s, 3H), 2.30-2.20 (m, 2H), 2.18 (s, 3H), 1.38 (t, J=7.2 Hz, 3H).

EXAMPLE 2(57)

8-cyclohexylamino-2-methyl-3-(2-methyl-4-methoxyphenyl)-6,7-dihydro-5H-cyclopenta[d]pyrazolo[1,5-a]pyrimidine

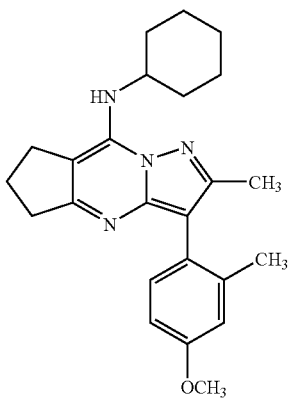

TLC: Rf 0.30 (n-hexane:ethyl acetate=3:1);

NMR (300 MHz, CDCl$_3$): δ 7.15 (d, J=8.1 Hz, 1H), 6.84 (d, J=2.7 Hz, 1H), 6.77 (dd, J=8.1, 2.7 Hz, 1H), 6.34 (brd, J=9.6 Hz, 1H), 3.81 (s, 3H), 3.80 (m, 1H), 3.10 (t, J=7.2 Hz, 2H), 2.88 (t, J=7.8 Hz, 2H), 2.30 (s, 3H), 2.17 (s, 3H), 2.18-2.00 (m, 4H), 1.90-1.80 (m, 2H), 1.75-1.60 (m, 1H), 1.50-1.20 (m, 5H).

EXAMPLE 2(58)

8-(N-propyl-N-(3-pentyl)amino)-2-methyl-3-(2-methyl-4-methoxyphenyl)-6,7-dihydro-5H-cyclopenta[d]pyrazolo[1,5-a]pyrimidine hydrochloride

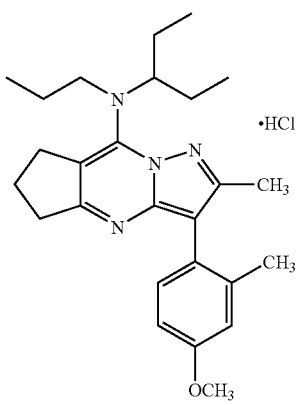

TLC: Rf 0.43 (n-hexane:ethyl acetate=3:1);

NMR (300 MHz, CDCl$_3$): δ 7.14 (d, J=8.1 Hz, 1H), 6.89 (d, J=2.7 Hz, 1H), 6.82 (dd, J=8.1, 2.7 Hz, 1H), 4.20 (m, 1H), 3.83 (s, 3H), 3.60 (m, 2H), 3.38 (t, J=7.5 Hz, 2H), 2.97 (t, J=7.5 Hz, 2H), 2.30-2.15 (m, 2H), 2.27 (s, 3H), 2.20 (s, 3H), 2.00-1.70 (m, 4H), 1.42 (m, 2H), 0.98 (t, J=7.5 Hz, 6H), 0.90 (t, J=7.5 Hz, 3H).

EXAMPLE 2(59)

8-(3-pentylamino)-2-methyl-3-(4-methoxyphenyl)-6,7-dihydro-5H-cyclopenta[d]pyrazolo[1,5-a]pyrimidine

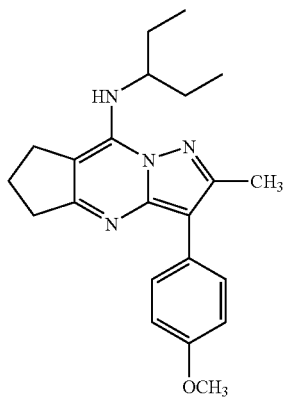

TLC: Rf 0.57 (n-hexane:ethyl acetate=2:1);

NMR (300 MHz, CDCl$_3$): δ 7.60 (d, J=9.0 Hz, 2H), 6.99 (d, J=9.0 Hz, 2H), 6.10 (br d, J=10.5 Hz, 1H), 3.84 (s, 3H), 3.81 (m, 1H), 3.08 (t, J=7.2 Hz, 2H), 2.94 (t, J=7.8 Hz, 2H), 2.53 (s, 3H), 2.15 (m, 2H), 1.53-1.82 (m, 4H), 1.00 (t, J=7.2 Hz, 6H).

EXAMPLE 2(60)

8-(3-pentylamino)-2-isopropyl-3-(4-methoxyphenyl)-6,7-dihydro-5H-cyclopenta[d]pyrazolo[1,5-a]pyrimidine

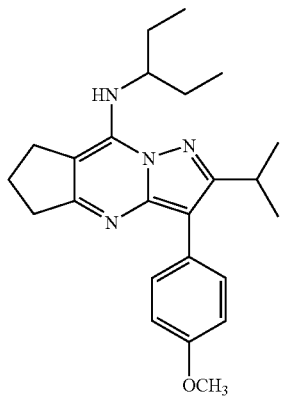

TLC: Rf 0.54 (n-hexane:ethyl acetate=3:1);

NMR (300 MHz, CDCl$_3$): δ 7.48 (d, J=8.7 Hz, 2H), 6.97 (d, J=8.7 Hz, 2H), 6.29 (br d, J=10.5 Hz, 1H), 3.84 (s, 3H), 3.80 (m, 1H), 3.32 (sept, J=6.9 Hz, 1H), 3.07 (t, J=7.2 Hz, 2H), 2.91 (t, J=7.5 Hz, 2H), 2.13 (m, 2H), 1.63-1.83 (m, 4H), 1.33 (d, J=6.9 Hz, 6H), 1.01 (t, J=7.5 HZ, 6H).

EXAMPLE 2(61)

8-t-butylamino-2-methyl-3-(2-methyl-4-methoxyphenyl)-6,7-dihydro-5H-cyclopenta[d]pyrazolo[1,5-a]pyrimidine

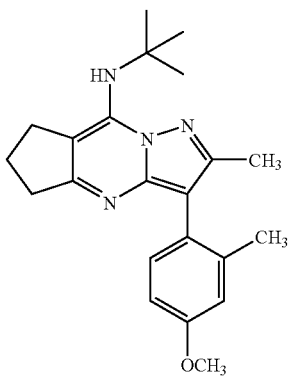

TLC: Rf 0.35 (n-hexane:ethyl acetate=3:1);

NMR (300 MHz, CDCl$_3$): δ 7.15 (brd, J=8.7 Hz, 1H), 6.97 (brs, 1H), 6.85 (d, J=2.7 Hz, 1H), 6.78 (dd, J=8.7, 2.7 Hz, 1H), 3.81 (s, 3H), 3.15 (t, J=7.2 Hz, 2H), 2.91 (t, J=7.5 Hz, 2H), 2.30 (s, 3H), 2.18 (s, 3H), 2.11 (m, 2H), 1.57 (s, 9H).

EXAMPLE 2(62)

8-(3-pentylamino)-3-(2,4,6-trimethylphenyl)-6,7-dihydro-5H-cyclopenta[d]pyrazolo[1,5-a]pyrimidine hydrochloride

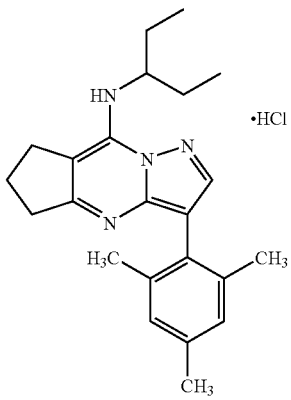

TLC: Rf 0.58 (n-hexane:ethyl acetate=3:1);

NMR (300 MHz, CDCl$_3$): δ 7.91 (s, 1H), 7.39 (brd, J=10.2 Hz, 1H), 6.99 (s, 2H), 4.03 (m, 1H), 3.52 (t, J=7.8 Hz, 2H), 3.17 (t, J=7.2 Hz, 2H), 2.32 (s, 3H), 2.31 (m, 2H), 2.13 (s, 6H), 1.67-1.96 (m, 4H), 1.07 (t, J=7.5 Hz, 6H).

EXAMPLE 2(63)

8-(1-cyclobutylethyl)amino-2-methyl-3-(2-methyl-4-methoxyphenyl)-6,7-dihydro-5H-cyclopenta[d]pyrazolo[1,5-a]pyrimidine hydrochloride

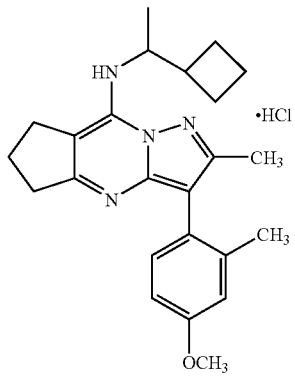

TLC: Rf 0.28 (n-hexane:ethyl acetate=3:1);

NMR (300 MHz, pyridine-$d_6$ 0.5 ml+CDCl$_3$ 0.1 ml): δ 7.46 (d, J=8.1 Hz, 1H), 7.06 (d, J=2.7 Hz, 1H), 6.97 (dd, J=8.1, 2.7 Hz, 1H), 6.80 (d, J=10.2 Hz, 1H), 3.96 (m, 1H), 3.74 (s, 3H), 2.97 (ddd, J=14.1, 7.2, 7.2 Hz, 2H), 2.86 (t, J=7.5 Hz, 2H), 2.50-2.36 (m, 1H), 2.47 (s, 3H), 2.39 (s, 3H), 2.05-1.65 (m, 8H), 1.15 (d, J=6.3 Hz, 3H).

EXAMPLE 2(64)

8-(3-pentylamino)-2-methyl-3-(2,3-dimethyl-4-methoxyphenyl)-6,7-dihydro-5H-cyclopenta[d]pyrazolo[1,5-a]pyrimidine

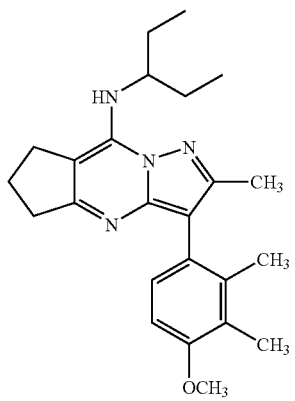

TLC: Rf 0.37 (benzene:ethyl acetate=10:1);

NMR (300 MHz, CDCl$_3$): δ 7.08 (d, J=8.1 Hz, 1H), 6.78 (d, J=8.1 Hz, 1H), 6.21 (d, J=10.8 Hz, 1H), 3.84 (s, 3H), 3.81 (m, 1H), 3.08 (t, J=6.6 Hz, 2H), 2.88 (t, J=8.1 Hz, 2H), 2.29 (s, 3H), 2.21 (s, 3H), 2.13 (m, 2H), 2.10 (s, 3H), 1.56-1.82 (m, 4H), 1.03 (t, J=7.5 Hz, 3H), 1.01 (t, J=6.9 Hz, 3H).

EXAMPLE 2(65)

8-(3-pentylamino)-2-methyl-3-(2,5-dimethyl-4-methoxyphenyl)-6,7-dihydro-5H-cyclopenta[d]pyrazolo[1,5-a]pyrimidine

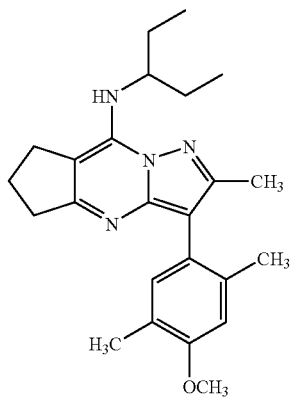

TLC: Rf 0.43 (benzene:ethyl acetate=10:1);

NMR (300 MHz, CDCl$_3$): δ 6.99 (s, 1H), 6.76 (s, 1H), 6.20 (d, J=10.5 Hz, 1H), 3.84 (s, 3H), 3.82 (m, 1H), 3.08 (t, J=6.9 Hz, 2H), 2.89 (t, J=7.2 Hz, 2H), 2.31 (s, 3H), 2.19 (s, 3H), 2.17 (s, 3H), 2.14 (m, 2H), 1.54-1.80 (m, 4H), 1.01 (m, 6H).

EXAMPLE 2(66)

8-(N-(2,2,2-trifluoroethyl)-N-cyclopropylmethylamino)-2-methyl-3-(2-methyl-4-methoxyphenyl)-6,7-dihydro-5H-cyclopenta[d]pyrazolo[1,5-a]pyrimidine

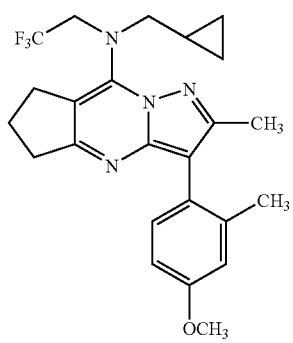

TLC: Rf 0.62 (n-hexane:ethyl acetate=2:1);

NMR (300 MHz, CDCl$_3$): δ 7.17 (d, J=8.1 Hz, 1H), 6.87 (d, J=2.7 Hz, 1H), 6.80 (dd, J=8.1, 2.7 Hz, 1H), 4.64 (q, J=9.6 Hz, 2H), 3.82 (s, 3H), 3.41 (d, J=6.6 Hz, 2H), 2.98 (t, J=6.9 Hz, 2H), 2.94 (t, J=7.5 Hz, 2H), 2.34 (s, 3H), 2.21-2.09 (m, 2H), 2.18 (s, 3H), 1.03 (m, 1H), 0.57 (m, 2H), 0.21 (m, 2H).

EXAMPLE 2(67)

8-(2,2,2-trifluoroethyl)amino-2-methyl-3-(2-methyl-4-methoxyphenyl)-6,7-dihydro-5H-cyclopenta[d]pyrazolo[1,5-a]pyrimidine

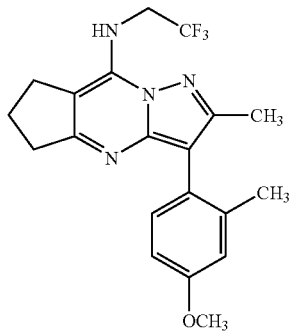

TLC: Rf 0.22 (n-hexane:ethyl acetate=3:1);

NMR (300 MHz, CDCl$_3$): δ 7.14 (d, J=8.1 Hz, 1H), 6.85 (d, J=2.7 Hz, 1H), 6.78 (dd, J=8.1, 2.7 Hz, 1H), 6.75 (brt, J=7.8 Hz, 1H), 4.22 (dq, J=7.8, 7.8 Hz, 2H), 3.82 (s, 3H), 3.12 (t, J=7.5 Hz, 2H), 2.92 (t, J=7.8 Hz, 2H), 2.31 (s, 3H), 2.23-2.09 (m, 2H), 2.17 (s, 3H).

EXAMPLE 2(68)

8-[(2R)-1-methoxybutan-2-yl]amino-2-methyl-3-(2-methyl-4-methoxyphenyl)-5,7-dihydro-furo[3,4-d]pyrazolo[1,5-a]pyrimidine hydrochloride

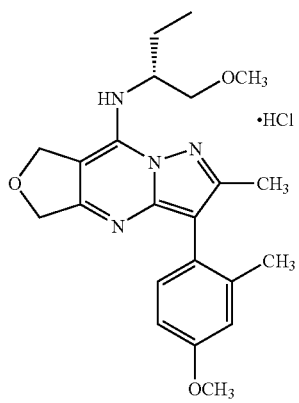

TLC: Rf 0.25 (n-hexane:ethyl acetate=2:1);

NMR (300 MHz, pyridine-d$_6$ 0.5 ml+CDCl$_3$ 0.1 ml): δ 7.39 (d, J=8.1 Hz, 1H), 7.37 (brd, J=9.3 Hz, 1H), 7.03 (d, J=2.7 Hz, 1H), 6.95 (dd, J=8.1, 2.7 Hz, 1H), 5.45 (d, J=9.9 Hz, 1H), 5.35 (d, J=9.9 Hz, 1H), 4.98 (brs, 2H), 3.74 (s, 3H), 3.63-3.48 (m, 3H), 3.26 (s, 3H), 2.41 (s, 3H), 2.34 (s, 3H), 1.82-1.60 (m, 2H), 0.97 (t, J=7.5 Hz, 3H).

EXAMPLE 2(69)

8-[(2R)-1-methoxybutan-2-yl]amino-2-methyl-3-(2-methyl-4-methoxyphenyl)-2,3-dihyciro-furo[3,2-d]pyrazolo[1,5-a]pyrimidine hydrochloride

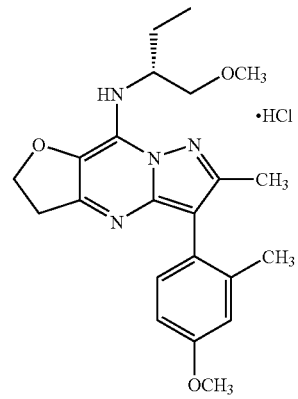

TLC: Rf 0.29 (n-hexane:ethyl acetate=2:1);

NMR (300 MHz, pyridine-d$_6$ 0.5 ml+CDCl$_3$ 0.1 ml): δ 7.40 (d, J=8.4 Hz, 1H), 7.03 (brs, 1H), 6.95 (dd, J=8.4, 2.4 Hz, 1H), 6.80 (brd, J=9.3 Hz, 1H), 4.47 (m, 1H), 4.47 (t, J=8.4 Hz, 2H), 3.74 (s, 3H), 3.56 (d, J=4.8 Hz, 2H), 3.28 (s, 3H), 3.12 (t, J=8.4 Hz, 2H), 2.43 (s, 3H), 2.35 (s, 3H), 1.87-1.46 (m, 2H), 1.00 (t, J=7.5 Hz, 3H).

EXAMPLE 2(70)

8-(3-pentylamino)-3-(2,6-dimethyl-4-methoxyphenyl)-6,7-dihydro-5H-cyclopenta[d]pyrazolo[1,5-a]pyrimidine hydrochloride

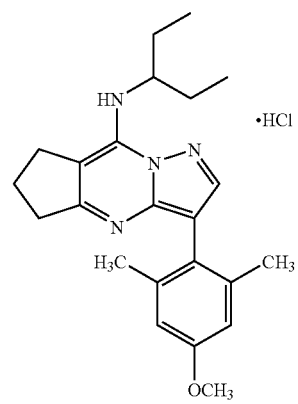

TLC: Rf 0.33 (n-hexane:ethyl acetate=3:1);

NMR (300 MHz, CDCl$_3$): δ 7.90 (s, 1H), 7.39 (br d, J=10.2 Hz, 1H), 6.72 (s, 2H), 4.02 (m, 1H), 3.81 (s, 3H), 3.53 (t, J=7.8 Hz, 2H), 3.17 (t, J=6.9 Hz, 2H), 2.32 (m, 2H), 2.14 (s, 6H), 1.66-1.96 (m, 4H), 1.08 (t, J=7.2 Hz, 6H).

EXAMPLE 2(71)

8-(3-pentylamino)-3-(4,6-dimethyl-2-methoxyphenyl)-6,7-dihydro-5H-cyclopenta[d]pyrazolo[1,5-a]pyrimidine hydrochloride

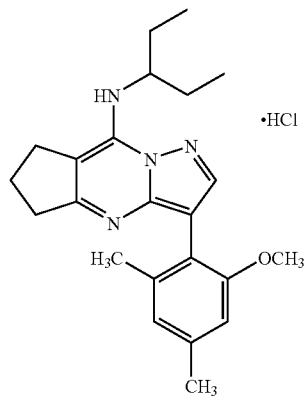

TLC: Rf 0.33 (n-hexane:ethyl acetate=3:1);

NMR (300 MHz, CDCl₃): δ 7.99 (s, 1H), 7.37 (br d, J=10.8 Hz, 1H), 6.75 (s, 1H), 6.70 (s, 1H), 4.01 (m, 1H), 3.85 (s, 3H), 3.57 (t, J=7.8 Hz, 2H), 3.16 (t, J=7.2 Hz, 2H), 2.36 (s, 3H), 2.31 (m, 2H), 2.23 (s, 3H), 1.63-1.92 (m, 4H), 1.06 (t, J=7.2 Hz, 6H).

EXAMPLE 2(72)

8-(3-pentylamino)-2-methyl-3-(2,6-dimethyl-4-methoxyphenyl)-6,7-dihydro-5H-cyclopenta[d]pyrazolo[1,5-a]pyrimidine

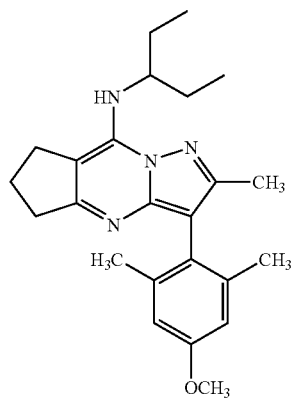

TLC: Rf 0.33 (benzene:ethyl acetate=10:1);
NMR (300 MHz, CDCl₃): δ6.68 (s, 2H), 6.21 (d, J=10.5 Hz, 1H), 3.81 (m, 1H), 3.80 (s, 3H), 3.09 (t, J=7.2 Hz, 2H), 2.88 (t, J=7.8 Hz, 2H), 2.19 (s, 3H), 2.13 (m, 2H), 2.04 (s, 6H), 1.55-1.83 (m, 4H), 1.03 (t, J=7.5 Hz, 6H).

EXAMPLE 2(73)

8-(3-pentylamino)-2-methyl-3-(4,6-dimethyl-2-methoxyphenyl)-6,7-dihydro-5H-cyclopenta[d]pyrazolo[1,5-a]pyrimidine

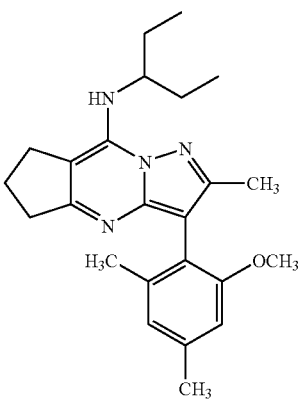

TLC: Rf 0.33 (benzene:ethyl acetate=10:1);
NMR (300 MHz, CDCl₃): δ6.75 (m, 1H), 6.62 (s, 1H), 6.21 (d, J=10.5 Hz, 1H), 3.80 (m, 1H), 3.71 (s, 3H), 3.06 (m, 2H), 2.87 (m, 2H), 2.34 (s, 3H), 2.24 (s, 3H), 2.12 (m, 2H), 2.09 (s, 3H), 1.53-1.80 (m, 4H), 1.03 (t, J=7.2 Hz, 3H), 1.00 (t, J=7.5 Hz, 3H).

EXAMPLE 2(74)

8-(3-methylpentan-3-yl)amino-2-methyl-3-(2-methyl-4-methoxyphenyl)-6,7-dihydro-5H-cyclopenta[d]pyrazolo[1,5-a]pyrimidine hydrochloride

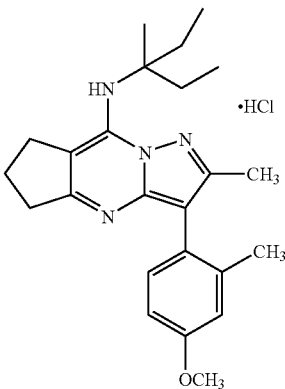

TLC: Rf 0.36 (n-hexane:ethyl acetate=3:1);
NMR (300 MHz, CDCl₃): δ 8.01 (brs, 1 H), 7.12 (d, J=8.1 Hz, 1 H), 6.89 (d, J=2.7 Hz, 1 H), 6.82 (dd, J=8.1, 2.7 Hz, 1 H), 3.83 (s, 3 H), 3.52 (t, J=7.8 Hz, 2 H), 3.16 (t, J=7.2 Hz, 2 H), 2.28 (s, 3 H), 2.24 (m, 2 H), 2.20 (s, 3 H), 2.00-1.85 (m, 4 H), 1.55 (s, 3 H), 1.03 (t, J=7.5 Hz, 6 H).

EXAMPLE 2(75)

8-(3-pentylamino)-2-methyl-3-(5-chloro-1,3-dioxaindan-6-yl)-6,7-dihydro-5H-cyclopenta[d]pyrazolo[1,5-a]pyrimidine

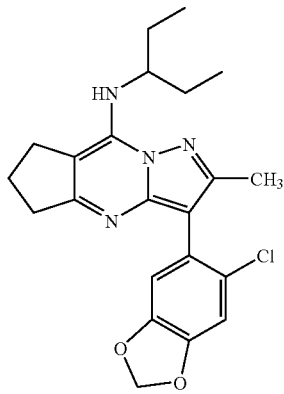

TLC: Rf 0.44 (benzene:ethyl acetate=10:1);

NMR (300 MHz, CDCl$_3$): δ 6.96 (s, 1H), 6.85 (s, 1H), 6.22 (br d, J=10.5 Hz, 1H), 5.99 (s, 2H), 3.80 (m, 1H), 3.08 (t, J=7.2 Hz, 2H), 2.91 (t, J=7.8 Hz, 2H), 2.34 (s, 3H), 2.16 (m, 2H), 1.53-1.81 (m, 4H), 1.01 (t, J=7.2 Hz, 6H).

EXAMPLE 2(76)

8-(N-ethyl-N-benzylamino)-2-methyl-3-(2-methyl-4-methoxyphenyl)-6,7-dihydro-5H-cyclopenta[d]pyrazolo[1,5-a]pyrimidine hydrochloride

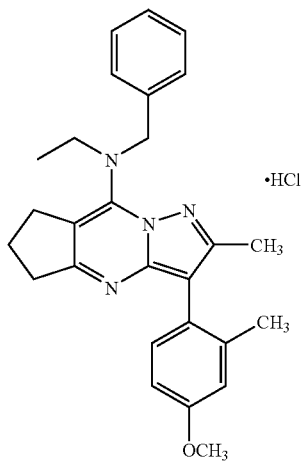

TLC: Rf 0.43 (n-hexane:ethyl acetate=2:1);

NMR (300 MHz, CDCl$_3$): δ 7.26-7.43 (m, 5H), 7.13 (d, J=8.4 Hz, 1H), 6.89 (d, J=2.7 Hz, 1H), 6.83 (dd, J=2.7, 8.4 Hz, 1H), 5.21 (s, 2H), 3.87 (q, J=6.9 Hz, 2H), 3.83 (s, 3H), 3.47 (t, J=7.2 Hz, 2H), 3.03 (t, J=7.2 Hz, 2H), 2.29 (s, 3H), 2.22 (m, 2H), 2.19 (s, 3H), 1.39 (t, J=6.9 Hz, 3H).

EXAMPLE 2(77)

8-(3-pentylamino)-2-methyl-3-(2-chloro-4-trifluoromethoxyphenyl)-6,7-dihydro-5H-cyclopenta[d]pyrazolo[1,5-a]pyrimidine hydrochloride

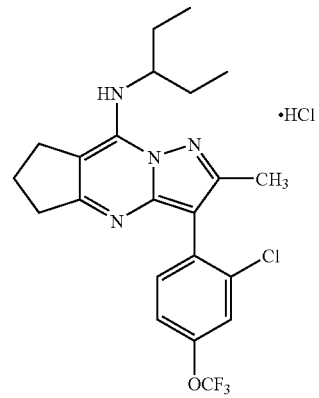

TLC: Rf 0.52 (n-hexane:ethyl acetate=3:1);

NMR (300 MHz, pyridene-d$_6$(0.5 ml), CDCl$_3$(0.1 ml)): δ 7.71 (d, J=8.4 Hz, 1H), 7.57 (m, 1H), 7.28 (m, 1H), 6.77 (d, J=10.5 Hz, 1H), 3.74 (m, 1H), 2.95 (t, J=7.5 Hz, 2H), 2.85 (t, J=7.8 Hz, 2H), 2.46 (s, 3H), 1.98 (m, 2H), 1.64-1.48 (m, 4H), 0.92 (t, J=7.5 Hz, 6H).

EXAMPLE 2(78)

8-(3-pentylamino)-2-methyl-3-(2-chloro-4-methoxyphenyl)-6,7-dihydro-5H-cyclopenta[d]pyrazolo[1,5-a]pyrimidine hydrochloride

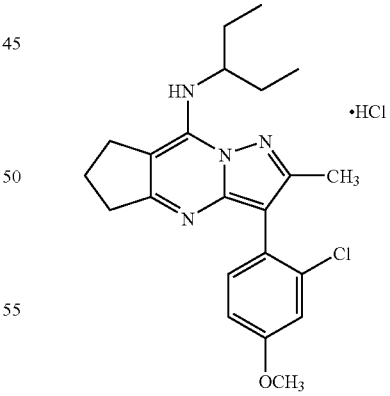

TLC: Rf 0.20 (n-hexane:ethyl acetate=3:1);

NMR (300 MHz, pyridene-d$_6$(0.5 ml), CDCl$_3$(0.1 ml)): δ 7.59 (d, J=8.4 Hz, 1H), 7.24 (d, J=2.4 Hz, 1H), 6.98 (dd, J=8.4, 2.4 Hz, 1H), 6.78 (d, J=10.5 Hz, 1H), 3.74 (m, 1H), 3.69 (s, 3H), 2.94 (t, J=7.2 Hz, 2H), 2.85 (t, J=7.8 Hz, 2H), 2.51 (s, 3H), 1.96 (m, 2H), 1.64-1.48 (m, 4H), 0.91 (t, J=7.5 Hz, 6H).

EXAMPLE 2(79)

8-(N-benzyl-N-(2-methoxyethyl)amino)-2-methyl-3-(2-methyl-4-methoxyphenyl)-6,7-dihydro-5H-cyclopenta[d]pyrazolo[1,5-a]pyrimidine hydrochloride

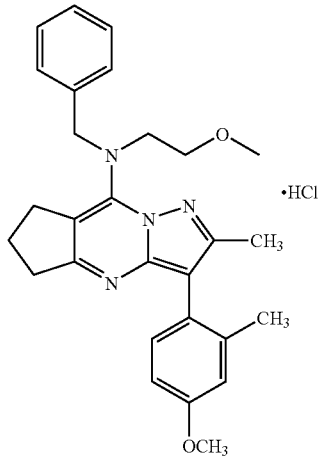

TLC: Rf 0.24 (hexane:ethyl acetate=2:1);

NMR (300 MHz, CDCl$_3$): δ 7.34-7.44 (m, 3H), 7.27-7.34 (m, 2H), 7.13 (d, J=8.4 Hz, 1H), 6.90 (d, J=2.7 Hz, 1H), 6.83 (dd, J=2.7, 8.4 Hz, 1H), 5.11 (s, 2H), 4.14 (t, J=4.8 Hz, 2H), 3.84 (s, 3H), 3.64 (t, J=4.8 Hz, 2H), 3.49 (t, J=7.8 Hz, 2H), 3.29 (s, 3H), 3.07 (t, J=7.2 Hz, 2H), 2.31 (s, 3H), 2.23 (m, 2H), 2.19 (s, 3H).

EXAMPLE 2(80)

8-(1, 2, 5, 6-tetrahydropyridyl)-2-methyl-3-(2-methyl-4-methoxyphenyl)-6,7-dihydro-5H-cyclopenta[d]pyrazolo[1,5-a]pyrimidine

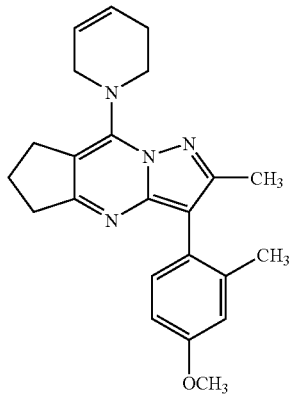

TLC: Rf 0.30 (hexane:ethyl acetate=3:1);

NMR (300 MHz, CDCl$_3$): δ 7.15 (d, J=8.1 Hz, 1H), 6.85 (d, J=2.7 Hz, 1H), 6.78 (dd, J=2.7, 8.1 Hz, CDCl$_3$), 5.97 (m, 1H), 5.83 (m, 1H), 4.21 (m, 2H), 3.85 (m, 2H), 3.82 (s, 3H), 3.07 (t, J=7.2 Hz, 2H), 2.89 (t, J=7.5 Hz, 2H), 2.41 (m, 2H), 2.32 (s, 3H), 2.16 (s, 3H), 2.11 (m, 2H).

EXAMPLE 2(81)

8-(3-pentylamino)-2-methyl-3-(2-methoxy-4,5-dimethylphenyl)-6,7-dihydro-5H-cyclopenta[d]pyrazolo[1,5-a]pyrimidine hydrochloride

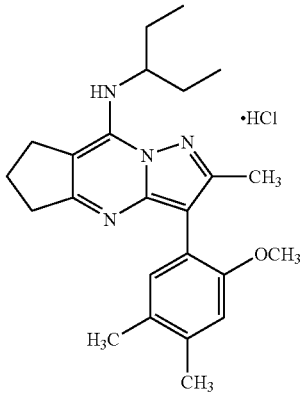

TLC: Rf 0.29 (hexane:ethyl acetate=3:1);

NMR (300 MHz, CDCl$_3$): δ 7.29 (brd, J=10.2 Hz, 1 H), 7.04 (s, 1 H), 6.83 (s, 1 H), 3.95 (m, 1 H), 3.90 (s, 3 H), 3.56 (t, J=7.8 Hz, 2H), 3.12 (t, J=7.5 Hz, 2 H), 2.42 (s, 3 H), 2.31 (s, 3 H), 2.28 (m, 2 H), 2.24 (s, 3 H), 1.90-1.62 (m, 4 H), 1.04 (t, J=7.5 Hz, 6 H).

EXAMPLE 2(82)

8-(1,2,3,4-tetrahydroisoquinolin-2-yl)-2-methyl-3-(2-methyl-4-methoxyphenyl)-6,7-dihydro-5H-cyclopenta[d]pyrazolo[1,5-a]pyrimidine

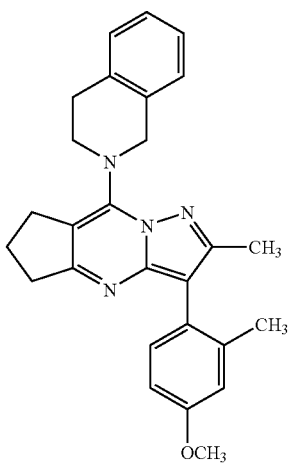

TLC: Rf 0.24 (hexane:ethyl acetate=3:1);

NMR (300 MHz, CDCl$_3$): δ 7.23-7.18 (m, 3 H), 7.16 (d, J=8.4 Hz, 1 H), 7.11 (m, 1 H), 6.86 (d, J=2.4 Hz, 1 H), 6.79 (dd, J=8.4, 2.4 Hz, 1 H), 4.86 (s, 2 H), 4.09 (t, J=5.7 Hz, 2 H), 3.82 (s, 3 H), 3.08 (t, J=5.7 Hz, 2 H), 2.97 (t, J=7.2 Hz, 2 H), 2.89 (t, J=7.8 Hz, 2 H), 2.33 (s, 3 H), 2.17 (s, 3 H), 2.08 (m, 2 H).

EXAMPLE 2(83)

8-phenylamino-2-methyl-3-(2-methyl-4-methoxyphenyl)-6,7-dihydro-5H-cyclopenta[d]pyrazolo[1,5-a]pyrimidine

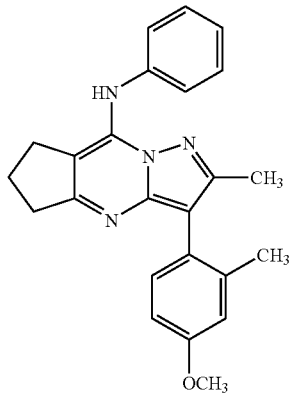

TLC: Rf 0.35 (hexane:ethyl acetate=3:1);

NMR (300 MHz, CDCl$_3$): δ 8.01 (br, 1H), 7.45-7.38 (m, 2H), 7.33-7.17 (m, 4H), 6.87 (d, J=2.4 Hz, 1H), 6.80 (dd, J=8.1, 2.4 Hz, 1H), 3.83 (s, 3H), 2.89 (t, J=7.8 Hz, 2H), 2.35 (s, 3H), 2.30 (t, J=7.5 Hz, 2H), 2.21 (s, 3H), 2.02-1.90 (m, 2H).

EXAMPLE 2(84)

8-(2-methylphenyl)amino-2-methyl-3-(2-methyl-4-methoxyphenyl)-6,7-dihydro-5H-cyclopenta[d]pyrazolo[1,5-a]pyrimidine

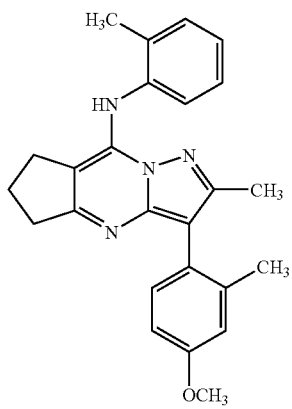

TLC: Rf 0.37 (hexane:ethyl acetate=3:1);

NMR (300 MHz, CDCl$_3$): δ 7.76 (br, 1H), 7.32-7.17 (m, 5H), 6.87 (d, J=2.4 Hz, 1H), 6.80 (dd, J=8.4, 2.4 Hz, 1H), 3.83 (s, 3H), 2.85 (t, J=7.5 Hz, 2H), 2.36 (s, 6H), 2.22 (s, 3H), 2.13 (t, J=7.5 Hz, 2H), 1.96-1.85 (m, 2H).

EXAMPLE 2(85)

8-(3-methylphenyl)amino-2-methyl-3-(2-methyl-4-methoxyphenyl)-6,7-dihydro-5H-cyclopenta[d]pyrazolo[1,5-a]pyrimidine

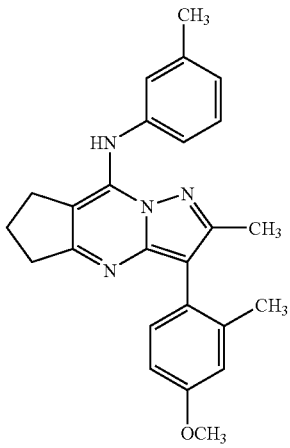

TLC: Rf 0.38 (hexane:ethyl acetate=3:1);

NMR (300 MHz, CDCl$_3$): δ 7.96 (br, 1H), 7.32-7.26 (m, 1H), 7.19 (d, J=8.4 Hz, 1H), 7.12-7.01 (m, 3H), 6.87 (d, J=2.7 Hz, 1H), 6.80 (dd, J=8.4, 2.7 Hz, 1H), 3.83 (s, 3H), 2.88 (t, J=7.8 Hz, 2H), 2.40 (s, 3H), 2.35 (s, 3H), 2.31 (t, J=6.9 Hz, 2H), 2.21 (s, 3H), 2.02-1.91 (m, 2H).

EXAMPLE 2(86)

8-(4-methylphenyl)amino-2-methyl-3-(2-methyl-4-methoxyphenyl)-6,7-dihydro-5H-cyclopenta[d]pyrazolo[1,5-a]pyrimidine

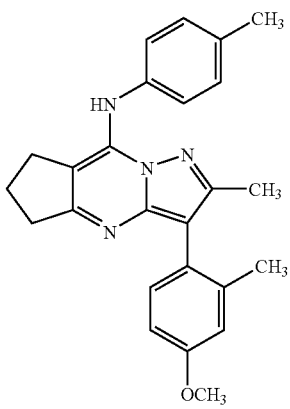

TLC: Rf 0.33 (hexane:ethyl acetate=3:1);

NMR (300 MHz, CDCl$_3$): δ 7.93 (br, 1H), 7.23-7.11 (m, 5H), 6.87 (d, J=2.7 Hz, 1H), 6.80 (dd, J=8.4, 2.7 Hz, 1H), 3.83 (s, 3H), 2.86 (t, J=7.5 Hz, 2H), 2.40 (s, 3H), 2.35 (s, 3H), 2.29 (t, J=7.5 Hz, 2H), 2.21 (s, 3H), 2.00-1.88 (m, 2H).

EXAMPLE 2(87)

8-(N-phenyl-N-propylamino)-2-methyl-3-(2-methyl-4-methoxyphenyl)-6,7-dihydro-5H-cyclopenta[d]pyrazolo[1,5-a]pyrimidine

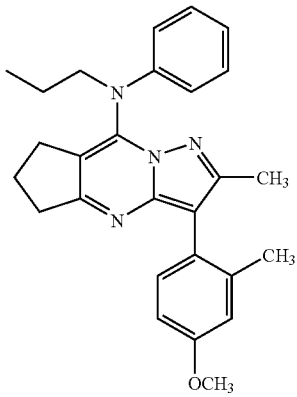

TLC: Rf 0.48 (hexane:ethyl acetate=3:1);

NMR (300 MHz, CDCl$_3$): δ 7.31-7.24 (m, 2H), 7.21 (d, J=8.4 Hz, 1H), 6.99-6.87 (m, 4H), 6.81 (dd, J=8.4, 2.7 Hz, 1H), 4.15-4.07 (m, 2H), 3.84 (s, 3H), 2.92 (t, J=7.5 Hz, 2H), 2.36 (s, 3H), 2.31 (t, J=7.5 Hz, 2H), 2.22 (s, 3H), 2.05-1.94 (m, 2H), 1.82-1.68 (m, 2H), 0.96 (t, J=7.2 Hz, 3H).

EXAMPLE 2(88)

8-(N-benzyl-N-propylamino)-2-methyl-3-(2-methyl-4-methoxyphenyl)-6,7-dihydro-5H-cyclopenta[d]pyrazolo[1,5-a]pyrimidine

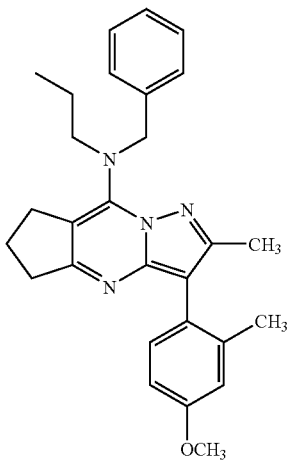

TLC: Rf 0.63 (hexane:ethyl acetate=3:1);

NMR (300 MHz, CDCl$_3$): δ 7.33-7.21 (m, 5H), 7.19 (d, J=8.4 Hz, 1H), 6.87 (d, J=2.7 Hz, 1H), 6.80 (dd, J=8.4, 2.7 Hz, 1H), 4.86 (s, 2H), 3.83 (s, 3H), 3.42-3.34 (m, 2H), 2.88 (t, J=7.8 Hz, 2H), 2.81 (t, J=7.1 Hz, 2H), 2.36 (s, 3H), 2.20 (s, 3H), 2.11-1.98 (m, 2H), 1.67-1.54 (m, 2H), 0.88 (t, J=7.5 Hz, 3H).

EXAMPLE 2(89)

8-(N,N-diallylamino)-2-methyl-3-(2-methyl-4-methoxyphenyl)-6,7-dihydro-5H-cyclopenta[d]pyrazolo[1,5-a]pyrimidine hydrochloride

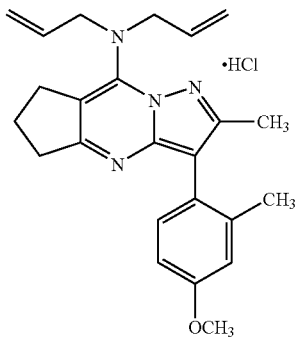

TLC: Rf 0.46 (hexane:ethyl acetate=2:1);

NMR (300 MHz, CDCl$_3$): δ 7.11 (d, J=8.4 Hz, 1H), 6.89 (d, J=2.7 Hz, 1H), 6.82 (dd, J=2.7, 8.4 Hz, 1H), 6.03 (m, 2H), 5.40 (d, J=10.5 Hz, 2H), 5.35 (d, J=18 Hz, 2H), 4.49 (d, J=6.0 Hz, 4H), 3.83 (s, 3H), 3.47 (t, J=7.8 Hz, 2H), 3.08 (t, J=7.2 Hz, 2H), 2.28 (s, 3H), 2.23 (m, 2H), 2.18 (s, 3H).

EXAMPLE 2(90)

8-(3-pentylamino)-2-methyl-3-(2-methyl-4-dimethylaminophenyl)-6,7-dihydro-5H-cyclopenta[d]pyrazolo[1,5-a]pyrimidine

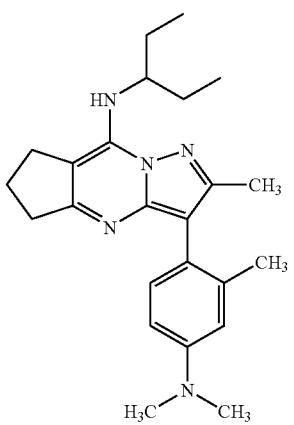

TLC: Rf 0.17 (hexane:ethyl acetate=3:1);

NMR (300 MHz, CDCl$_3$): δ 7.11 (d, J=8.1 Hz, 1 H), 6.70 (d, J=2.7 Hz, 1 H), 6.64 (dd, J=8.1, 2.7 Hz, 1 H), 6.19 (d, J=10.2 Hz, 1 H), 3.80 (m, 1 H), 3.08 (t, J=7.5 Hz, 2 H), 2.95 (s, 6 H), 2.89 (t, J=7.5 Hz, 2 H), 2.32 (s, 3 H), 2.18 (s, 3 H), 2.18-2.08 (m, 2 H), 1.80-1.56 (m, 4 H), 1.01 (brs, 6 H).

EXAMPLE 2(91)

8-(1-phenylpropylamino)-2-methyl-3-(2-methyl-4-methoxyphenyl)-6,7-dihydro-5H-cyclopenta[d]pyrazolo[1,5-a]pyrimidine hydrochloride

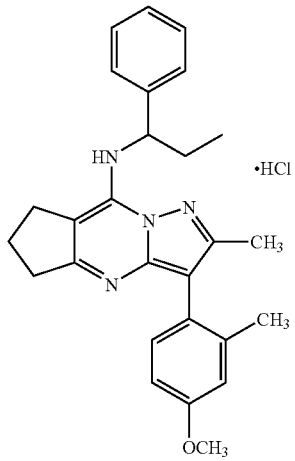

TLC: Rf 0.45 (hexane:ethyl acetate=2:1);
NMR (300 MHz, CDCl$_3$): δ 7.83 (d, J=8.7 Hz, 1H), 7.27-7.48 (m, 5H), 7.12 (d, J=8.4 Hz, 1H), 6.88 (m, 1H), 6.81 (dd, J=2.7, 8.4 Hz, 1H), 5.10 (m, 1H), 3.82 (s, 3H), 3.41 (m, 2H), 3.16 (m, 1H), 2.83 (m, 1H), 2.32 (s, 3H), 2.20 and 2.19 (s, total 3H), 2.12 (m, 4H), 1.12 and 1.01 (t, J=7.2 Hz, total 3H).

EXAMPLE 2(92)

8-(N-(2-phenylethyl)-N-propylamino)-2-methyl-3-(2-methyl-4-methoxyphenyl)-6,7-dihydro-5H-cyclopenta[d]pyrazolo[1,5-a]pyrimidine hydrochloride

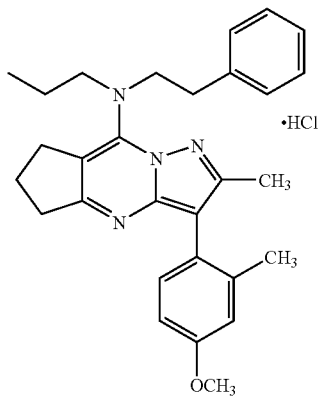

TLC: Rf 0.35 (hexane:ethyl acetate=3:1);
NMR (300 MHz, CDCl$_3$): δ 7.23-7.05 (m, 6H), 6.90 (d, J=2.4 Hz, 1H), 6.83 (dd, J=8.4, 2.4 Hz, 1H), 4.33 (t, J=6.6 Hz, 2H), 3.84 (s, 3H), 3.71 (t, J=6.9 Hz, 2H), 3.37 (t, J=7.5 Hz, 2H), 2.98 (t, J=7.2 Hz, 2H), 2.77 (t, J=7.5 Hz, 2H), 2.32 (s, 3H), 2.20 (s, 3H), 2.20-2.06 (m, 2H), 1.81-1.68 (m, 2H), 0.97 (t, J=7.5 Hz, 3H).

EXAMPLE 2(93)

8-(N-(3-phenylpropyl)-N-propylamino)-2-methyl-3-(2-methyl-4-methoxyphenyl)-6,7-dihydro-5H-cyclopenta[d]pyrazolo[1,5-a]pyrimidine

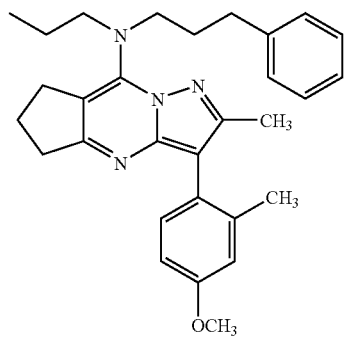

TLC: Rf 0.40 (hexane:ethyl acetate=3:1);
NMR (300 MHz, CDCl$_3$): δ 7.26-7.05 (m, 6H), 6.86 (d, J=2.7 Hz, 1H), 6.79 (dd, J=8.4, 2.7 Hz, 1H), 3.83 (s, 3H), 3.66-3.53 (m, 4H), 2.88 (t, J=7.5 Hz, 2H), 2.87 (t, J=7.5 Hz, 2H), 2.62 (t, J=7.8 Hz, 2H), 2.32 (s, 3H), 2.19 (s, 3H), 2.15-2.04 (m, 2H), 1.95-1.83 (m, 2H), 1.61-1.49 (m, 2H), 0.88 (t, J=7.2 Hz, 3H).

EXAMPLE 2(94)

8-(N-(4-phenylbutyl)-N-propylamino)-2-methyl-3-(2-methyl-4-methoxyphenyl)-6,7-dihydro-5H-cyclopenta[d]pyrazolo[1,5-a]pyrimidine

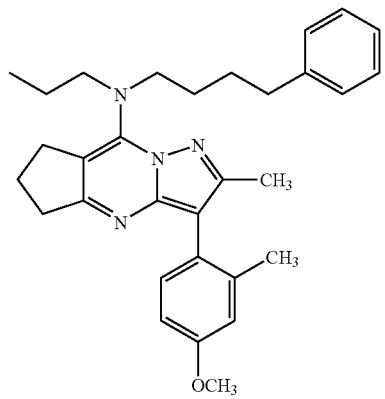

TLC: Rf 0.48 (hexane:ethyl acetate=3:1);
NMR (300 MHz, CDCl$_3$): δ 7.25-7.05 (m, 6H), 6.86 (d, J=2.7 Hz, 1H), 6.78 (dd, J=8.1, 2.7 Hz, 1H), 3.83 (s, 3H), 3.63 (t, J=6.6 Hz, 2H), 3.57-3.49 (m, 2H), 2.90 (t, J=7.5 Hz, 2H), 2.88 (t, J=7.5 Hz, 2H), 2.57 (t, J=6.9 Hz, 2H), 2.32 (s, 3H), 2.19 (s, 3H), 2.15-2.05 (m, 2H), 1.66-1.49 (m, 6H), 0.88 (t, J=7.5 Hz, 3H).

EXAMPLE 2(95)

8-(1-phenyl-2-butyl)amino-2-methyl-3-(2-methyl-4-methoxyphenyl)-6,7-dihydro-5H-cyclopenta[d]pyrazolo[1,5-a]pyrimidine hydrochloride

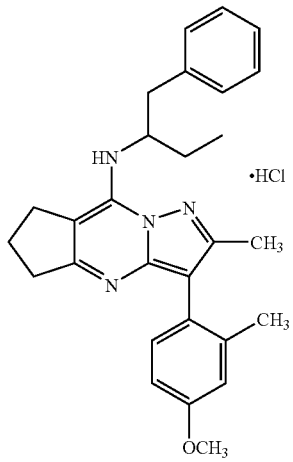

TLC: Rf 0.41 (hexane:ethyl acetate=2:1);

NMR (300 MHz, DMSO-$d_6$): δ 9.24 (m, 1H), 7.04-7.30 (m, 6H), 6.95 (brs, 1H), 6.86 (dd, J=2.7, 8.4 Hz, 1H), 4.20 (brs, 1H), 3.78 (s, 3H), 2.87-3.17 (m, 3H), 2.64-2.87 (m, 3H), 2.26 (s, 3H), 1.82-2.18 (m, 5H), 1.63-1.82 (m, 2H), 0.93 (br t, J=6.9 Hz, 3H).

EXAMPLE 2(96)

8-(1-phenyl-3-pentyl)amino-2-methyl-3-(2-methyl-4-methoxyphenyl)-6,7-dihydro-5H-cyclopenta[d]pyrazolo[1,5-a]pyrimidine hydrochloride

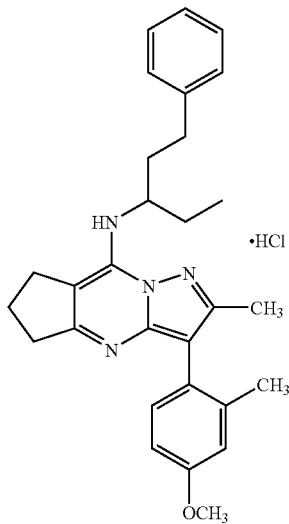

TLC: Rf 0.43 (hexane:ethyl acetate=2:1);

NMR (300 MHz, DMSO-$d_6$): δ 8.53 (m, 1H), 7.09-7.28 (m, 6H), 6.96 (d, J=3.0 Hz, 1H), 6.85 (dd, J=3.0, 8.4 Hz, 1H), 4.10 (m, 1H), 3.82 (s, 3H), 2.89-3.02 (m, 3H), 2.68-2.85 (m, 3H), 2.25 (s, 3H), 2.00-2.22 (m, 7H), 1.79 (m, 2H), 0.93 (t, J=7.5 Hz, 3H).

EXAMPLE 2(97)

8-(N-(4-methylphenyl)-N-propylamino)-2-methyl-3-(2-methyl-4-methoxyphenyl)-6,7-dihydro-5H-cyclopenta[d]pyrazolo[1,5-a]pyrimidine hydrochloride

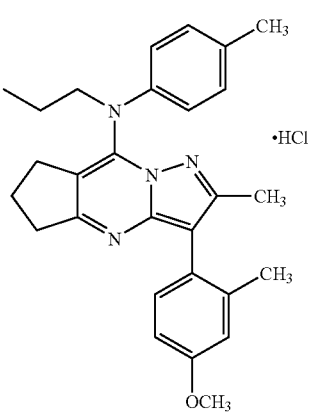

TLC: Rf 0.43 (hexane:ethyl acetate=3:1);

NMR (300 MHz, CDCl$_3$): δ 7.27 (d, J=8.1 Hz, 2H), 7.13-7.22 (m, 3H), 6.90 (d, J=2.4 Hz, 1H), 6.84 (dd, J=2.4, 8.7 Hz, 1H), 4.46 (m, 2H), 3.84 (s, 3H), 3.35 (m, 2H), 2.43 (s, 3H), 2.31 (s, 3H), 2.22 (s, 3H), 1.77-1.97 (m, 6H), 0.98 (t, J=7.5 Hz, 3H).

EXAMPLE 2(98)

8-(N-(4-methylphenyl)methyl-N-propylamino)-2-methyl-3-(2-methyl-4-methoxyphenyl)-6,7-dihydro-5H-cyclopenta[d]pyrazolo[1,5-a]pyrimidine hydrochloride

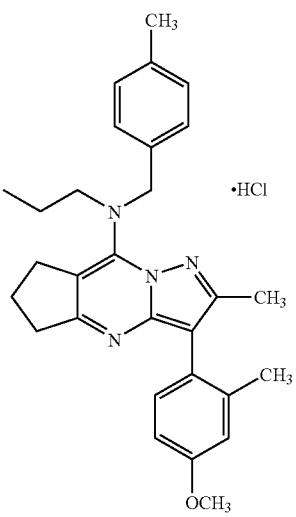

TLC: Rf 0.45 (hexane:ethyl acetate=3:1);

NMR (300 MHz, CDCl$_3$): δ 7.11-7.21 (m, 5H), 6.90 (d, J=2.7 Hz, 1H), 6.83 (dd, J=2.7, 8.7 Hz, 1H), 5.13 (s, 2H), 3.84

(s, 3H), 3.72 (t, J=7.5 Hz, 2H), 3.48 (t, J=8.1 Hz, 2H), 3.01 (t, J=6.9 Hz, 2H), 2.36 (s, 3H), 2.29 (s, 3H), 2.22 (m, 2H), 2.19 (s, 3H), 1.77 (m, 2H), 0.94 (t, J=7.5 Hz, 3H).

EXAMPLE 2(99)

8-(N-(3-methylphenyl)-N-propylamino)-2-methyl-3-(2-methyl-4-methoxyphenyl)-6,7-dihydro-5H-cyclopenta[d]pyrazolo[1,5-a]pyrimidine hydrochloride

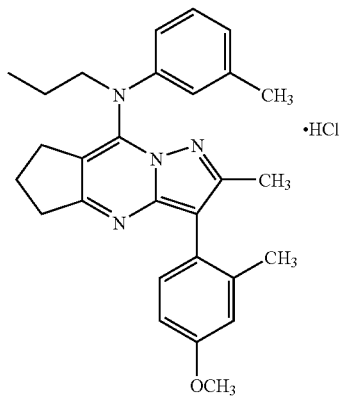

TLC: Rf 0.41 (hexane:ethyl acetate=3:1);
NMR (300 MHz, CDCl$_3$): δ 7.36 (m, 1H), 7.06-7.24 (m, 4H), 6.91 (d, J=2.4 Hz, 1H), 6.84 (dd, J=2.4, 8.1 Hz, 1H), 4.46 (m, 2H), 3.84 (s, 3H), 3.36 (m, 2H), 2.42 (s, 3H), 2.32 (s, 3H), 2.23 (s, 3H), 1.77-2.00 (m, 6H), 0.99 (t, J=7.2 Hz, 3H).

EXAMPLE 2(100)

8-(N-(4-methoxyphenyl)methyl-N-propylamino)-2-methyl-3-(2-methyl-4-methoxyphenyl)-6,7-dihydro-5H-cyclopenta[d]pyrazolo[1,5-a]pyrimidine hydrochloride

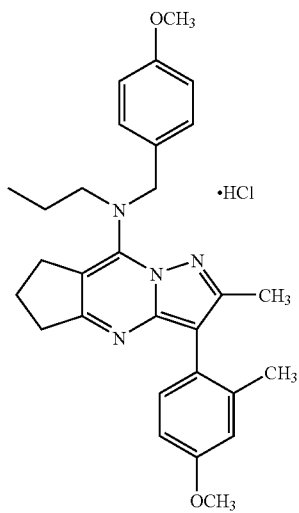

TLC: Rf 0.26 (hexane:ethyl acetate=3:1);
NMR (300 MHz, CDCl$_3$): δ 7.18 (d, J=8.7 Hz, 2H), 7.13 (d, J=8.4 Hz, 1H), 6.90 (d, J=8.7 Hz, 2H), 6.90 (d, J=3.0 Hz, 1H), 6.83 (dd, J=3.0, 8.4 Hz, 1H), 5.10 (s, 2H), 3.84 (s, 3H), 3.82 (s, 3H), 3.70 (t, J=7.5 Hz, 2H), 3.49 (t, J=8.1 Hz, 2H), 3.01 (t, J=6.9 Hz, 2H), 2.30 (s, 3H), 2.22 (m, 2H), 2.19 (s, 3H), 1.75 (m, 2H), 0.93 (t, J=7.2 Hz, 3H).

EXAMPLE 2(101)

8-(N-(4-chlorophenyl)methyl-N-propylamino)-2-methyl-3-(2-methyl-4-methoxyphenyl)-6,7-dihydro-5H-cyclopenta[d]pyrazolo[1,5-a]pyrimidine hydrochloride

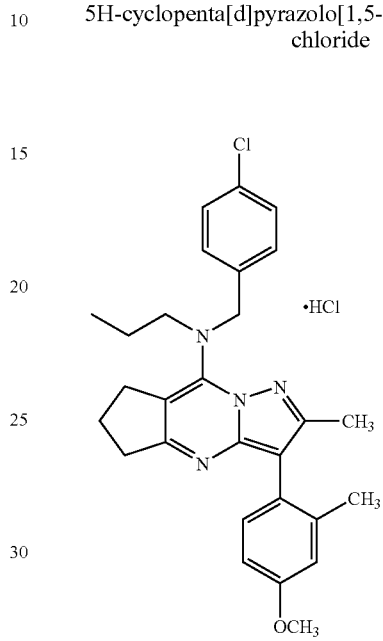

TLC: Rf 0.26 (hexane:ethyl acetate=3:1);
NMR (300 MHz, CDCl$_3$): δ 7.37 (d, J=8.7 Hz, 2H), 7.24 (d, J=8.7 Hz, 2H), 7.12 (d, J=8.4 Hz, 1H), 6.90 (d, J=2.7 Hz, 1H), 6.83 (dd, J=2.7, 8.4 Hz, 1H), 5.15 (s, 2H), 3.83 (s, 3H), 3.68 (m, 2H), 3.50 (t, J=7.8 Hz, 2H), 3.02 (t, J=7.2 Hz, 2H), 2.29 (s, 3H), 2.25 (m, 2H), 2.19 (s, 3H), 1.74 (m, 2H), 0.93 (t, J=7.2 Hz, 3H).

EXAMPLE 2(102)

8-(N-(2-methylphenyl)-N-propylamino)-2-methyl-3-(2-methyl-4-methoxyphenyl)-6,7-dihydro-5H-cyclopenta[d]pyrazolo[1,5-a]pyrimidine hydrochloride

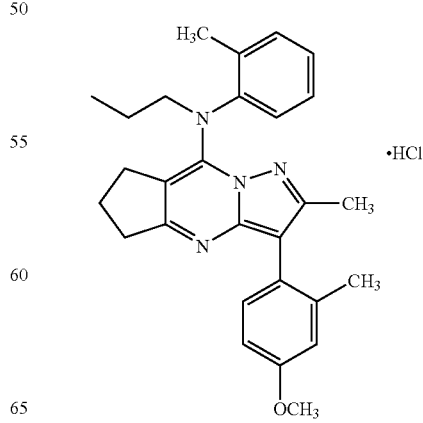

TLC: Rf 0.46 (hexane:ethyl acetate=3:1);

NMR (300 MHz, CDCl$_3$): δ 7.27-7.45 (m, 4H), 7.16 (d, J=8.4 Hz, 1H), 6.90 (d, J=2.4 Hz, 1H), 6.84 (dd, J=2.4, 8.4 Hz, 1H), 4.53 (m, 1H), 4.37 (m, 1H), 3.84 (s, 3H), 3.34 (m, 2H), 2.31 (s, 3H), 2.23 (s, 3H), 2.10 (s, 3H), 1.50-2.07 (m, 6H), 0.97 (t, J=7.5 Hz, 3H).

EXAMPLE 2(103)

8-((3S)-3-methoxymethyl-1, 2, 3, 4-tetrahydroisoquinolin-2-yl)-2-methyl-3-(2-methyl-4-methoxyphenyl)-6,7-dihydro-5H-cyclopenta[d]pyrazolo[1,5-a]pyrimidine hydrochloride

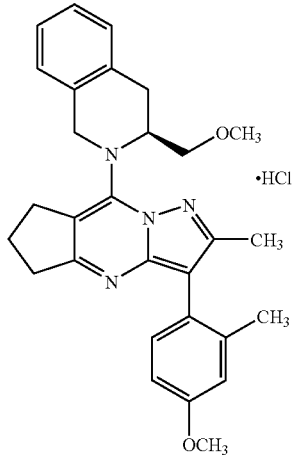

TLC: Rf 0.56 (hexane:ethyl acetate=1:1);

NMR (300 MHz, CDCl$_3$): δ 7.30-7.05 (m, 5H), 6.90-6.75 (m, 2H), 5.48 (m, 1H), 5.03 (d, J=15.6 Hz, 1H), 4.72 (dd, J=15.6, 3.9 Hz, 1H), 3.82 (s, 3H), 3.33 and 3.32 (s, 3H), 3.87-3.05 (m, 7H), 2.82 (d, J=15.6 Hz, 1H), 2.40-2.10 (m, 2H), 2.29 (s, 3H), 2.25 and 2.11 (s, 3H).

EXAMPLE 2(104)

8-(3-pentylamino)-2-methyl-3-(2-dimethylamino-4-methylpyridin-5-yl)-6,7-dihydro-5H-cyclopenta[d]pyrazolo[1,5-a]pyrimidine dihydrochloride

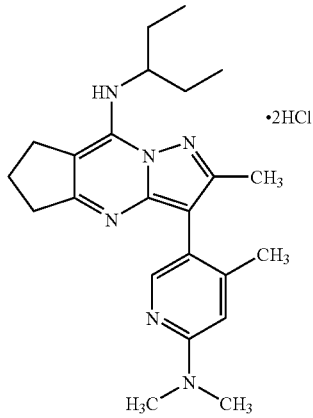

TLC: Rf 0.42 (chloroform:methanol=20:1);

NMR (300 MHz, CDCl$_3$): δ 8.01 (s, 1H), 7.32 (d, J=10.2 Hz, 1H), 6.85 (s, 1H), 4.00 (m, 1H), 3.41 (s, 6H), 3.40 (m, 2H), 3.17 (m, 2H), 2.37 (s, 3H), 2.33 (m, 2H), 2.32 (s, 3H), 1.65-1.95 (m, 4H), 1.07 (t, J=7.5 Hz, 3H), 1.06 (t, J=7.2 Hz, 3H).

EXAMPLE 2(105)

8-((2S)-1-methoxy-3-phenyl-2-propyl)amino-2-methyl-3-(2-methyl-4-methoxyphenyl)-6,7-dihydro-5H-cyclopenta[d]pyrazolo[1,5-a]pyrimidine hydrochloride

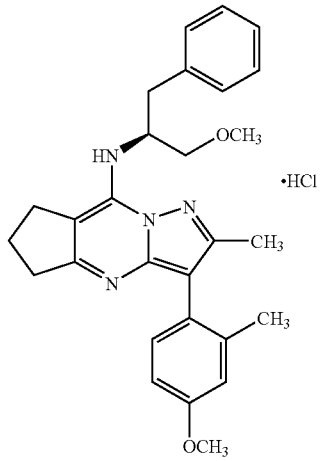

TLC: Rf 0.26 (hexane:ethyl acetate=2:1);

NMR (300 MHz, CDCl$_3$): δ 7.77 (m, 1H), 7.25-7.36 (m, 3H), 7.16-7.23 (m, 2H), 7.11 (m, 1H), 6.88 (m, 1H), 6.80 (m, 1H), 4.44 (m, 1H), 3.82 (s, 3H), 3.53-3.68 (m, 2H), 3.47 and 3.46 (s, 3H), 3.38 (m, 2H), 3.11 (t, J=7.2 Hz, 2H), 3.08 (m, 1H), 2.81 (m, 1H), 2.31 (s, 3H), 2.20 and 2.17 (s, 3H), 2.15 (m, 2H).

EXAMPLE 2(106)

8-(N-(4-methylthiophenyl)methyl-N-propylamino)-2-methyl-3-(2-methyl-4-methoxyphenyl)-6,7-dihydro-5H-cyclopenta[d]pyrazolo[1,5-a]pyrimidine hydrochloride

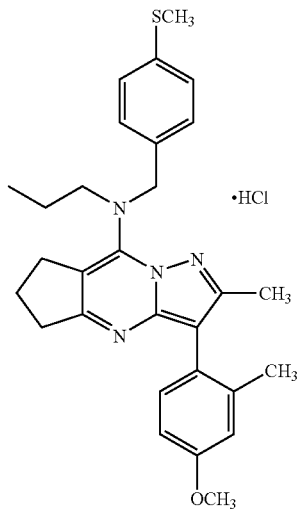

TLC: Rf 0.50 (hexane:ethyl acetate=2:1);

NMR (300 MHz, CDCl$_3$): δ 7.25 (d, J=8.4 Hz, 2H), 7.18 (d, J=8.4 Hz, 2H), 7.13 (d, J=8.1 Hz, 1H), 6.90 (d, J=2.4 Hz, 1H), 6.83 (dd, J=2.4, 8.1 Hz, 1H), 5.13 (s, 2H), 3.84 (s, 3H), 3.70 (m, 2H), 3.50 (t, J=7.8 Hz, 2H), 3.01 (t, J=6.9 Hz, 2H), 2.50 (s, 3H), 2.29 (s, 3H), 2.23 (m, 2H), 2.19 (s, 3H), 1.75 (m, 2H), 0.93 (t, J=7.5 Hz, 3H).

EXAMPLE 2(107)

8-(4-phenylpiperazin-1-yl)-2-methyl-3-(2-methyl-4-methoxyphenyl)-6,7-dihydro-5H-cyclopenta[d]pyrazolo[1,5-a]pyrimidine dihydrochloride

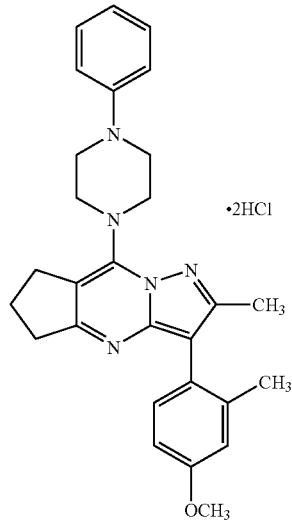

TLC: Rf 0.30 (hexane:ethyl acetate=2:1);

NMR (300 MHz, DMSO-d$_6$): δ 7.30-7.38 (m, 2H), 7.21-7.29 (m, 2H), 7.12 (d, J=8.4 Hz, 1H), 7.00 (brd, J=6.9 Hz, 1H), 6.95 (d, J=2.7 Hz, 1H), 6.86 (dd, J=2.7, 8.4 Hz, 1H), 4.22 (brs, 4H), 3.79 (s, 3H), 3.53 (brs, 4H), 3.14 (m, 2H), 2.97 (t, J=7.8 Hz, 2H), 2.21 (s, 3H), 2.15 (m, 2H), 2.06 (s, 3H).

EXAMPLE 2(108)

8-(4-(2-chlorophenyl)piperazin-1-yl)-2-methyl-3-(2-methyl-4-methoxyphenyl)-6,7-dihydro-5H-cyclopenta[d]pyrazolo[1,5-a]pyrimidine

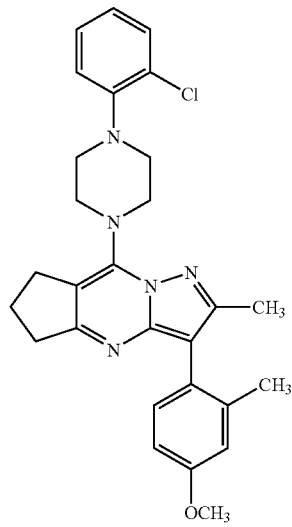

TLC: Rf 0.38 (hexane:ethyl acetate=2:1);

NMR (300 MHz, CDCl$_3$): δ 7.41 (dd, J=1.5, 7.8 Hz, 1H), 7.28 (m, 1H), 7.16 (d, J=8.1 Hz, 1H), 7.15 (d, J=8.7 Hz, 1H), 7.03 (m, 1H), 6.86 (d, J=2.7 Hz, 1H), 6.79 (dd, J=2.7, 8.1 Hz, 1H), 3.90 (m, 4H), 3.82 (s, 3H), 3.33 (t, J=4.8H, 4H), 3.16 (t, J=7.5 Hz, 2H), 2.91 (t, J=7.8 Hz, 2H), 2.33 (s, 3H), 2.17 (s, 3H), 2.14 (m, 2H).

EXAMPLE 2(109)

8-(N,N-dibutylamino)-2-methyl-3-(2-methyl-4-methoxyphenyl)-6,7-dihydro-5H-cyclopenta[d]pyrazolo[1,5-a]pyrimidine hydrochloride

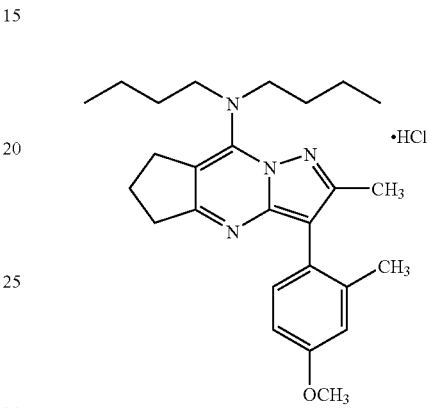

TLC: Rf 0.57 (hexane:ethyl acetate=2:1);

NMR (300 MHz, CDCl$_3$): δ 7.12 (d, J=7.8 Hz, 1H), 6.89 (d, J=2.4 Hz, 1H), 6.82 (dd, J=2.4, 7.8 Hz, 1H), 3.90 (t, J=7.5 Hz, 4H), 3.83 (s, 3H), 3.48 (m, 2H), 3.02 (m, 2H), 2.27 (s, 3H), 2.25 (m, 2H), 2.19 (s, 3H), 1.71 (m, 4H), 1.38 (m, 4H), 0.97 (t, J=6.9 Hz, 6H).

EXAMPLE 2(110)

8-(N-methyl-N-butylamino)-2-methyl-3-(2-methyl-4-methoxyphenyl)-6,7-dihydro-5H-cyclopenta[d]pyrazolo[1,5-a]pyrimidine hydrochloride

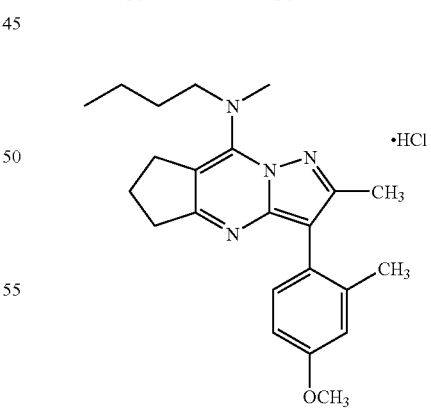

TLC: Rf 0.36 (hexane:ethyl acetate=2:1);

NMR (300 MHz, CDCl$_3$): δ 7.10 (d, J=8.1 Hz, 1H), 6.88 (d, J=3.0 Hz, 1H), 6.81 (dd, J=3.0, 8.1 Hz, 1H), 3.97 (m, 2H), 3.83 (s, 3H), 3.51 (s, 3H), 3.45 (t, J=8.1 Hz, 2H), 3.12 (t, J=6.9 Hz, 2H), 2.26 (s, 3H), 2.23 (m, 2H), 2.18 (s, 3H), 1.85 (m, 2H), 1.40 (m, 2H), 0.99 (t, J=7.2 Hz, 3H).

EXAMPLE 2(111)

8-(N-(4-methylphenyl)methyl-N-butylamino)-2-methyl-3-(2-methyl-4-methoxyphenyl)-6,7-dihydro-5H-cyclopenta[d]pyrazolo[1,5-a]pyrimidine hydrochloride

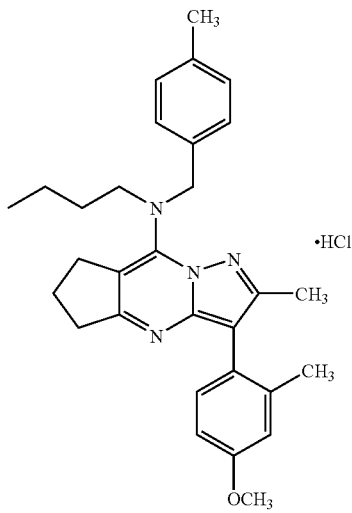

TLC: Rf 0.53 (hexane:ethyl acetate=2:1);
NMR (300 MHz, CDCl$_3$): δ 7.10-7.21 (m, 5H), 6.89 (d, J=2.4 Hz, 1H), 6.83 (dd, J=2.4, 8.1 Hz, 1H), 5.13 (s, 2H), 3.83 (s, 3H), 3.77 (t, J=7.2 Hz, 2H), 3.48 (t, J=7.8 Hz, 2H), 3.01 (t, J=6.9 Hz, 2H), 2.36 (s, 3H), 2.29 (s, 3H), 2.21 (m, 2H), 2.19 (s, 3H), 1.73 (m, 2H), 1.34 (m, 2H), 0.93 (t, J=7.2 Hz, 3H).

EXAMPLE 2(112)

8-(N-(4-methylphenyl)methyl-N-(2-methoxyethyl)amino)-2-methyl-3-(2-methyl-4-methoxyphenyl)-6,7-dihydro-5H-cyclopenta[d]pyrazolo[1,5-a]pyrimidine hydrochloride

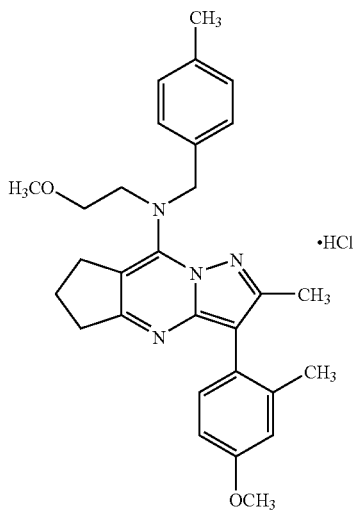

TLC: Rf 0.23 (hexane:ethyl acetate=2:1);
NMR (300 MHz, CDCl$_3$): δ 7.25-7.05 (m, 5H), 6.98-6.78 (m, 2H), 5.06 (s, 2H), 4.22-4.03 (m, 2H), 3.84 (s, 3H), 3.75-3.58 (m, 2H), 3.58-3.38 (m, 2H), 3.30 (s, 3H), 3.20-2.90 (m, 2H), 2.36 (s, 3H), 2.30 (s, 3H), 2.21 (m, 2H), 2.19 (s, 3H).

EXAMPLE 2(113)

8-(N-cyclopropyl-N-(4-methylphenyl)methylamino)-2-methyl-3-(2-methyl-4-methoxyphenyl)-6,7-dihydro-5H-cyclopenta[d]pyrazolo[1,5-a]pyrimidine hydrochloride

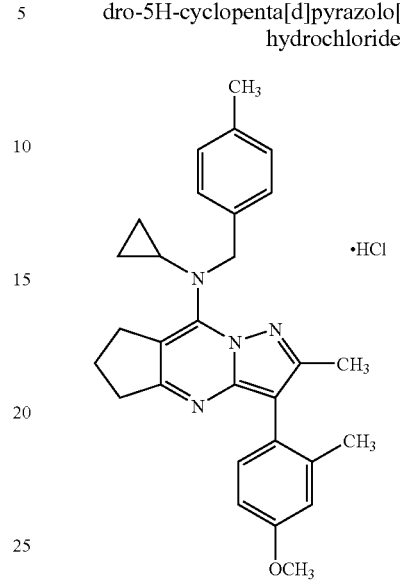

TLC: Rf 0.35 (hexane:ethyl acetate=2:1);
NMR (300 MHz, CDCl$_3$): δ 7.25-6.95 (m, 5H), 6.95-6.73 (m, 2H), 5.40-5.15 (m, 2H), 3.83 (s, 3H), 3.65-3.30 (m, 2H), 3.30-2.95 (m, 2H), 2.35 (s, 3H), 2.31 (s, 3H), 2.30-2.10 (m, 3H), 2.19 (s, 3H), 1.10-0.80 (m, 4H).

EXAMPLE 2(114)

8-(N-cyclopropylmethyl-N-(4-methylphenyl)methylamino)-2-methyl-3-(2-methyl-4-methoxyphenyl)-6,7-dihydro-5H-cyclopenta[d]pyrazolo[1,5-a]pyrimidine hydrochloride

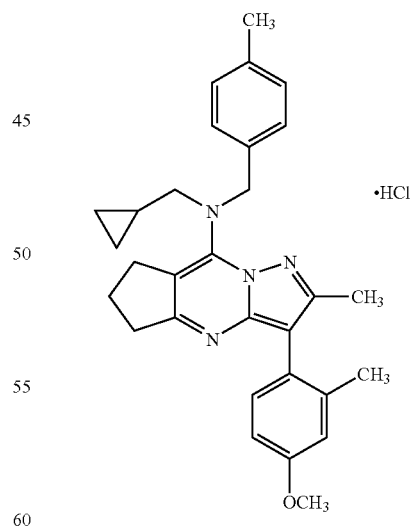

TLC: Rf 0.37 (hexane:ethyl acetate=2:1);
NMR (300 MHz, CDCl$_3$): δ 7.30-7.00 (m, 5H), 7.00-6.75 (m, 2H), 5.24 (s, 2H), 3.84 (s, 3H), 3.80-3.60 (m, 2H), 3.60-3.35 (m, 2H), 3.20-2.90 (m, 2H), 2.34 (s, 3H), 2.29 (s, 3H), 2.22 (s, 2H), 2.11 (s, 3H), 1.38-1.05 (m, 1H), 0.75-0.50 (m, 2H), 0.35-0.10 (m, 2H).

EXAMPLE 2(115)

8-(N,N-dipropylamino)-2-methyl-3-(2-methyl-4-methoxyphenyl)-6,7-dihydro-5H-cyclopenta[d]pyrazolo[1,5-a]pyrimidine

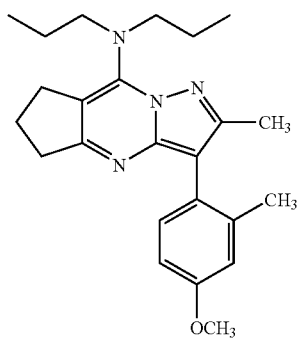

TLC: Rf 0.59 (hexane:ethyl acetate=2:1);

NMR (300 MHz, CDCl₃): δ 7.17 (d, J=8.4 Hz, 1H), 6.86 (d, J=2.4 Hz, 1H), 6.79 (dd, J=2.4, 8.4 Hz, 1H), 3.82 (s, 3H), 3.56 (m, 4H), 2.95 (t, J=7.2 Hz, 2H), 2.90 (t, J=7.8 Hz, 2H), 2.33 (s, 3H), 2.19 (s, 3H), 2.13 (m, 2H), 1.58 (m, 4H), 0.89 (t, J=7.5 Hz, 6H).

EXAMPLE 2(116)

8-(N-(4-methylphenyl)methyl-N-(2-butynyl)amino)-2-methyl-3-(2-methyl-4-methoxyphenyl)-6,7-dihydro-5H-cyclopenta[d]pyrazolo[1,5-a]pyrimidine hydrochloride

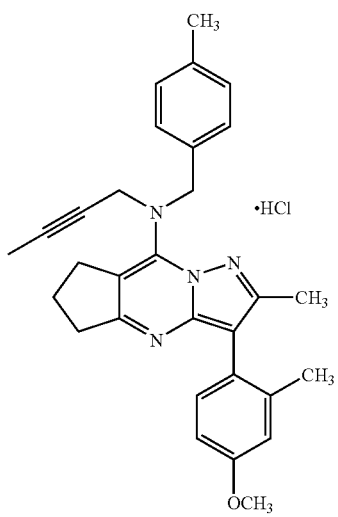

TLC: Rf 0.47 (hexane:ethyl acetate=2:1);

NMR (300 MHz, CDCl₃): δ 7.33 (d, J=8.1 Hz, 2H), 7.19 (d, J=8.1 Hz, 2H), 7.11 (d, J=8.7 Hz, 1H), 6.89 (d, J=2.7 Hz, 1H), 6.82 (dd, J=2.7, 8.7 Hz, 1H), 5.27 (d, J=15.0 Hz, 1H), 5.24 (d, J=15.0 Hz, 1H), 4.41 (m, 2H), 3.83 (s, 3H), 3.51 (t, J=7.5 Hz, 2H), 3.22 (t, J=6.9 Hz, 2H), 2.37 (s, 3H), 2.28 (s, 3H), 2.25 (m, 2H), 2.17 (s, 3H), 1.91 (t, J=2.4 Hz, 3H).

EXAMPLE 2(117)

8-(N-propyl-N-(2-butynyl)amino)-2-methyl-3-(2-methyl-4-methoxyphenyl)-6,7-dihydro-5H-cyclopenta[d]pyrazolo[1,5-a]pyrimidine

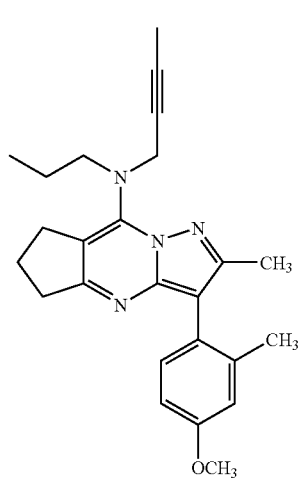

TLC: Rf 0.55 (hexane:ethyl acetate=2:1);

NMR (300 MHz, CDCl₃): δ 7.16 (d, J=8.1 Hz, 1H), 6.86 (d, J=2.7 Hz, 1H), 6.79 (dd, J=2.7, 8.1 Hz, 1H), 4.40 (m, 2H), 3.82 (s, 3H), 3.55 (m, 2H), 3.11 (t, J=7.2 Hz, 2H), 2.91 (t, J=7.8 Hz, 2H), 2.32 (s, 3H), 2.18 (s, 3H), 2.13 (m, 2H), 1.81 (t, J=2.4 Hz, 3H), 1.66 (m, 2H), 0.95 (t, J=7.5 Hz, 3H).

EXAMPLE 2(118)

8-(5-nonylamino)-2-methyl-3-(2-methyl-4-methoxyphenyl)-6,7-dihydro-5H-cyclopenta[d]pyrazolo[1,5-a]pyrimidine hydrochloride

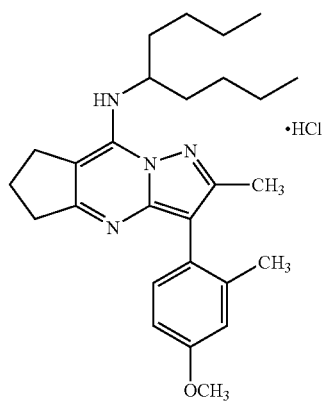

TLC: Rf 0.58 (hexane:ethyl acetate=2:1);

NMR (300 MHz, CDCl₃): δ 7.33 (brd, J=10.5 Hz, 1H), 7.12 (d, J=8.7 Hz, 1H), 6.88 (d, J=2.7 Hz, 1H), 6.81 (dd, J=2.7, 8.7 Hz, 1H), 4.10 (m, 1H), 3.83 (s, 3H), 3.49 (t, J=8.1 Hz, 2H), 3.12 (t, J=6.6 Hz, 2H), 2.29 (s, 3H), 2.27 (m, 2H), 2.20 (s, 3H), 1.61-1.88 (m, 4H), 1.30-1.53 (m, 8H), 0.94 (m, 6H).

EXAMPLE 2(119)

8-(N-cyclopentyl-N-(4-methylphenyl)methylamino)-2-methyl-3-(2-methyl-4-methoxyphenyl)-6,7-dihydro-5H-cyclopenta[d]pyrazolo[1,5-a]pyrimidine hydrochloride

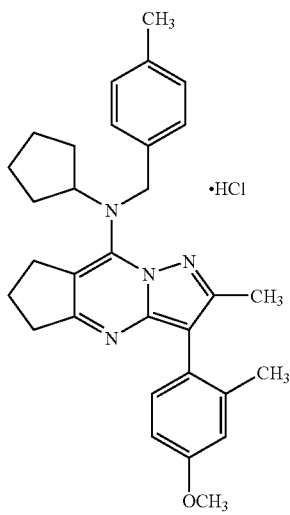

TLC: Rf 0.38 (hexane:ethyl acetate=2:1);
NMR (300 MHz, CD$_3$OD): δ 7.20-6.98 (m, 5H), 6.93 (d, J=2.4 Hz, 1H), 6.85 (dd, J=8.6, 2.4 Hz, 1H), 5.20 (d, J=16.5 Hz, 1H), 5.09 (d, J=16.5 Hz, 1H), 5.02-4.70 (m, 1H), 3.81 (s, 3H), 3.17 (t, J=7.2 Hz, 2H), 2.98 (t, J=7.8 Hz, 2H), 2.29 (s, 3H), 2.22 (s, 3H), 1.98 (s, 3H), 2.40-1.60 (m, 10H).

EXAMPLE 2(120)

8-(N-cyclopropylmethyl-N-(4-methylthiophenyl)methylamino)-2-methyl-3-(2-methyl-4-methoxyphenyl)-6,7-dihydro-5H-cyclopenta[d]pyrazolo[1,5-a]pyrimidine

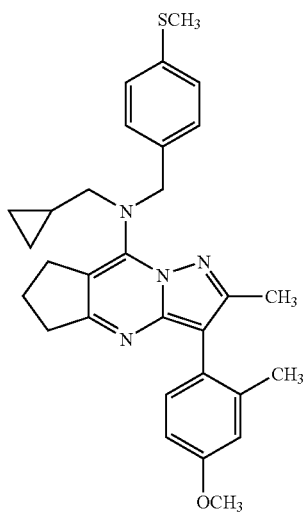

TLC: Rf 0.85 (hexane:ethyl acetate=1:1);
NMR (300 MHz, CDCl$_3$): δ 7.28-7.16 (m, 5H), 6.87 (d, J=3.0 Hz, 1H), 6.79 (dd, J=3.0, 8.4 Hz, 1H), 4.89 (s, 2H), 3.83 (s, 3H), 3.38 (d, J=6.9 Hz, 2H), 2.96 (t, J=7.2 Hz, 2H), 2.89 (t, J=7.2 Hz, 2H), 2.47 (s, 3H), 2.36 (s, 3H), 2.19 (s, 3H), 2.09 (quint, J=7.2 Hz, 2H), 1.10-0.95 (m, 1H), 0.52-0.42 (m, 2H), 0.10-0.05 (m, 2H).

EXAMPLE 2(121)

8-(N-(4-fluorophenyl)methyl-N-propylamino)-2-methyl-3-(2-methyl-4-methoxyphenyl)-6,7-dihydro-5H-cyclopenta[d]pyrazolo[1,5-a]pyrimidine

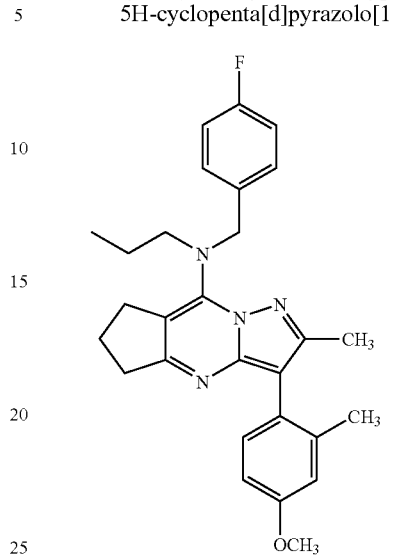

TLC: Rf 0.87 (hexane ethyl acetate=1:1);
NMR (300 MHz, CDCl$_3$): δ 7.28-7.16 (m, 3H), 7.03-6.95 (m, 2H), 6.87 (d, J=2.4 Hz, 1H), 6.79 (dd, J=2.4, 8.4 Hz, 1H), 4.80 (s, 2H), 3.83 (s, 3H), 3.40-3.32 (m, 2H), 2.89 (t, J=7.5 Hz, 2H), 2.81 (t, J=7.5 Hz, 2H), 2.36 (s, 3H), 2.20 (s, 3H), 2.07 (quint, J=7.5 Hz, 2H), 1.62-1.50 (m, 2H), 0.88 (t, J=7.2 Hz, 3H).

EXAMPLE 2(122)

8-(N-cyclobutyl-N-(4-methylphenyl)methylamino)-2-methyl-3-(2-methyl-4-methoxyphenyl)-6,7-dihydro-5H-cyclopenta[d]pyrazolo[1,5-a]pyrimidine

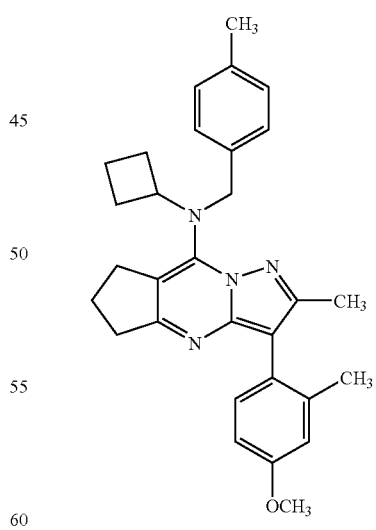

TLC: Rf 0.48 (hexane:ethyl acetate=2:1);
NMR (300 MHz, CDCl$_3$): δ 7.19 (d, J=8.4 Hz, 1H), 7.02 (d, J=7.5 Hz, 2H), 6.89 (d, J=7.5 Hz, 2H), 6.87 (d, J=3.0 Hz, 1H), 6.80 (dd, J=8.4, 3.0 Hz, 1H), 4.90-4.70 (m, 2H), 4.08 (m, 1H), 3.83 (s, 3H), 2.84 (t, J=7.5 Hz, 2H), 2.61 (m, 2H), 2.39 (s, 3H), 2.30 (s, 3H), 2.19 (s, 3H), 2.20-2.06 (m, 4H), 1.96 (m, 2H), 1.80-1.60 (m, 2H).

EXAMPLE 2(123)

8-(N-ethyl-N-(4-methylphenyl)methylamino)-2-methyl-3-(2-methyl-4-methoxyphenyl)-6,7-dihydro-5H-cyclopenta[d]pyrazolo[1,5-a]pyrimidine

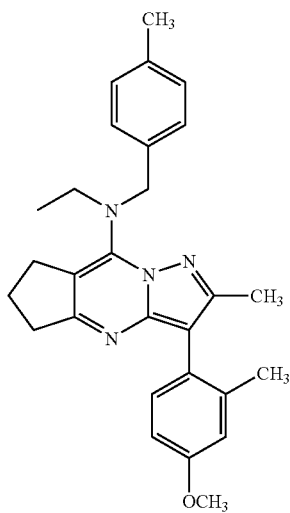

TLC: Rf 0.69 (hexane:ethyl acetate=1:1);
NMR (300 MHz, CDCl₃): δ 7.19 (d, J=8.1 Hz, 1H), 7.14-7.06 (m, 4H), 6.87 (d, J=2.7 Hz, 1H), 6.80 (dd, J=2.7, 8.1 Hz, 1H), 4.81 (s, 2H), 3.87 (s, 3H), 3.47 (q, J=6.9 Hz, 2H), 2.88 (t, J=7.8 Hz, 2H), 2.81 (brt, J=7.8 Hz, 2H), 2.36 (s, 3H), 2.33 (s, 3H), 2.20 (s, 3H), 2.04 (quint, J=7.8 Hz, 2H), 1.18 (t, J=6.9 Hz, 3H).

EXAMPLE 2(124)

8-(N-propyl-N-(4-trifluoromethylphenyl)methylamino)-2-methyl-3-(2-methyl-4-methoxyphenyl)-6,7-dihydro-5H-cyclopenta[d]pyrazolo[1,5-a]pyrimidine

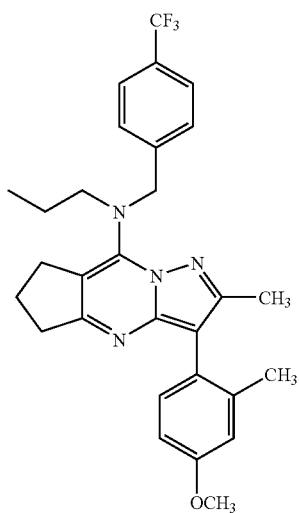

TLC: Rf 0.79 (hexane:ethyl acetate=1:1);
NMR (300 MHz, CDCl₃): δ 7.57 (brd, J=8.1 Hz, 2H), 7.44 (brd, J=8.1 Hz, 2H), 7.18 (d, J=8.7 Hz, 1H), 6.87 (d, J=2.4 Hz, 1H), 6.79 (dd, J=2.4, 8.7 Hz, 1H), 4.91 (s, 2H), 3.83 (s, 3H), 3.49-3.25 (m, 2H), 2.90 (t, J=7.8 Hz, 2H), 2.87 (t, J=7.8 Hz, 2H), 2.35 (s, 3H), 2.19 (s, 3H), 2.18-2.00 (m, 2H), 1.62-1.50 (m, 2H), 0.88 (t, J=7.5 Hz, 3H).

EXAMPLE 2(125)

8-(N-propyl-N-(tetrahydrofuran-2-yl)methylamino)-2-methyl-3-(2-methyl-4-methoxyphenyl)-6,7-dihydro-5H-cyclopenta[d]pyrazolo[1,5-a]pyrimidine

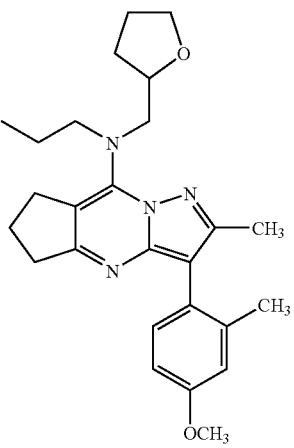

TLC: Rf 0.31 (hexane:ethyl acetate=2:1);
NMR (300 MHz, CDCl₃): δ 7.16 (d, J=8.1 Hz, 1H), 6.86 (d, J=2.7 Hz, 1H), 6.78 (dd, J=2.7, 8.1 Hz, 1H), 3.84-4.06 (m, 2H), 3.82 (s, 3H), 3.64-3.80 (m, 3H), 3.50-3.64 (m, 2H), 2.99 (t, J=7.2 Hz, 2H), 2.91 (t, J=8.1 Hz, 2H), 2.32 (s, 3H), 2.19 (s, 3H), 2.13 (m, 2H), 1.74-2.00 (m, 3H), 1.42-1.65 (m, 3H), 0.89 (t, J=7.5 Hz, 3H).

EXAMPLE 2(126)

8-(N-butyl-N-(2-methoxyethyl)amino)-2-methyl-3-(2-methyl-4-methoxyphenyl)-6,7-dihydro-5H-cyclopenta[d]pyrazolo[1,5-a]pyrimidine

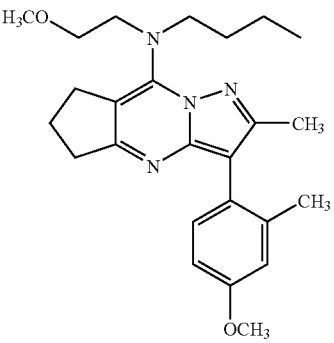

TLC: Rf 0.30 (hexane:ethyl acetate=2:1);
NMR (300 MHz, CDCl₃): δ 7.16 (d, J=8.4 Hz, 1H), 6.86 (d, J=2.7 Hz, 1H), 6.79 (dd, J=2.7, 8.4 Hz, 1H), 3.92 (t, J=5.7 Hz, 2H), 3.82 (s, 3H), 3.57 (m, 2H), 3.50 (t, J=5.7 Hz, 2H), 3.28 (s, 3H), 2.98 (t, J=7.8 Hz, 2H), 2.91 (t, J=7.8 Hz, 2H), 2.32 (s, 3H), 2.18 (s, 3H), 2.13 (m, 2H), 1.55 (m, 2H), 1.33 (m, 2H), 0.90 (t, J=7.2 Hz, 3H).

EXAMPLE 2(127)

8-(N-propyl-N-cyclopropylamino)-2-methyl-3-(2-methyl-4-methoxyphenyl)-6,7-dihydro-5H-cyclopenta[d]pyrazolo[1,5-a]pyrimidine

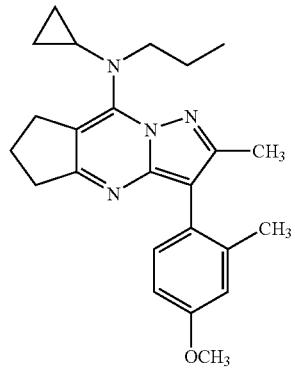

TLC: Rf 0.45 (hexane:ethyl acetate=2:1);
NMR (300 MHz, CDCl$_3$): δ 7.16 (d, J=8.1 Hz, 1H), 6.85 (d, J=2.7 Hz, 1H), 6.78 (dd, J=8.1, 2.7 Hz, 1H), 3.85 (m, 2H), 3.82 (s, 3H), 3.19 (t, J=7.5 Hz, 2H), 3.07 (m, 1H), 2.92 (t, J=7.5 Hz, 2H), 2.31 (s, 3H), 2.18 (s, 3H), 2.12 (m, 2H), 1.62 (m, 2H), 0.89 (t, J=7.2 Hz, 3H), 0.80-0.68 (m, 4H).

EXAMPLE 2(128)

8-(N-cyclobutylmethyl-N-(2-methoxyethyl)amino)-2-methyl-3-(2-methyl-4-methoxyphenyl)-6,7-dihydro-5H-cyclopenta[d]pyrazolo[1,5-a]pyrimidine

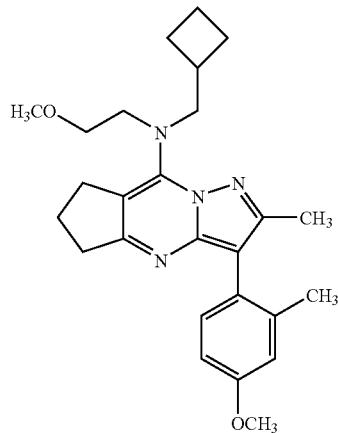

TLC: Rf 0.57 (hexane:ethyl acetate=1:1);
NMR (300 MHz, CDCl$_3$): δ 7.17 (d, J=8.4 Hz, 1H), 6.86 (d, J=2.7 Hz, 1H), 6.78 (dd, J=2.7, 8.4 Hz, 1H), 3.82 (s, 3H), 3.82 (t, J=6.0 Hz, 2H), 3.64 (d, J=7.5 Hz, 2H), 3.49 (t, J=6.0 Hz, 2H), 3.28 (s, 3H), 2.96 (t, J=7.2 Hz, 2H), 2.91 (t, J=7.8 Hz, 2H), 2.62-2.50 (m, 1H), 2.32 (s, 3H), 2.18 (s, 3H), 2.20-2.05 (m, 2H), 2.06-1.58 (m, 6H).

EXAMPLE 2(129)

8-(3-ethoxycarbonyl-1, 2, 5, 6-tetrahydropyridyl)-2-methyl-3-(2-methyl-4-methoxyphenyl)-6,7-dihydro-5H-cyclopenta[d]pyrazolo[1,5-a]pyrimidine hydrochloride

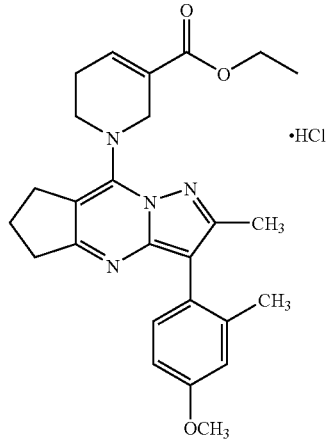

TLC: Rf 0.27 (hexane:ethyl acetate=2:1);
NMR (300 MHz, CDCl$_3$): δ 7.27 (m, 1H), 7.09 (d, J=8.1 Hz, 1H), 6.88 (d, J=2.7 Hz, 1H), 6.81 (dd, J=2.7, 8.1 Hz, 1H), 4.62 (m, 2H), 4.27 (q, J=6.9 Hz, 2H), 4.20 (t, J=5.7 Hz, 2H), 3.83 (s, 3H), 3.47 (t, J=7.2 Hz, 2H), 3.16 (t, J=6.0 Hz, 2H), 2.85 (m, 2H), 2.27 (s, 3H), 2.26 (m, 2H), 2.17 (s, 3H), 1.34 (t, J=6.9 HZ, 3H).

EXAMPLE 2(130)

8-(N-cyclopropylmethyl-N-(4-methylphenyl)methylamino)-2-methyl-3-(2-methyl-4-methoxyphenyl)-5,7-dihydro-furo[3,4-d]pyrazolo[1,5-a]pyrimidine hydrochloride

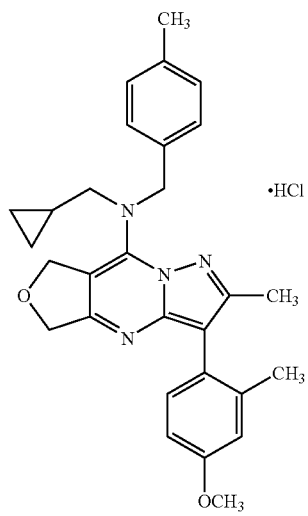

TLC: Rf 0.68 (hexane:ethyl acetate=1:1);

NMR (300 MHz, CDCl$_3$): δ 7.21 (d, J=7.8 Hz, 2H), 7.16 (d, J=7.8 Hz, 2H), 7.13 (d, J=8.4 Hz, 1H), 6.90 (d, J=2.7 Hz, 1H), 6.83 (dd, J=2.7, 8.4 Hz, 1H), 5.41 (brs, 2H), 5.27 (m, 2H), 5.22 (brs, 2H), 3.83 (s, 3H), 3.74 (m, 2H), 2.37 (s, 3H), 2.31 (s, 3H), 2.20 (s, 3H), 1.24 (m, 1H), 0.67 (m, 2H), 0.24 (m, 2H).

EXAMPLE 2(131)

8-(3-(3-methyl-1,2,4-oxadiazol-5-yl)-1,2,5,6-tetrahydropyridyl)-2-methyl-3-(2-methyl-4-methoxyphenyl)-6,7-dihydro-5H-cyclopenta[d]pyrazolo[1,5-a]pyrimidine

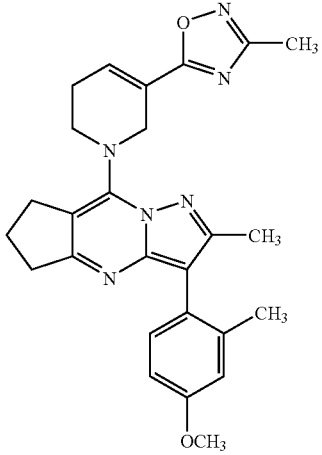

TLC: Rf 0.18 (hexane:ethyl acetate=2:1);

NMR (300 MHz, CDCl$_3$): δ 7.29 (m, 1H), 7.15 (d, J=8.7 Hz, 1H), 6.86 (d, J=2.7 Hz, 1H), 6.79 (dd, J=2.7, 8.7 Hz, 1H), 4.57 (m, 2H), 3.94 (m, 2H), 3.82 (s, 3H), 3.09 (t, J=7.5 Hz, 2H), 2.91 (t, J=7.8 Hz, 2H), 2.71 (m, 2H), 2.42 (s, 3H), 2.32 (s, 3H), 2.17 (s, 3H), 2.14 (m, 2H).

EXAMPLE 2(132)

8-(4-heptylamino)-2-methyl-3-(2-chloro-4-methoxyphenyl)-6,7-dihydro-5H-cyclopenta[d]pyrazolo[1,5-a]pyrimidine hydrochloride

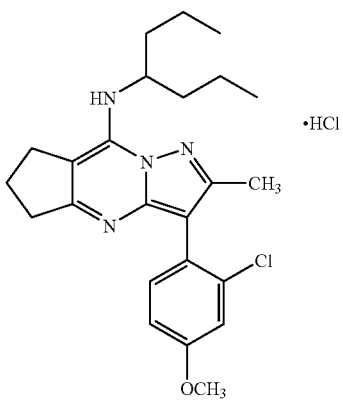

TLC: Rf 0.48 (hexane:ethyl acetate=2:1);

NMR (300 MHz, CDCl$_3$): δ 7.37 (d, J=8.7 Hz, 1H), 7.07 (d, J=2.4 Hz, 1H), 6.97 (dd, J=2.4, 8.7 Hz, 1H), 4.13 (m, 1H), 3.85 (s, 3H), 3.35-3.66 (m, 2H), 3.13 (t, J=7.5 Hz, 2H), 2.34 (s, 3H), 2.29 (m, 2H), 1.60-1.84 (m, 4H), 1.34-1.60 (m, 4H), 1.00 (t, J=7.2 Hz, 3H), 0.99 (t, J=7.5 Hz, 3H).

EXAMPLE 2(133)

8-(N-cyclopropylmethyl-N-(2-butyryl)amino)-2-methyl-3-(2-methyl-4-methoxyphenyl)-6,7-dihydro-5H-cyclopenta[d]pyrazolo[1,5-a]pyrimidine

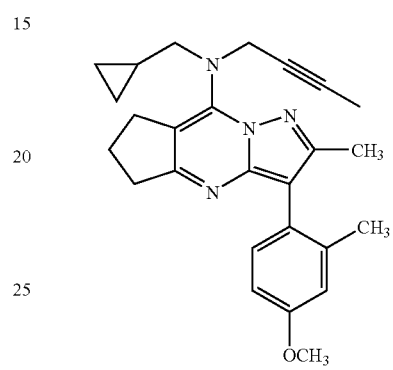

TLC: Rf 0.73 (hexane:ethyl acetate=1:1);

NMR (300 MHz, CDCl$_3$): δ 7.16 (d, J=8.1 Hz, 1H), 6.86 (d, J=2.7 Hz, 1H), 6.78 (dd, J=8.1, 2.7 Hz, 1H), 4.54 (brs, 2H), 3.82 (s, 3H), 3.53 (d, J=6.9 Hz, 2H), 3.13 (t, J=7.2 Hz, 2H), 2.91 (t, J=7.8 Hz, 2H), 2.33 (s, 3H), 2.17 (s, 3H), 2.17-2.08 (m, 2H), 1.81 (t, J=2.7 Hz, 3H), 1.20-1.16 (m, 1H), 0.60-0.52 (m, 2H), 0.36-0.28 (m, 2H).

EXAMPLE 2(134)

8-(N-(2-methoxyethyl)-N-(2-butyryl)amino)-2-methyl-3-(2-methyl-4-methoxyphenyl)-6,7-dihydro-5H-cyclopenta[d]pyrazolo[1,5-a]pyrimidine

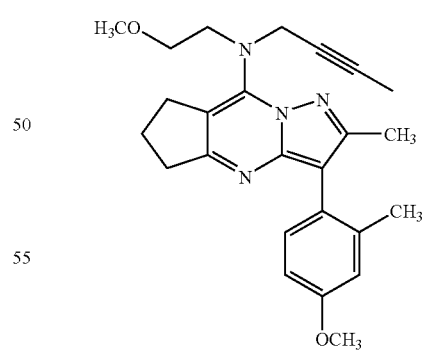

TLC: Rf 0.13 (hexane:ethyl acetate=3:1);

NMR (300 MHz, CDCl$_3$): δ 7.15 (d, J=8.4 Hz, 1H), 6.86 (d, J=2.7 Hz, 1H), 6.79 (dd, J=8.4, 2.7 Hz, 1H), 4.44-4.39 (m, 2H), 3.92 (t, J=6.0 Hz, 2H), 3.82 (s, 3H), 3.65 (t, J=6.0 Hz, 2H), 3.34 (s, 3H), 3.13 (t, J=7.2 Hz, 2H), 2.91 (t, J=7.8 Hz, 2H), 2.32 (s, 3H), 2.17 (s, 3H), 2.17-2.08 (m, 2H), 1.81 (t, J=2.7 Hz, 3H).

EXAMPLE 2(135)

8-(2-butyrylamino)-2-methyl-3-(2-methyl-4-methoxyphenyl)-6,7-dihydro-5H-cyclopenta[d]pyrazolo[1,5-a]pyrimidine

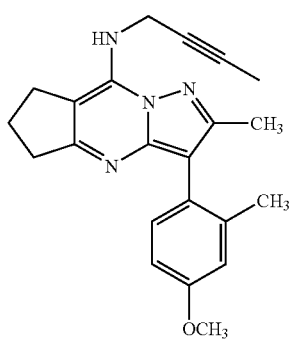

TLC: Rf 0.80 (hexane:ethyl acetate=1:1);
NMR (300 MHz, CDCl$_3$): δ 7.15 (d, J=8.4 Hz, 1H), 6.85 (d, J=2.4 Hz, 1H), 6.78 (dd, J=8.4, 2.4 Hz, 1H), 6.53 (t, J=6.9 Hz, 1H), 4.36-4.30 (m, 2H), 3.82 (s, 3H), 3.25 (t, J=7.2 Hz, 2H), 2.90 (t, J=7.8 Hz, 2H), 2.31 (s, 3H), 2.18 (s, 3H), 2.20-2.08 (m, 2H), 1.83 (t, J=2.1 Hz, 3H).

EXAMPLE 2(136)

8-(4-(4-chlorophenyl)-1, 2, 5, 6-tetrahydropyridyl)-2-methyl-3-(2-methyl-4-methoxyphenyl)-6,7-dihydro-5H-cyclopenta[d]pyrazolo[1,5-a]pyrimidine

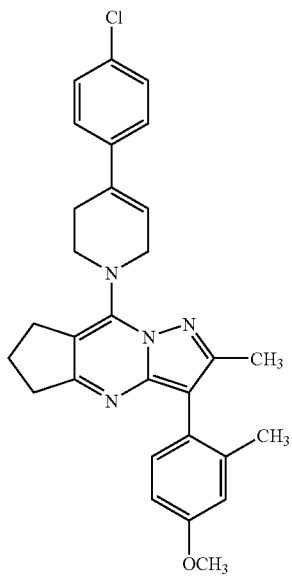

TLC: Rf 0.10 (hexane:ethyl acetate=3:1);
NMR (300 MHz, CDCl$_3$): δ 7.42-7.30 (m, 4H), 7.16 (d, J=8.1 Hz, 1H), 6.86 (d, J=2.4 Hz, 1H), 6.79 (dd, J=8.1, 2.4 Hz, 1H), 6.22-6.18 (m, 1H), 4.50-4.32 (m, 2H), 4.10-3.90 (m, 2H), 3.82 (s, 3H), 3.10 (t, J=6.9 Hz, 2H), 2.91 (t, J=7.5 Hz, 2H), 2.82-2.69 (m, 2H), 2.33 (s, 3H), 2.17 (s, 3H), 2.17-2.08 (m, 2H).

EXAMPLE 2(137)

8-(N-cyclopropylmethyl-N-(4-methylphenyl)methylamino)-2-methyl-3-(2-methyl-4-methoxyphenyl)-6,7-dihydro-5H-cyclopenta[d]pyrazolo[1,5-a]pyrimidine hydrochloride

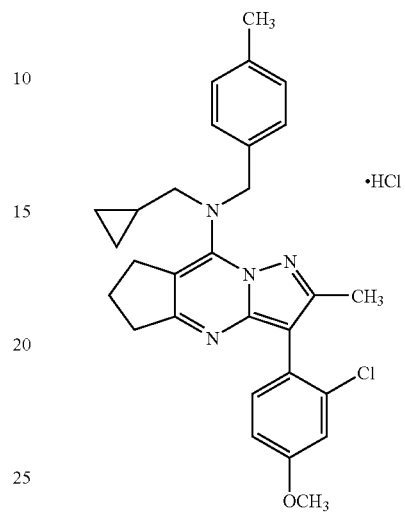

TLC: Rf 0.53 (hexane:ethyl acetate=2:1);
NMR (300 MHz, CDCl$_3$): δ 7.36 (d, J=8.4 Hz, 1H), 7.18 (d, J=8.1 Hz, 2H), 7.15 (d, J=8.1 Hz, 2H), 7.08 (d, J=2.7 Hz, 1H), 6.97 (dd, J=8.4, 2.7 Hz, 1H), 5.25 (d, J=15.9 Hz, 1H), 0.5.21 (d, J=15.9 Hz, 1H), 3.85 (s, 3H), 3.70 (m, 2H), 3.36-3.62 (m, 2H), 3.07 (t, J=7.2 Hz, 2H), 2.36 (s, 3H), 2.35 (s, 3H), 2.23 (m, 2H), 1.23 (m, 1H), 0.63 (m, 2H), 0.18 (m, 2H).

EXAMPLE 2(138)

8-(N-propyl-N-(4-trifluoromethyloxyphenyl)methylamino)-2-methyl-3-(2-methyl-4-methoxyphenyl)-6,7-dihydro-5H-cyclopenta[d]pyrazolo[1,5-a]pyrimidine

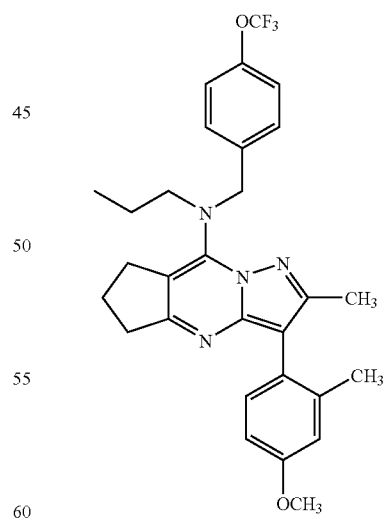

TLC: Rf 0.55 (hexane:ethyl acetate=3:1);
NMR (300 MHz, CDCl$_3$): δ 7.32 (brd, J=8.7 Hz, 2H), 7.18 (d, J=8.4 Hz, 1H), 7.15 (brd, J=8.7 Hz, 2H), 6.87 (d, J=2.7 Hz, 1H), 6.80 (dd, J=8.4, 2.7 Hz, 1H), 4.84 (s, 2H), 3.83 (s, 3H), 3.41-3.35 (m, 2H), 2.89 (t, J=7.5 Hz, 2H), 2.83 (t, J=7.8 Hz, 2H), 2.36 (s, 3H), 2.19 (s, 3H), 2.19-2.00 (m, 2H), 1.66-1.54 (m, 2H), 0.88 (t, J=7.5 Hz, 3H).

EXAMPLE 2(139)

8-(N-(2-butyryl)-N-cyclopropylmethylamino)-2-methyl-3-(2-chloro-4-methoxyphenyl)-6,7-dihydro-5H-cyclopenta[d]pyrazolo[1,5-a]pyrimidine

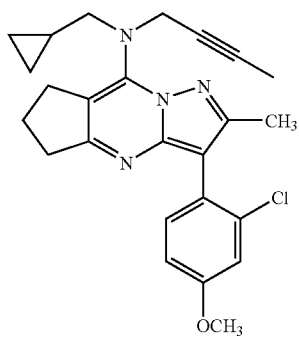

TLC: Rf 0.40 (hexane:ethyl acetate=3:1);

NMR (300 MHz, CDCl$_3$): δ 7.29 (d, J=8.7 Hz, 1H), 7.05 (d, J=2.4 Hz, 1H), 6.88 (dd, J=8.7, 2.4 Hz, 1H), 4.54 (q, J=2.1 Hz, 2H), 3.83 (s, 3H), 3.52 (d, J=6.6 Hz, 2H), 3.13 (t, J=7.5 Hz, 2H), 2.92 (t, J=7.5 Hz, 2H), 2.37 (s, 3H), 2.13 (quint, J=7.5 Hz, 2H), 1.81 (t, J=2.1 Hz, 3H), 1.16-1.02 (m, 1H), 0.60-0.52 (m, 2H), 0.32-0.26 (m, 2H).

EXAMPLE 2(140)

8-(N-propyl-N-(3-methylphenyl)methylamino)-2-methyl-3-(2-methyl-4-methoxyphenyl)-6,7-dihydro-5H-cyclopenta[d]pyrazolo[1,5-a]pyrimidine hydrochloride

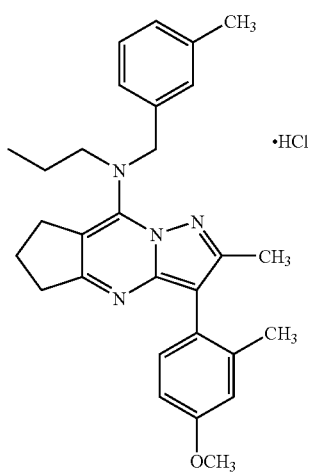

TLC: Rf 0.52 (hexane:ethyl acetate=2:1);

NMR (300 MHz, CDCl$_3$): δ 7.27 (m, 1H), 7.15 (m, 1H), 7.13 (d, J=8.1 Hz, 1H), 7.05 (m, 2H), 6.90 (d, J=2.7 Hz, 1H), 6.83 (dd, J=2.7, 8.1 Hz, 1H), 5.14 (s, 2H), 3.83 (s, 3H), 3.74 (m, 2H), 3.49 (t, J=7.2 Hz, 2H), 3.02 (t, J=6.9 Hz, 2H), 2.36 (s, 3H), 2.29 (s, 3H), 2.22 (m, 2H), 2.20 (s, 3H), 1.77 (m, 2H), 0.94 (t, J=7.2 Hz, 3H).

EXAMPLE 2(141)

8-(N-propyl-N-(2-methylphenyl)methylamino)-2-methyl-3-(2-methyl-4-methoxyphenyl)-6,7-dihydro-5H-cyclopenta[d]pyrazolo[1,5-a]pyrimidine hydrochloride

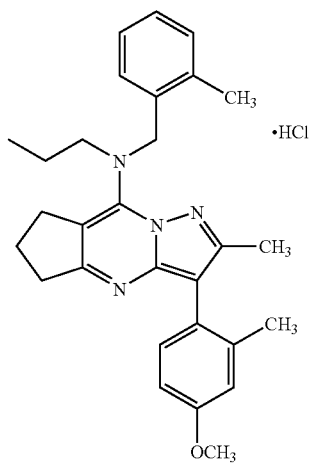

TLC: Rf 0.52 (hexane:ethyl acetate=2:1);

NMR (300 MHz, CDCl$_3$): δ 7.18-7.30 (m, 4H), 7.13 (d, J=8.1 Hz, 1H), 6.90 (d, J=2.4 Hz, 1H), 6.83 (dd, J=2.4, 8.1 Hz, 1H), 5.13 (s, 2H), 3.83 (s, 3H), 3.78 (m, 2H), 3.49 (t, J=6.9 Hz, 2H), 3.00 (t, J=6.9 Hz, 2H), 2.28 (s, 3H), 2.24 (s, 3H), 2.21 (m, 2H), 2.19 (s, 3H), 1.79 (m, 2H), 0.94 (t, J=7.2 Hz, 3H).

EXAMPLE 2(142)

8-(3-pentylamino)-2-methyl-3-(2-chloro-4-ethoxyphenyl)-6,7-dihydro-5H-cyclopenta[d]pyrazolo[1,5-a]pyrimidine hydrochloride

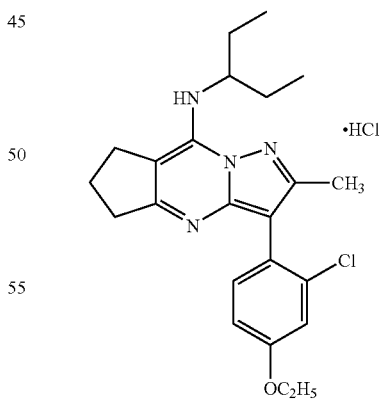

TLC: Rf 0.49 (hexane:ethyl acetate=2:1);

NMR (300 MHz, CDCl$_3$): δ 7.34 (d, J=8.7 Hz, 1H), 7.06 (d, J=2.4 Hz, 1H), 6.95 (dd, J=2.4, 8.7 Hz, 1H), 4.07 (m, 2H), 3.99 (m, 1H), 3.34-3.65 (m, 2H), 3.13 (t, J=7.8 Hz, 2H), 2.35 (s, 3H), 2.29 (m, 2H), 1.62-1.93 (m, 4H), 1.42 (t, J=6.9 Hz, 3H), 1.06 (t, J=7.5 Hz, 3H), 1.05 (t, J=7.2 Hz, 3H).

EXAMPLE 2(143)

8-(3-pentylamino)-2-methyl-3-(2-chloro-4-ethoxyphenyl)-5,7-dihydro-furo[3,4-d]pyrazolo[1,5-a]pyrimidine hydrochloride

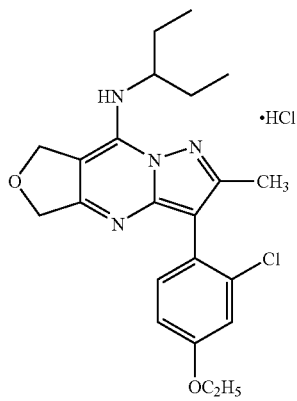

TLC: Rf 0.40 (hexane:ethyl acetate=2:1);

NMR (300 MHz, CDCl$_3$): δ 7.52 (brd, J=10.2 Hz, 1H), 7.32 (d, J=8.4 Hz, 1H), 7.07 (d, J=2.4 Hz, 1H), 6.95 (dd, J=2.4, 8.4 Hz, 1H), 5.49 (d, J=16.5 Hz, 1H), 5.39 (d, J=16.5 Hz, 1H), 5.28 (brs, 2H), 4.07 (m, 2H), 3.40 (m, 1H), 2.40 (s, 3H), 1.68-1.98 (m, 4H), 1.43 (t, J=6.9 Hz, 3H), 1.07 (t, J=7.2 Hz, 3H), 1.06 (t, J=7.2 Hz, 3H).

EXAMPLE 2(144)

8-(N-methyl-N-hexylamino)-2-methyl-3-(2-methyl-4-methoxyphenyl)-6,7-dihydro-5H-cyclopenta[d]pyrazolo[1,5-a]pyrimidine hydrochloride

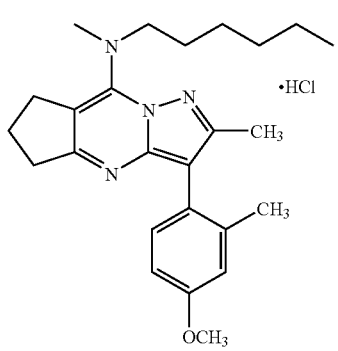

TLC: Rf 0.09 (hexane:ethyl acetate=3:1);

NMR (300 MHz, CDCl$_3$): δ 7.11 (d, J=8.4 Hz, 1H), 6.89 (d, J=2.4 Hz, 1H), 6.82 (dd, J=8.4, 2.4 Hz, 1H), 4.01-3.95 (m, 2H), 3.83 (s, 3H), 3.51 (s, 3H), 3.51-3.42 (m, 2H), 3.18-3.06 (m, 2H), 2.26 (s, 3H), 2.26-2.18 (m, 2H), 2.18 (s, 3H), 1.96-1.80 (m, 2H), 1.44-1.25 (m, 6H), 0.90 (brt, J=6.6 Hz, 3H).

EXAMPLE 2(145)

8-(N-methyl-N-(3-pentyl)amino)-2-methyl-3-(2-methyl-4-methoxyphenyl)-6,7-dihydro-5H-cyclopenta[d]pyrazolo[1,5-a]pyrimidine hydrochloride

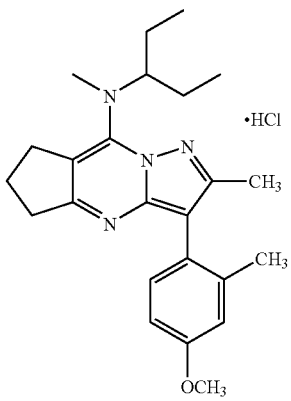

TLC: Rf 0.47 (hexane:ethyl acetate=2:1);

NMR (300 MHz, CDCl$_3$): δ 7.11 (d, J=8.4 Hz, 1H), 6.89 (d, J=2.7 Hz, 1H), 6.82 (m, 1H), 4.55 (m, 1H), 3.83 (s, 3H), 3.46 (t, J=7.8 Hz, 2H), 3.27 (s, 3H), 3.10 (t, J=6.9 Hz, 2H), 2.26 (s, 3H), 2.45 (m, 2H), 2.19 (s, 3H), 1.76-1.98 (m, 4H), 1.01 (t, J=7.2 Hz, 6H).

EXAMPLE 2(146)

8-(N-methyl-N-(4-heptyl)amino)-2-methyl-3-(2-methyl-4-methoxyphenyl)-6,7-dihydro-5H-cyclopenta[d]pyrazolo[1,5-a]pyrimidine hydrochloride

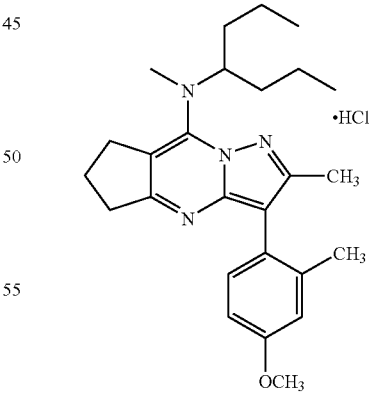

TLC: Rf 0.51 (hexane:ethyl acetate=2:1);

NMR (300 MHz, CDCl$_3$): δ 7.11 (d, J=8.4 Hz, 1H), 6.89 (d, J=3.0 Hz, 1H), 6.82 (dd, J=3.0, 8.4 Hz, 1H), 4.80 (m, 1H), 3.83 (s, 3H), 3.47 (t, J=7.5 Hz, 2H), 3.27 (s, 3H), 3.09 (t, J=7.5 Hz, 2H), 2.25 (s, 3H), 2.24 (m, 2H), 2.19 (s, 3H), 1.64-1.94 (m, 4H), 1.28-1.58 (m, 4H), 0.97 (t, J=7.2 Hz, 6H).

EXAMPLE 2(147)

8-(N-cyclopropyl-N-(4-methylphenyl)methylamino)-2-methyl-3-(2-chloro-4-methoxyphenyl)-5,7-dihydro-furo[3,4-d]pyrazolo[1,5-a]pyrimidine hydrochloride

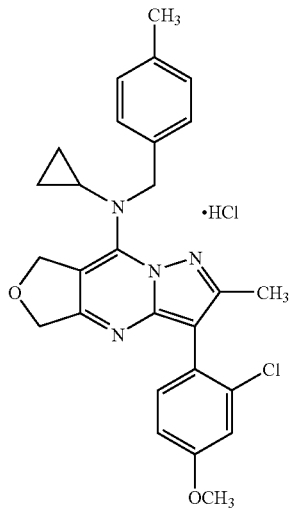

TLC: Rf 0.54 (hexane:ethyl acetate=1:1);
NMR (300 MHz, CDCl$_3$): δ 7.34 (d, J=8.4 Hz, 1H), 7.11 (d, J=7.8 Hz, 2H), 7.09 (d, J=2.4 Hz, 1H), 7.02 (d, J=7.8 Hz, 2H), 6.94 (dd, J=2.4, 8.4 Hz, 1H), 5.18-5.30 (m, 4H), 5.15 (s, 2H), 3.85 (s, 3H), 2.67 (m, 1H), 2.41 (s, 3H), 2.33 (s, 3H), 0.85-1.00 (m, 4H).

EXAMPLE 2(148)

8-(N-cyclopropylmethyl-N-(4-methylphenyl)methylamino)-2-methyl-3-(2-chloro-4-methoxyphenyl)-5,7-dihydro-furo[3,4-d]pyrazolo[1,5-a]pyrimidine hydrochloride

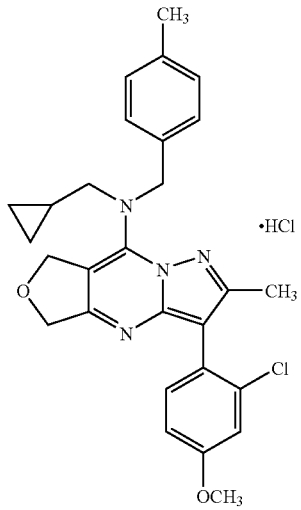

TLC: Rf 0.58 (hexane:ethyl acetate=1:1);
NMR (300 MHz, CDCl$_3$): δ 7.35 (d, J=8.4 Hz, 1H), 7.19 (d, J=8.1 Hz, 2H), 7.17 (d, J=8.1 Hz, 2H), 7.08 (d, J=2.7 Hz, 1H), 6.96 (dd, J=2.7, 8.4 Hz, 1H), 5.10-5.50 (m, 6H), 3.85 (s, 3H), 3.69 (m, 2H), 2.37 (s, 3H), 2.36 (s, 3H), 1.21 (m, 1H), 0.65 (m, 2H), 0.22 (m, 2H).

EXAMPLE 2(149)

8-(N-cyclobutyl-N-propylamino)-2-methyl-3-(2-methyl-4-methoxyphenyl)-6,7-dihydro-5H-cyclopenta[d]pyrazolo[1,5-a]pyrimidine

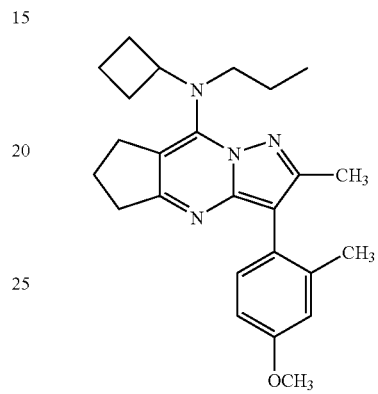

TLC: Rf 0.45 (hexane:ethyl acetate=3:1);
NMR (300 MHz, CDCl$_3$): δ 7.17 (,d J=8.1 Hz, 1H), 6.86 (d, J=2.7 Hz, 1H), 6.78 (dd, J=8.1, 2.7 Hz, 1H), 4.35 (quint, J=7.5 Hz, 1H), 3.82 (s, 3H), 3.69-3.10 (m, 2H), 2.94 (t, J=6.9 Hz, 2H), 2.90 (t, J=7.8 Hz, 2H), 2.33 (s, 3H), 2.22-2.02 (m, 9H), 1.78-1.58 (m, 2H), 1.39 (sext, J=7.8 Hz, 2H), 0.84 (t, J=7.8 Hz, 3H).

EXAMPLE 2(150)

8-(N-isobutyl-N-(2-dimethylaminoethyl)amino)-2-methyl-3-(2-methyl-4-methoxyphenyl)-6,7-dihydro-5H-cyclopenta[d]pyrazolo[1,5-a]pyrimidine dihydrochloride

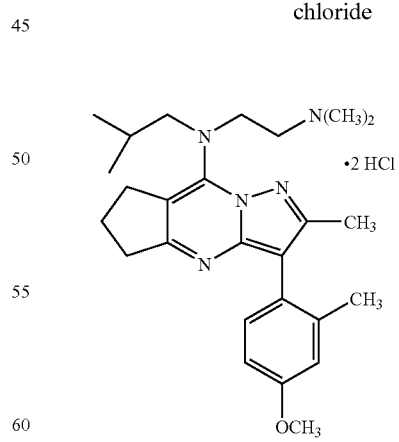

TLC: Rf 0.63 (ethyl acetate: acetic acid:water=3:1:1);
NMR (300 MHz, DMSO-d$_6$): δ 7.11 (d, J=8.4 Hz, 1H), 6.91 (d, J=2.7 Hz, 1H), 6.82 (dd, J=8.4, 2.7 Hz, 1H), 4.08-3.98 (m, 2H), 3.78 (s, 3H), 3.50-3.42 (m, 2H), 3.42-3.32 (m, 2H), 3.01 (brt, J=6.9 Hz, 2H), 2.87 (brt, J=7.8 Hz, 2H), 2.79 (s, 3H), 2.77 (s, 3H), 2.25 (s, 3H), 2.18-2.00 (m, 2H), 2.08 (s, 3H), 1.80-1.64 (m, 1H), 0.83 (d, J=6.6 Hz, 6H).

EXAMPLE 2(151)

8-(N-propyl-N-(4-fluorophenyl)methylamino)-2-methyl-3-(2-chloro-4-methoxyphenyl)-5,7-dihydro-furo[3,4-d]pyrazolo[1,5-a]pyrimidine

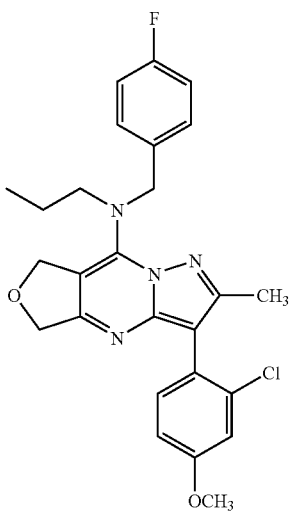

TLC: Rf 0.34 (hexane:ethyl acetate=3:1);
NMR (300 MHz, CDCl₃): δ 7.31 (d, J=8.7 Hz, 1H), 7.28-7.24 (m, 2H), 7.08 (d, J=3.0 Hz, 1H), 7.05-6.97 (m, 2H), 6.90 (dd, J=8.7, 3.0 Hz, 1H), 5.09 (s, 2H), 4.91 (s, 2H), 4.89 (s, 2H), 3.84 (s, 3H), 3.33-3.27 (m, 2H), 2.40 (s, 3H), 1.63 (sext, J=7.8 Hz, 2H), 0.39 (t, J=7.8 Hz, 3H).

EXAMPLE 2(152)

8-(N-propyl-N-(4-fluorophenyl)methylamino)-2-methyl-3-(2-chloro-4-methoxyphenyl)-6,7-dihydro-5H-cyclopenta[d]pyrazolo[1,5-a]pyrimidine

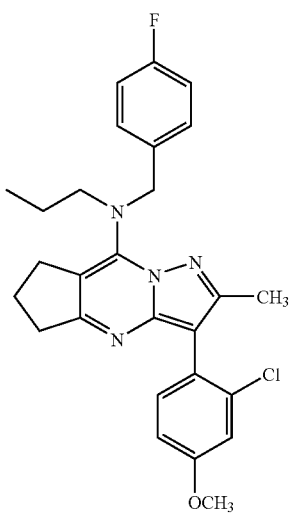

TLC: Rf 0.36 (hexane:ethyl acetate=3:1);
NMR (300 MHz, CDCl₃): δ 7.32 (d, J=8.4 Hz, 1H), 7.28-7.20 (m, 2H), 7.07 (d, J=2.7 Hz, 1H), 7.02-6.94 (m, 2H), 6.89 (dd, J=8.4, 2.7 Hz, 1H), 4.80 (s, 2H), 3.84 (s, 3H), 3.36 (brt, J=7.5 Hz, 2H), 2.90 (t, J=7.5 Hz, 2H), 2.82 (t, J=7.5 Hz, 2H), 2.39 (s, 3H), 2.07 (quint, J=7.5 Hz, 2H), 1.68-1.48 (m, 2H), 0.87 (t, J=7.5 Hz, 3H).

EXAMPLE 2(153)

8-(N-cyclopropylmethyl-N-(4-methylthiophenyl)methylamino)-2-methyl-3-(2-chloro-4-methoxyphenyl)-5,7-dihydro-furo[3,4-d]pyrazolo[1,5-a]pyrimidine hydrochloride

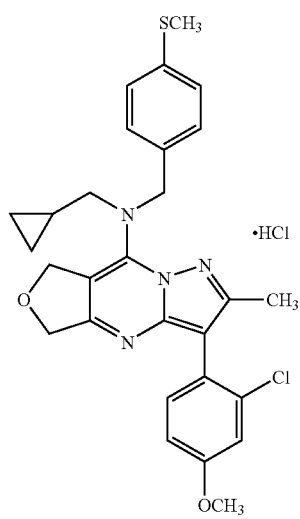

TLC: Rf 0.67 (hexane:ethyl acetate=1:1);
NMR (300 MHz, CDCl₃): δ 7.35 (d, J=8.4 Hz, 1H), 7.27 (d, J=8.4 Hz, 2H), 7.22 (d, J=8.4 Hz, 2H), 7.09 (d, J=2.7 Hz, 1H), 6.97 (dd, J=2.7, 8.4 Hz, 1H), 5.48 (d, J=16.5 Hz, 1H), 5.37 (d, J=16.5 Hz, 1H), 5.33 (d, J=15.9 Hz, 1H), 5.24 (s, 2H), 5.24 (d, J=15.9 Hz, 1H), 3.85 (s, 3H), 3.69 (m, 2H), 2.50 (s, 3H), 2.36 (s, 3H), 1.19 (m, 1H), 0.69 (m, 2H), 0.24 (m, 2H).

EXAMPLE 2(154)

8-(N,N-dipropylamino)-2-methyl-3-(2-chloro-4-methoxyphenyl)-5,7-dihydro-furo[3,4-d]pyrazolo[1,5-a]pyrimidine hydrochloride

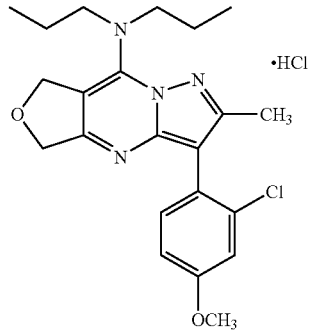

TLC: Rf 0.69 (hexane:ethyl acetate=1:1);
NMR (300 MHz, CDCl₃): δ 7.33 (d, J=8.7 Hz, 1H), 7.08 (d, J=2.4 Hz, 1H), 6.96 (dd, J=2.4, 8.7 Hz, 1H), 5.48 (td, J=1.8, 16.8 Hz, 1H), 5.36 (td, J=1.8, 16.8 Hz, 1H), 5.21 (t, J=1.8 Hz, 2H), 3.85 (m, 4H), 3.85 (s, 3H), 2.35 (s, 3H), 1.83 (m, 4H), 1.02 (t, J=7.2 Hz, 6H).

EXAMPLE 2(155)

8-(N,N-dibutylamino)-2-methyl-3-(2-chloro-4-methoxyphenyl)-5,7-dihydro-furo[3,4-d]pyrazolo[1,5-a]pyrimidine hydrochloride

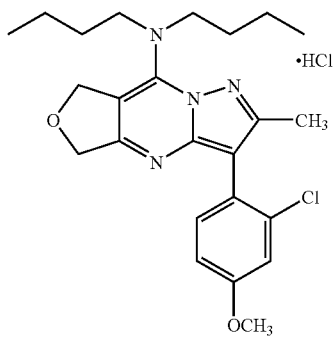

TLC: Rf 0.74 (hexane:ethyl acetate=1:1);

NMR (300 MHz, CDCl$_3$): δ 7.34 (d, J=8.4 Hz, 1H), 7.08 (d, J=2.4 Hz, 1H), 6.96 (dd, J=2.4, 8.4 Hz, 1H), 5.47 (d, J=16.5 Hz, 1H), 5.36 (d, J=16.5 Hz, 1H), 5.21 (s, 2H), 3.88 (m, 4H), 3.85 (s, 3H), 2.34 (s, 3H), 1.79 (m, 4H), 1.42 (m, 4H), 1.00 (t, J=7.2 Hz, 6H).

EXAMPLE 2(156)

8-(N-cyclopropylmethyl-N-(4-fluorophenyl)methylamino)-2-methyl-3-(2-chloro-4-methoxyphenyl)-6,7-dihydro-5H-cyclopenta[d]pyrazolo[1,5-a]pyrimidine

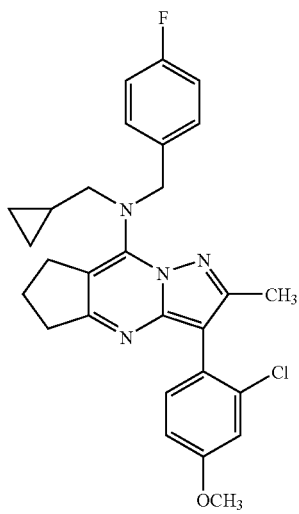

TLC: Rf 0.27 (hexane:ethyl acetate=1:1);

NMR (300 MHz, CDCl$_3$): δ 7.33-7.26 (m, 3H), 7.06 (d, J=2.7 Hz, 1H), 7.01-6.95 (m, 2H), 6.88 (dd, J=8.4, 2.7 Hz, 1H), 4.88 (s, 2H), 3.84 (s, 3H), 3.38 (d, J=6.9 Hz, 2H), 2.96 (t, J=7.2 Hz, 2H), 2.91 (t, J=7.2 Hz, 2H), 2.39 (s, 3H), 2.10 (quint, J=7.2 Hz, 2H), 1.10-0.98 (m, 1H), 0.49-0.42 (m, 2H), 0.08-0.02 (m, 2H).

EXAMPLE 2(157)

8-(N-propyl-N-(4-methylphenyl)methylamino)-2-methyl-3-(2-chloro-4-methoxyphenyl)-5,7-dihydro-furo[3,4-d]pyrazolo[1,5-a]pyrimidine hydrochloride

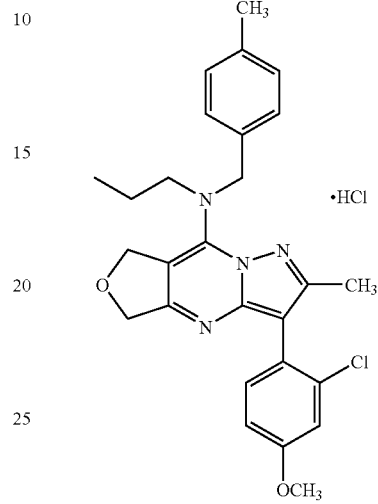

TLC: Rf 0.43 (hexane:ethyl acetate=2:1);

NMR (300 MHz, CDCl$_3$): δ 7.33 (d, J=8.7 Hz, 1H), 7.19 (d, J=8.1 Hz, 2H), 7.13 (d, J=8.1 Hz, 2H), 7.08 (d, J=2.7 Hz, 1H), 6.95 (dd, J=2.7, 8.1 Hz, 1H), 5.28 (m, 2H), 5.13 (m, 2H), 5.08 (m, 2H), 3.85 (s, 3H), 3.64 (m, 2H), 2.37 (s, 3H), 2.36 (s, 3H), 1.80 (m, 2H), 0.95 (t, J=7.5 Hz, 3H).

EXAMPLE 2(158)

8-(3-pentylamino)-2-methyl-3-(3-chloro-5-trifluoromethylpyridin-2-yl)-6,7-dihydro-5H-cyclopenta[d]pyrazolo[1,5-a]pyrimidine dihydrochloride

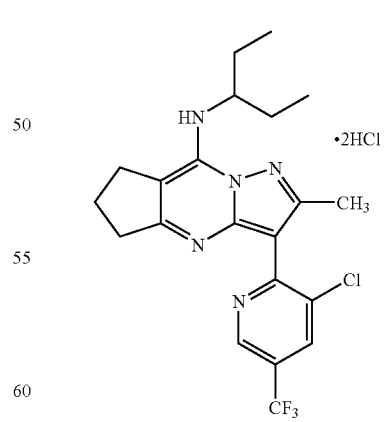

TLC: Rf 0.19 (hexane:ethyl acetate=3:1);

NMR (300 MHz, CDCl$_3$): δ 8.91 (s, 1H), 8.12 (s, 1H), 3.99 (m, 1H), 3.50 (m, 2H), 3.15 (m, 2H), 2.47 (s, 3H), 2.32 (m, 2H), 1.94-1.64 (m, 4H), 1.06 (brt, J=6.9 Hz, 6H).

EXAMPLE 2(159)

8-(N-butyl-N-propylamino)-2-methyl-3-(2-chloro-4-methoxyphenyl)-5,7-dihydro-furo[3,4-d]pyrazolo[1,5-a]pyrimidine hydrochloride

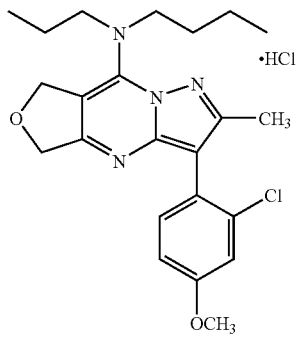

TLC: Rf 0.21 (hexane ethyl acetate=3:1);

NMR (300 MHz, CDCl$_3$): δ 7.34 (d, J=8.1 Hz, 1H), 7.08 (d, J=2.4 Hz, 1H), 6.96 (dd, J=8.1, 2.4 Hz, 1H), 5.47 and 5.35 (ABd, J=16.5 Hz, 2H), 5.21 (brs, 2H), 4.00-3.75 (m) and 3.85 (s) total 7H, 2.34 (s, 3H), 1.90-1.75 (m, 4H), 1.42 (sext, J=7.2 Hz, 2H), 1.05-0.98 (m, 6H).

EXAMPLE 2(160)

8-(N-butyl-N-propylamino)-2-methyl-3-(2-methyl-4-methoxyphenyl)-6,7-dihydro-5H-cyclopenta[d]pyrazolo[1,5-a]pyrimidine hydrochloride

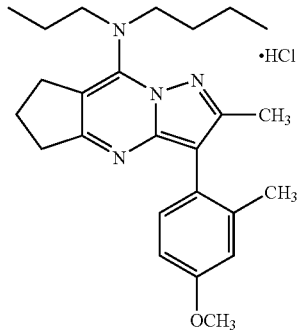

TLC: Rf 0.33 (hexane:ethyl acetate=3:1);

NMR (300 MHz, CDCl$_3$): δ 7.12 (d, J=8.7 Hz, 1H), 6.89 (d, J=2.4 Hz, 1H), 6.82 (dd, J=8.7, 2.4 Hz, 1H), 3.95-3.80 (m) and 3.83 (s) total 7H, 3.48 (t, J=7.5 Hz, 2H), 3.02 (t, J=7.5 Hz, 2H), 2.30-2.18 (m) and 2.27 (s) total 5H, 2.19 (s, 3H), 1.80-1.65 (m, 4H), 1.38 (sext, J=7.2 Hz, 2H), 0.96 (t, J=7.2 Hz, 6H).

EXAMPLE 2(161)

8-(4-heptylamino)-2-methyl-3-(2-chloro-4-methoxyphenyl)-5,7-dihydro-furo[3,4-d]pyrazolo[1,5-a]pyrimidine hydrochloride

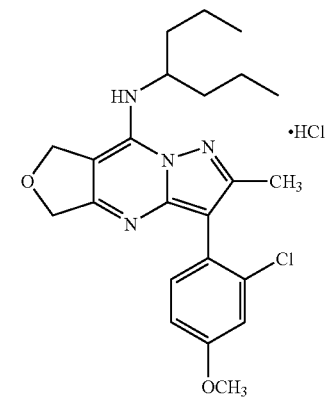

TLC: Rf 0.54 (hexane:ethyl acetate=2:1);

NMR (300 MHz, CDCl$_3$): δ 7.52 (d, J=10.2 Hz, 1H), 7.34 (d, J=8.7 Hz, 1H), 7.08 (d, J=2.4 Hz, 1H), 6.97 (dd, J=2.4, 8.7 Hz, 1H), 5.49 (brd. J=16.8 Hz, 1H), 5.39 (d, J=16.8 Hz, 1H), 5.28 (m, 2H), 3.85 (s, 3H), 3.53 (m, 1H), 2.39 (s, 3H), 1.75 (m, 4H), 1.47 (m, 4H), 1.00 (t, J=7.2 Hz, 6H).

EXAMPLE 2(162)

8-(N-butyl-N-ethylamino)-2-methyl-3-(2-chloro-4-methoxyphenyl)-5,7-dihydro-furo[3,4-d]pyrazolo[1,5-a]pyrimidine hydrochloride

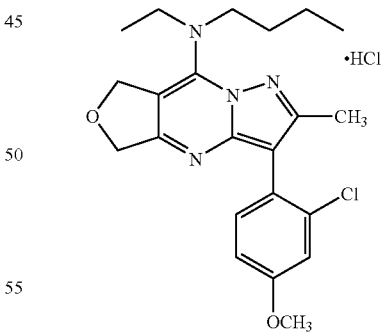

TLC: Rf 0.48 (hexane:ethyl acetate=2:1);

NMR (300 MHz, CDCl$_3$): δ 7.33 (d, J=8.7 Hz, 1H), 7.08 (d, J=2.4 Hz, 1H), 6.96 (dd, J=2.4, 8.7 Hz, 1H), 5.46 (m, 1H), 5.35 (m, 1H), 5.23 (t, J=1.5 Hz, 2H), 3.80-4.00 (m, 4H), 3.85 (s, 3H), 2.34 (s, 3H), 1.80 (m, 2H), 1.46 (t, J=7.2 Hz, 3H), 1.44 (m, 2H), 1.01 (t, J=7.2 Hz, 3H).

EXAMPLE 2(163)

8-(N-cyclopropyl-N-(4-fluorophenyl)methylamino)-2-methyl-3-(2-chloro-4-methoxyphenyl)-6,7-dihydro-5H-cyclopenta[d]pyrazolo[1,5-a]pyrimidine

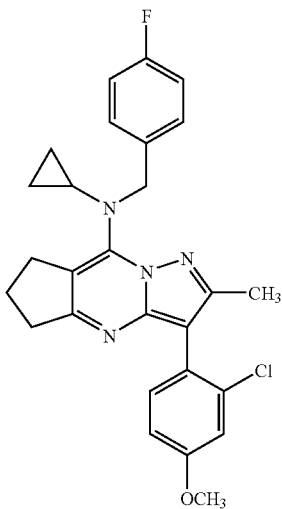

TLC: Rf 0.80 (hexane:ethyl acetate=1:1);
NMR (300 MHz, CDCl$_3$): δ 7.32 (d, J=8.4 Hz, 1H), 7.17-7.09 (m, 2H), 7.07 (d, J=2.7 Hz, 1H), 6.96-6.93 (m, 2H), 6.90 (dd, J=8.4, 2.7 Hz, 1H), 5.01 (s, 2H), 3.84 (s, 3H), 2.97-2.86 (m, 4H), 2.75 (m, 1H), 2.39 (s, 3H), 2.03 (m, 2H), 0.80-0.68 (m, 4H).

EXAMPLE 2(164)

8-(N-propyl-N-(2-fluorophenyl)methylamino)-2-methyl-3-(2-methyl-4-methoxyphenyl)-6,7-dihydro-5H-cyclopenta[d]pyrazolo[1,5-a]pyrimidine

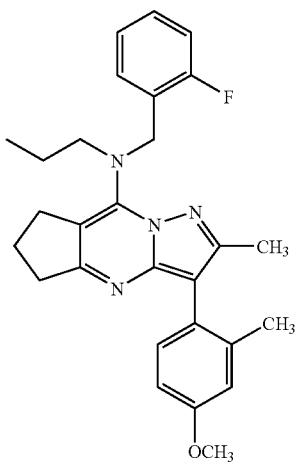

TLC: Rf 0.85 (hexane:ethyl acetate=2:1);
NMR (300 MHz, CDCl$_3$): δ 7.24-7.12 (m, 2H), 7.19 (d, J=8.1 Hz, 1H), 7.06-6.97 (m, 2H), 6.87 (d, J=2.7 Hz, 1H), 6.80 (dd, J=8.1, 2.7 Hz, 1H), 5.00-4.92 (m, 2H), 3.83 (s, 3H), 3.42-3.36 (m, 2H), 2.86 (t, J=7.5 Hz, 2H), 2.75 (t, J=7.5 Hz, 2H), 2.37 (s, 3H), 2.19 (s, 3H), 2.02 (quint, J=7.5 Hz, 2H), 1.68-1.46 (m, 2H), 0.90 (t, J=7.2 Hz, 3H).

EXAMPLE 2(165)

8-(N-propyl-N-(3-fluorophenyl)methylamino)-2-methyl-3-(2-methyl-4-methoxyphenyl)-6,7-dihydro-5H-cyclopenta[d]pyrazolo[1,5-a]pyrimidine

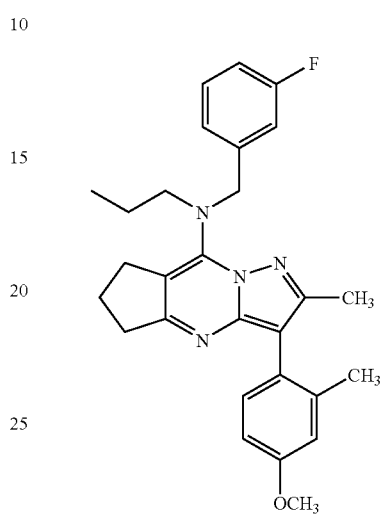

TLC: Rf 0.86 (hexane:ethyl acetate=2:1);
NMR (300 MHz, CDCl$_3$): δ 7.30-7.22 (m, 1H), 7.18 (d, J=8.4 Hz, 1H), 7.08-7.01 (m, 2H), 6.98-6.90 (m, 1H), 6.87 (d, J=2.4 Hz, 1H), 6.80 (dd, J=8.4, 2.4 Hz, 1H), 4.85 (s, 2H), 3.83 (s, 3H), 3.42-3.36 (m, 2H), 2.89 (t, J=7.5 Hz, 2H), 2.86 (t, J=7.5 Hz, 2H), 2.36 (s, 3H), 2.19 (s, 3H), 2.09 (quint, J=7.5 Hz, 2H), 1.68-1.52 (m, 2H), 0.88 (t, J=7.5 Hz, 3H).

EXAMPLE 2(166)

8-dicyclopropylmethylamino-2-methyl-3-(2-chloro-4-methoxyphenyl)-5,7-dihydro-furo[3,4-d]pyrazolo[1,5-a]pyrimidine

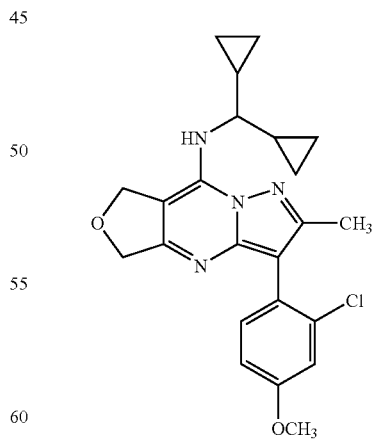

TLC: Rf 0.39 (hexane:ethyl acetate=2:1);
NMR (300 MHz, CDCl$_3$): δ 7.29 (d, J=8.7 Hz, 1H), 7.06 (d, J=2.4 Hz, 1H), 6.89 (dd, J=2.4, 8.7 Hz, 1H), 6.48 (brd, J=9.9 Hz, 1H), 5.22 (brs, 2H), 4.89 (brs, 2H), 3.83 (s, 3H), 2.87 (m, 1H), 2.37 (s, 3H), 1.15 (m, 2H), 0.61 (m, 4H), 0.42 (m, 4H).

EXAMPLE 2(167)

8-dicyclopropylmethylamino-2-methyl-3-(2-chloro-4-methoxyphenyl)-6,7-dihydro-5H-cyclopenta[d]pyrazolo[1,5-a]pyrimidine

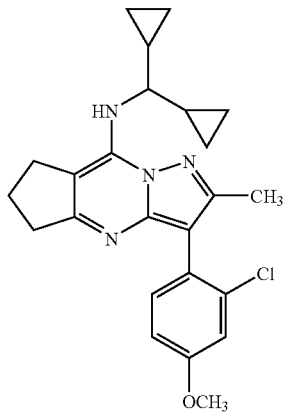

TLC: Rf 0.40 (hexane:ethyl acetate=2:1);

NMR (300 MHz, CDCl$_3$): δ 7.29 (d, J=8.4 Hz, 1H), 7.04 (d, J=2.4 Hz, 1H), 6.87 (dd, J=2.4, 8.4 Hz, 1H), 6.37 (brd, J=9.9 Hz, 1H), 3.82 (s, 3H), 3.40 (m, 1H), 3.01 (t, J=6.9 Hz, 2H), 2.88 (t, J=7.8 Hz, 2H), 2.35 (s, 3H), 2.11 (m, 2H), 1.14 (m, 2H), 0.50-0.66 (m, 4H), 0.35-0.50 (m; 4H).

EXAMPLE 2(168)

8-(N-butyl-N-propylamino)-2-methyl-3-(2-chloro-4-methoxyphenyl)-6,7-dihydro-5H-cyclopenta[d]pyrazolo[1,5-a]pyrimidine hydrochloride

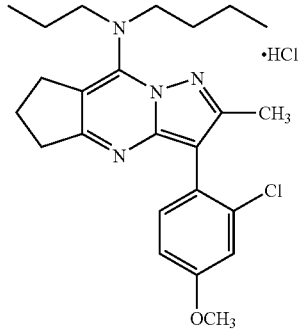

TLC: Rf 0.52 (hexane:ethyl acetate=2:1);

NMR (300 MHz, CDCl$_3$): δ 7.40-7.30 (m, 1H), 7.08 (s, 1H), 7.00-6.90 (m, 1H), 4.00-3.80 (m) and 3.85 (s) total 7H, 3.65-3.30 (m, 2H), 3.10-2.95 (m, 2H), 2.40-2.20 (m) and 2.33 (s) total 5H, 1.80-1.65 (m, 4H), 1.43-1.30 (m, 2H), 0.97 (t, J=6.6 Hz, 6H).

EXAMPLE 2(169)

8-(N-cyclopropylmethyl-N-propylamino)-2-methyl-3-(2-chloro-4-methoxyphenyl)-6,7-dihydro-5H-cyclopenta[d]pyrazolo[1,5-a]pyrimidine

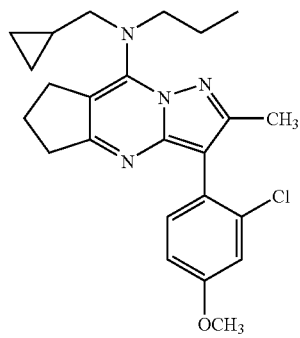

TLC: Rf 0.54 (hexane:ethyl acetate=2:1);

NMR (300 MHz, CDCl$_3$): δ 7.31 (d, J=8.4 Hz, 1H), 7.05 (d, J=2.7 Hz, 1H), 6.88 (dd, J=8.4, 2.7 Hz, 1H), 3.83 (s, 3H), 3.64-3.58 (m, 2H), 3.53 (d, J=6.9 Hz, 2H), 3.01 (t, J=7.2 Hz, 2H), 2.92 (t, J=7.2 Hz, 2H), 2.36 (s, 3H), 2.14 (quint, J=7.2 Hz, 2H), 1.65-1.55 (m, 2H), 1.05-0.90 (m, 1H), 0.91 (t, J=7.5 Hz, 3H), 0.50-0.40 (m, 2H), 0.15-0.05 (m, 2H).

EXAMPLE 2(170)

8-(N-cyclopropylmethyl-N-propylamino)-2-methyl-3-(2-chloro-4-methoxyphenyl)-5,7-dihydro-furo[3,4-d]pyrazolo[1,5-a]pyrimidine

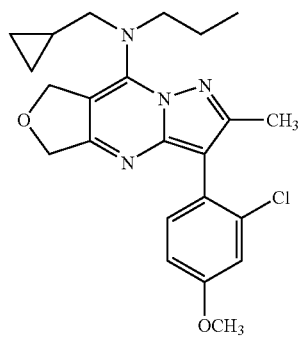

TLC: Rf 0.42 (hexane:ethyl acetate=2:1);

NMR (300 MHz, CDCl$_3$) δ 7.30 (d, J=8.4 Hz, 1H), 7.07 (d, J=2.7 Hz, 1H), 6.89 (dd, J=8.4, 2.7 Hz, 1H), 5.23 (s, 2H), 4.91 (s, 2H), 3.83 (s, 3H), 3.65-3.50 (m, 4H), 2.38 (s, 3H), 1.63 (quint, J=7.2 Hz, 2H), 1.10-0.98 (m, 1H), 0.94 (t, J=7.2 Hz, 3H), 0.56-0.46 (m, 2H), 0.15 (dd, J=10.8, 5.1 Hz, 2H).

EXAMPLE 2(171)

8-(N-(2-butynyl)-N-propylamino)-2-methyl-3-(2-chloro-4-methoxyphenyl)-6,7-dihydro-5H-cyclopenta[d]pyrazolo[1,5-a]pyrimidine hydrochloride

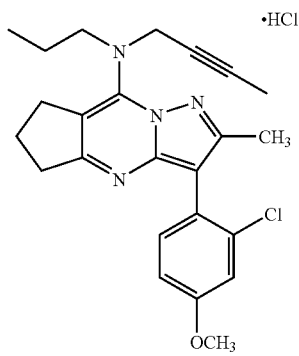

TLC: Rf 0.44 (hexane:ethyl acetate=2:1);

NMR (300 MHz, CDCl$_3$): δ 7.34 (d, J=8.7 Hz, 1H), 7.08 (d, J=1.8 Hz, 1H), 6.96 (brd, J=8.7 Hz, 1H), 4.56 (d, J=2.1 Hz, 2H), 4.05-3.80 (m) and 3.85 (s) total 5H, 3.65-3.30 (m, 2H), 3.25-3.10 (m, 2H), 2.40-2.20 (m) and 2.33 (s) total 5H, 1.95-1.80 (m) and 1.89 (s) total 5H, 1.01 (t, J=7.2 Hz, 3H).

EXAMPLE 2(173)

8-(N-butyl-N-(2-methoxyethyl)amino)-2-methyl-3-(2-chloro-4-methoxyphenyl)-6,7-dihydro-5H-cyclopenta[d]pyrazolo[1,5-a]pyrimidine hydrochloride

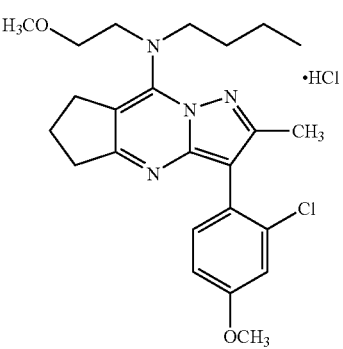

TLC: Rf 0.34 (hexane:ethyl acetate=2:1);

NMR (300 MHz, CDCl$_3$): δ 7.35 (d, J=7.8 Hz, 1H), 7.08 (d, J=2.1 Hz, 1H), 6.97 (brd, J=7.8 Hz, 1H), 4.30-4.18 (m, 2H), 3.90-3.78 (m) and 3.85 (s) total 5H, 3.70-3.30 (m) and 3.64 (m) total 4H, 3.30 (s, 3H), 3.08-2.98 (m, 2H), 2.40-2.18 (m) and 2.33 (s) total 5H, 1.80-1.65 (m, 2H), 1.43-1.35 (m, 2H), 0.96 (t, J=7.2 Hz, 3H).

EXAMPLE 2(172)

8-(N-(2-butynyl)-N-propylamino)-2-methyl-3-(2-chloro-4-methoxyphenyl)-5,7-dihydro-furo[3,4-d]pyrazolo[1,5-a]pyrimidine

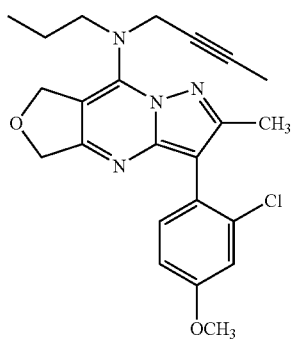

TLC: Rf 0.36 (hexane:ethyl acetate=2:1);

NMR (300 MHz, CDCl$_3$): δ 7.28 (d, J=8.7 Hz, 1H), 7.07 (d, J=2.7 Hz, 1H), 6.90 (dd, J=8.7, 2.7 Hz, 1H), 5.32 (s, 2H), 4.91 (s, 2H), 4.45 (q, J=2.1 Hz, 2H), 3.84 (s, 3H), 3.55-3.45 (m, 2H), 2.38 (s, 3H), 1.82 (t, J=2.1 Hz, 3H), 1.72 (sext, J=7.2 Hz, 2H), 0.98 (t, J=7.2 Hz, 3H).

EXAMPLE 2(174)

8-(N-butyl-N-(2-methoxyethyl)amino)-2-methyl-3-(2-chloro-4-methoxyphenyl)-5,7-dihydro-furo[3,4-d]pyrazolo[1,5-a]pyrimidine hydrochloride

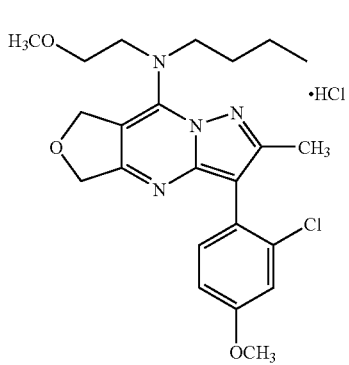

TLC: Rf 0.39 (hexane:ethyl acetate=2:1);

NMR (300 MHz, CDCl$_3$): δ 7.40-7.30 (m, 1H), 7.08 (brs, 1H), 7.05-6.95 (m, 1H), 5.60-5.35 (m, 2H), 5.30-5.15 (m, 2H), 4.40-4.20 (m, 2H), 3.90-3.70 (m) and 3.85 (s) total 7H, 3.35 (s, 3H), 2.35 (s, 3H), 1.85-1.70 (m, 2H), 1.50-1.38 (m, 2H), 0.99 (t, J=6.9 Hz, 3H).

EXAMPLE 2(175)

8-(N-propyl-N-(4-trifluoromethyloxyphenyl)methylamino)-2-methyl-3-(2-chloro-4-methoxyphenyl)-5,7-dihydro-furo[3,4-d]pyrazolo[1,5-a]pyrimidine

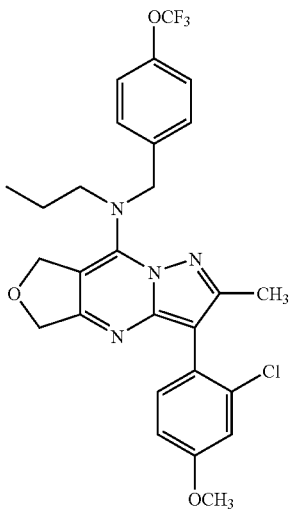

TLC: Rf 0.42 (hexane:ethyl acetate=3:1);
NMR (300 MHz, CDCl₃): δ 7.39-7.33 (m, 2H), 7.31 (d, J=8.4 Hz, 1H), 7.21-7.15 (m, 2H), 7.08 (d, J=2.4 Hz, 1H), 6.91 (dd, J=8.4, 2.4 Hz, 1H), 5.12 (s, 2H), 4.95 (s, 2H), 4.90 (s, 2H), 3.84 (s, 3H), 3.36-3.28 (m, 2H), 2.40 (s, 3H), 1.70-1.54 (m, 2H), 0.89 (t, J=7.5 Hz, 3H).

EXAMPLE 2(176)

8-(N-cyclopropylmethyl-N-(4-fluorophenyl)methylamino)-2-methyl-3-(2-methyl-4-methoxyphenyl)-6,7-dihydro-5H-cyclopenta[d]pyrazolo[1,5-a]pyrimidine

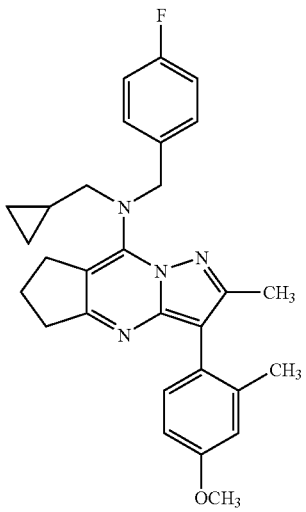

TLC: Rf 0.28 (hexane:ethyl acetate=3:1);
NMR (300 MHz, CDCl₃): δ 7.33-7.26 (m, 2H), 7.18 (d, J=8.4 Hz, 1H), 7.03-6.94 (m, 2H), 6.87 (d, J=2.7 Hz, 1H), 6.80 (dd, J=8.4, 2.7 Hz, 1H), 4.88 (s, 2H), 3.83 (s, 3H), 3.38 (d, J=6.9 Hz, 2H), 2.95 (t, J=6.9 Hz, 2H), 2.89 (t, J=6.9 Hz, 2H), 2.36 (s, 3H), 2.19 (s, 3H), 2.09 (quint, J=6.9 Hz, 2H), 1.01 (m, 1H), 0.58-0.42 (m, 2H), 0.20-0.01 (m, 2H).

EXAMPLE 2(177)

8-(3-pentylamino)-2-methyl-3-(3,5-dichloropyridin-2-yl)-6,7-dihydro-5H-cyclopenta[d]pyrazolo[1,5-a]pyrimidine

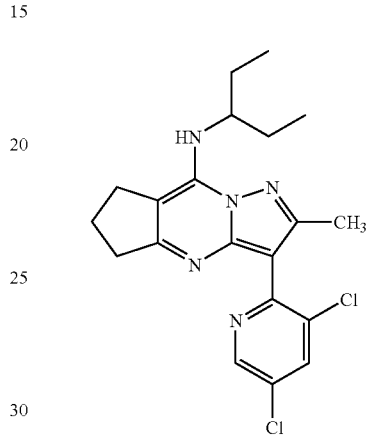

TLC: Rf 0.38 (hexane:ethyl acetate=3:1);
NMR (300 MHz, CDCl₃): δ 8.58 (d, J=2.1 Hz, 1H), 7.81 (d, J=2.1 Hz, 1H), 6.24 (brd, J=11.1 Hz, 1H), 3.80 (m, 1H), 3.08 (t, J=7.5 Hz, 2H), 2.93 (t, J=7.5 Hz, 2H), 2.41 (s, 3H), 2.15 (quint, J=7.5 Hz, 2H), 1.80-1.52 (m, 4H), 1.00 (t, J=7.5 Hz, 6H).

EXAMPLE 2(178)

8-(N-butyl-N-ethylamino)-2-methyl-3-(2-chloro-4-methoxyphenyl)-6,7-dihydro-5H-cyclopenta[d]pyrazolo[1,5-a]pyrimidine hydrochloride

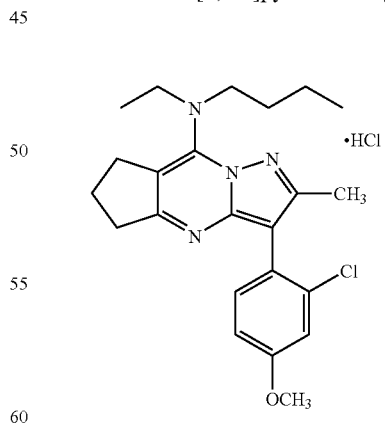

TLC: Rf 0.61 (hexane:ethyl acetate=2:1);
NMR (300 MHz, CDCl₃): δ 7.35 (d, J=8.4 Hz, 1H), 7.07 (d, J=2.7 Hz, 1H), 6.96 (dd, J=2.7, 8.4 Hz, 1H), 3.94 (m, 4H), 3.85 (s, 3H), 3.30-3.62 (m, 2H), 3.05 (m, 2H), 2.32 (s, 3H), 2.25 (m, 2H), 1.74 (m, 2H), 1.32-1.48 (m, 5H), 0.98 (t, J=7.8 Hz, 3H).

EXAMPLE 2(179)

8-(N-cyclopropylmethyl-N-(4-trifluoromethylphenyl)methylamino)-2-methyl-3-(2-methyl-4-methoxyphenyl)-6,7-dihydro-5H-cyclopenta[d]pyrazolo[1,5-a]pyrimidine hydrochloride

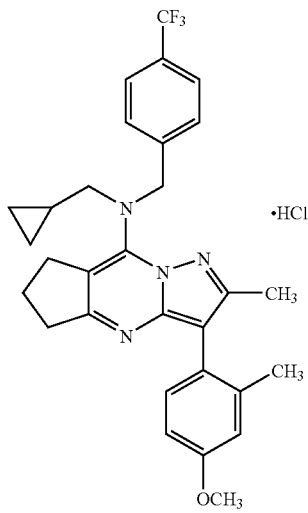

TLC: Rf 0.54 (hexane:ethyl acetate=2:1);
NMR (300 MHz, CDCl$_3$): δ 7.65 (d, J=8.4 Hz, 2H), 7.47 (d, J=8.4 Hz, 2H), 7.13 (d, J=8.7 Hz, 1H), 6.90 (d, J=2.4 Hz, 1H), 6.83 (dd, J=2.4, 8.7 Hz, 1H), 5.37 (s, 2H), 3.83 (s, 3H), 3.66 (m, 2H), 3.52 (t, J=7.5 Hz, 2H), 3.11 (t, J=7.2 Hz, 2H), 2.29 (s, 3H), 2.27 (m, 2H), 2.19 (s, 3H), 1.14 (m, 1H), 0.65 (m, 2H), 0.17 (m, 2H).

EXAMPLE 2(180)

8-(3-pentylamino)-2-methyl-3-(2-chloro-4-methoxyphenyl)-5,7-dihydro-furo[3,4-d]pyrazolo[1,5-a]pyrimidine hydrochloride

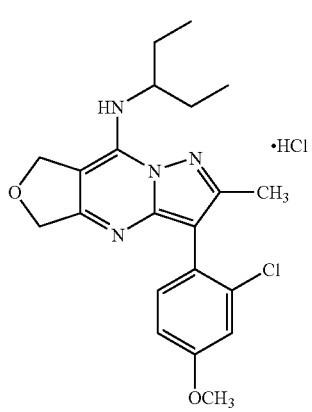

TLC: Rf 0.40 (hexane:ethyl acetate=2:1);
NMR (300 MHz, CDCl$_3$): δ 7.52 (brd, J=10.2 Hz, 1H), 7.35 (d, J=8.7 Hz, 1H), 7.08 (d, J=2.7 Hz, 1H), 6.96 (dd, J=2.7, 8.7 Hz, 1H), 5.50 (d, J=16.5 Hz, 1H), 5.39 (d, J=16.5 Hz, 1H), 5.29 (s, 2H), 3.85 (s, 3H), 3.39 (m, 1H), 2.40 (s, 3H), 1.68-1.98 (m, 4H), 1.06 (m, 6H).

EXAMPLE 2(181)

8-(N-cyclopropylmethylamino-N-(4-fluorophenyl)methylamino)-2-methyl-3-(2-chloro-4-methoxyphenyl)-5,7-dihydro-furo[3,4-d]pyrazolo[1,5-a]pyrimidine

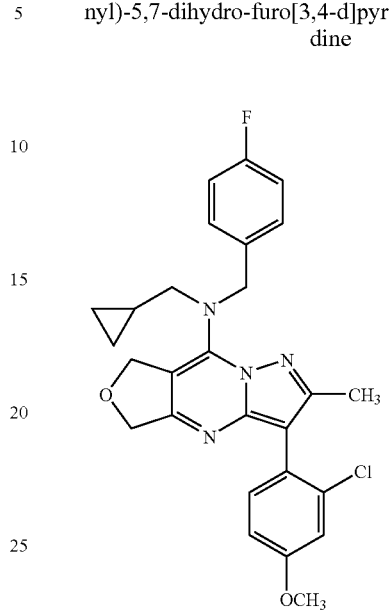

TLC: Rf 0.28 (hexane:ethyl acetate=3:1);
NMR (300 MHz, CDCl$_3$): δ 7.34-7.28 (m, 2H), 7.30 (d, J=8.4 Hz, 1H), 7.08 (d, J=2.7 Hz, 1H), 7.05-6.98 (m, 2H), 6.901 (dd, J=8.4, 2.7 Hz, 1H), 5.21 (s, 2H), 4.93 (s, 2H), 4.90 (s, 2H), 3.84 (s, 3H), 3.38 (d, J=6.9 Hz, 2H), 2.40 (s, 3H), 1.08-0.94 (m, 1H), 0.56-0.48 (m, 2H), 0.14-0.06 (m, 2H).

EXAMPLE 2(182)

8-(N-benzyl-N-(2-dimethylaminoethyl)amino)-2-methyl-3-(2-methyl-4-methoxyphenyl)-6,7-dihydro-5H-cyclopenta[d]pyrazolo[1,5-a]pyrimidine dihydrochloride

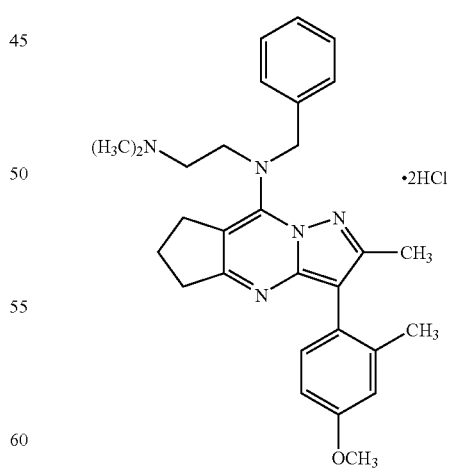

TLC: Rf 0.60 (ethyl acetate:acetic acid:water=3:1:1);
NMR (300 MHz, CD$_3$OD): δ 7.45-7.32 (m, 5H), 7.18 (d, J=8.4 Hz, 1H), 6.98 (d, J=2.7 Hz, 1H), 6.90 (dd, J=8.4, 2.7 Hz, 1H), 5.20 (s, 2H), 4.40 (m, 2H), 3.84 (s, 3H), 3.75 (m, 2H), 3.16 (m, 2H), 3.06 (m, 2H), 2.96 (s, 6H), 2.35 (s, 3H), 2.38-2.18 (m, 2H), 2.11 (s, 3H).

EXAMPLE 2(183)

8-(N-benzyl-N-(2-dimethylaminoethyl)amino)-2-methyl-3-(2-chloro-4-methoxyphenyl)-5,7-dihydro-furo[3,4-d]pyrazolo[1,5-a]pyrimidine dihydrochloride

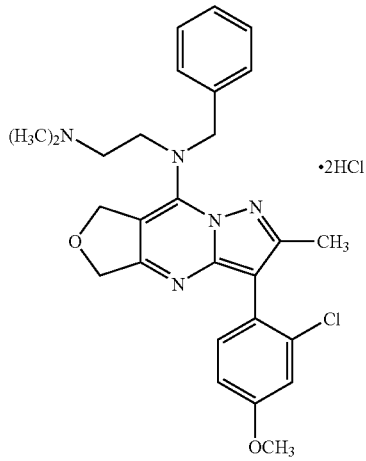

TLC: Rf 0.80 (ethyl acetate:acetic acid:water=3:1:1);

NMR (300 MHz, CD₃OD): δ 7.60-7.30 (m, 6H), 7.19 (d, J=2.4 Hz, 1H), 7.08-7.02 (m, 1H), 5.13 (s, 2H), 4.96 (s, 2H), 4.94 (s, 2H), 4.40-4.24 (m, 2H), 3.87 (s, 3H), 3.76 (m, 1H), 3.56 (m, 1H), 2.99 (s, 3H), 2.98 (s, 3H), 2.44 (s, 3H).

EXAMPLE 2(184)

8-(N-benzyl-N-(2-dimethylaminoethyl)amino)-2-methyl-3-(2-chloro-4-methoxyphenyl)-6,7-dihydro-5H-cyclopenta[d]pyrazolo[1,5-a]pyrimidine dihydrochloride

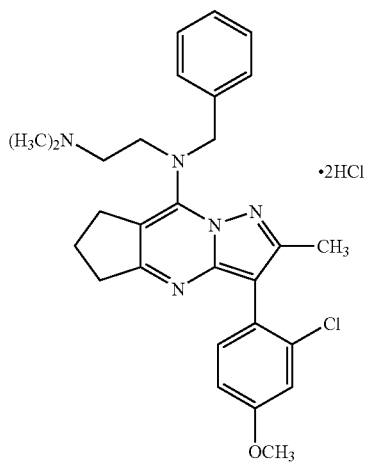

TLC: Rf 0.27 (chloroform:methanol=9:1);

NMR (300 MHz, CD₃OD): δ 7.46-7.26 (m, 6H), 7.20 (d, J=2.1 Hz, 1H), 7.08-7.02 (m, 1H), 5.11 (brs, 2H), 4.34-4.20 (m, 2H), 3.87 (s, 3H), 3.76-3.64 (m, 2H), 3.34-2.86 (m) and 2.96 (s) total 10H, 2.41 (s, 3H), 2.26-2.10 (m, 2H).

EXAMPLE 2(185)

8-(N-(2-butynyl)-N-ethylamino)-2-methyl-3-(2-methyl-4-methoxyphenyl)-6,7-dihydro-5H-cyclopenta[d]pyrazolo[1,5-a]pyrimidine hydrochloride

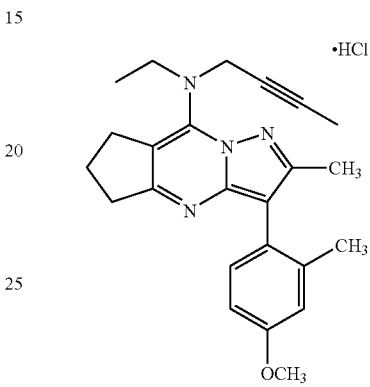

TLC: Rf 0.36 (hexane:ethyl acetate=2:1);

NMR (300 MHz, CDCl₃): δ 7.10 (d, J=8.4 Hz, 1H), 6.88 (d, J=2.7 Hz, 1H), 6.82 (dd, J=2.7, 8.4 Hz, 1H), 4.55 (q, J=2.1 Hz, 2H), 4.08 (m, 2H), 3.83 (s, 3H), 3.48 (t, J=7.5 Hz, 2H), 3.22 (t, J=6.9 Hz, 2H), 2.28 (s, 3H), 2.24 (m, 2H), 2.17 (s, 3H), 1.90 (t, J=2.1 Hz, 3H), 1.47 (t, J=7.2 Hz, 3H).

EXAMPLE 2(186)

8-(N-(2-butynyl)-N-ethylamino)-2-methyl-3-(2-chloro-4-methoxyphenyl)-5,7-dihydro-furo[3,4-d]pyrazolo[1,5-a]pyrimidine hydrochloride

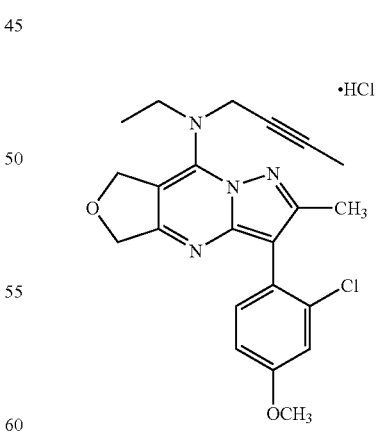

TLC: Rf 0.26 (hexane:ethyl acetate=2:1);

NMR (300 MHz, CDCl₃): δ 7.32 (d, J=8.4 Hz, 1H), 7.08 (d, J=2.4 Hz, 1H), 6.95 (dd, J=2.4, 8.4 Hz, 1H), 5.41 (s, 2H), 5.36 (m, 2H), 4.46 (m, 2H), 4.08 (m, 2H), 3.85 (s, 3H), 2.36 (s, 3H), 1.89 (t, J=2.7 Hz, 3H), 1.51 (t, J=7.2 Hz, 3H).

EXAMPLE 2(187)

8-(N-(2-butynyl)-N-ethylamino)-2-methyl-3-(2-chloro-4-methoxyphenyl)-6,7-dihydro-5H-cyclopenta[d]pyrazolo[1,5-a]pyrimidine hydrochloride

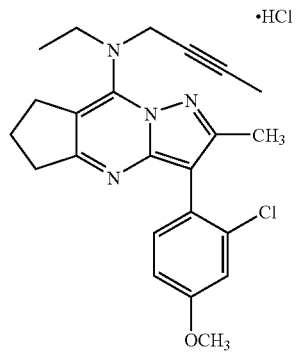

TLC: Rf 0.32 (hexane:ethyl acetate=2:1);

NMR (300 Hz, CDCl$_3$): δ 7.34 (d, J=8.4 Hz, 1H), 7.07 (d, J=2.7 Hz, 1H), 6.96 (dd, J=2.7, 8.4 Hz, 1H), 4.54 (m, 2H), 4.09 (m, 2H), 3.85 (s, 3H), 3.35-3.64 (m, 2H), 3.22 (t, J=7.2 Hz, 2H), 2.34 (S, 3H), 2.26 (m, 2H), 1.90 (t, J=2.4 Hz, 3H), 1.47 (t, J=7.2 Hz, 3H).

EXAMPLE 2(188)

8-(N,N-dipropylamino)-2-methyl-3-(2-chloro-4-methoxyphenyl)-6,7-dihydro-5H-cyclopenta[d]pyrazolo[1,5-a]pyrimidine

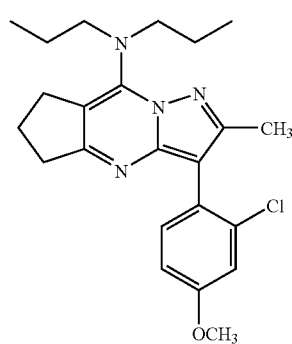

TLC: Rf 0.40 (hexane:ethyl acetate=3:1);

NMR (300 MHz, CDCl$_3$): δ 7.30 (d, J=8.4 Hz, 1H), 7.05 (d, J=2.7 Hz, 1H), 6.88 (dd, J=2.7, 8.4 Hz, 1H), 3.83 (s, 3H), 3.56 (m, 4H), 2.95 (t, J=7.2 Hz, 2H), 2.91 (t, J=8.1 Hz, 2H), 2.36 (s, 3H), 2.13 (m, 2H), 1.58 (m, 4H), 0.89 (t, J=7.2 Hz, 6H).

EXAMPLE 2(189)

8-(N-(2-butynyl)-N-cyclopropylmethylamino)-2-methyl-3-(2-chloro-4-methoxyphenyl)-5,7-dihydrofuro[3,4-d]pyrazolo[1,5-a]pyrimidine

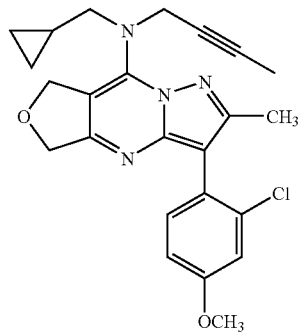

TLC: Rf 0.50 (toluene: acetone=5:1);

NMR (300 MHz, CDCl$_3$): δ 7.28 (d, J=8.4 Hz, 1H), 7.07 (d, J=2.7 Hz, 1H), 6.90 (dd, J=8.4, 2.7 Hz, 1H), 5.35 (s, 2H), 4.91 (s, 2H), 4.56 (m, 2H), 3.83 (s, 3H), 3.50 (m, 2H), 2.39 (s, 3H), 1.82 (t, J=2.4 Hz, 3H), 1.15 (m, 1H), 0.64-0.56 (m, 2H), 0.38-0.28 (m, 2H).

EXAMPLE 2(190)

8-(N-propyl-N-(4-cyanophenyl)methylamino)-2-methyl-3-(2-methyl-4-methoxyphenyl)-6,7-dihydro-5H-cyclopenta[d]pyrazolo[1,5-a]pyrimidine

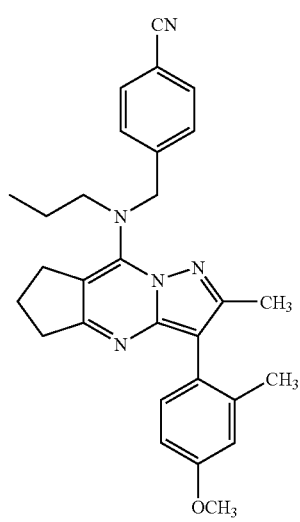

TLC: Rf 0.22 (hexane:ethyl acetate=3:1);

NMR (300 MHz, CDCl$_3$): δ 7.60 (brd, J=8.1 Hz, 2H), 7.47 (brd, J=8.1 Hz, 2H), 7.17 (d, J=8.7 Hz, 1H), 6.87 (d, J=2.7 Hz, 1H), 6.79 (dd, J=8.7, 2.7 Hz, 1H), 4.90 (s, 2H), 3.83 (s, 3H), 3.39 (m, 2H), 2.94-2.82 (m, 4H), 2.34 (s, 3H), 2.18 (s, 3H), 2.11 (m, 2H), 1.59 (m, 2H), 0.88 (t, J=7.2 Hz, 3H).

EXAMPLE 2(191)

8-(N-cyclopropyl-N-(4-methylthiophenyl)methylamino)-2-methyl-3-(2-chloro-4-methoxyphenyl)-5,7-dihyclro-furo[3,4-d]pyrazolo[1,5-a]pyrimidine

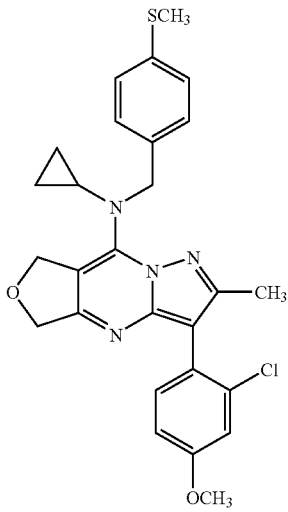

TLC: Rf 0.20 (hexane:ethyl acetate=3:1);
NMR (300 MHz, CDCl$_3$): δ 7.32 (d, J=8.4 Hz, 1H), 7.19-7.13 (m, 2H), 7.08 (d, J=2.7 Hz, 1H), 7.06-7.01 (m, 2H), 6.91 (dd, J=8.4, 2.7 Hz, 1H), 5.20 (s, 2H), 5.15 (s, 2H), 4.91 (s, 2H), 3.84 (s, 3H), 2.56 (m, 1H), 2.46 (s, 3H), 2.41 (s, 3H), 0.95-0.88 (m, 4H).

EXAMPLE 2(192)

8-(N-propyl-N-(4-methylthiophenyl)methylamino)-2-methyl-3-(2-chloro-4-methoxyphenyl)-5,7-dihydro-furo[3,4-d]pyrazolo[1,5-a]pyrimidine

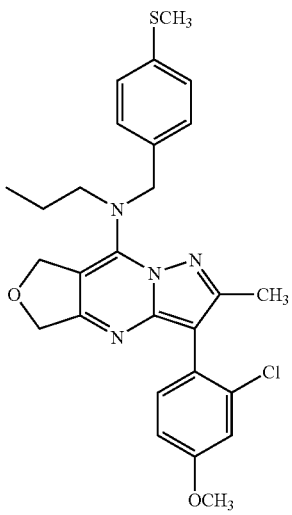

TLC: Rf 0.25 (hexane:ethyl acetate=3:1);
NMR (300 MHz, CDCl$_3$): δ 7.31 (d, J=8.7 Hz, 1H), 7.20 (s, 4H), 7.08 (d, J=2.7 Hz, 1H), 6.90 (dd, J=8.7, 2.7 Hz, 1H), 5.10 (s, 2H), 4.90 (s, 2H), 4.89 (s, 2H), 3.84 (s, 3H), 3.34 (m, 2H), 2.48 (s, 3H), 2.40 (s, 3H), 1.70-1.50 (m, 2H), 0.89 (t, J=7.5 Hz, 3H).

EXAMPLE 2(193)

8-(N-cyclopropyl-N-(4-fluorophenyl)methylamino)-2-methyl-3-(2-chloro-4-methoxyphenyl)-5,7-dihydro-furo[3,4-d]pyrazolo[1,5-a]pyrimidine

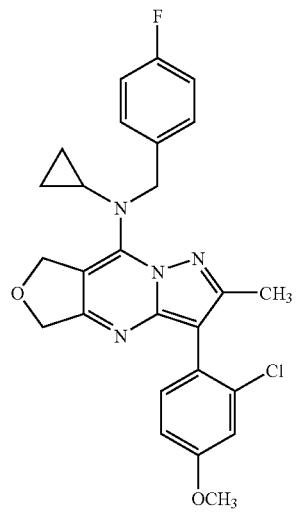

TLC: Rf 0.19 (hexane:ethyl acetate=3:1);
NMR (300 MHz, CDCl$_3$): δ 7.32 (d, J=8.4 Hz, 1H), 7.14-7.04 (m, 3H), 7.02-6.94 (m, 2H), 6.92 (dd, J=8.4, 2.4 Hz, 1H), 5.19 (s, 2H), 5.16 (s, 2H), 4.91 (s, 2H), 3.84 (s, 3H), 2.55 (m, 1H), 2.41 (s, 3H), 0.90-0.76 (m, 4H).

EXAMPLE 2(194)

8-(N-propyl-N-(3-fluorophenyl)methylamino)-2-methyl-3-(2-chloro-4-methoxyphenyl)-6,7-dihydro-5H-cyclopenta[d]pyrazolo[1,5-a]pyrimidine

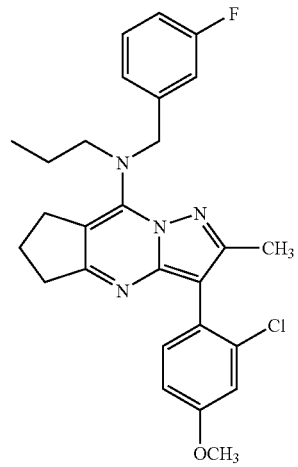

TLC: Rf 0.48 (hexane:ethyl acetate=3:1);
NMR (300 MHz, CDCl$_3$): δ 7.33 (d, J=8.4 Hz, 1H), 7.26-7.15 (m, 2H), 7.07 (d, J=2.4 Hz, 1H), 7.05-6.98 (m, 2H), 6.89 (dd, J=8.4, 2.4 Hz, 1H), 4.94 (s, 2H), 3.84 (s, 3H), 3.39 (m, 2H), 2.88 (t, J=7.5 Hz, 2H), 2.77 (t, J=7.5 Hz, 2H), 2.40 (s, 3H), 2.04 (quint, J=7.5 Hz, 2H), 1.63 (m, 2H), 0.90 (t, J=7.5 Hz, 3H).

EXAMPLE 2(195)
8-(N-propyl-N-(3-fluorophenyl)methylamino)-2-methyl-3-(2-chloro-4-methoxyphenyl)-5,7-dihydro-furo[3,4-d]pyrazolo[1,5-a]pyrimidine

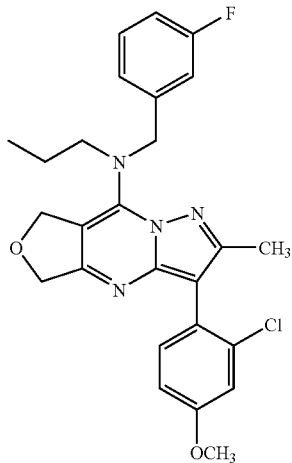

TLC: Rf 0.46 (hexane:ethyl acetate=3:1);
NMR (300 MHz, CDCl$_3$): δ 7.32 (d, J=8.4 Hz, 1H), 7.28-7.16 (m, 2H), 7.08 (d, J=2.4 Hz, 1H), 7.07-6.99 (m, 2H), 6.91 (dd, J=8.4, 2.4 Hz, 1H), 5.07 (s, 2H), 5.04 (s, 2H), 4.88 (s, 2H), 3.84 (s, 3H), 3.13 (m, 2H), 2.41 (s, 3H), 1.68 (sext, J=7.5 Hz, 2H), 0.93 (t, J=7.5 Hz, 3H).

EXAMPLE 2(196)
8-dipropylamino-2-methyl-3-(2,5-dichlorophenyl)-6,7-dihydro-5H-cyclopenta[d]pyrazolo[1,5-a]pyrimidine

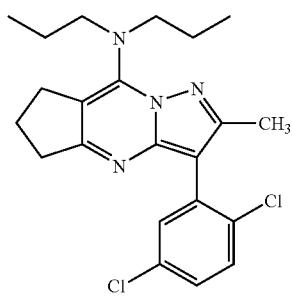

TLC: Rf 0.64 (hexane:ethyl acetate=3:1);
NMR (300 MHz, CDCl$_3$): δ 7.41 (d, J=8.7 Hz, 1H), 7.40 (d, J=2.4 Hz, 1H), 7.23 (dd, J=8.7, 2.4 Hz, 1H), 3.60-3.52 (m, 4H), 2.96 (t, J=7.8 Hz) and 2.93 (t, J=7.8 Hz) total 4H, 2.37 (s, 3H), 2.15 (quint, J=7.8 Hz, 2H), 1.65-1.50 (m, 4H), 0.89 (t, J=7.2 Hz, 6H).

EXAMPLE 2(197)
8-dipropylamino-2-methyl-3-(2,4-dichlorophenyl)-6,7-dihydro-5H-cyclopenta[d]pyrazolo[1,5-a]pyrimidine

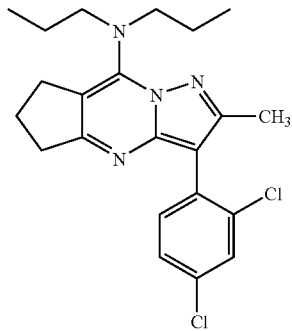

TLC: Rf 0.57 (hexane:ethyl acetate=3:1);
NMR (300 MHz, CDCl$_3$): δ 7.51 (d, J=2.4 Hz, 1H), 7.35 (d, J=8.1 Hz, 1H), 7.29 (dd, J=8.1, 2.4 Hz, 1H), 3.65-3.50 (m, 4H), 2.96 (t, J=7.2 Hz) and 2.92 (t, J=7.2 Hz) total 4H, 2.36 (s, 3H), 2.14 (quint, J=7.2 Hz, 2H), 1.63-1.45 (m, 4H), 0.89 (t, J=7.5 Hz, 6H).

EXAMPLE 2(198)
8-dipropylamino-2-methyl-3-(4-methylphenyl)-6,7-dihydro-5H-cyclopenta[d]pyrazolo[1,5-a]pyrimidine

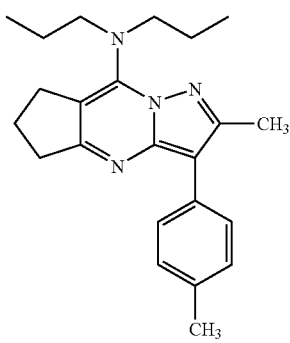

TLC: Rf 0.58 (hexane:ethyl acetate=3:1);
NMR (300 MHz, CDCl$_3$): δ 7.58 (d, J=7.8 Hz, 2H), 7.24 (d, J=7.8 Hz, 2H), 3.60-3.52 (m, 4H), 3.00-2.90 (m, 4H), 2.56 (s, 3H), 2.37 (s, 3H), 2.14 (quint, J=7.5 Hz, 2H), 1.64-1.48 (m, 4H), 0.87 (t, J=7.2 Hz, 6H).

EXAMPLE 2(199)
8-dipropylamino-2-methyl-3-(3-methylphenyl)-6,7-dihydro-5H-cyclopenta[d]pyrazolo[1,5-a]pyrimidine

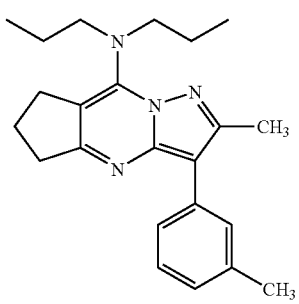

TLC: Rf 0.61 (hexane:ethyl acetate=3:1);
NMR (300 MHz, CDCl$_3$): δ 7.50 (s) and 7.47 (d, J=7.5 Hz) total 2H, 7.32 (t, J=7.5 Hz, 1H), 7.06 (t, J=7.5 Hz, 1H), 3.60-3.52 (m, 4H), 2.96 (t, J=7.8 Hz, 4H), 2.57 (s, 3H), 2.41 (s, 3H), 2.15 (quint, J=7.8 Hz, 2H), 1.64-1.45 (m, 4H), 0.88 (t, J=7.2 Hz, 6H).

EXAMPLE 2(200)

8-dipropylamino-2-methyl-3-(2-methylphenyl)-6,7-dihydro-5H-cyclopenta[d]pyrazolo[1,5-a]pyrimidine

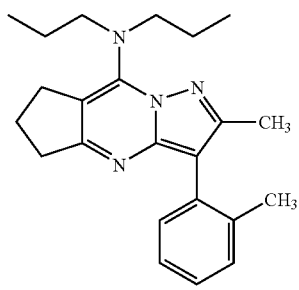

TLC: Rf 0.56 (hexane:ethyl acetate=3:1);

NMR (300 MHz, CDCl$_3$): δ 7.35-7.20 (m, 4H), 3.62-3.54 (m, 4H), 2.96 (t, J=7.2 Hz) and 2.90 (t, J=7.2 Hz) total 4H, 2.34 (s, 3H), 2.22 (s, 3H), 2.13 (quint, J=7.2 Hz, 2H), 1.63-1.50 (m, 4H), 0.89 (t, J=7.5 Hz, 6H).

EXAMPLE 2(201)

8-(N-propyl-N-(benz[d]1,3-dioxolan-5-yl)methylamino)-2-methyl-3-(2-methyl-4-methoxyphenyl)-6,7-dihydro-5H-cyclopenta[d]pyrazolo[1,5-a]pyrimidine

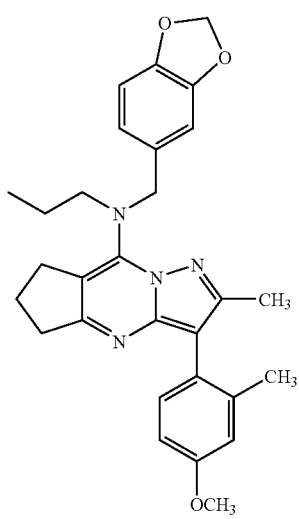

TLC: Rf 0.31 (hexane:ethyl acetate=3:1);

NMR (300 MHz, CDCl$_3$): δ 7.18 (d, J=8.1 Hz, 1H), 6.87 (d, J=2.7 Hz, 1H), 6.77-6.83 (m, 2H), 6.67-6.75 (m, 2H), 5.94 (s, 2H), 4.74 (s, 2H), 3.83 (s, 3H), 3.37 (m, 2H), 2.89 (t, J=7.8 Hz, 2H), 2.85 (t, J=7.5 Hz, 2H), 2.35 (s, 3H), 2.20 (s, 3H), 2.08 (m, 2H), 1.58 (m, 2H), 0.88 (t, J=7.2 Hz, 3H).

EXAMPLE 2(202)

8-(N-propyl-N-(benz[d]1,3-dioxolan-5-yl)methylamino)-2-methyl-3-(2-chloro-4-methoxyphenyl)-6,7-dihydro-5H-cyclopenta[d]pyrazolo[1,5-a]pyrimidine hydrochloride

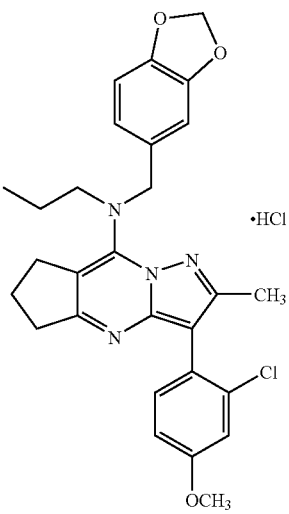

TLC: Rf 0.38 (hexane:ethyl acetate=2:1);

NMR (300 MHz, CDCl$_3$): δ 7.36 (d, J=8.4 Hz, 1H), 7.08 (d, J=2.7 Hz, 1H), 6.97 (dd, J=8.4, 2.7 Hz, 1H), 6.70-6.82 (m, 3H), 6.00 (s, 2H), 5.07 (s, 2H), 3.85 (s, 3H), 3.71 (m, 2H), 3.36-3.64 (m, 2H), 3.03 (t, J=7.4 Hz, 2H), 2.35 (s, 3H), 2.24 (m, 2H), 1.74 (m, 2H), 0.93 (t, J=7.5 Hz, 3H).

EXAMPLE 2(203)

8-(3-pentylamino)-2-methyl-3-(2-methylphenyl)-6,7-dihydro-5H-cyclopenta[d]pyrazolo[1,5-a]pyrimidine

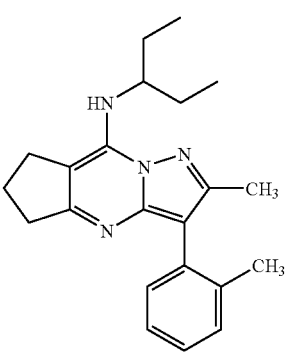

TLC: Rf 0.39 (hexane:ethyl acetate=3:1);

NMR (300 MHz, CDCl$_3$): δ 7.30-7.18 (m, 4H), 6.23 (d, J=10.5 Hz, 1H), 3.90-3.75 (m, 1H), 3.09 (t, J=7.2 Hz, 2H), 2.90 (t, J=7.2 Hz, 2H), 2.32 (s, 3H), 2.22 (s, 3H), 2.14 (quint, J=7.2 Hz, 2H), 1.80-1.58 (m, 4H), 1.08-0.96 (m, 6H).

EXAMPLE 2(204)

8-(3-pentylamino)-2-methyl-3-(3-methylphenyl)-6,7-dihydro-5H-cyclopenta[d]pyrazolo[1,5-a]pyrimidine

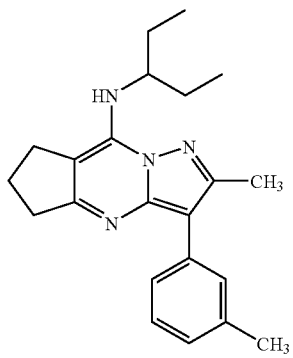

TLC: Rf 0.45 (hexane:ethyl acetate=3:1);

NMR (300 MHz, CDCl$_3$): δ 7.50 (s, 1H), 7.46 (d, J=7.8 Hz, 1H), 7.31 (t, J=7.8 Hz, 1H), 7.05 (d, J=7.8 Hz, 1H), 6.21 (d, J=10.8 Hz, 1H), 3.86-3.74 (m, 1H), 3.08 (t, J=7.2 Hz, 2H), 2.95 (t, J=7.2 Hz, 2H), 2.55 (s, 3H), 2.41 (s, 3H), 2.15 (quint, J=7.2 Hz, 2H), 1.82-1.55 (m, 4H), 1.01 (t, J=7.5 Hz, 6H).

EXAMPLE 2(205)

8-(3-pentylamino)-2-methyl-3-(4-methylphenyl)-6,7-dihydro-5H-cyclopenta[d]pyrazolo[1,5-a]pyrimidine

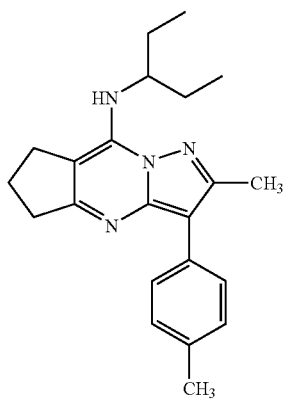

TLC: Rf 0.47 (hexane:ethyl acetate=3:1);

NMR (300 MHz, CDCl$_3$): δ 7.57 (d, J=7.8 Hz, 2H), 7.24 (d, J=7.8 Hz, 2H), 6.20 (10.5 Hz, 1H), 3.83-3.75 (m, 1H), 3.08 (t, J=7.2 Hz, 2H), 2.94 (t, J=7.2 Hz, 2H), 2.55 (s, 3H), 2.37 (s, 3H), 2.15 (quint, J=7.2 Hz, 2H), 1.80-1.52 (m, 4H), 1.00 (t, J=7.2 Hz, 6H).

EXAMPLE 2(206)

8-(3-pentylamino)-2-methyl-3-(2-methylthio-4-methoxyphenyl)-6,7-dihydro-5H-cyclopenta[d]pyrazolo[1,5-a]pyrimidine hydrochloride

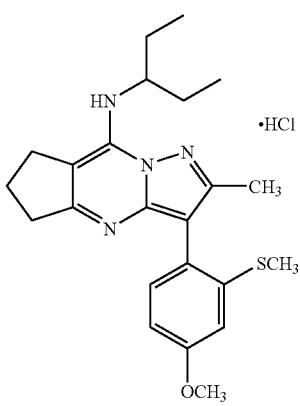

TLC: Rf 0.10 (hexane:ethyl acetate=3:1);

NMR (300 MHz, CDCl$_3$): δ 7.26-7.16 (m, 1H), 6.83 (m, 1H), 6.84-6.76 (m, 1H), 3.97 (m, 1H), 3.86 (s, 3H), 3.48 (m, 2H), 3.12 (m, 2H), 2.44 (s, 3H), 2.33 (s, 3H), 2.28 (m, 2H), 1.95-1.44 (m, 4H), 1.11-0.99 (m, 6H).

EXAMPLE 2(207)

8-(N-propyl-N-(benz[d]1,3-dioxolan-5-yl)methylamino)-2-methyl-3-(2-chloro-4-methoxyphenyl)-5,7-dihydro-furo[3,4-d]pyrazolo[1,5-a]pyrimidine hydrochloride

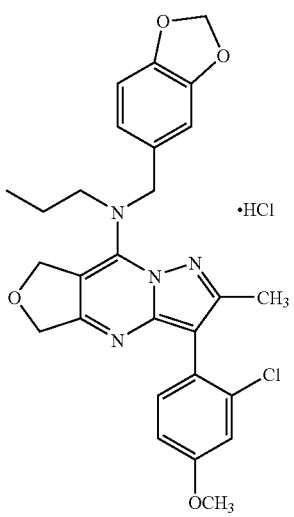

TLC: Rf 0.40 (hexane:ethyl acetate=2:1);

NMR (300 MHz, CDCl$_3$): δ 7.34 (d, J=8.7 Hz, 1H), 7.08 (d, J=2.7 Hz, 1H), 6.95 (dd, J=2.7, 8.7 Hz, 1H), 6.78-6.83 (m, 2H), 6.72 (m, 1H), 5.99 (s, 2H), 5.28 (m, 2H), 5.16 (s, 2H), 5.04 (m, 2H), 3.85 (s, 3H), 3.60 (m, 2H), 2.38 (s, 3H), 1.77 (m, 2H), 0.95 (t, J=7.2 Hz, 3H).

EXAMPLE 2(208)

8-(N-benzyl-N-cyclopropylmethylamino)-2-methyl-3-(2-methyl-4-methoxyphenyl)-6,7-dihydro-5H-cyclopenta[d]pyrazolo[1,5-a]pyrimidine hydrochloride

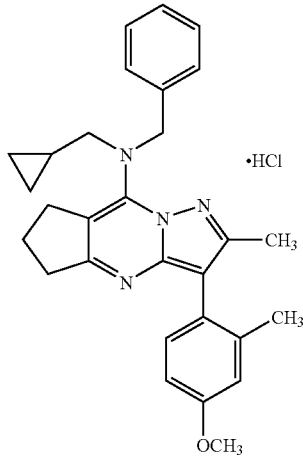

TLC: Rf 0.58 (hexane:ethyl acetate=2:1);

NMR (300 MHz, CDCl$_3$): δ 7.25-7.43 (m, 5H), 7.13 (d, J=7.8 Hz, 1H), 6.90 (d, J=2.4 Hz, 1H), 6.83 (dd, J=2.4, 7.8 Hz, 1H), 5.28 (s, 2H), 3.84 (s, 3H), 3.69 (m, 2H), 3.48 (t, J=8.1 Hz, 2H), 3.07 (t, J=7.2 Hz, 2H), 2.30 (s, 3H), 2.24 (m, 2H), 2.19 (s, 3H), 1.16 (m, 1H), 0.63 (m, 2H), 0.18 (m, 2H).

EXAMPLE 2(209)

8-(N-benzyl-N-cyclopropylmethylamino)-2-methyl-3-(2-chloro-4-methoxyphenyl)-6,7-dihydro-5H-cyclopenta[d]pyrazolo[1,5-a]pyrimidine hydrochloride

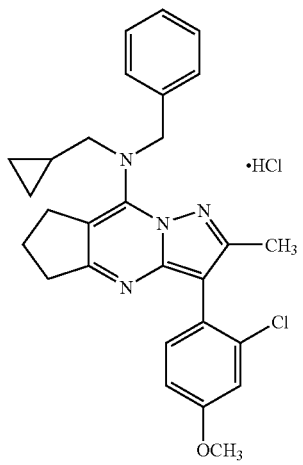

TLC: Rf 0.56 (hexane:ethyl acetate=2:1);

NMR (300 MHz, CDCl$_3$): δ 7.25-7.43 (m, 6H), 7.09 (d, J=2.7 Hz, 1H), 6.96 (dd, J=2.7, 8.4 Hz, 1H), 5.27 (m, 2H), 3.85 (s, 3H), 3.68 (m, 2H), 3.48 (m, 2H), 3.07 (t, J=6.9 Hz, 2H), 2.35 (s, 3H), 2.23 (m, 2H), 1.16 (m, 1H), 0.64 (m, 2H), 0.18 (m, 2H).

EXAMPLE 2(210)

8-(N-benzyl-N-cyclopropylmethylamino)-2-methyl-3-(2-chloro-4-methoxyphenyl)-5,7-dihydro-furo[3,4-d]pyrazolo[1,5-a]pyrimidine hydrochloride

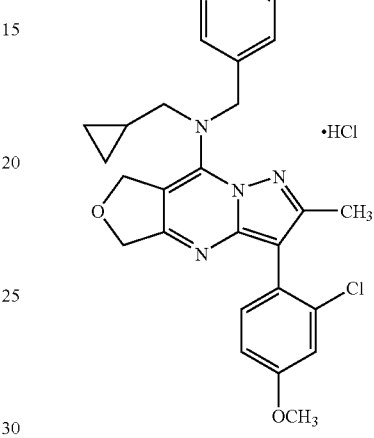

TLC: Rf 0.47 (hexane:ethyl acetate=2:1);

NMR (300 MHz, CDCl$_3$): δ 7.26-7.45 (m, 6H), 7.09 (d, J=2.4 Hz, 1H), 6.96 (dd, J=2.4, 8.1 Hz, 1H), 5.36 (m, 2H), 5.28 (m, 2H), 5.23 (s, 2H), 3.85 (s, 3H), 3.69 (m, 2H), 2.37 (s, 3H), 1.21 (m, 1H), 0.66 (m, 2H), 0.22 (m, 2H).

EXAMPLE 2(211)

8-(N-butyl-N-(2-butynyl)amino)-2-methyl-3-(2-methyl-4-methoxyphenyl)-6,7-dihydro-5H-cyclopenta[d]pyrazolo[1,5-a]pyrimidine

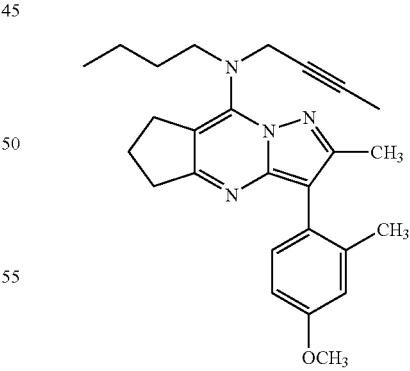

TLC: Rf 0.38 (hexane:ethyl acetate=3:1);

NMR (300 MHz, CDCl$_3$): δ 7.16 (d, J=8.4 Hz, 1H), 6.86 (d, J=2.7 Hz, 1H), 6.79 (dd, J=8.4, 2.7 Hz, 1H), 4.40 (brs, 2H), 3.82 (s, 3H), 3.59 (m, 2H), 3.11 (t, J=7.2 Hz, 2H), 2.91 (t, J=7.8 Hz, 2H), 2.32 (s, 3H), 2.18 (s, 3H), 2.13 (m, 2H), 1.81 (t, J=2.1 Hz, 3H), 1.63 (m, 2H), 1.38 (m, 2H), 0.94 (t, J=7.5 Hz, 3H).

EXAMPLE 2(212)

8-(3-pentylamino)-2-methyl-3-(2-methyl-4-fluorophenyl)-6,7-dihydro-5H-cyclopenta[d]pyrazolo[1,5-a]pyrimidine hydrochloride

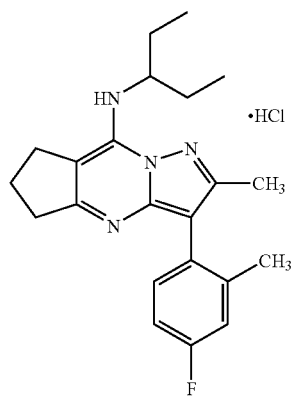

TLC: Rf 0.44 (hexane:ethyl acetate=3:1);

NMR (300 MHz, DMSO-$d_6$): δ 7.34-7.24 (m, 2H), 7.20-7.10 (m, 1H), 4.03-3.85 (m, 1H), 3.14 (brt, J=8.1 Hz, 2H), 2.95 (brt, J=8.1 Hz, 2H), 2.25 (s, 3H), 2.25-2.10 (m) and 2.12 (s) total 5H, 1.85-1.60 (m, 4H), 0.95-0.85 (m, 6H).

EXAMPLE 2(213)

8-(3-pentylamino)-2-methyl-3-(2,5-dichlorophenyl)-6,7-dihydro-5H-cyclopenta[d]pyrazolo[1,5-a]pyrimidine hydrochloride

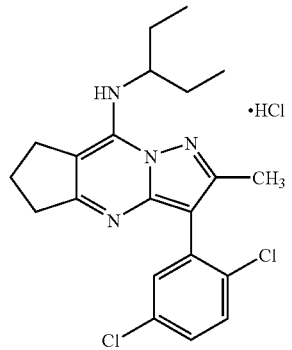

TLC: Rf 0.46 (hexane:ethyl acetate=3:1);

NMR (300 MHz, DMSO-$d_6$): δ 7.68 (d, J=8.4 Hz, 1H), 7.62-7.55 (m) and 7.59 (s) total 2H, 4.03-3.85 (m, 1H), 3.14 (brt, J=7.8 Hz, 2H), 2.96 (brt, J=7.8 Hz, 2H), 2.32 (s, 3H), 2.25-2.10 (m, 2H), 1.85-1.60 (m, 4H), 0.89 (t, J=7.5 Hz, 6H).

EXAMPLE 2(214)

8-(3-pentylamino)-2-methyl-3-(2,4-dimethoxyphenyl)-6,7-dihydro-5H-cyclopenta[d]pyrazolo[1,5-a]pyrimidine hydrochloride

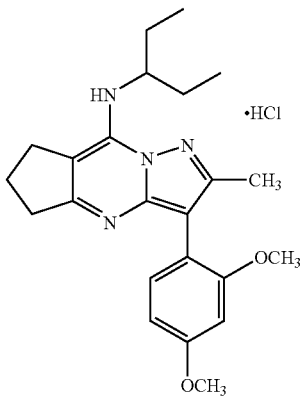

TLC: Rf 0.43 (hexane:ethyl acetate=1:1);

NMR (300 MHz, DMSO-$d_6$): δ 7.24 (d, J=8.1 Hz, 1H), 6.71 (d, J=2.4 Hz, 1H), 6.66 (dd, J=8.1, 2.4 Hz, 1H), 4.05-3.85 (m, 1H), 3.85 (s, 3H), 3.74 (s, H), 3.15 (brt, J=8.1 Hz, 2H), 2.99 (brt, J=8.1 Hz, 2H), 2.33 (s, 3H), 2.25-2.10 (m, 2H), 1.85-1.63 (m, 4H), 0.89 (t, J=7.5 Hz, 6H).

EXAMPLE 2(215)

8-(3-pentylamino)-2-methyl-3-(2-fluoro-4-methylphenyl)-6,7-dihydro-5H-cyclopenta[d]pyrazolo[1,5-a]pyrimidine hydrochloride

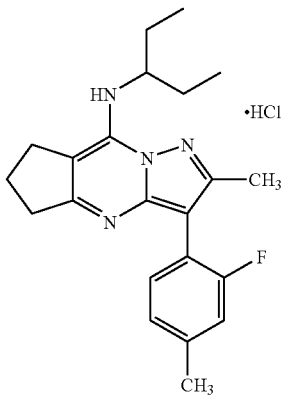

TLC: Rf 0.43 (hexane:ethyl acetate=3:1);

NMR (300 MHz, DMSO-$d_6$): 69.20-9.00 (m, 1H), 7.39 (t, J=7.8 Hz, 1H), 7.22 (d, J=11.1 Hz, 1H), 7.17 (d, J=7.8 Hz, 1H), 4.05-3.60 (m, 1H, covered with $H_2O$ in DMSO-$d_6$), 3.14

(brt, J=7.8 Hz, 2H), 2.99 (brt, J=7.8 Hz, 2H), 2.40 (s, 3H), 2.37 (s, 3H), 2.18 (quint, J=7.8 Hz, 2H), 1.83-1.60 (m, 4H), 0.89 (t, J=7.5 Hz, 6H).

EXAMPLE 2(216)

8-(N-butyl-N-(2-butynyl)amino)-2-methyl-3-(2-chloro-4-methoxyphenyl)-6,7-dihydro-5H-cyclopenta[d]pyrazolo[1,5-a]pyrimidine

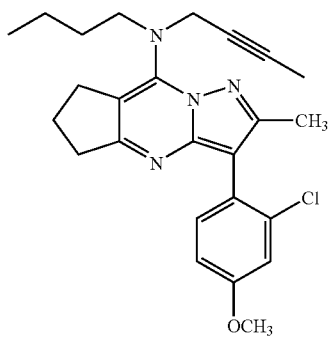

TLC: Rf 0.80 (hexane:ethyl acetate=1:1);

NMR (300 MHz, CDCl$_3$): 7.29 (d, J=8.7 Hz, 1H), 7.06 (d, J=2.4 Hz, 1H), 6.88 (dd, J=8.7, 2.4 Hz, 1H), 4.39 (q, J=2.1 Hz, 2H), 3.83 (s, 3H), 3.59 (m, 2H), 3.11 (t, J=7.5 Hz, 2H), 2.93 (t, J=7.5 Hz, 2H), 2.36 (s, 3H), 2.14 (quint, J=7.5 Hz, 2H), 1.81 (t, J=2.1 Hz, 3H), 1.68-1.54 (m, 2H), 1.39 (sext, J=7.5 Hz, 2H), 0.94 (t, J=7.5 Hz, 3H).

EXAMPLE 2(217)

8-(N-butyl-N-(2-butynyl)amino)-2-methyl-3-(2-chloro-4-methoxyphenyl)-5,7-dihydro-furo[3,4-d]pyrazolo[1,5-a]pyrimidine

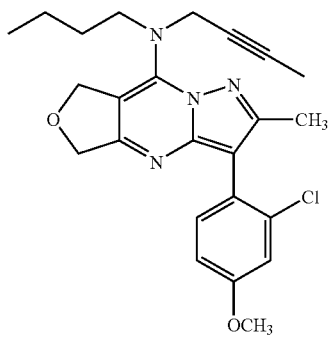

TLC: Rf 0.78 (hexane:ethyl acetate=1:1);

NMR (300 MHz, CDCl$_3$): δ 7.28 (d, J=8.7 Hz, 1H), 7.07 (d, J=2.7 Hz, 1H), 6.89 (dd, J=8.7, 2.7 Hz, 1H), 5.33 (s, 2H), 4.91 (s, 2H), 4.44 (q, J=2.4 Hz, 2H), 3.83 (s, 3H), 3.54 (m, 2H), 2.38 (s, 3H), 1.82 (t, J=2.4 Hz, 3H), 1.74-1.61 (m, 2H), 1.41 (sext, J=7.5 Hz, 2H), 0.96 (t, J=7.5 Hz, 3H).

EXAMPLE 2(218)

8-(3-methyl-2-butylamino)-2-methyl-3-(2-methyl-4-methoxyphenyl)-6,7-dihydro-5H-cyclopenta[d]pyrazolo[1,5-a]pyrimidine hydrochloride

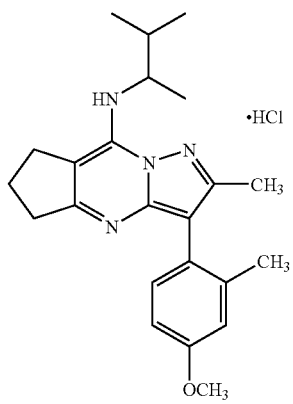

TLC: Rf 0.36 (hexane:ethyl acetate=3:1);

NMR (300 MHz, CDCl$_3$): δ 7.45 (brd, J=10.2 Hz, 1H), 7.11 (dd J=4.2, 8.4 Hz, 1H), 6.89 (d, J=2.4 Hz, 1H), 6.82 (dd, J=2.4, 8.4 Hz, 1H), 4.07 (m, 1H), 3.83 (s, 3H), 3.49 (m, 2H), 3.15 (t, J=6.9 Hz, 2H), 2.29 (m, 2H), 2.28 (s, 3H), 2.20 and 2.19 (s, total 3H), 1.99 (m, 1H), 1.42 and 1.41 (d, J=6.6 Hz, total 3H), 1.05-1.14 (m, 6H).

EXAMPLE 2(219)

8-(1-cyclohexylethylamino)-2-methyl-3-(2-methyl-4-methoxyphenyl)-6,7-dihydro-5H-cyclopenta[d]pyrazolo[1,5-a]pyrimidine hydrochloride

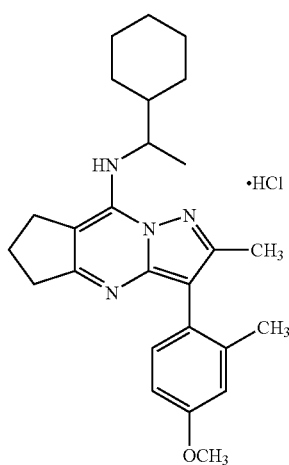

TLC: Rf 0.36 (hexane:ethyl acetate=3:1);

NMR (300 MHz, CDCl$_3$): δ 7.42 (brd, J=10.5 Hz, 1H), 7.11 and 7.10 (d, J=8.1 Hz, total 1H), 6.88 (d, J=2.7 Hz, 1H), 6.81 (dd, J=2.7, 8.1 Hz, 1H), 4.03 (m, 1H), 3.82 (s, 3H), 3.48 (m, 2H), 3.12 (t, J=7.5 Hz, 2H), 2.28 (m, 2H), 2.28 (s, 3H), 2.20 and 2.18 (s, total 3H), 1.52-1.95 (m, 6H), 1.41 and 1.40 (d, J=6.6 Hz, total 3H), 1.01-1.37 (m, 5H).

EXAMPLE 2(220)

8-(2-pentylamino)-2-methyl-3-(2-methyl-4-methoxyphenyl)-6,7-dihydro-5H-cyclopenta[d]pyrazolo[1,5-a]pyrimidine hydrochloride

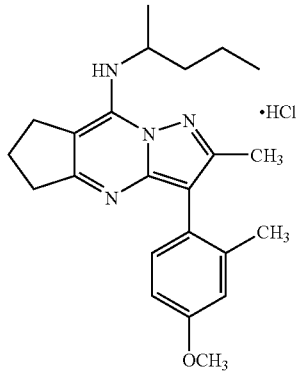

TLC: Rf 0.36 (hexane:ethyl acetate=3:1);

NMR (300 MHz, CDCl$_3$): δ 7.34 (brd, J=9.6 Hz, 1H), 7.11 and 7.10 (d, J=8.7 Hz, total 1H), 6.89 (d, J=2.7 Hz, 1H), 6.81 (dd, J=2.7, 8.7 Hz, 1H), 4.25 (m, 1H), 3.83 (s, 3H), 3.49 (m, 2H), 3.16 (t, J=6.9 Hz, 2H), 2.29 (m, 2H), 2.28 (s, 3H), 2.20 and 2.19 (s, total 3H), 1.70-1.80 (m, 2H), 1.44-1.58 (m, 2H), 1.47 and 1.46 (d, J=6.6 Hz, total 3H), 1.01 (m, 3H).

EXAMPLE 2(221)

8-(2-heptylamino)-2-methyl-3-(2-methyl-4-methoxyphenyl)-6,7-dihydro-5H-cyclopenta[d]pyrazolo[1,5-a]pyrimidine hydrochloride

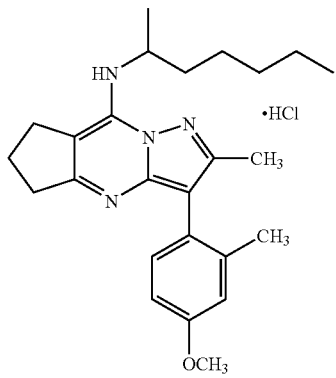

TLC: Rf 0.43 (hexane:ethyl acetate=3:1);

NMR (300 MHz, CDCl$_3$): δ 7.32 (brd, J=10.2 Hz, 1H), 7.12 and 7.11 (d, J=8.4 Hz, total 1H), 6.89 (d, J=2.7 Hz, 1H), 6.82 (dd, J=2.7, 8.4 Hz, 1H), 4.22 (m, 1H), 3.83 (s, 3H), 3.50 (m, 2H), 3.15 (t, J=6.9 Hz, 2H), 2.29 (m, 2H), 2.28 (s, 3H), 2.20 and 2.19 (s, total 3H), 1.71-1.81 (m, 2H), 1.30-1.55 (m, 9H), 0.92 (m, 3H).

EXAMPLE 2(222)

8-(1-methoxy-2-propylamino)-2-methyl-3-(2-methyl-4-methoxyphenyl)-6,7-dihydro-5H-cyclopenta[d]pyrazolo[1,5-a]pyrimidine hydrochloride

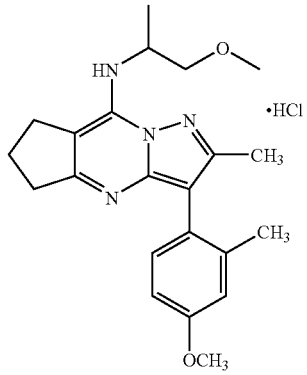

TLC: Rf 0.30 (hexane:ethyl acetate=2:1);

NMR (300 MHz, CDCl$_3$): δ 7.66 (brd, J=8.4 Hz, 1H), 7.11 and 7.10 (d, J=8.7 Hz, total 1H), 6.88 (d, J=2.7 Hz, 1H), 6.80 (dd, J=2.7, 8.7 Hz, 1H), 4.46 (m, 1H), 3.82 (s, 3H), 3.64 (dd, J=3.9, 9.9 Hz, 1H), 3.42-3.58 (m, 3H), 3.46 and 3.45 (s, total 3H), 3.23 (m, 1H), 3.11 (m, 1H), 2.29 (m, 2H), 2.29 (s, 3H), 2.19 and 2.18 (s, total, 3H), 1.49 (d, J=6.6 Hz, 3H).

EXAMPLE 2(223)

8-(2-octylamino)-2-methyl-3-(2-methyl-4-methoxyphenyl)-6,7-dihydro-5H-cyclopenta[d]pyrazolo[1,5-a]pyrimidine hydrochloride

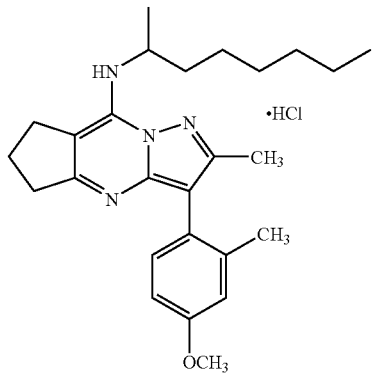

TLC: Rf 0.60 (hexane:ethyl acetate=2:1);

NMR (300 MHz, CDCl$_3$): δ 7.33 (brd, J=10.2 Hz, 1H), 7.12 and 7.11 (d, J=8.1 Hz, total 1H), 6.89 (d, J=2.7 Hz, 1H), 6.82 (dd, J=2.7, 8.1 Hz, 1H), 4.23 (m, 1H), 3.83 (s, 3H), 3.50 (brt, J=7.2 Hz, 2H), 3.15 (t, J=6.6 Hz, 2H), 2.29 (m, 2H), 2.28 (s, 3H), 2.20 and 2.19 (s, total 3H), 1.75 (m, 2H), 1.46 and 1.45 (d, J=6.3 Hz, total 3H), 1.26-1.45 (m, 8H), 0.90 (m, 3H).

EXAMPLE 2(224)

8-(1,2,3,4-tetrahydronaphthalen-1-yl)amino-2-methyl-3-(2-methyl-4-methoxyphenyl)-6,7-dihydro-5H-cyclopenta[d]pyrazolo[1,5-a]pyrimidine

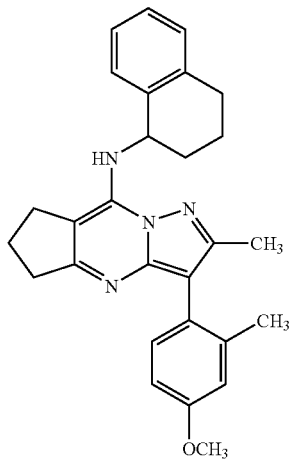

TLC: Rf 0.16 (hexane:ethyl acetate=3:1);

NMR (300 MHz, CDCl₃): δ 7.44 (m, 1H), 7.27-7.14 (m, 4H), 6.85 (d, J=2.7 Hz, 1H), 6.78 (dd, J=8.1, 2.7 Hz, 1H), 6.69 (brd, J=9.9 Hz, 1H), 5.22 (m, 1H), 3.82 (s, 3H), 3.24-3.08 (m, 2H), 3.00-2.76 (m, 4H), 2.26 (s, 3H), 2.24-1.82 (m, 6H), 2.20 (s, 3H).

EXAMPLE 2(225)

8-((1S,2S,3S,5R)-2,6,6-trimethylbicyclo[3.1.1]-3-heptyl)amino-2-methyl-3-(2-methyl-4-methoxyphenyl)-6,7-dihydro-5H-cyclopenta[d]pyrazolo[1,5-a]pyrimidine

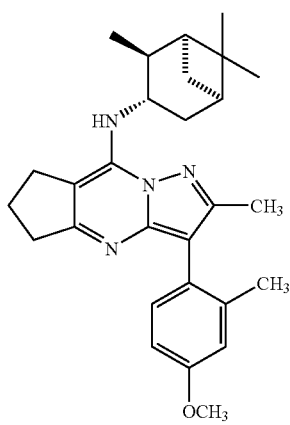

TLC: Rf 0.25 (hexane:ethyl acetate=3:1);

NMR (300 MHz, CDCl₃): δ 7.16 (d, J=8.1 Hz, 1H), 6.85 (d, J=2.4 Hz, 1H), 6.78 (dd, J=8.1, 2.4 Hz, 1H), 6.35 (brd, J=10.8 Hz, 1H), 4.31 (m, 1H), 3.82 (s, 3H), 3.22-3.06 (m, 2H), 2.91 (t, J=8.1 Hz, 2H), 2.62-2.46 (m, 2H), 2.31 (s, 3H), 2.19 (s, 3H), 2.19-1.82 (m, 6H), 1.29 (s, 3H), 1.20 (d, J=6.0 Hz, 3H), 1.11-1.08 (m, 1H), 1.09 (s, 3H).

EXAMPLE 2(226)

8-(3-pentylamino)-2-methyl-3-(2-methyl-4-chlorophenyl)-6,7-dihydro-5H-cyclopenta[d]pyrazolo[1,5-a]pyrimidine hydrochloride

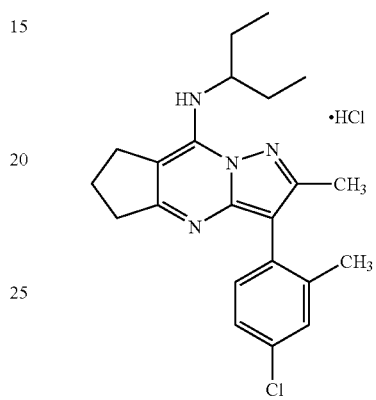

TLC: Rf 0.41 (hexane:ethyl acetate=3:1);

NMR (300 MHz, CDCl₃): δ 7.38-7.32 (m, 2H), 7.26-7.10 (m, 2H), 4.04-3.90 (m, 1H), 3.60-3.30 (m, 2H), 3.13 (t, J=6.6 Hz, 2H), 2.39 (s, 3H), 2.35 (s, 3H), 2.28 (quint, J=6.6 Hz, 2H), 1.92-1.40 (m, 4H), 1.06 (t, J=7.2 Hz, 6H).

EXAMPLE 2(227)

8-(3-pentylamino)-2-methyl-3-(2,5-dimethoxyphenyl)-6,7-dihydro-5H-cyclopenta[d]pyrazolo[1,5-a]pyrimidine hydrochloride

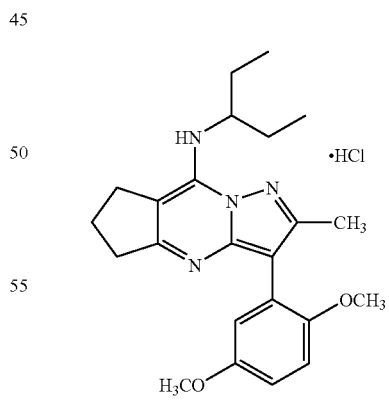

TLC: Rf 0.52 (hexane:ethyl acetate=1:1);

NMR (300 MHz, CDCl₃): δ 7.32-7.24 (m, 1H), 7.00-6.90 (m, 2H), 6.85 (d, J=2.4 Hz, 1H), 4.05-3.95 (m, 1H), 3.90 (s, 3H), 3.84 (s, 3H), 3.56 (t, J=7.8 Hz, 2H), 3.12 (t, J=7.8 Hz, 2H), 2.43 (s, 3H), 2.29 (quint, J=7.8 Hz, 2H), 1.90-1.40 (m, 4H), 1.05 (t, J=7.5 Hz, 6H).

EXAMPLE 2(228)

8-(3-pentylamino)-2-methyl-3-(2-methoxyphenyl)-6,7-dihydro-5H-cyclopenta[d]pyrazolo[1,5-a]pyrimidine hydrochloride

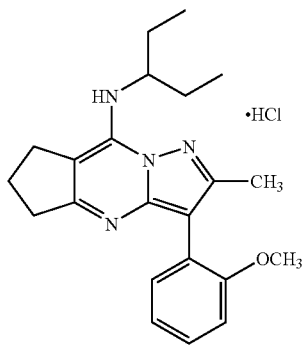

TLC: Rf 0.24 (hexane:ethyl acetate=3:1);

NMR (300 MHz, CDCl$_3$): δ 7.41 (t, J=8.1 Hz, 1H), 7.34-7.24 (m, 2H), 7.10-7.02 (m, 2H), 4.03-3.90 (m, 1H), 3.94 (s, 3H), 3.56 (t, J=7.5 Hz, 2H), 3.12 (t, J=7.5 Hz, 2H), 2.43 (s, 3H), 2.36-2.20 (m, 2H), 1.90-1.40 (m, 4H), 1.05 (t, J=7.5 Hz, 6H).

EXAMPLE 2(229)

8-dicyclopropylmethylamino-2-methyl-3-(2-methyl-4-methoxyphenyl)-5,7-dihydro-furo[3,4-d]pyrazolo[1,5-a]pyrimidine hydrochloride

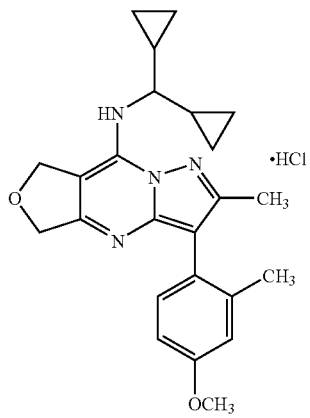

TLC: Rf 0.46 (hexane:ethyl acetate=2:1);

NMR (300 MHz, CDCl$_3$): δ 7.87 (m, 1H), 7.11 (d, J=8.7 Hz, 1H), 6.89 (d, J=2.7 Hz, 1H), 6.82 (dd, J=2.7, 8.7 Hz, 1H), 5.37 (s, 2H), 5.19 (m, 2H), 3.83 (s, 3H), 2.90 (m, 1H), 2.36 (s, 3H), 2.20 (s, 3H), 1.26 (m, 2H), 0.66-0.85 (m, 4H), 0.47 (m, 4H).

EXAMPLE 2(230)

8-(N-butyl-N-ethylamino)-2-methyl-3-(2-methyl-4-methoxyphenyl)-5,7-dihydro-furo[3,4-d]pyrazolo[1,5-a]pyrimidine hydrochloride

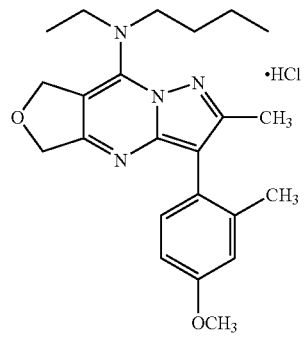

TLC: Rf 0.49 (hexane:ethyl acetate=2:1);

NMR (300 MHz, CDCl$_3$): δ 7:10 (d, J=8.7 Hz, 1H), 6.89 (d, J=2.7 Hz, 1H), 6.82 (dd, J=2.7, 8.7 Hz, 1H), 5.40 (s, 2H), 5.23 (s, 2H), 3.85-4.00 (m, 4H), 3.83 (s, 3H), 2.29 (s, 3H), 2.19 (s, 3H), 1.82 (m, 2H), 1.46 (t, J=6.9 Hz, 3H), 1.44 (m, 2H), 1.02 (t, J=6.9 Hz, 3H).

EXAMPLE 2(231)

8-(N-butyl-N-propylamino)-2-methyl-3-(2-methyl-4-methoxyphenyl)-5,7-dihydro-furo[3,4-d]pyrazolo[1,5-a]pyrimidine hydrochloride

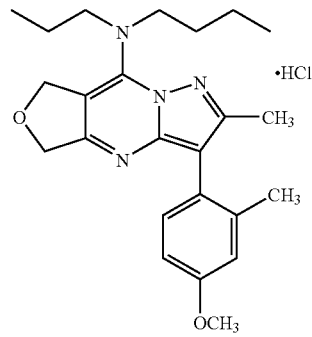

TLC: Rf 0.54 (hexane:ethyl acetate=2:1);

NMR (300 MHz, CDCl$_3$): δ 7.10 (d, J=8.4 Hz, 1H), 6.89 (d, J=2.4 Hz, 1H), 6.82 (dd, J=2.4, 8.4 Hz, 1H), 5.40 (s, 2H), 5.21 (s, 2H), 3.87 (m, 4H), 3.83 (s, 3H), 2.29 (s, 3H), 2.19 (s, 3H), 1.82 (m, 4H), 1.42 (m, 2H), 1.02 (t, J=7.2 Hz, 3H), 1.00 (t, J=7.2 Hz, 3H).

EXAMPLE 2(232)

8-(N,N-dipropylamino)-2-methyl-3-(2-methyl-4-methoxyphenyl)-5,7-dihydro-furo[3,4-d]pyrazolo[1,5-a]pyrimidine hydrochloride

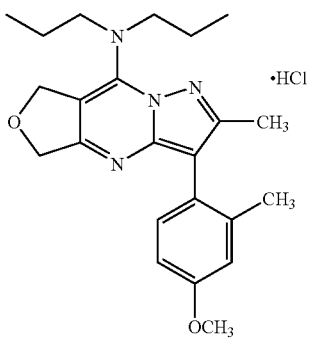

TLC: Rf 0.51 (hexane:ethyl acetate=2:1);
NMR (300 MHz, CDCl$_3$): δ 7.10 (d, J=8.4 Hz, 1H), 6.89 (d, J=3.0 Hz, 1H), 6.82 (dd, J=3.0, 8.4 Hz, 1H), 5.39 (brs, 2H), 5.21 (brs, 2H), 3.85 (m, 4H), 3.83 (s, 3H), 2.29 (s, 3H), 2.19 (s, 3H), 1.83 (m, 4H), 1.02 (t, J=7.2 Hz, 6H).

EXAMPLE 2(233)

8-(N-ethyl-N-(4-hydroxybutyl)amino)-2-methyl-3-(2-methyl-4-methoxyphenyl)-6,7-dihydro-5H-cyclopenta[d]pyrazolo[1,5-a]pyrimidine hydrochloride

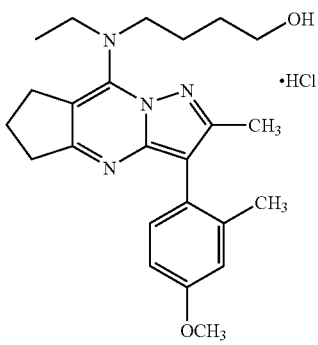

TLC: Rf 0.29 (hexane:ethyl acetate=1:2);
NMR (300 MHz, CDCl$_3$): δ 7.10 (d, J=8.4 Hz, 1H), 6.87 (d, J=3.0 Hz, 1H), 6.79 (dd, J=3.0, 8.4 Hz, 1H), 3.87-4.01 (m, 4H), 3.82 (s, 3H), 3.65 (t, J=6.0 Hz, 2H), 3.38 (t, J=7.5 Hz, 2H), 3.06 (t, J=7.2 Hz, 2H), 2.27 (s, 3H), 2.24 (m, 2H), 2.17 (s, 3H), 1.86 (m, 2H), 1.61 (m, 2H), 1.38 (t, J=7.2 Hz, 3H).

EXAMPLE 2(234)

8-bis(2-methoxyethyl)amino-2-methyl-3-(2-chloro-4-methoxyphenyl)-5,7-dihydro-furo[3,4-d]pyrazolo[1,5-a]pyrimidine hydrochloride

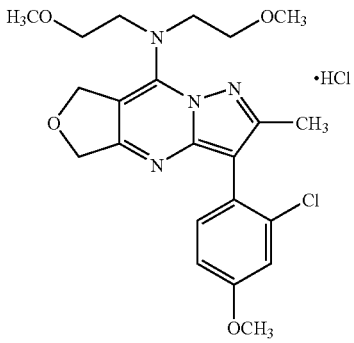

TLC: Rf 0.35 (hexane:ethyl acetate=1:2);
NMR (300 MHz, CDCl$_3$): δ 7.33 (d, J=8.4 Hz, 1H), 7.08 (d, J=2.4 Hz, 1H), 6.96 (dd, J=2.4, 8.4 Hz, 1H), 5.40 (m, 1H), 5.33 (m, 1H), 5.25 (m, 2H), 4.15 (m, 4H), 3.85 (s, 3H), 3.71 (t, J=5.1 Hz, 4H), 3.35 (s, 6H), 2.35 (s, 3H).

EXAMPLE 2(235)

8-(3-pentylamino)-2-methyl-3-(2-methoxy-5-isopropylphenyl)-6,7-dihydro-5H-cyclopenta[d]pyrazolo[1,5-a]pyrimidine hydrochloride

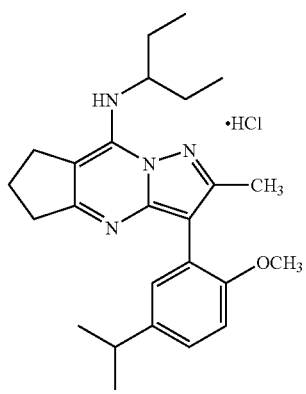

TLC: Rf 0.36 (hexane:ethyl acetate=3:1);
NMR (300 MHz, CDCl$_3$): δ 7.23 (dd, J=8.4, 2.1 Hz, 1H), 7.12 (d, J=2.1 Hz, 1H), 6.98 (d, J=8.4 Hz, 1H), 4.00-3.85 (m) and 3.91 (s) total 4H, 3.58-3.30 (m, 2H), 3.11 (t, J=6.9 Hz, 2H), 2.92 (m, 1H), 2.43 (s, 3H), 2.35-2.20 (m, 2H), 1.90-1.50 (m, 4H), 1.26 (d, J=6.9 Hz, 6H), 1.04 (t, J=7.5 Hz, 6H).

EXAMPLE 2(236)

8-(3-pentylamino)-2-methyl-3-(2-methoxy-5-fluorophenyl)-6,7-dihydro-5H-cyclopenta[d]pyrazolo[1,5-a]pyrimidine hydrochloride

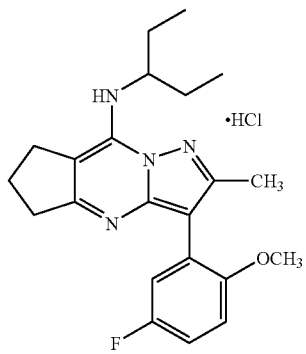

TLC: Rf 0.26 (hexane:ethyl acetate=3:1);
NMR (300 MHz, CDCl$_3$): δ 7.20-6.95 (m, 4H), 4.04-3.80 (m) and 3.91 (s) total 4H, 3.52-3.40 (m, 2H), 3.12 (t, J=7.2 Hz, 2H), 2.43 (s, 3H), 2.27 (quint, J=7.2 Hz, 2H), 1.90-1.40 (m, 4H), 1.05 (t, J=7.5 Hz, 6H).

EXAMPLE 2(237)

8-(N-butyl-N-(4-fluorophenyl)methylamino)-2-methyl-3-(2-chloro-5-methoxyphenyl)-6,7-dihydro-5H-cyclopenta[d]pyrazolo[1,5-a]pyrimidine hydrochloride

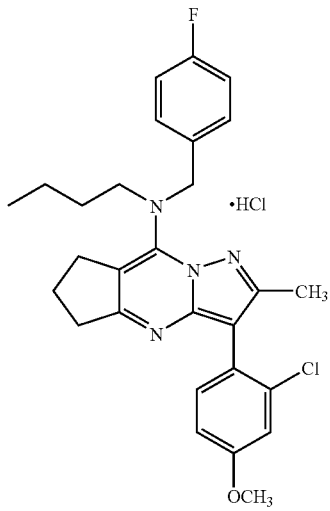

TLC: Rf 0.40 (hexane:ethyl acetate=3:1);
NMR (300 MHz, CDCl$_3$): δ 7.44-7.20 (m, 3H), 7.14-6.90 (m, 4H), 5.03 (brs, 2H), 3.85 (s, 3H), 3.62 (m, 2H), 3.29 (m, 2H), 2.96 (m, 2H), 2.37 (s, 3H), 2.19 (m, 2H), 1.65 (m, 2H), 1.32 (m, 2H), 0.90 (m, 3H).

EXAMPLE 2(238)

8-(N-butyl-N-(4-fluorophenyl)methylamino)-2-methyl-3-(2-chloro-4-methoxyphenyl)-5,7-dihydro-furo[3,4-d]pyrazolo[1,5-a]pyrimidine hydrochloride

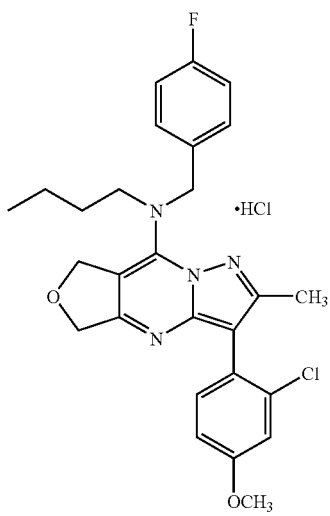

TLC: Rf 0.20 (hexane:ethyl acetate=3:1);
NMR (300 MHz, CDCl$_3$): δ 7.40-7.26 (m, 3H), 7.12 (brd, J=7.8 Hz, 2H), 7.09 (d, J=2.1 Hz, 1H), 6.99-6.92 (m, 1H), 5.40 (m, 2H), 5.30-5.08 (m, 4H), 3.85 (s, 3H), 3.70 (m, 2H), 2.37 (s, 3H), 1.76 (m, 2H), 1.36 (m, 2H), 0.94 (t, J=7.5 Hz, 3H).

EXAMPLE 2(239)

8-(N-butyl-N-(4-fluorophenyl)methylamino)-2-methyl-3-(2-methyl-4-methoxyphenyl)-5,7-dihydro-furo[3,4-d]pyrazolo[1,5-a]pyrimidine hydrochloride

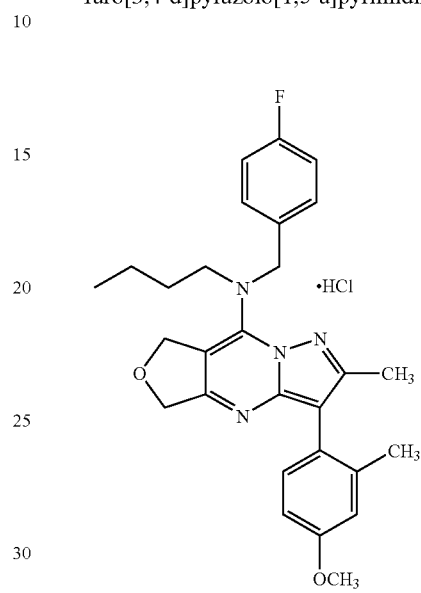

TLC: Rf 0.28 (hexane ethyl acetate=3:1);
NMR (300 MHz, CDCl$_3$): δ 7.29 (m, 2H), 7.18-7.04 (m, 3H), 6.89 (d, J=2.1 Hz, 1H), 6.85-6.78 (m, 1H), 5.23 (m, 2H), 5.15 (m, 2H), 5.11 (m, 2H), 3.83 (s, 3H), 3.58 (m, 2H), 2.33 (s, 3H), 2.20 (s, 3H), 1.71 (m, 2H), 1.35 (m, 2H), 0.95-0.84 (m, 3H).

EXAMPLE 2(240)

8-(3-pentylamino)-2-methyl-3-(2-methoxy-5-chlorophenyl)-6,7-dihydro-5H-cyclopenta[d]pyrazolo[1,5-a]pyrimidine hydrochloride

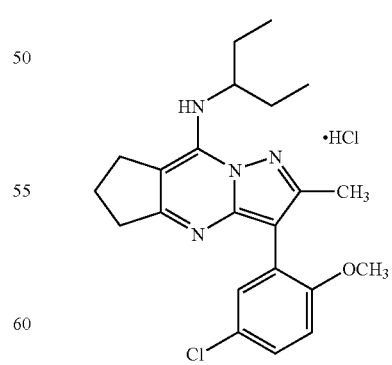

TLC: Rf 0.26 (hexane:ethyl acetate=3:1);
NMR (300 MHz, CDCl$_3$): δ 7.33 (dd, J=9.0, 3.0 Hz, 1H), 7.25-7.05 (m) and 7.22 (d, J=3.0 Hz) total 2H, 6.98 (d, J=9.0 Hz, 1H), 4.03-3.85 (m) and 3.93 (s) total 4H, 3.55-3.40 (m, 2H), 3.13 (t, J=7.2 Hz, 2H), 2.43 (s, 3H), 2.28 (quint, J=7.2 Hz, 2H), 1.90-1.40 (m, 4H), 1.05 (t, J=7.5 Hz, 6H).

EXAMPLE 2(241)

8-(N-ethyl-N-(2-butyryl)amino)-2-methyl-3-(2-methyl-4-methoxyphenyl)-5,7-dihydro-furo[3,4-d]pyrazolo[1,5-a]pyrimidine hydrochloride

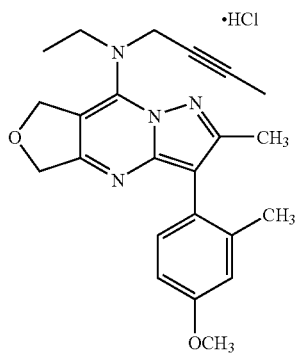

TLC: Rf 0.37 (hexane:ethyl acetate=2:1);

NMR (300 MHz, CDCl$_3$): δ 7.10 (d, J=8.4 Hz, 1H), 6.89 (d, J=2.7 Hz, 1H), 6.82 (dd, J=2.7, 8.4 Hz, 1H), 5.41 (s, 4H), 4.48 (m, 2H), 4.14 (m, 2H), 3.83 (s, 3H), 2.31 (s, 3H), 2.18 (s, 3H), 1.90 (t, J=2.4 Hz, 3H), 1.54 (t, J=7.2 Hz, 3H).

EXAMPLE 2(242)

8-(N-propyl-N-(2-butyryl)amino)-2-methyl-3-(2-methyl-4-methoxyphenyl)-5,7dihydro-furo[3,4-d]pyrazolo[1,5-a]pyrimidine hydrochloride

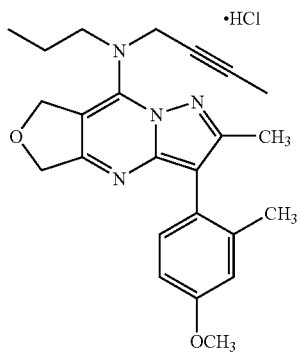

TLC: Rf 0.47 (hexane:ethyl acetate=2:1);

NMR (300 MHz, CDCl$_3$): δ 7.10 (d, J=8.1 Hz, 1H), 6.89 (d, J=2.7 Hz, 1H), 6.82 (dd, J=2.7, 8.1 Hz, 1H), 5.41 (m, 2H), 5.39 (m, 2H), 5.42 (m, 2H), 3.98 (m, 2H), 3.83 (s, 3H), 2.31 (s, 3H), 2.18 (s, 3H), 1.94 (m, 2H), 1.89 (t, J=2.7 Hz, 3H), 1.05 (t, J=7.2 Hz, 3H).

EXAMPLE 2(243)

8-(N-propyl-N-(4-methylthiophenyl)methylamino)-2-methyl-3-(2-methyl-4-methoxyphenyl)-5,7-dihydro-furo[3,4-d]pyrazolo[1,5-a]pyrimidine hydrochloride

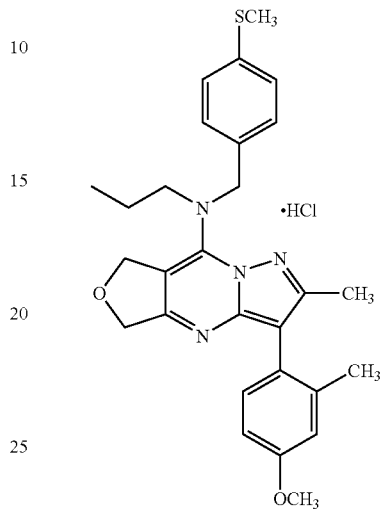

TLC: Rf 0.45 (hexane:ethyl acetate=2:1);

NMR (300 MHz, CDCl$_3$): δ 7.27 (d, J=8.4 Hz, 2H), 7.20 (d, J=8.4 Hz, 2H), 7.12 (d, J=8.4 Hz, 1H), 6.90 (d, J=2.7 Hz, 1H), 6.83 (dd, J=2.7, 8.4 Hz, 1H), 5.40 (s, 2H), 5.11-5.26 (m, 4H), 3.84 (s, 3H), 3.70 (m, 2H), 2.50 (s, 3H), 2.31 (s, 3H), 2.20 (s, 3H), 1.84 (m, 2H), 0.97 (t, J=7.2 Hz, 3H).

EXAMPLE 2(244)

8-(N-propyl-N-(benz[d]1,3-dioxolan-5-yl)methylamino)-2-methyl-3-(2-methyl-4-methoxyphenyl)-5,7-dihydro-furo[3,4-d]pyrazolo[1,5-a]pyrimidine hydrochloride

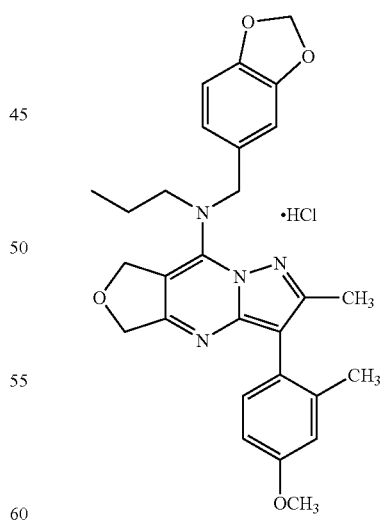

TLC: Rf 0.45 (hexane:ethyl acetate=2:1);

NMR (300 MHz, CDCl$_3$): δ 7.13 (d, J=8.1 Hz, 1H), 6.90 (d, J=2.7 Hz, 1H), 6.83 (dd, J=2.7, 8.1 Hz, 1H), 6.82 (d, J=7.5 Hz, 1H), 6.78 (d, J=1.5 Hz, 1H), 6.73 (dd, J=1.5, 7.5 Hz, 1H), 6.01 (s, 2H), 5.39 (s, 2H), 5.17 (s, 2H), 5.11 (m, 2H), 3.84 (s, 3H), 3.69 (m, 2H), 2.32 (s, 3H), 2.21 (s, 3H), 1.81 (m, 2H), 0.96 (t, J=7.2 Hz, 3H).

EXAMPLE 2(245)

8-(N-benzyl-N-cyclopropylmethylamino)-2-methyl-3-(2-methyl-4-methoxyphenyl)-5,7-dihydro-furo[3,4-d]pyrazolo[1,5-a]pyrimidine hydrochloride

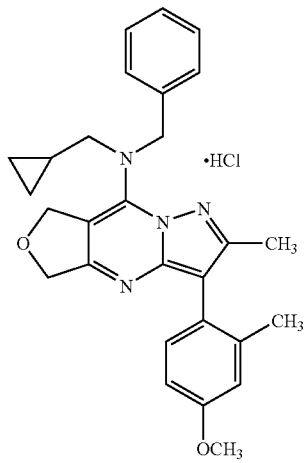

TLC: Rf 0.47 (hexane:ethyl acetate=2:1);
NMR (300 MHz, CDCl₃): δ 7.34-7.46 (m, 3H), 7.26-7.33 (m, 2H), 7.13 (d, J=8.7 Hz, 1H), 6.90 (d, J=2.7 Hz, 1H), 6.84 (dd, J=2.7, 8.7 Hz, 1H), 5.42 (s, 2H), 5.33 (m, 2H), 5.24 (s, 2H), 3.84 (s, 3H), 3.73 (m, 2H), 2.31 (s, 3H), 2.20 (s, 3H), 1.24 (m, 1H), 0.69 (m, 2H), 0.24 (m, 2H).

EXAMPLE 2(246)

8-(N-cyclopropylmethyl-N-(4-trifluoromethylphenyl)methylamino)-2-methyl-3-(2-chloro-5-methoxyphenyl)-6,7-dihydro-5H-cyclopenta[d]pyrazolo[1,5-a]pyrimidine hydrochloride

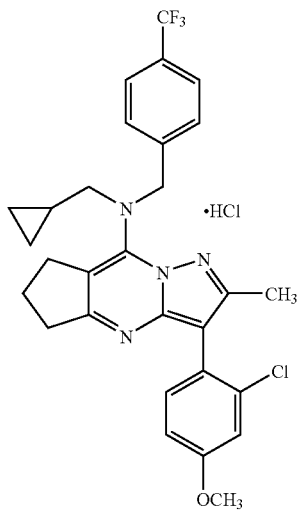

TLC: Rf 0.48 (hexane:ethyl acetate=2:1);
NMR (300 MHz, CDCl₃): δ 7.62 (brd, J=7.8 Hz, 2H), 7.48 (brd, J=7.8 Hz, 2H), 7.34 (brd, J=8.1 Hz, 1H), 7.08 (d, J=2.4 Hz, 1H), 6.90-6.88 (m, 1H), 5.19 (brs, 2H), 3.85 (s, 3H), 3.54 (m, 2H), 3.36-3.14 (m, 2H), 3.14-2.98 (m, 2H), 2.36 (s, 3H), 2.22 (m, 2H), 1.12-0.98 (m, 1H), 0.64-0.52 (m, 2H), 0.18-0.08 (m, 2H).

EXAMPLE 2(247)

8-(N-cyclopropylmethyl-N-(4-trifluoromethylphenyl)methylamino)-2-methyl-3-(2-chloro-4-methoxyphenyl)-5,7-dihydro-furo[3,4-d]pyrazolo[1,5-a]pyrimidine hydrochloride

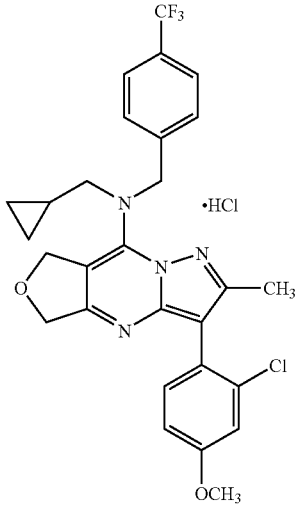

TLC: Rf 0.42 (hexane:ethyl acetate=2:1);
NMR (300 MHz, CDCl₃): δ 7.65 (brd, J=7.5 Hz, 2H), 7.49 (brd, J=7.5 Hz, 2H), 7.33 (d, J=8.4 Hz, 1H), 7.08 (d, J=2.4 Hz, 1H), 6.95 (dd, J=8.4, 2.4 Hz, 1H), 5.35-5.18 (m, 6H), 3.85 (s, 3H), 3.54 (d, J=6.6 Hz, 2H), 2.36 (s, 3H), 1.11 (m, 1H), 0.72-0.60 (m, 2H), 0.22-0.14 (m, 2H).

EXAMPLE 2(248)

8-(N-cyclopropylmethyl-N-(4-trifluoromethylphenyl)methylamino)-2-methyl-3-(2-methyl-4-methoxyphenyl)-5,7-dihydro-furo[3,4-d]pyrazolo[1,5-a]pyrimidine hydrochloride

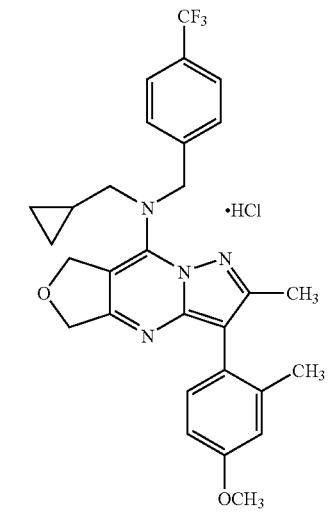

TLC: Rf 0.42 (hexane:ethyl acetate=2:1);
NMR (300 MHz, CDCl₃): δ 7.68 (d, J=7.8 Hz, 2H), 7.49 (d, J=7.8 Hz, 2H), 7.12 (d, J=8.4 Hz, 1H), 6.90 (d, J=2.7 Hz, 1H), 6.83 (dd, J=8.4, 2.7 Hz, 1H), 5.42 (m, 2H), 5.38 (s, 2H), 5.27 (s, 2H), 3.83 (s, 3H), 3.61 (m, 2H), 2.30 (s, 3H), 2.19 (s, 3H), 1.15 (m, 1H), 0.74-0.66 (m, 2H), 0.26-0.18 (m, 2H).

EXAMPLE 2(249)

8-(N-propyl-N-(4-cyanophenyl)methylamino)-2-methyl-3-(2-methyl-4-methoxyphenyl)-5,7-dihydro-furo[3,4-d]pyrazolo[1,5-a]pyrimidine hydrochloride

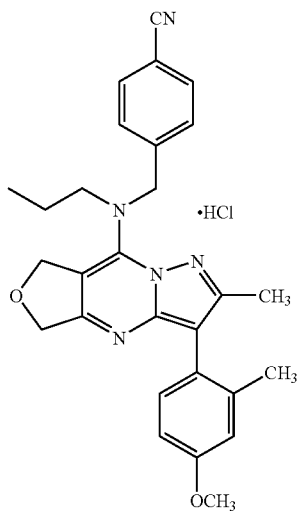

TLC: Rf 0.29 (hexane:ethyl acetate=2:1);
NMR (300 MHz, CDCl$_3$): δ 7.66 (brd, J=7.8 Hz, 2H), 7.49 (brd, J=7.8 Hz, 2H), 7.15 (d, J=8.4 Hz, 1H), 6.88 (d, J=2.7 Hz, 1H), 6.81 (dd, J=8.4, 2.7 Hz, 1H), 5.15 (brs, 2H), 5.09 (brs, 2H), 5.01 (brs, 2H), 3.83 (s, 3H), 3.37 (m, 2H), 2.33 (s, 3H), 2.18 (s, 3H), 1.74-1.60 (m, 2H), 0.91 (t, J=6.9 Hz, 3H).

EXAMPLE 2(250)

8-(N-cyclopropyl-N-(4-fluorophenyl)methylamino)-2-methyl-3-(2-chloro-4-methoxyphenyl)-5,7-dihydro-furo[3,4-d]pyrazolo[1,5-a]pyrimidine hydrochloride

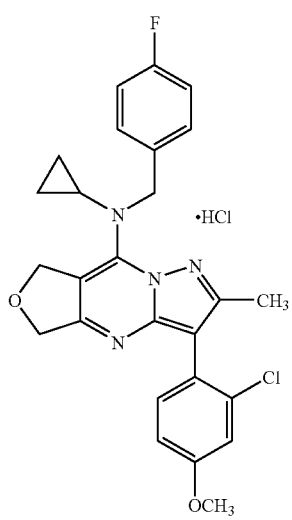

TLC: Rf 0.40 (hexane:ethyl acetate=2:1);
NMR (300 MHz, CDCl$_3$): δ 7.32 (d, J=8.4 Hz, 1H), 7.16-7.07 (m, 3H), 7.02-6.94 (m 2H), 6.92 (dd, J=8.4, 3.0 Hz, 1H), 5.20 (s, 2H), 5.18 (s, 2H), 4.94 (s, 2H), 3.84 (s, 3H), 2.56 (m, 1H), 2.41 (s, 3H), 0.89-0.79 (m, 4H).

EXAMPLE 2(251)

8-(N-cyclopropyl-N-(4-fluorophenyl)methylamino)-2-methyl-3-(2-methyl-4-methoxyphenyl)-5,7-dihydro-furo[3,4-d]pyrazolo[1,5-a]pyrimidine hydrochloride

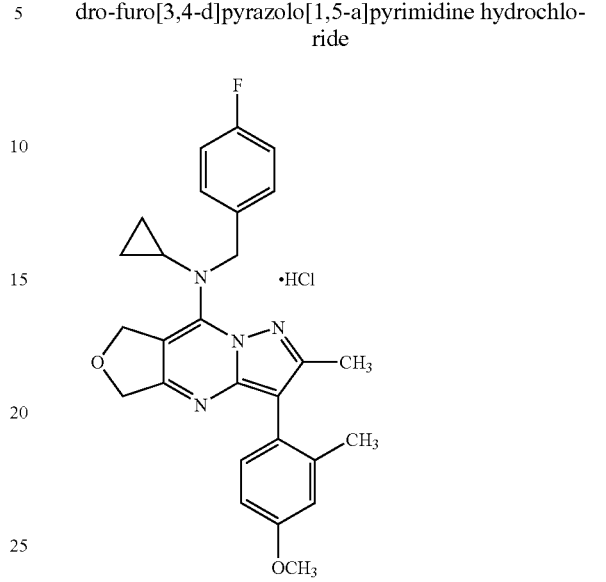

TLC: Rf 0.44 (hexane:ethyl acetate=2:1);
NMR (300 MHz, CDCl$_3$): δ 7.19-7.08 (m, 3H), 7.04-6.96 (m, 2H), 6.88 (d, J=2.7 Hz, 1H), 6.82 (dd, J=8.4, 2.7 Hz, 1H), 5.28-5.18 (m, 4H), 5.00 (s, 2H), 3.83 (s, 3H), 2.60 (m, 1H), 2.38 (s, 3H), 2.18 (s, 3H), 0.90-0.80 (m, 4H).

EXAMPLE 2(252)

8-(N-cyclopropylmethyl-N-(4-fluorophenyl)methylamino)-2-methyl-3-(2-methyl-4-methoxyphenyl)-5,7-dihydro-furo[3,4-d]pyrazolo[1,5-a]pyrimidine hydrochloride

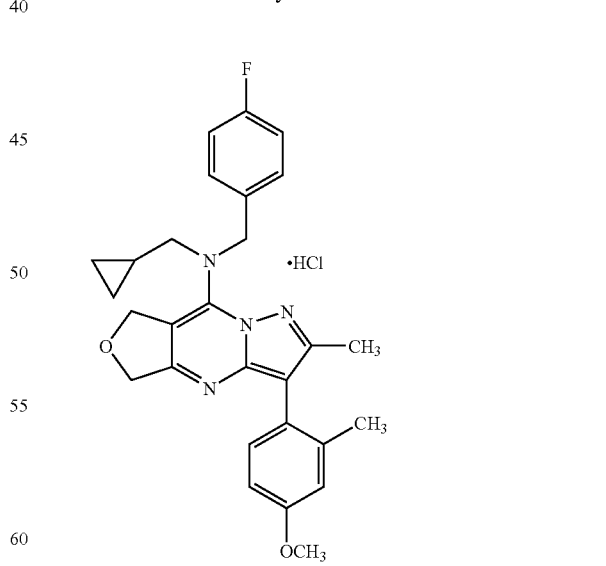

TLC: Rf 0.49 (hexane:ethyl acetate=2:1);
NMR (300 MHz, CDCl$_3$): δ 7.36-7.29 (m, 2H), 7.15-7.05 (m, 3H), 6.90 (d, J=2.7 Hz, 1H), 6.84 (dd, J=8.1, 2.7 Hz, 1H), 5.39 (s, 2H), 5.32-5.20 (m, 4H), 3.84 (s, 3H), 3.62 (m, 2H), 2.32 (s, 3H), 2.20 (s, 3H), 1.20-1.08 (m, 1H), 0.72-0.62 (m, 2H), 0.28-0.18 (m, 2H).

EXAMPLE 2(253)
8-(N-propyl-N-(2-methoxyethyl)amino)-2-methyl-3-(2-chloro-4-methoxyphenyl)-5,7-dihydro-furo[3,4-d]pyrazolo[1,5-a]pyrimidine hydrochloride

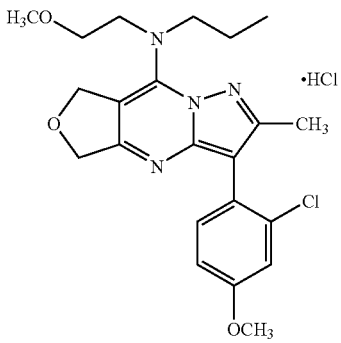

TLC: Rf 0.35 (hexane:ethyl acetate=2:1);
NMR (300 MHz, CDCl$_3$): δ 7.34 (d, J=8.7 Hz, 1H), 7.08 (d, J=2.4 Hz, 1H), 6.97 (dd, J=8.7, 2.4 Hz, 1H), 5.48 (d, J=16.8 Hz, 1H), 5.36 (d, J=16.8 Hz, 1H), 5.23 (s, 2H), 4.38-4.22 (m, 2H), 3.85 (s, 3H), 3.78-3.66 (m, 4H), 3.34 (s, 3H), 2.35 (s, 3H), 1.81 (sext, J=7.5 Hz, 2H), 1.01 (t, J=7.5 Hz, 3H).

EXAMPLE 2(254)
8-(N-propyl-N-(2-methoxyethyl)amino)-2-methyl-3-(2-methyl-4-methoxyphenyl)-5,7-dihydro-furo[3,4-d]pyrazolo[1,5-a]pyrimidine hydrochloride

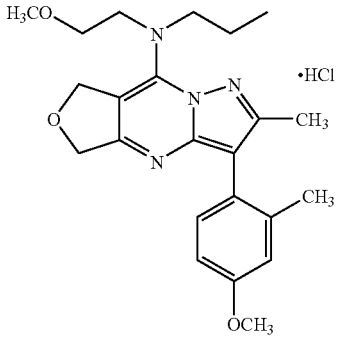

TLC: Rf 0.33 (hexane:ethyl acetate=2:1);
NMR (300 MHz, CDCl$_3$): δ 7.11 (d, J=8.4 Hz, 1H), 6.89 (d, J=2.4 Hz, 1H), 6.83 (dd, J=8.4, 2.4 Hz, 1H) 5.41 (s, 2H), 5.22 (s, 2H), 4.30 (m, 2H), 3.83 (s, 3H), 3.80-3.60 (m, 4H), 3.34 (s, 3H), 2.30 (s, 3H), 2.19 (s, 3H), 1.81 (sext, J=7.5 Hz, 2H), 1.01 (t, J=7.5 Hz, 3H).

EXAMPLE 2(255)
8-(3-pentylamino)-2-methyl-3-(2-methyl-4-cyanophenyl)-6,7-dihydro-5H-cyclopenta[d]pyrazolo[1,5-a]pyrimidine hydrochloride

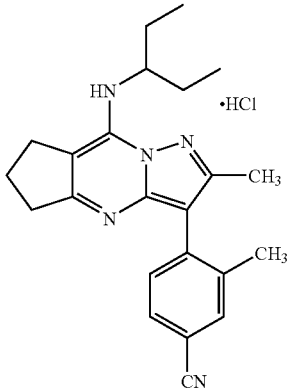

TLC: Rf 0.45 (hexane:ethyl acetate=2:1);
NMR (300 MHz, CDCl$_3$): δ 7.65 (s, 1H), 7.57 (d. J=7.8 Hz, 1H), 7.34 (d, J=7.8 Hz, 1H), 7.24-7.08 (m, 1H), 4.06-3.88 (m, 1H), 3.41 (brt, J=7.2 Hz, 2H), 3.15 (t, J=7.2 Hz, 2H), 2.40-2.20 (m) and 2.30 (s) total 8H, 1.90-1.40 (m, 4H), 1.06 (t, J=6.6 Hz, 6H).

EXAMPLE 2(256)
8-(N-propyl-N-(2-methoxyethyl)amino)-2-methyl-3-(2-chloro-5-methoxyphenyl)-6,7-dihydro-5H-cyclopenta[d]pyrazolo[1,5-a]pyrimidine hydrochloride

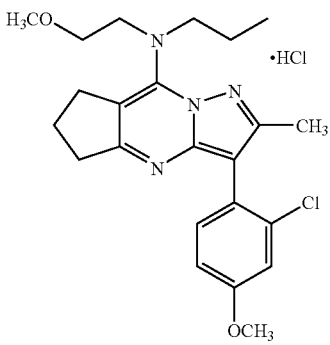

TLC: Rf 0.46 (hexane:ethyl acetate=2:1);
NMR (300 MHz, CDCl$_3$): δ 7.34 (brd, J=8.4 Hz, 1H), 7.08 (d, J=2.4 Hz, 1H), 6.99-6.91 (m, 1H), 4.20 (m, 2H), 3.85 (s, 3H), 3.75 (m, 2H), 3.62 (m, 2H), 3.52-3.30 (m, 2H), 3.30 (s, 3H), 3.03 (m, 2H), 2.33 (s, 3H), 2.24 (m, 2H), 1.72 (m, 2H), 0.96 (t, J=7.5 Hz, 3H).

EXAMPLE 2(257)
8-(N-ethyl-N-(4-methylthiophenyl)methylamino)-2-methyl-3-(2-chloro-4-methoxyphenyl)-6,7-dihydro-5H-cyclopenta[d]pyrazolo[1,5-a]pyrimidine hydrochloride

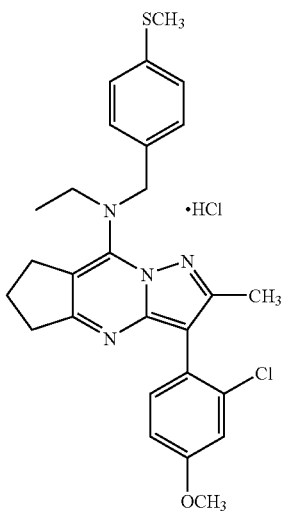

TLC: Rf 0.42 (hexane:ethyl acetate=2:1);
NMR (300 MHz, CDCl$_3$): δ 7.40-7.30 (m, 1H), 7.30-7.16 (m, 4H), 7.08 (d, J=2.4 Hz, 1H), 6.99-6.92 (m, 1H), 5.11 (brs, 2H), 3.85 (s, 3H), 3.78 (m, 2H), 3.42 (m, 2H), 3.00 (m, 2H), 2.50 (s, 3H), 2.35 (s, 3H), 2.21 (m, 2H), 1.34 (m, 3H).

EXAMPLE 2(258)

8-(N-ethyl-N-(4-methylthiophenyl)methylamino)-2-methyl-3-(2-chloro-4-methoxyphenyl)-5,7-dihydro-furo[3,4-d]pyrazolo[1,5-a]pyrimidine hydrochloride

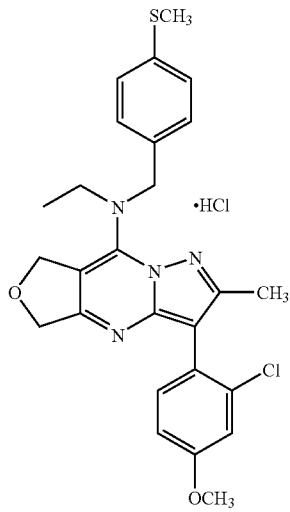

TLC: Rf 0.35 (hexane:ethyl acetate=2:1);
NMR (300 MHz, CDCl$_3$): δ 7.35 (d, J=8.7 Hz, 1H), 7.28 (brd, J=8.1 Hz, 2H), 7.21 (brd, J=8.1 Hz, 2H), 7.09 (d, J=2.7 Hz, 1H), 6.97 (dd, J=8.7, 2.7 Hz, 1H), 5.48-5.27 (m, 2H), 5.27-5.06 (m, 4H), 3.85 (s, 3H), 3.88-3.78 (m, 2H), 2.50 (s, 3H), 2.36 (s, 3H), 1.42 (t, J=6.9 Hz, 3H).

EXAMPLE 2(259)

8-(N-ethyl-N-(4-methylthiophenyl)methylamino)-2-methyl-3-(2-methyl-4-methoxyphenyl)-5,7-dihydro-furo[3,4-d]pyrazolo[1,5-a]pyrimidine hydrochloride

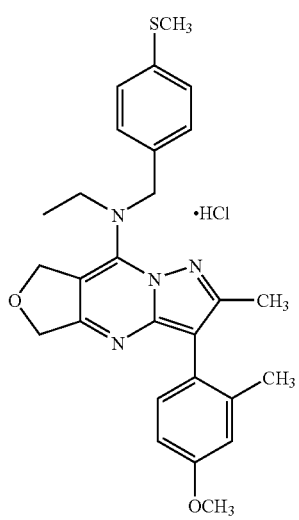

TLC: Rf 0.40 (hexane:ethyl acetate=2:1);
NMR (300 MHz, CDCl$_3$): δ 7.28 (brd, J=8.4 Hz, 2H), 7.22 (brd, J=8.4 Hz, 2H), 7.13 (d, J=8.4 Hz, 1H), 6.90 (d, J=2.7 Hz, 1H), 6.84 (dd, J=8.4, 2.7 Hz, 1H), 5.40 (brs, 2H), 5.22-5.08 (m, 4H), 3.86 (m, 2H), 3.84 (s, 3H), 2.50 (s, 3H), 2.31 (s, 3H), 2.20 (s, 3H), 1.43 (t, J=6.6 Hz, 3H).

EXAMPLE 2(260)

8-(3-pentylamino)-2-methyl-3-(4-methylthiophenyl)-6,7-dihydro-5H-cyclopenta[d]pyrazolo[1,5-a]pyrimidine hydrochloride

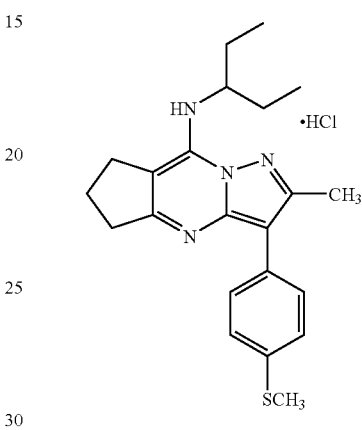

TLC: Rf 0.46 (hexane:ethyl acetate=3:1);
NMR (300 MHz, CDCl$_3$): δ 7.52 (d, J=8.4 Hz, 2H), 7.39 (d, J=8.4 Hz, 2H), 7.31 (d, J=10.5 Hz, 1H), 4.06-3.90 (m, 1H), 3.60 (t, J=7.8 Hz, 2H), 3.13 (t, J=7.8 Hz, 2H), 2.52 (s, 3H), 2.49 (s, 3H), 2.30 (quint, J=7.8 Hz, 2H), 1.94-1.64 (m, 4H), 1.05 (t, J=7.2 Hz, 6H).

EXAMPLE 2(261)

8-(N-butyl-N-(2-methoxyethyl)amino)-2-methyl-3-(2-methyl-4-methoxyphenyl)-5,7-dihydro-furo[3,4-d]pyrazolo[1,5-a]pyrimidine hydrochloride

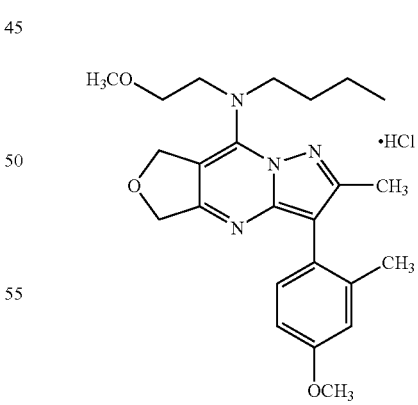

TLC: Rf 0.61 (hexane:ethyl acetate=1:2);
NMR (300 MHz, CDCl$_3$): δ 7.11 (d, J=8.4 Hz, 1H), 6.89 (d, J=2.4 Hz, 1H), 6.82 (dd, J=8.4, 2.4 Hz, 1H), 5.40 (s, 2H), 5.22 (s, 2H), 4.29 (m, 2H), 3.83 (s, 3H), 3.78 (m, 2H), 3.72 (t, J=5.1 Hz, 2H), 3.34 (s, 3H), 2.30 (s, 3H), 2.19 (s, 3H), 1.77 (quintet, J=7.5 Hz, 2H), 1.42 (sixtet, J=7.5 Hz, 2H), 1.00 (t, J=7.5 Hz, 3H).

EXAMPLE 2(262)

8-(3-pentylamino)-2-methyl-3-(4-dimethylaminophenyl)-6,7-dihydro-5H-cyclopenta[d]pyrazolo[1,5-a]pyrimidine hydrochloride

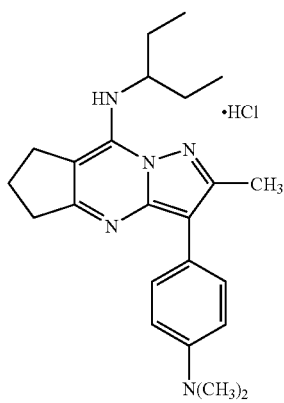

TLC: Rf 0.57 (hexane:ethyl acetate=1:1);

NMR (300 MHz, CDCl$_3$): δ 7.72 (d, J=7.8 Hz, 2H), 7.60-7.40 (m, 2H), 6.88-6.75 (m, 1H), 3.98-3.85 (m, 1H), 3.35-3.25 (m, 2H), 3.15-3.05 (m) and 3.13 (s) total 8H, 2.52 (s, 3H), 2.25 (quint, J=7.8 Hz, 2H), 1.85-1.60 (m, 4H), 1.03 (t, J=7.5 Hz, 6H).

EXAMPLE 2(263)

8-(N-cyclopropylmethyl-N-propylamino)-2-methyl-3-(2-methyl-4-methoxyphenyl)-5,7-dihydro-furo[3,4-d]pyrazolo[1,5-a]pyrimidine hydrochloride

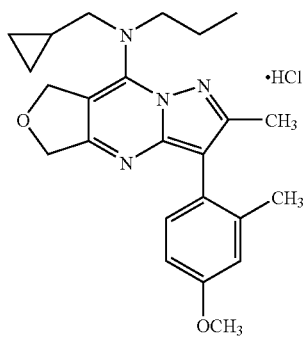

TLC: Rf 0.55 (hexane:ethyl acetate=2:1);

NMR (300 MHz, CDCl$_3$): δ 7.15 (d, J=8.4 Hz, 1H), 6.88 (d, J=2.4 Hz, 1H), 6.81 (dd, J=8.4, 2.4 Hz, 1H), 5.24 (s, 2H), 5.04 (s, 2H), 3.83 (s, 3H), 3.69-3.63 (m, 4H), 2.33 (s, 3H), 2.18 (s, 3H), 1.70 (sixt, J=7.5 Hz, 2H), 1.07 (m, 1H), 0.96 (t, J=7.5 Hz, 3H), 0.56 (m, 2H), 0.20 (m, 2H).

EXAMPLE 2(264)

8-(N-propyl-N-(5-methylfuran-2-yl)methylamino)-2-methyl-3-(2-chloro-4-methoxyphenyl)-5,7-dihydro-furo[3,4-d]pyrazolo[1,5-a]pyrimidine

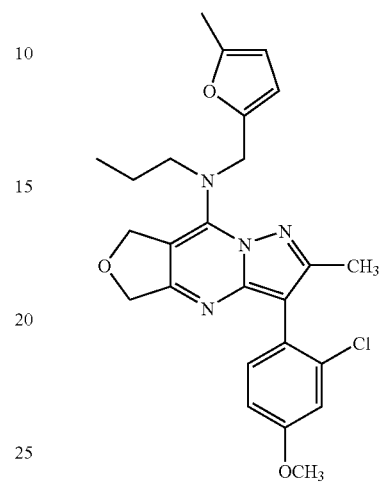

TLC: Rf 0.47 (hexane:ethyl acetate=2:1);

NMR (300 MHz, CDCl$_3$): δ 7.31 (d, J=8.4 Hz, 1H), 7.08 (d, J=2.7 Hz, 1H), 6.90 (dd, J=2.7, 8.4 Hz, 1H), 6.02 (d, J=3.0 Hz, 1H), 5.86 (m, 1H), 5.08 (s, 2H), 4.91 (s, 2H), 4.90 (s, 2H), 3.84 (s, 3H), 3.26 (m, 2H), 2.41 (s, 3H), 2.23 (s, 3H), 1.66 (m, 2H), 0.94 (t, J=7.2 Hz, 3H).

EXAMPLE 2(265)

8-(N-propyl-N-(5-methylfuran-2-yl)methylamino)-2-methyl-3-(2-methyl-4-methoxyphenyl)-5,7-dihydro-furo[3,4-d]pyrazolo[1,5-a]pyrimidine

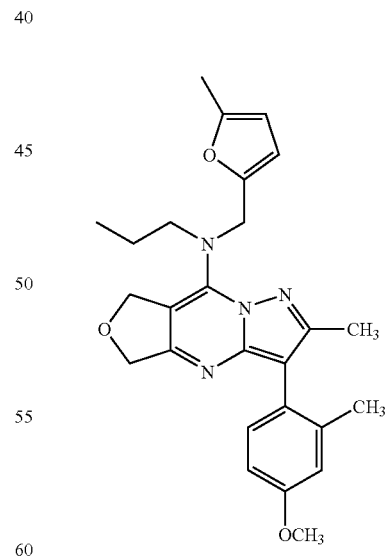

TLC: Rf 0.49 (hexane:ethyl acetate=2:1);

NMR (300 MHz, CDCl$_3$): δ 7.18 (d, J=8.1 Hz, 1H), 6.88 (d, J=2.4 Hz, 1H), 6.81 (d, J=2.4, 8.1 Hz, 1H), 6.01 (d, J=3.0 Hz, 1H), 5.86 (m, 1H), 5.07 (s, 2H), 4.91 (s, 2H), 4.88 (s, 2H), 3.83 (s, 3H), 3.25 (m, 2H), 2.37 (s, 3H), 2.22 (s, 3H), 2.18 (s, 3H), 1.67 (m, 2H), 0.94 (t, J=7.5 Hz, 3H).

EXAMPLE 2(266)

8-(N-cyclopropylmethyl-N-(2-methoxyethyl)amino)-2-methyl-3-(2-methyl-4-methoxyphenyl)-5,7-dihydro-furo[3,4-d]pyrazolo[1,5-a]pyrimidine hydrochloride

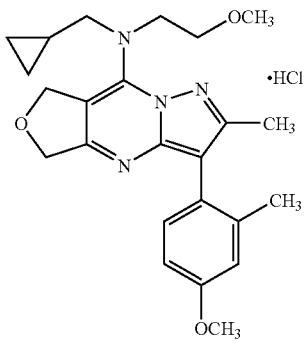

TLC: Rf 0.29 (hexane:ethyl acetate=2:1);

NMR (300 MHz, CDCl$_3$): δ 7.16 (d, J=8.1 Hz, 1H), 6.86 (d, J=2.4 Hz, 1H), 6.80 (dd, J=8.1, 2.4 Hz, 1H), 5.25 (s, 2H), 4.90 (s, 2H), 4.05 (t, J=5.4 Hz, 2H), 3.83 (s, 3H), 3.56 (t, J=5.4 Hz, 2H), 3.48 (d, J=6.9 Hz, 2H), 3.29 (s, 3H), 2.34 (s, 3H), 2.17 (s, 3H), 1.04 (m, 1H), 0.56 (m, 2H), 0.22 (m, 2H).

EXAMPLE 2(267)

8-(N-propyl-N-(4-trifluoromethyloxyphenyl)methylamino)-2-methyl-3-(2-methyl-4-methoxyphenyl)-5,7-dihydro-furo[3,4-d]pyrazolo[1,5-a]pyrimidine hydrochloride

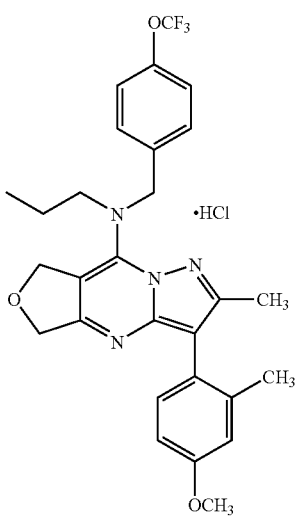

TLC: Rf 0.51 (hexane:ethyl acetate=2:1);

NMR (300 MHz, CDCl$_3$): δ 7.36 (brd, J=8.1 Hz, 2H), 7.18 (brd, J=8.1 Hz, 2H), 7.17 (d, J=8.4 Hz, 1H), 6.88 (d, J=2.4 Hz, 1H), 6.81 (dd, J=8.4, 2.4 Hz, 1H), 5.13 (brs, 2H), 4.97 (brs, 2H), 4.92 (brs, 2H), 3.83 (s, 3H), 3.34 (m, 2H), 2.36 (s, 3H), 2.18 (s, 3H), 1.64 (m, 2H), 0.90 (t, J=7.2 Hz, 3H).

EXAMPLE 2(268)

8-(N-propyl-N-(4-fluorophenyl)methylamino)-2-methyl-3-(2-methyl-4-methoxyphenyl)-5,7-dihydro-furo[3,4-d]pyrazolo[1,5-a]pyrimidine hydrochloride

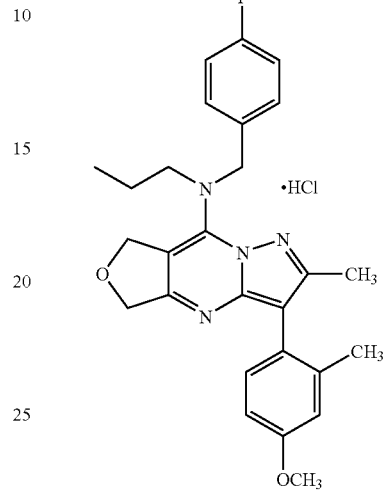

TLC: Rf 0.53 (hexane:ethyl acetate=2:1);

NMR (300 MHz, CDCl$_3$): δ 7.32-7.22 (m, 2H), 7.17 (brd, J=8.7 Hz, 1H), 7.02 (m, 2H), 6.88 (d, J=2.4 Hz, 1H), 6.82 (brd, J=8.7 Hz, 1H), 5.11 (brs, 2H), 4.95 (brs, 4H), 3.83 (s, 3H), 3.34 (m, 2H), 2.36 (s, 3H), 2.19 (s, 3H), 1.65 (m, 2H), 0.90 (t, J=6.9 Hz, 3H).

EXAMPLE 2(269)

8-(3-pentylamino)-2-methyl-3-(2-chloro-4-methylthiophenyl)-6,7-dihydro-5H-cyclopenta[d]pyrazolo[1,5-a]pyrimidine hydrochloride

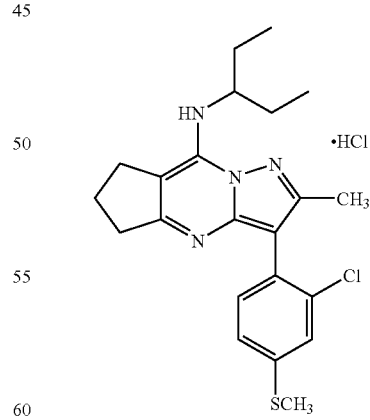

TLC: Rf 0.64 (hexane:ethyl acetate=2:1);

NMR (300 MHz, CDCl$_3$): δ 7.40-7.34 (m, 2H), 7.33-7.24 (m, 2H), 3.99 (m, 1H), 3.66-3.35 (m, 2H), 3.13 (t, J=7.5 Hz, 2H), 2.52 (s, 3H), 2.35 (s, 3H), 2.30 (m, 2H), 1.94-1.64 (m, 4H), 1.10-1.00 (m, 6H).

EXAMPLE 2(270)

8-(N-cyclopropylmethyl-N-(2-butynyl)amino)-2-methyl-3-(2-methyl-4-methoxyphenyl)-5,7-dihydro-furo[3,4-d]pyrazolo[1,5-a]pyrimidine hydrochloride

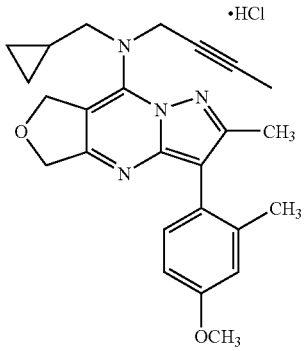

TLC: Rf 0.52 (hexane:ethyl acetate=2:1);
NMR (300 MHz, CDCl₃): δ 7.14 (d, J=8.1 Hz, 1H), 6.88 (d, J=2.7 Hz, 1H), 6.81 (dd, J=8.1, 2.7 Hz, 1H), 5.37 (s, 2H), 5.05 (s, 2H), 4.58 (s, 2H), 3.83 (s, 3H), 3.62 (m, 2H), 2.35 (s, 3H), 2.17 (s, 3H), 1.84 (s, 3H), 1.20 (m, 1H), 0.63 (m, 2H), 0.36 (m, 2H).

EXAMPLE 2(271)

8-(N-(2-methoxyethyl)-N-(2-butynyl)amino)-2-methyl-3-(2-methyl-4-methoxyphenyl)-5,7-dihydro-furo[3,4-d]pyrazolo[1,5-a]pyrimidine hydrochloride

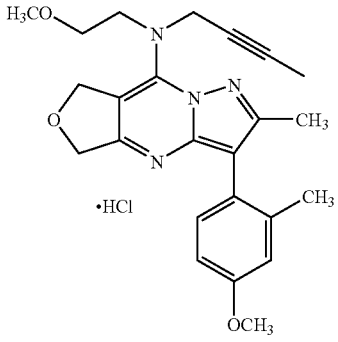

TLC: Rf 0.29 (hexane:ethyl acetate=2:1);
NMR (300 MHz, CDCl₃): δ 7.13 (d, J=8.1 Hz, 1H), 6.87 (d, J=2.4 Hz, 1H), 6.81 (dd, J=8.1, 2.4 Hz, 1H), 5.39 (s, 2H), 5.06 (s, 2H), 4.42 (s, 2H), 4.06 (m, 2H), 3.83 (s, 3H), 3.81 (m, 2H), 3.37 (s, 3H), 2.33 (s, 3H), 2.17 (s, 3H), 1.85 (s, 3H).

EXAMPLE 2(272)

8-(N-(2-methoxyethyl)-N-(2-butynyl)amino)-2-methyl-3-(2-chloro-4-methoxyphenyl)-5,7-dihydro-furo[3,4-d]pyrazolo[1,5-a]pyrimidine hydrochloride

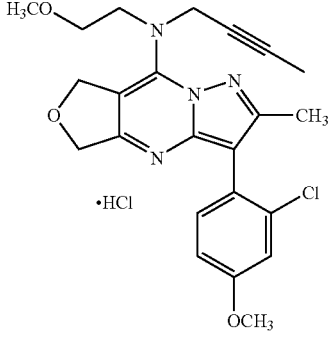

TLC: Rf 0.39 (hexane:ethyl acetate=2:1);
NMR (300 MHz, CDCl₃): δ 7.28 (d, J=8.4 Hz, 1H), 7.06 (d, J=2.4 Hz, 1H), 6.89 (dd, J=8.4, 2.4 Hz, 1H), 5.37 (s, 2H), 4.92 (s, 2H), 4.36 (m, 2H), 3.95 (t, J=5.4 Hz, 2H), 3.83 (s, 3H), 3.76 (t, J=5.4 Hz, 2H), 3.36 (s, 3H), 2.37 (s, 3H), 1.83 (s, 3H).

EXAMPLE 2(273)

8-(N-(2-methoxyethyl)-N-(2-butynyl)amino)-2-methyl-3-(2-chloro-4-methoxyphenyl)-6,7-dihydro-5H-cyclopenta[d]pyrazolo[1,5-a]pyrimidine hydrochloride

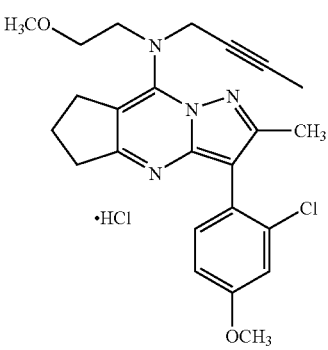

TLC: Rf 0.44 (hexane:ethyl acetate=2:1);
NMR (300 MHz, CDCl₃): δ 7.32 (d, J=8.4 Hz, 1H), 7.06 (d, J=2.7 Hz, 1H), 6.93 (dd, J=8.4, 2.7 Hz, 1H), 4.53 (m, 2H), 4.18 (m, 2H), 3.84 (s, 3H), 3.81 (t, J=4.8 Hz, 2H), 3.36 (s, 3H), 3.30 (m, 2H), 3.20 (t, J=7.2 Hz, 2H), 2.34 (s, 3H), 2.22 (quint, J=7.2 Hz, 2H), 1.86 (t, J=2.4 Hz, 3H).

EXAMPLE 2(274)

8-(N-propyl-N-(5-methylfuran-2-yl)methylamino)-2-methyl-3-(2-chloro-4-methoxyphenyl)-6,7-dihydro-5H-cyclopenta[d]pyrazolo[1,5-a]pyrimidine

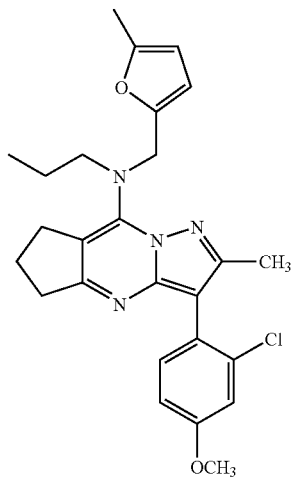

TLC: Rf 0.53 (hexane:ethyl acetate=2:1);
NMR (300 MHz, CDCl₃): δ 7.32 (d, J=8.4 Hz, 1H), 7.06 (d, J=2.7 Hz, 1H), 6.89 (dd, J=2.7, 8.4 Hz, 1H), 5.99 (d, J=3.0 Hz, 1H), 5.85 (dd, J=1.6, 3.0 Hz, 1H), 4.78 (s, 2H), 3.84 (s, 3H), 3.35 (m, 2H), 2.90 (t, J=7.5 Hz, 2H), 2.81 (t, J=7.2 Hz, 2H), 2.39 (s, 3H), 2.22 (m, 3H), 2.07 (m, 2H), 1.62 (m, 2H), 0.91 (t, J=7.5 Hz, 3H).

EXAMPLE 2(275)

8-(N-benzyl-N-cyclopropylamino)-2-methyl-3-(2-chloro-4-methoxyphenyl)-6,7-dihydro-5H-cyclopenta[d]pyrazolo[1,5-a]pyrimidine hydrochloride

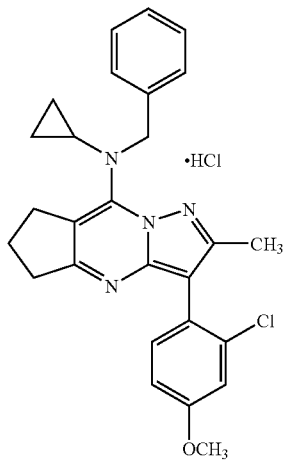

TLC: Rf 0.49 (hexane:ethyl acetate=2:1);

NMR (300 MHz, CDCl$_3$): δ 7.42-7.30 (m, 4H), 7.25-7.15 (m, 2H), 7.09 (d, J=2.4 Hz, 1H), 7.00-6.94 (m, 1H), 5.39 (d, J=14.7 Hz, 1H), 5.27 (d, J=14.7 Hz, 1H), 3.85 (s, 3H), 3.70-3.32 (m, 2H), 3.12 (m, 2H), 2.96 (m, 1H), 2.37 (s, 3H), 2.21 (m, 2H), 1.20-0.92 (m, 4H).

EXAMPLE 2(276)

8-(N-benzyl-N-cyclopropylamino)-2-methyl-3-(2-chloro-4-methoxyphenyl)-5,7-dihydro-furo[3,4-d]pyrazolo[1,5-a]pyrimidine hydrochloride

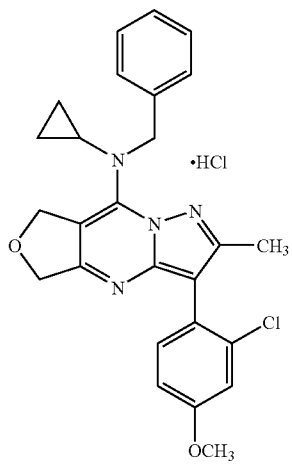

TLC: Rf 0.42 (hexane:ethyl acetate=2:1);

NMR (300 MHz, CDCl$_3$): δ 7.32 (d, J=8.4 Hz, 1H), 7.30-7.26 (m, 3H), 7.15-7.09 (m, 2H), 7.08 (d, J=2.4 Hz, 1H), 6.91 (dd, J=8.4, 2.4 Hz, 1H), 5.20 (s, 2H), 5.19 (s, 2H), 4.91 (s, 2H), 3.84 (s, 3H), 2.56 (m, 1H), 2.41 (s, 3H), 0.92-0.78 (m, 4H).

EXAMPLE 2(277)

8-(N-benzyl-N-cyclopropylamino)-2-methyl-3-(2-methyl-4-methoxyphenyl)-5,7-dihydro-furo[3,4-d]pyrazolo[1,5-a]pyrimidine hydrochloride

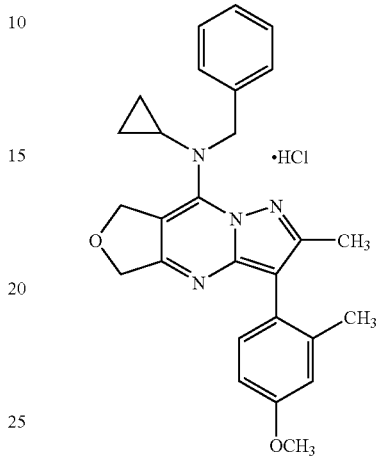

TLC: Rf 0.40 (hexane:ethyl acetate=2:1);

NMR (300 MHz, CDCl$_3$): δ 7.33-7.19 (m, 3H), 7.19 (d, J=8.1 Hz, 1H), 7.14-7.08 (m, 2H), 6.88 (d, J=2.7 Hz, 1H), 6.82 (dd, J=8.1, 2.7 Hz, 1H), 5.32-5.12 (m, 2H), 5.19 (s, 2H), 4.89 (s, 2H), 3.83 (s, 3H), 2.57 (m, 1H), 2.38 (s, 3H), 2.18 (s, 3H), 0.92-0.78 (m, 4H).

EXAMPLE 2(278)

8-(N-cyclopropylmethyl-N-(2-methoxyethyl)amino)-2-methyl-3-(2-chloro-4-methoxyphenyl)-5,7-dihydro-furo[3,4-d]pyrazolo[1,5-a]pyrimidine hydrochloride

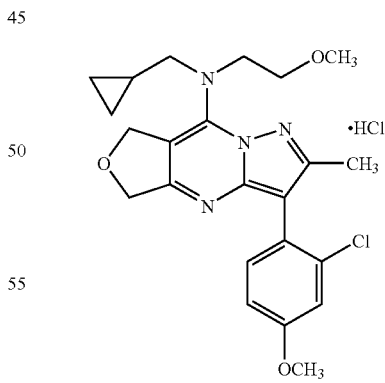

TLC: Rf 0.30 (hexane:ethyl acetate=2:1);

NMR (300 MHz, CDCl$_3$): δ 7.33 (d, J=8.4 Hz, 1H), 7.08 (d, J=2.4 Hz, 1H), 6.94 (dd, J=8.4, 2.4 Hz, 1H), 5.30 (m) and 5.27 (s) total 4H, 4.32 (m, 2H), 3.84 (s, 3H), 3.72-3.67 (m, 4H), 3.31 (s, 3H), 2.36 (s, 3H), 1.11 (m, 1H), 0.71 (m, 2H), 0.36 (m, 2H).

EXAMPLE 2(279)

8-(N-cyclopropylmethyl-N-(2-methoxyethyl)amino)-2-methyl-3-(2-chloro-4-methoxyphenyl)-6,7-dihydro-5H-cyclopenta[d]pyrazolo[1,5-a]pyrimidine hydrochloride

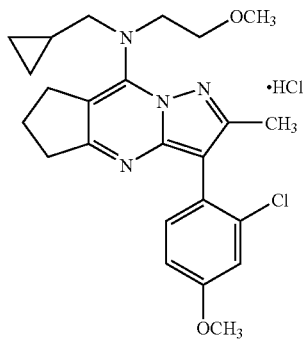

TLC: Rf 0.33 (hexane:ethyl acetate=2:1);

NMR (300 MHz, CDCl$_3$): δ 7.34 (d, J=8.4 Hz, 1H), 7.08 (d, J=2.4 Hz, 1H), 6.95 (dd, J=8.4, 2.4 Hz, 1H), 4.30 (m, 2H), 3.85 (s, 3H), 3.71 (d, J=6.6 Hz, 2H), 3.64 (t, J=5.1 Hz, 2H), 3.41 (m, 2H), 3.29 (s, 3H), 3.07 (t, J=7.2 Hz, 2H), 2.34 (s, 3H), 2.24 (quint, J=7.2 Hz, 2H), 1.09 (m, 1H), 0.65 (m, 2H), 0.31 (m, 2H).

EXAMPLE 2(280)

8-(3-pentylamino)-2-methyl-3-(2-chloro-4-bromophenyl)-6,7-dihydro-5H-cyclopenta[d]pyrazolo[1,5-a]pyrimidine

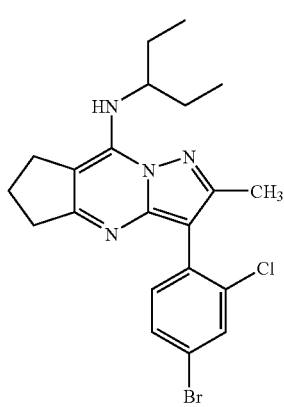

TLC: Rf 0.61 (hexane:ethyl acetate=2:1);

NMR (300 MHz, CDCl$_3$): δ 7.65 (d, J=2.1 Hz, 1H), 7.44 (dd, J=2.1, 8.1 Hz, 1H), 7.28 (d, J=8.1 Hz, 1H), 6.23 (br d, J=10.5 Hz, 1H), 3.81 (m, 1H), 3.09 (t, J=7.2 Hz, 2H), 2.90 (t, J=7.8 Hz, 2H), 2.34 (s, 3H), 2.15 (m, 2H), 1.60-1.82 (m, 4H), 1.01 (t, J=7.5 Hz, 6H).

EXAMPLE 2(281)

8-(3-pentylamino)-2-methyl-3-(2,5-dichloro-4-methoxyphenyl)-6,7-dihydro-5H-cyclopenta[d]pyrazolo[1,5-a]pyrimidine

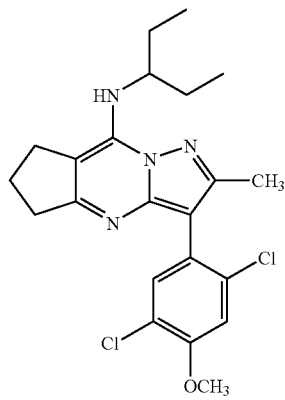

TLC: Rf 0.65 (hexane:ethyl acetate=2:1);

NMR (300 MHz, CDCl$_3$): δ 7.40 (s, 1H), 7.06 (s, 1H), 6.22 (br d, J=10.5 Hz, 1H), 3.92 (s, 3H), 3.81 (m, 1H), 3.08 (t, J=6.9 Hz, 2H), 2.91 (t, J=7.8 Hz, 1H), 2.33 (s, 3H), 2.15 (m, 2H), 1.58-1.82 (m, 4H), 1.01 (t, J=7.5 Hz, 6H).

EXAMPLE 2(282)

8-(3-pentylamino)-2-methyl-3-(2,5-dichloro-4-methoxyphenyl)-5,7-dihydro-furo[3,4-d]pyrazolo[1,5-a]pyrimidine

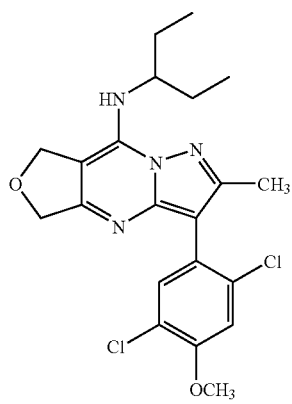

TLC: Rf 0.61 (hexane:ethyl acetate=2:1);

NMR (300 MHz, CDCl$_3$): δ 7.39 (s, 1H), 7.07 (s, 1H), 6.34 (brd, J=10.5 Hz, 1H), 5.29 (m, 2H), 4.93 (m, 2H), 3.93 (s, 3H), 3.24 (m, 1H), 2.36 (s, 3H), 1.67-1.84 (m, 4H), 1.02 (t, J=7.2 Hz, 6H).

EXAMPLE 2(283)

8-(N-cyclopropyl-N-(4-cyanophenyl)methylamino)-2-methyl-3-(2-chloro-4-methoxyphenyl)-5,7-dihydro-furo[3,4-d]pyrazolo[1,5-a]pyrimidine hydrochloride

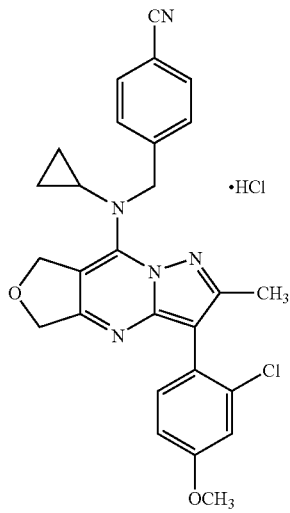

TLC: Rf 0.26 (hexane:ethyl acetate=2:1);

NMR (300 MHz, CDCl$_3$): δ 7.61 (d, J=7.8 Hz, 2H), 7.33 (d, J=7.8 Hz, 2H), 7.30 (d, J=8.7 Hz, 1H), 7.08 (d, J=2.7 Hz, 1H), 6.91 (dd, J=8.7, 2.7 Hz, 1H), 5.27 (s, 2H), 5.25 (s, 2H), 4.93 (s, 2H), 3.84 (s, 3H), 2.58 (m, 1H), 2.40 (s, 3H), 0.84 (m, 4H).

EXAMPLE 2(284)

8-(N-cyclopropyl-N-(4-cyanophenyl)methylamino)-2-methyl-3-(2-methyl-4-methoxyphenyl)-5,7-dihydro-furo[3,4-d]pyrazolo[1,5-a]pyrimidine hydrochloride

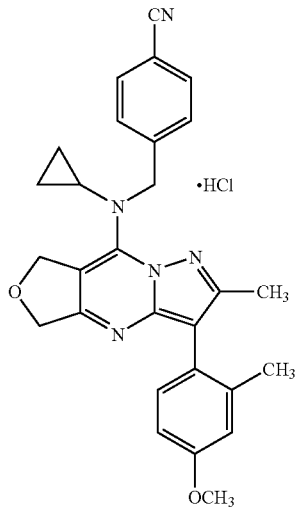

TLC: Rf 0.24 (hexane:ethyl acetate=2:1);

NMR (300 MHz, CDCl$_3$): δ 7.61 (d, J=7.8 Hz, 2H), 7.33 (d, J=7.8 Hz, 2H), 7.17 (d, J=8.1 Hz, 1H), 6.88 (d, J=2.7 Hz, 1H), 6.82 (dd, J=8.1, 2.7 Hz, 1H), 5.40-5.20 (m, 2H), 5.25 (s, 2H), 4.91 (s, 2H), 3.83 (s, 3H), 2.58 (m, 1H), 2.36 (s, 3H), 2.17 (s, 3H), 0.84 (m, 4H).

EXAMPLE 2(285)

8-dibutylamino-2-methyl-3-(2-chloro-4-methoxyphenyl)-6,7-dihydro-5H-cyclopenta[d]pyrazolo[1,5-a]pyrimidine hydrochloride

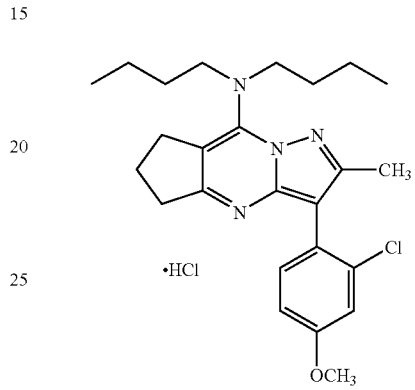

TLC: Rf 0.66 (hexane:ethyl acetate=2:1);

NMR (300 MHz, CDCl$_3$): δ 7.35 (d, J=8.4 Hz, 1H), 7.07 (d, J=2.1 Hz, 1H), 6.94 (dd, J=8.4, 2.1 Hz, 1H), 3.84 (s and m, total 7H), 3.35 (m, 2H), 3.01 (t, J=7.5 Hz, 2H), 2.33 (s, 3H), 2.22 (quint, J=7.5 Hz, 2H), 1.67 (quint, J=7.5 Hz, 4H), 1.36 (sixt, J=7.5 Hz, 2H), 0.95 (t, J=7.5 Hz, 6H).

EXAMPLE 2(286)

8-dibutylamino-2-methyl-3-(2-methyl-4-methoxyphenyl)-5,7-dihydro-furo[3,4-d]pyrazolo[1,5-a]pyrimidine hydrochloride

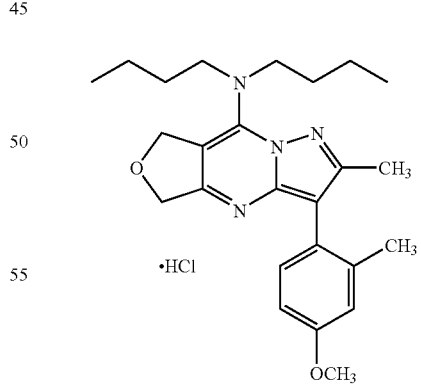

TLC: Rf 0.63 (hexane:ethyl acetate=2:1);

NMR (300 MHz, CDCl$_3$): δ 7.11 (d, J=8.4 Hz, 1H), 6.89 (d, J=2.4 Hz, 1H), 6.83 (dd, J=8.4, 2.4 Hz, 1H), 5.43 (s, 2H), 5.21 (s, 2H), 3.88 (m, 4H), 3.83 (s, 3H), 2.29 (s, 3H), 2.20 (s, 3H), 1.78 (quint, J=7.5 Hz, 4H), 1.42 (sixt, J=7.5 Hz, 4H), 1.00 (t, J=7.5 Hz, 6H).

EXAMPLE 2(287)

8-bis(2-methoxyethyl)amino-2-methyl-3-(2-chloro-4-methoxyphenyl)-6,7-dihydro-5H-cyclopenta[d]pyrazolo[1,5-a]pyrimidine hydrochloride

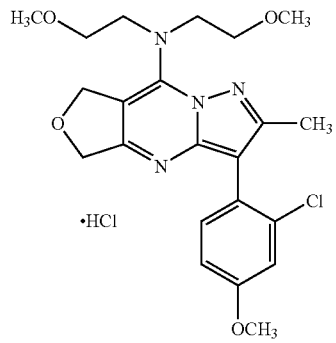

TLC: Rf 0.26 (hexane:ethyl acetate=2:1);

NMR (300 MHz, CDCl$_3$): δ 7.35 (d, J=9.0 Hz, 1H), 7.08 (d, J=2.7 Hz, 1H), 6.96 (dd, J=9.0, 2.7 Hz, 1H), 4.15 (m, 4H), 3.85 (s, 3H), 3.64 (t, J=5.4 Hz, 4H), 3.53 (m, 1H), 3.45 (m, 1H), 3.31 (s, 6H), 3.05 (t, J=7.2 Hz, 2H), 2.34 (s, 3H), 2.22 (quint, J=7.2 Hz, 2H).

EXAMPLE 2(288)

8-(N-ethyl-N-cyclopropylmethylamino)-2-methyl-3-(2-chloro-4-methoxyphenyl)-5,7-dihydro-furo[3,4-d]pyrazolo[1,5-a]pyrimidine hydrochloride

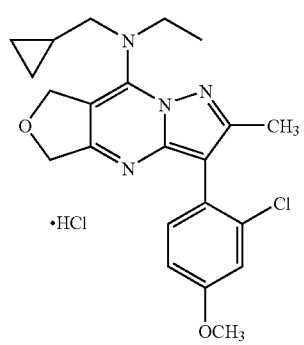

TLC: Rf 0.49 (hexane:ethyl acetate=2:1);

NMR (300 MHz, CDCl$_3$): δ 7.31 (d, J=7.8 Hz, 1H), 7.07 (d, J=2.1 Hz, 1H), 6.92 (m, 1H), 5.28 (s, 2H), 5.11 (s, 2H), 3.84 (s, 3H), 3.81 (m, 2H), 3.69 (m, 2H), 2.37 (s, 3H), 1.33 (s, 3H), 1.09 (m, 1H), 0.60 (m, 2H), 0.24 (m, 2H).

EXAMPLE 2(289)

8-(N-ethyl-N-cyclopropylmethylamino)-2-methyl-3-(2-methyl-4-methoxyphenyl)-5,7-dihydro-furo[3,4-d]pyrazolo[1,5-a]pyrimidine hydrochloride

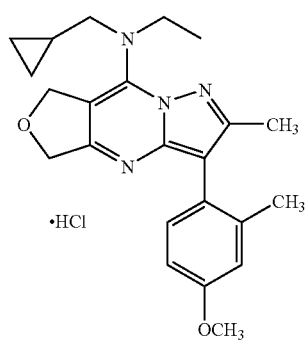

TLC: Rf 0.50 (hexane:ethyl acetate=2:1);

NMR (300 MHz, CDCl$_3$): δ 7.12 (m, 1H), 6.89 (s, 1H), 6.82 (m, 1H), 5.38 (m, 2H), 5.31 (m, 2H), 3.99 (m, 2H), 3.83 (s and m, total 5H), 2.31 (s, 3H), 2.20 (s, 3H), 1.44 (m, 3H), 1.19 (m, 1H), 0.72 (m, 2H), 0.36 (m, 2H).

EXAMPLE 2(290)

8-(N-ethyl-N-cyclopropylmethylamino)-2-methyl-3-(2-chloro-4-methoxyphenyl)-6,7-dihydro-5H-cyclopenta[d]pyrazolo[1,5-a]pyrimidine hydrochloride

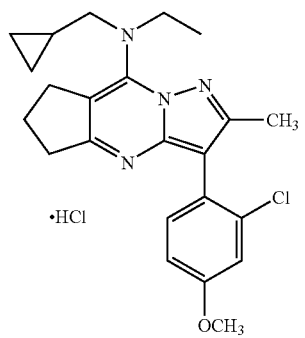

TLC: Rf 0.51 (hexane:ethyl acetate=2:1);

NMR (300 MHz, CDCl$_3$): δ 7.31 (d, J=8.4 Hz, 1H), 7.06 (d, J=2.4 Hz, 1H), 6.89 (dd, J=8.4, 2.4 Hz, 1H), 3.84 (s, 3H), 3.77 (q, J=7.2 Hz, 2H), 3.59 (d, J=6.6 Hz, 2H), 3.04 (t, J=7.5 Hz, 4H), 2.36 (s, 3H), 2.16 (quint, J=7.5 Hz, 2H), 1.23 (t, J=7.2 Hz, 3H), 1.03 (m, 1H), 0.50 (m, 2H), 0.15 (m, 2H).

EXAMPLE 2(291)

8-(N-cyclopropyl-N-(4-cyanophenyl)methylamino)-2-methyl-3-(2-chloro-4-methoxyphenyl)-6,7-dihydro-5H-cyclopenta[d]pyrazolo[1,5-a]pyrimidine hydrochloride

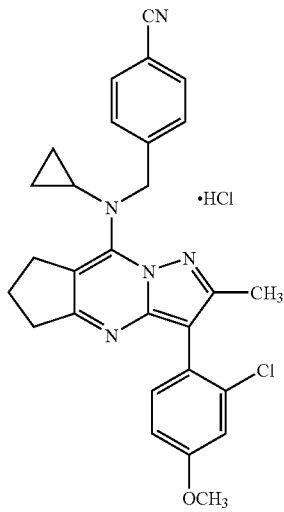

TLC: Rf 0.29 (hexane:ethyl acetate=2:1);

NMR (300 MHz, DMSO-$d_6$): δ 7.83-7.76 (m, 2H), 7.54-7.48 (m, 2H), 7.30 (dd, J=8.7, 1.2 Hz, 1H), 7.16 (m, 1H), 7.02-6.96 (m, 1H), 5.12 (m, 2H), 3.82 (s, 3H), 3.06 (m, 2H), 2.94-2.78 (m, 3H), 2.25 (s, 3H), 2.05 (m, 2H), 0.79-0.70 (m, 2H), 0.61 (m, 2H).

EXAMPLE 2(292)

8-(N-cyclopropylmethyl-N-(4-cyanophenyl)methylamino)-2-methyl-3-(2-chloro-4-methoxyphenyl)-6,7-dihydro-5H-cyclopenta[d]pyrazolo[1,5-a]pyrimidine hydrochloride

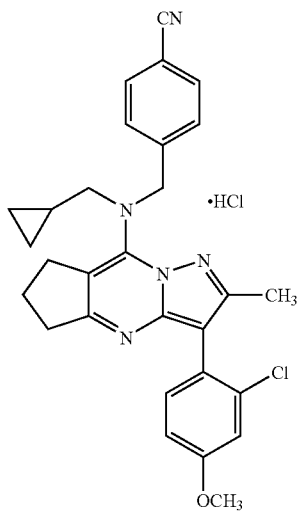

TLC: Rf 0.37 (hexane:ethyl acetate=2:1);

NMR (300 MHz, CDCl$_3$): δ 7.69 (brd, J=7.2 Hz, 2H), 7.49 (brd, J=7.2 Hz, 2H), 7.34 (brd, J=8.4 Hz, 1H), 7.09 (d, J=2.1 Hz, 1H), 6.96 (m, 1H), 5.33 (m, 2H), 3.85 (s, 3H), 3.60 (m, 2H), 3.48 (m, 2H), 3.10 (m, 2H), 2.33 (s, 3H), 2.28 (m, 2H), 1.18-1.02 (m, 1H), 0.70-0.58 (m, 2H), 0.22-0.10 (m, 2H).

EXAMPLE 2(293)

8-(N-cyclopropylmethyl-N-(4-cyanophenyl)methylamino)-2-methyl-3-(2-chloro-4-methoxyphenyl)-5,7-dihydro-furo[3,4-d]pyrazolo[1,5-a]pyrimidine hydrochloride

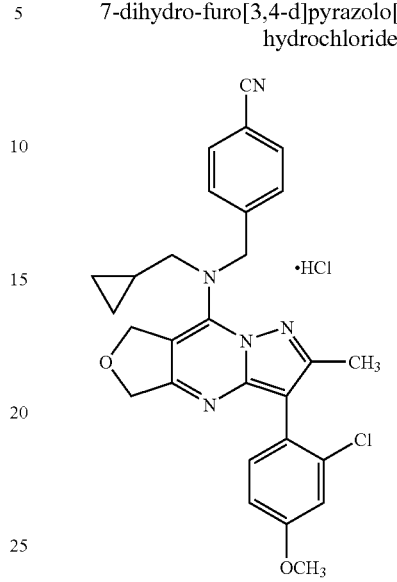

TLC: Rf 0.21 (hexane:ethyl acetate=2:1);

NMR (300 MHz, CDCl$_3$): δ 7.68 (d, J=8.1 Hz, 2H), 7.52 (d, J=8.1 Hz, 2H), 7.31 (d, J=8.7 Hz, 1H), 7.08 (d, J=2.4 Hz, 1H), 6.94 (dd, J=8.7, 2.4 Hz, 1H), 5.26 (m, 4H), 5.14 (s, 2H), 3.84 (s, 3H), 3.45 (d, J=6.6 Hz, 2H), 2.36 (s, 3H), 1.05 (m, 1H), 0.68-0.56 (m, 2H), 0.18-0.10 (m, 2H).

EXAMPLE 2(294)

8-(N-cyclopropylmethyl-N-(4-cyanophenyl)methylamino)-2-methyl-3-(2-methyl-4-methoxyphenyl)-5,7-dihydro-furo[3,4-d]pyrazolo[1,5-a]pyrimidine hydrochloride

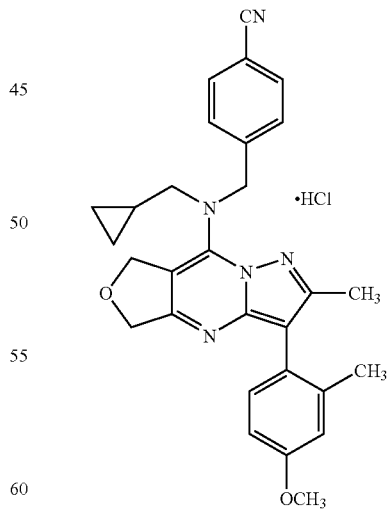

TLC: Rf 0.37 (hexane:ethyl acetate=2:1);

NMR (300 MHz, CDCl$_3$): δ 7.66 (d, J=7.8 Hz, 2H), 7.52 (d, J=7.8 Hz, 2H), 7.15 (d, J=8.1 Hz, 1H), 6.88 (d, J=2.4 Hz, 1H), 6.82 (dd, J=8.1, 2.4 Hz, 1H), 5.25 (s, 2H), 5.13 (s, 2H), 5.00 (s, 2H), 3.83 (s, 3H), 3.41 (d, J=6.6 Hz, 2H), 2.34 (s, 3H), 2.18 (s, 3H), 1.02 (m, 1H), 0.60-0.52 (m, 2H), 0.12-0.06 (m, 2H).

EXAMPLE 2(295)

8-(N-propyl-N-(thiophen-3-yl)methylamino)-2-methyl-3-(2-chloro-4-methoxyphenyl)-5,7-dihydro-furo[3,4-d]pyrazolo[1,5-a]pyrimidine

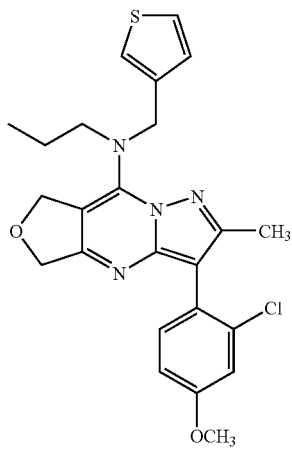

TLC: Rf 0.48 (hexane:ethyl acetate=2:1);

NMR (300 MHz, CDCl$_3$): δ 7.31 (d, J=8.7 Hz, 1H), 7.28 (m, 1H), 7.13 (m, 1H), 7.08 (d, J=2.4 Hz, 1H), 6.98 (dd, J=0.9, 4.8 Hz, 1H), 6.90 (dd, J=2.4, 8.7 Hz, 1H), 5.08 (s, 2H), 4.96 (s, 2H), 4.89 (s, 2H), 3.84 (s, 3H), 3.32 (m, 2H), 2.41 (s, 3H), 1.64 (m, 2H), 0.90 (t, J=7.5 Hz, 3H).

EXAMPLE 2(296)

8-(N-propyl-N-(5-methylthiophen-2-yl)methylamino)-2-methyl-3-(2-chloro-4-methoxyphenyl)-5,7-dihydro-furo[3,4-d]pyrazolo[1,5-a]pyrimidine

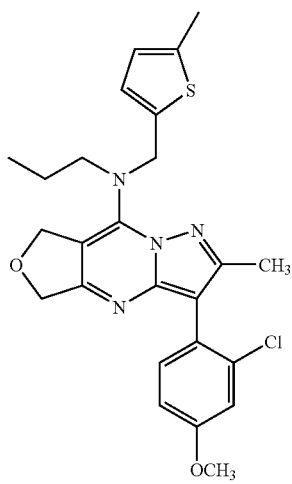

TLC: Rf 0.50 (hexane:ethyl acetate=2:1);

NMR (300 MHz, CDCl$_3$): δ 7.31 (d, J=8.7 Hz, 1H), 7.07 (d, J=2.4 Hz, 1H), 6.90 (dd, J=2.4, 8.7 Hz, 1H), 6.66 (d, J=3.3 Hz, 1H), 6.56 (m, 1H), 5.02-5.17 (m, 4H), 4.90 (s, 2H), 3.84 (s, 3H), 3.27 (m, 2H), 2.44 (s, 3H), 2.42 (s, 3H), 1.64 (m, 2H), 0.92 (t, J=7.5 Hz, 3H).

EXAMPLE 2(297)

8-(N-butyl-N-cyclopropylmethylamino)-2-methyl-3-(2-chloro-4-methoxyphenyl)-6,7-dihydro-5H-cyclopenta[d]pyrazolo[1,5-a]pyrimidine hydrochloride

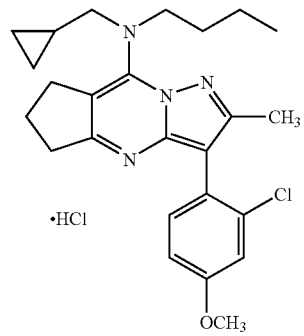

TLC: Rf 0.61 (hexane:ethyl acetate=2:1);

NMR (300 MHz, CDCl$_3$): δ 7.31 (d, J=8.7 Hz, 1H), 7.06 (d, J=2.1 Hz, 1H), 6.89 (dd, J=8.7, 2.1 Hz, 1H), 3.83 (s, 3H), 3.69 (t, J=7.2 Hz, 2H), 3.56 (d, J=7.2 Hz, 2H), 3.02 (m, 4H), 2.36 (s, 3H), 2.15 (quint, J=7.2 Hz, 2H), 1.58 (quint, J=7.5 Hz, 2H), 1.34 (sixt, J=7.5 Hz, 2H), 1.02 (m, 1H), 0.91 (t, J=7.5 Hz, 3H), 0.48 (m, 2H), 0.13 (m, 2H).

EXAMPLE 2(298)

8-(N-butyl-N-cyclopropylmethylamino)-2-methyl-3-(2-chloro-4-methoxyphenyl)-5,7-dihydro-furo[3,4-d]pyrazolo[1,5-a]pyrimidine hydrochloride

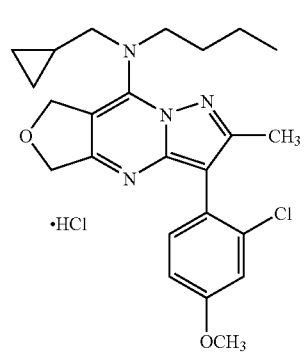

TLC: Rf 0.40 (hexane:ethyl acetate=2:1);

NMR (300 MHz, CDCl$_3$): δ 7.32 (d, J=8.4 Hz, 1H), 7.07 (d, J=2.1 Hz, 1H), 6.93 (dd, J=8.4, 2.1 Hz, 1H), 5.25 (s, 2H), 5.17 (s, 2H), 3.84 (s, 3H), 3.77 (m, 2H), 3.71 (m, 2H), 2.37 (s, 3H), 1.70 (quint, J=7.2 Hz, 2H), 1.39 (sixt, J=7.2 Hz, 2H), 1.10 (m, 1H), 0.96 (t, J=7.2 Hz, 3H), 0.62 (m, 2H), 0.25 (m, 2H).

EXAMPLE 2(299)

8-(N-butyl-N-cyclopropylmethylamino)-2-methyl-3-(2-methyl-4-methoxyphenyl)-5,7-dihydro-furo[3,4-d]pyrazolo[1,5-a]pyrimidine hydrochloride

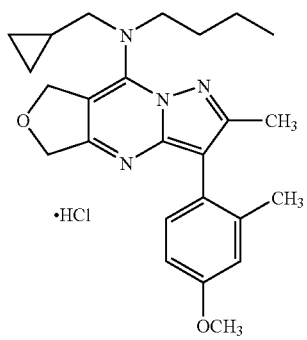

TLC: Rf 0.45 (hexane:ethyl acetate=2:1);

NMR (300 MHz, CDCl$_3$): δ 7.15 (d, J=8.7 Hz, 1H), 6.88 (d, J=2.1 Hz, 1H), 6.81 (dd, J=8.7, 2.1 Hz, 1H), 5.25 (s, 2H), 5.13 (s, 2H), 3.83 (s, 3H), 3.75 (m, 2H), 3.70 (m, 2H), 2.33 (s, 3H), 2.18 (s, 3H), 1.69 (m, 2H), 1.39 (sixt, J=7.5 Hz, 2H), 1.09 (m, 1H), 0.96 (t, J=7.5 Hz, 3H), 0.60 (m, 2H), 0.23 (m, 2H).

EXAMPLE 2(300)

8-(N-propyl-N-(thiophen-3-yl)methylamino)-2-methyl-3-(2-methyl-4-methoxyphenyl)-5,7-dihydro-furo[3,4-d]pyrazolo[1,5-a]pyrimidine

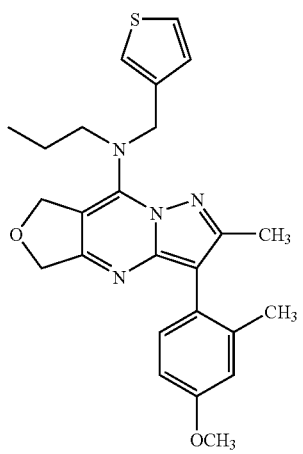

TLC: Rf 0.48 (hexane:ethyl acetate=2:1);

NMR (300 MHz, CDCl$_3$): δ 7.28 (dd, J=2.7, 5.1 Hz, 1H), 7.18 (d, J=8.7 Hz, 1H), 7.13 (m, 1H), 6.97 (dd, J=1.5, 5.1 Hz, 1H), 6.88 (d, J=3.0 Hz, 1H), 6.81 (dd, J=3.0, 8.7 Hz, 1H), 5.07 (s, 2H), 4.96 (s, 2H), 4.87 (s, 2H), 3.83 (s, 3H), 3.31 (m, 2H), 2.37 (s, 3H), 2.19 (s, 3H), 1.64 (m, 2H), 0.91 (t, J=7.2 Hz, 3H).

EXAMPLE 2(301)

8-(N-propyl-N-(5-methylthiophen-2-yl)methylamino)-2-methyl-3-(2-methyl-4-methoxyphenyl)-5,7-dihydro-furo[3,4-d]pyrazolo[1,5-a]pyrimidine

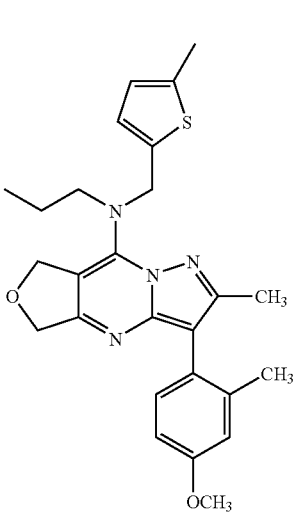

TLC: Rf 0.47 (hexane:ethyl acetate=2:1);

NMR (300 MHz, CDCl$_3$): δ 7.18 (d, J=8.4 Hz, 1H), 6.88 (d, J=3.0 Hz, 1H), 6.81 (dd, J=3.0, 8.4 Hz, 1H), 6.65 (d, J=3.3 Hz, 1H), 6.55 (m, 1H), 5.11 (s, 4H), 4.88 (s, 2H), 3.83 (s, 3H), 3.27 (m, 2H), 2.43 (s, 3H), 2.38 (s, 3H), 2.19 (s, 3H), 1.65 (m, 2H), 0.92 (t, J=7.5 Hz, 3H).

EXAMPLE 2(302)

8-(3-pentylamino)-2-methyl-3-(2-chloro-4-ethoxycarbonylphenyl)-6,7-dihydro-5H-cyclopenta[d]pyrazolo[1,5-a]pyrimidine hydrochloride

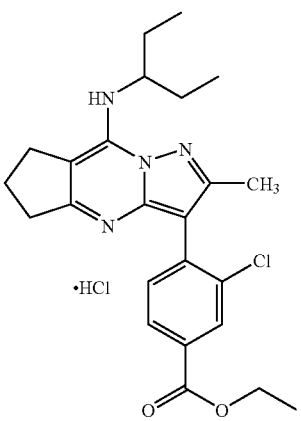

TLC: Rf 0.56 (hexane:ethyl acetate=2:1);

NMR (300 MHz, CDCl$_3$): δ 8.21 (d, J=1.5 Hz, 1H), 8.08 (dd, J=1.5, 7.8 Hz, 1H), 7.56 (d, J=7.8 Hz, 1H), 7.30 (brd, J=10.8 Hz, 1H), 4.38 (q, J=6.9 Hz, 2H), 4.00 (m, 1H), 3.34-3.64 (m, 2H), 3.15 (t, J=6.9 Hz, 2H), 2.35 (s, 3H), 2.31 (m, 2H), 1.65-1.96 (m, 4H), 1.41 (t, J=6.9 Hz, 3H), 1.07 (t, J=7.5 Hz, 3H), 1.06 (t, J=7.5 Hz, 3H).

EXAMPLE 2(303)

8-(N-propyl-N-(2-fluorophenyl)methylamino)-2-methyl-3-(2-chloro-4-methoxyphenyl)-6,7-dihydro-5H-cyclopenta[d]pyrazolo[1,5-a]pyrimidine hydrochloride

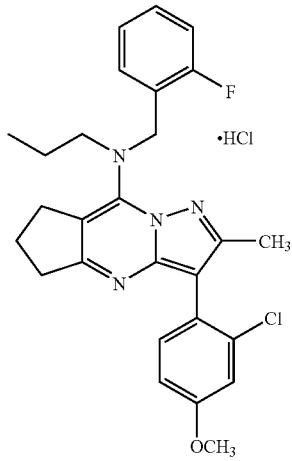

TLC: Rf 0.52 (hexane:ethyl acetate=2:1);

NMR (300 MHz, CDCl$_3$): δ 7.35 (m, 2H), 7.10-6.92 (m, 5H), 5.16 (m, 2H), 3.85 (s, 3H), 3.70 (m, 2H), 3.60-3.34 (m, 2H), 3.03 (m, 2H), 2.35 (s, 3H), 2.26 (m, 2H), 1.75 (m, 2H), 0.94 (m, 3H).

EXAMPLE 2(304)

8-(N-propyl-N-(2-fluorophenyl)methylamino)-2-methyl-3-(2-chloro-4-methoxyphenyl)-5,7-dihydro-furo[3,4-d]pyrazolo[1,5-a]pyrimidine hydrochloride

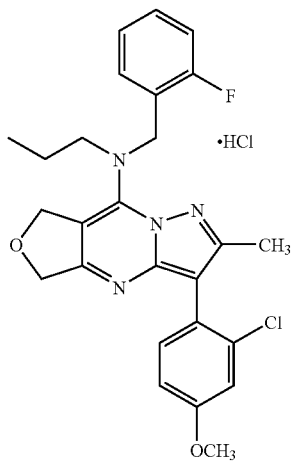

TLC: Rf 0.45 (hexane:ethyl acetate=2:1);

NMR (300 MHz, CDCl$_3$): δ 7.48-7.33 (m, 2H), 7.13-7.04 (m, 4H), 6.97 (dd, J=8.4, 2.4 Hz, 1H), 5.50-5.15 (m, 4H), 5.17 (s, 2H), 3.85 (s, 3H), 3.74-3.60 (m, 2H), 2.37 (s, 3H), 1.82 (sext, J=7.2 Hz, 2H), 0.97 (t, J=7.2 Hz, 3H).

EXAMPLE 2(305)

8-(N-propyl-N-(2-fluorophenyl)methylamino)-2-methyl-3-(2-methyl-4-methoxyphenyl)-5,7-dihydro-furo[3,4-d]pyrazolo[1,5-a]pyrimidine hydrochloride

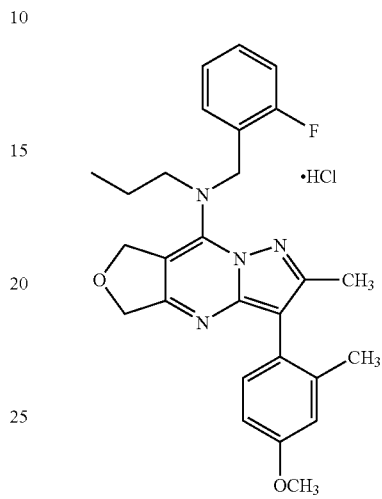

TLC: Rf 0.55 (hexane:ethyl acetate=2:1);

NMR (300 MHz, CDCl$_3$): δ 7.36-7.26 (m, 1H), 7.16 (d, J=8.7 Hz, 1H), 7.09-6.96 (m, 3H), 6.88 (d, J=2.7 Hz, 1H), 6.82 (dd, J=8.7, 2.7 Hz, 1H), 5.13 (s, 2H), 5.03 (s, 2H), 5.02 (s, 2H), 3.83 (s, 3H), 3.41 (m, 2H), 2.35 (s, 3H), 2.19 (s, 3H), 1.69 (sext, J=7.2 Hz, 2H), 0.92 (t, J=7.2 Hz, 3H).

EXAMPLE 2(306)

8-(N-propyl-N-(5-methylthiophen-2-yl)methylamino)-2-methyl-3-(2-chloro-4-methoxyphenyl)-6,7-dihydro-5H-cyclopenta[d]pyrazolo[1,5-a]pyrimidine

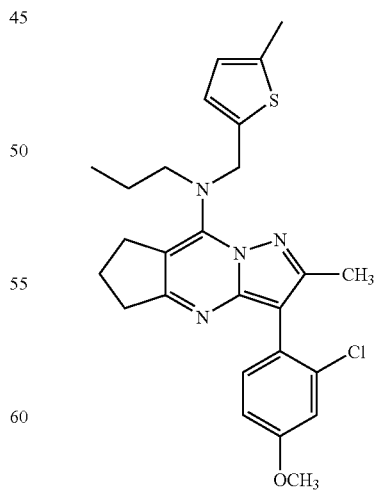

TLC: Rf 0.57 (hexane:ethyl acetate=2:1);

NMR (300 MHz, CDCl$_3$): δ 7.32 (d, J=8.4 Hz, 1H), 7.06 (d, J=2.7 Hz, 1H), 6.89 (dd, J=2.7, 8.4 Hz, 1H), 6.64 (d, J=3.3 Hz,

1H), 6.54 (m, 1H), 4.96 (s, 2H), 3.84 (s, 3H), 3.38 (m, 2H), 2.90 (t, J=7.5 Hz, 2H), 2.86 (t, J=7.2 Hz, 2H), 2.43 (s, 3H), 2.40 (s, 3H), 2.08 (m, 2H), 1.61 (m, 2H), 0.90 (t, J=7.5 Hz, 3H).

EXAMPLE 2(307)

8-(N-propyl-N-(thiophen-3-yl)methylamino)-2-methyl-3-(2-chloro-4-methoxyphenyl)-6,7-dihydro-5H-cyclopenta[d]pyrazolo[1,5-a]pyrimidine

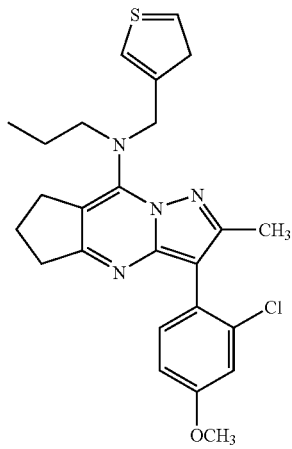

TLC: Rf 0.53 (hexane:ethyl acetate=3:1);
NMR (300 MHz, CDCl$_3$): δ 7.32 (d, J=8.7 Hz, 1H), 7.25 (m, 1H), 7.11 (m, 1H), 7.07 (d, J=2.7 Hz, 1H), 6.95 (dd, J=1.5, 5.1 Hz, 1H), 6.89 (dd, J=2.7, 8.7 Hz, 1H), 4.85 (s, 2H), 3.84 (s, 3H), 3.39 (m, 2H), 2.90 (t, J=7.5 Hz, 2H), 2.81 (t, J=7.2 Hz, 2H), 2.39 (s, 3H), 2.07 (m, 2H), 1.60 (m, 2H), 0.89 (t, J=7.2 Hz, 3H).

EXAMPLE 2(308)

8-(N-ethyl-N-propylamino)-2-methyl-3-(2-chloro-4-methoxyphenyl)-6,7-dihydro-5H-cyclopenta[d]pyrazolo[1,5-a]pyrimidine

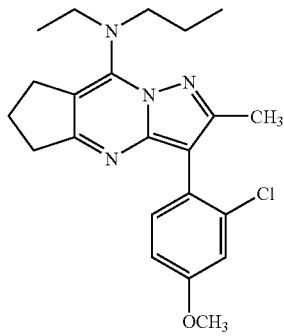

TLC: Rf 0.58 (hexane:ethyl acetate=2:1);
NMR (300 MHz, CDCl$_3$): δ 7.30 (d, J=8.4 Hz, 1H), 7.06 (d, J=2.7 Hz, 1H), 6.88 (dd, J=8.4, 2.7 Hz, 1H), 3.83 (s, 3H), 3.66 (q, J=6.9 Hz, 2H), 3.60-3.50 (m, 2H), 3.02-2.84 (m, 4H), 2.37 (s, 3H), 2.20-2.04 (m, 2H), 1.64-1.52 (m, 2H), 1.17 (t, J=6.9 Hz, 3H), 0.90 (t, J=6.9 Hz, 3H).

EXAMPLE 2(309)

8-(N-ethyl-N-propylamino)-2-methyl-3-(2-methyl-4-methoxyphenyl)-5,7-dihydro-furo[3,4-d]pyrazolo[1,5-a]pyrimidine

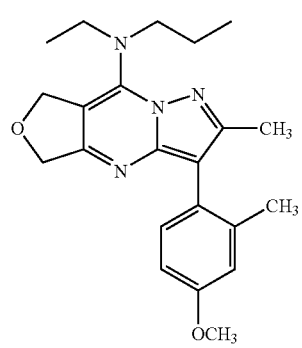

TLC: Rf 0.55 (hexane:ethyl acetate=2:1);
NMR (300 MHz, CDCl$_3$): δ 7.16 (d, J=8.7 Hz, 1H), 6.87 (d, J=2.7 Hz, 1H), 6.80 (dd, J=8.7, 2.7 Hz, 1H), 5.20 (s, 2H), 4.89 (s, 2H), 3.82 (s, 3H), 3.67 (q, J=7.2 Hz, 2H), 3.60-3.48 (m, 2H), 2.34 (s, 3H), 2.18 (s, 3H), 1.72-1.56 (m, 2H), 1.23 (t, J=7.2 Hz, 3H), 0.93 (t, J=7.2 Hz, 3H).

EXAMPLE 2(310)

8-(N-ethyl-N-propylamino)-2-methyl-3-(2-chloro-4-methoxyphenyl)-5,7-dihydro-furo[3,4-d]pyrazolo[1,5-a]pyrimidine

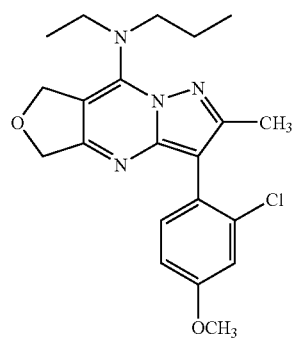

TLC: Rf 0.51 (hexane:ethyl acetate=2:1);
NMR (300 MHz, CDCl$_3$): δ 7.29 (d, J=8.7 Hz, 1H), 7.06 (d, J=2.7 Hz, 1H), 6.89 (dd, J=8.7, 2.7 Hz, 1H), 5.19 (s, 2H), 4.90 (s, 2H), 3.83 (s, 3H), 3.67 (q, J=7.2 Hz, 2H), 3.60-3.48 (m, 2H), 2.38 (s, 3H), 1.70-1.50 (m, 2H), 1.24 (t, J=7.2 Hz, 3H), 0.93 (t, J=7.2 Hz, 3H).

EXAMPLE 2(311)

8-(3-pentylamino)-2-methyl-3-(2-chloro-4-carbamoylphenyl)-6,7-dihydro-5H-cyclopenta[d]pyrazolo[1,5-a]pyrimidine

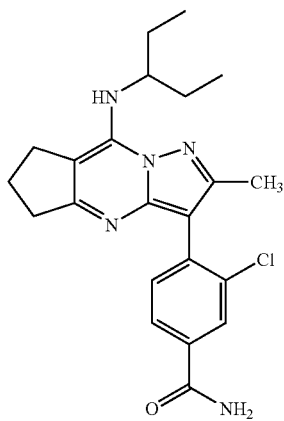

TLC: Rf 0.53 (methylene chloride:ethyl acetate=10:1);

NMR (300 MHz, CDCl$_3$): δ 7.96 (d, J=1.8 Hz, 1H), 7.70 (dd, J=8.1, 1.8 Hz, 1H), 7.50 (d, J=8.1 Hz, 1H), 6.26 (d, J=10.5 Hz, 1H), 3.82 (m, 1H), 3.14-3.05 (m, 2H), 2.91 (t, J=7.8 Hz, 2H), 2.36 (s, 3H), 2.22-2.10 (m, 2H), 1.85-1.50 (m, 4H), 1.02 (t, J=7.5 Hz, 6H).

EXAMPLE 2(312)

8-(3-pentylamino)-2-methyl-3-(2-chloro-4-(N-methylcarbamoyl)phenyl)-6,7-dihydro-5H-cyclopenta[d]pyrazolo[1,5-a]pyrimidine

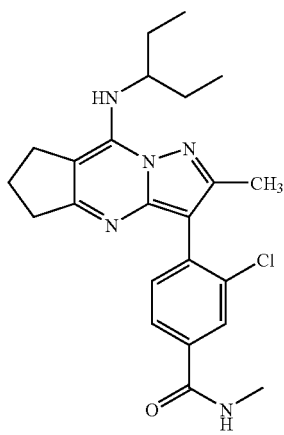

TLC: Rf 0.55 (methylene chloride:ethyl acetate=10:1);

NMR (300 MHz, CDCl$_3$): δ 7.89 (d, J=1.8 Hz, 1H), 7.64 (dd, J=7.8, 1.8 Hz, 1H), 7.45 (d, J=7.8 Hz, 1H), 6.42 (brs, 1H), 6.26 (d, J=10.2 Hz, 1H), 3.82 (m, 1H), 3.14-3.05 (m, 2H), 3.01 (d, J=4.5 Hz, 3H), 2.91 (t, J=7.8 Hz, 2H), 2.35 (s, 3H), 2.22-2.09 (m, 2H), 1.82-1.55 (m, 4H), 1.02 (t, J=7.5 Hz, 6H).

EXAMPLE 2(313)

8-(3-pentylamino)-2-methyl-3-(2-chloro-4-(N,N-dimethylcarbamoyl)phenyl)-6,7-dihydro-5H-cyclopenta[d]pyrazolo[1,5-a]pyrimidine

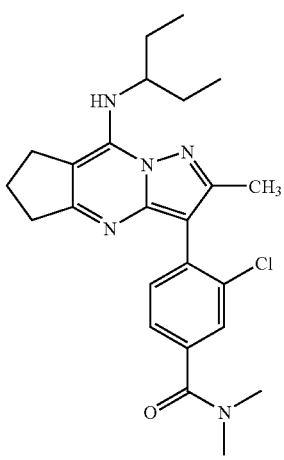

TLC: Rf 0.65 (methylene chloride:ethyl acetate=10:1);

NMR (300 MHz, CDCl$_3$): δ 7.56 (d, J=1.5 Hz, 1H), 7.46 (d, J=7.8 Hz, 1H), 7.36 (dd, J=7.8, 1.5 Hz, 1H), 6.26 (d, J=9.9 Hz, 1H), 3.82 (m, 1H), 3.17-3.02 (m, 8H), 2.92 (t, J=7.8 Hz, 2H), 2.34 (s, 3H), 2.21-2.06 (m, 2H), 1.85-1.42 (m, 4H), 1.02 (t, J=7.5 Hz, 6H).

EXAMPLE 2(314)

8-(3-pentylamino)-2-methyl-3-(2,6-dimethyl-4-methoxyphenyl)-5,7-dihydro-furo[3,4-d]pyrazolo[1,5-a]pyrimidine

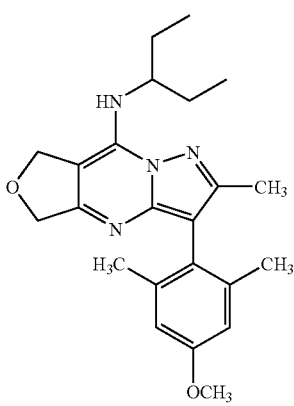

TLC: Rf 0.29 (hexane:ethyl acetate=3:1);

NMR (300 MHz, CDCl$_3$): δ 6.69 (s, 2H), 6.32 (d, J=10.8 Hz, 1H), 5.29 (s, 2H), 4.88 (s, 2H), 3.80 (s, 3H), 3.30-3.18 (m, 1H), 2.22 (s, 3H), 2.04 (s, 6H), 1.83-1.55 (m, 4H), 1.03 (t, J=7.2 Hz, 6H).

EXAMPLE 2(315)

8-(N-ethyl-N-(4-fluorophenyl)methylamino)-2-methyl-3-(2-methyl-4-methoxyphenyl)-5,7-dihydro-furo[3,4-d]pyrazolo[1,5-a]pyrimidine

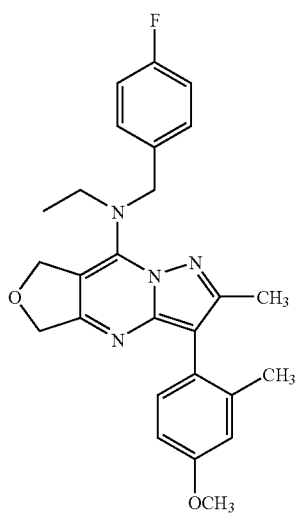

TLC: Rf 0.49 (hexane:ethyl acetate=2:1);
NMR (300 MHz, CDCl$_3$): δ 7.30-7.22 (m, 2H), 7.18 (d, J=8.1 Hz, 1H), 7.06-6.94 (m, 2H), 6.88 (d, J=2.7 Hz, 1H), 6.81 (dd, J=8.1, 2.7 Hz, 1H), 5.09 (s, 2H), 4.96-4.80 (m, 4H), 3.83 (s, 3H), 3.41 (q, J=7.2 Hz, 2H), 2.37 (s, 3H), 2.18 (s, 3H), 1.23 (t, J=7.2 Hz, 3H).

EXAMPLE 2(316)

8-(N-ethyl-N-(4-fluorophenyl)methylamino)-2-methyl-3-(2-chloro-4-methoxyphenyl)-6,7-dihydro-5H-cyclopenta[d]pyrazolo[1,5-a]pyrimidine

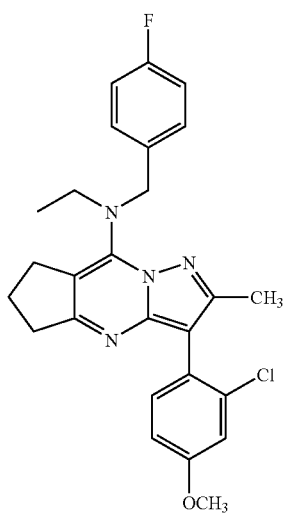

TLC: Rf 0.42 (hexane:ethyl acetate=2:1);
NMR (300 MHz, CDCl$_3$): δ 7.32 (d, J=8.4 Hz, 1H), 7.26-7.22 (m, 2H), 7.07 (d, J=2.4 Hz, 1H), 7.04-6.94 (m, 2H), 6.90 (dd, J=8.4, 2.4 Hz, 1H), 4.81 (s, 2H), 3.84 (s, 3H), 3.47 (q, J=7.2 Hz, 2H), 2.90 (t, J=7.2 Hz, 2H), 2.82 (t, J=7.2 Hz, 2H), 2.40 (s, 3H), 2.16-1.98 (m, 2H), 1.18 (t, J=7.2 Hz, 3H).

EXAMPLE 2(317)

8-(N-ethyl-N-(4-fluorophenyl)methylamino)-2-methyl-3-(2-chloro-4-methoxyphenyl)-5,7-dihydro-furo[3,4-d]pyrazolo[1,5-a]pyrimidine

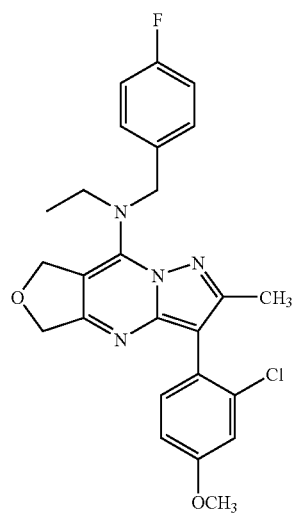

TLC: Rf 0.46 (hexane:ethyl acetate=2:1);
NMR (300 MHz, CDCl$_3$): δ 7.31 (d, J=8.1 Hz, 1H), 7.30-7.24 (m, 2H), 7.08 (d, J=2.7 Hz, 1H), 7.06-6.94 (m, 2H), 6.91 (dd, J=8.1, 2.7 Hz, 1H), 5.10 (s, 2H), 4.90 (s, 2H), 4.89 (s, 2H), 3.84 (s, 3H), 3.42 (q, J=7.2 Hz, 2H), 2.40 (s, 3H), 1.22 (t, J=7.2 Hz, 3H).

EXAMPLE 2(318)

8-(3-pentylamino)-2-methyl-3-(2-chloro-4,6-dimethoxyphenyl)-6,7-dihydro-5H-cyclopenta[d]pyrazolo[1,5-a]pyrimidine

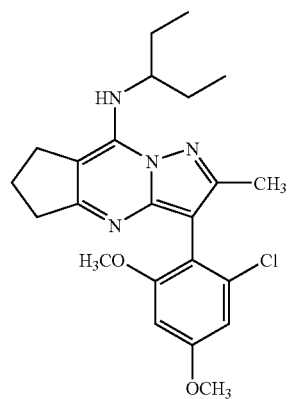

TLC: Rf 0.26 (hexane:ethyl acetate 2:1);
NMR (300 MHz, CDCl$_3$): δ 6.67 (d, J=2.7 Hz, 1H), 6.45 (d, J=2.7 Hz, 1H), 6.23 (d, J=10.8 Hz, 1H), 3.82 (s, 3H), 3.80 (m, 1H), 3.70 (s, 3H), 3.07 (m, 2H), 2.90 (m, 2H), 2.25 (s, 3H), 2.13 (m, 2H), 1.52-1.80 (m, 4H), 1.02 (t, J=7.2 Hz, 3H), 1.01 (t, J=7.2 Hz, 3H).

EXAMPLE 2(319)

8-(3-pentylamino)-2-methyl-3-(2-chloro-4,6-dimethoxyphenyl)-5,7-dihydro-furo[3,4-d]pyrazolo[1,5-a]pyrimidine

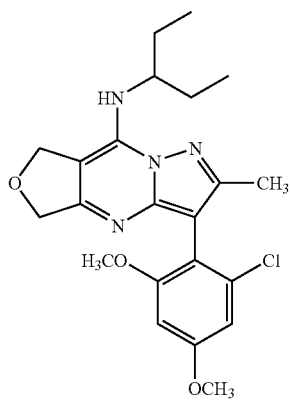

TLC: Rf 0.22 (hexane:ethyl acetate=2:1);

NMR (300 MHz, CDCl$_3$): δ 6.68 (d, J=2.7 Hz, 1H), 6.47 (d, J=2.7 Hz, 1H), 6.34 (d, J=10.8 Hz, 1H), 5.28 (s, 2H), 4.92 (d, J=13.5 Hz, 1H), 4.90 (d, J=13.5 Hz, 1H), 3.83 (s, 3H), 3.71 (s, 3H), 3.23 (m, 1H), 2.28 (s, 3H), 1.53-1.82 (m, 4H), 1.02 (t, J=7.5 Hz, 3H), 1.01 (t, J=7.5 Hz, 3H).

EXAMPLE 2(320)

8-(3-pentylamino)-2-methyl-3-(2-chloro-4-aminophenyl)-6,7-dihydro-5H-cyclopenta[d]pyrazolo[1,5-a]pyrimidine

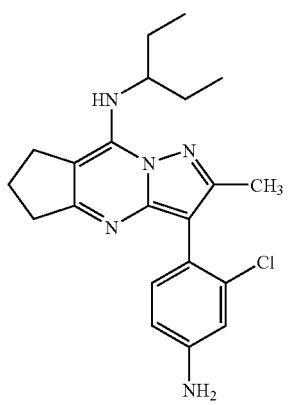

TLC: Rf 0.22 (hexane:ethyl acetate=1:1);

NMR (300 MHz, CDCl$_3$): δ 7.16 (d, J=8.4 Hz, 1H), 6.82 (d, J=2.1 Hz, 1H), 6.63 (dd, J=8.4, 2.1 Hz, 1H), 6.21 (d, J=10.2 Hz, 1H), 3.87-3.62 (m, 3H), 3.12-3.03 (m, 2H), 2.95-2.86 (m, 2H), 2.34 (s, 3H), 2.20-2.07 (m, 2H), 1.85-1.50 (m, 4H), 1.01 (t, J=7.5 Hz, 6H).

EXAMPLE 2(321)

8-(4-heptylamino)-2-methyl-3-(2-methyl-4-methoxyphenyl)-5,7-dihydro-furo[3,4-d]pyrazolo[1,5-a]pyrimidine

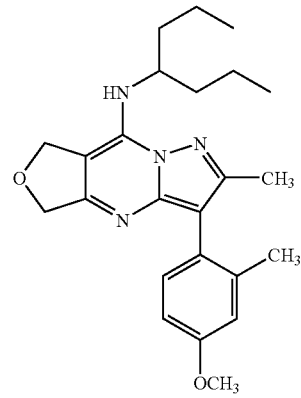

TLC: Rf 0.48 (hexane:ethyl acetate=2:1);

NMR (300 MHz, CDCl$_3$): δ 7.15 (d, J=8.7 Hz, 1H), 6.86 (d, J=2.7 Hz, 1H), 6.79 (dd, J=8.7, 2.7 Hz, 1H), 6.32 (d, J=10.8 Hz, 1H), 5.29 (s, 2H), 4.90 (s, 2H), 3.82 (s, 3H), 3.40 (m, 1H), 2.32 (s, 3H), 2.18 (s, 3H), 1.78-1.38 (m, 8H), 0.95 (t, J=7.2 Hz, 6H).

EXAMPLE 2(322)

8-(3-pentylamino)-2-methyl-3-(2-chloro-4-methylaminophenyl)-6,7-dihydro-5H-cyclopenta[d]pyrazolo[1,5-a]pyrimidine

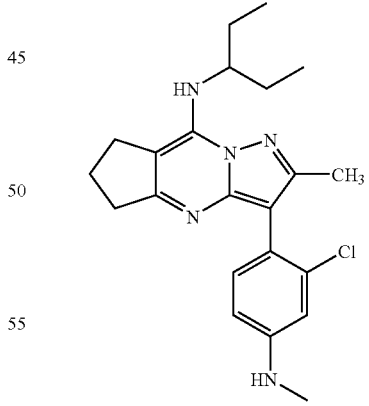

TLC: Rf 0.45 (hexane:ethyl acetate=1:1);

NMR (300 MHz, CDCl$_3$): δ 7.18 (d, J=8.4 Hz, 1H), 6.73 (d, J=2.4 Hz, 1H), 6.56 (dd, J=8.4, 2.4 Hz, 1H), 6.21 (d, J=10.5 Hz, 1H), 3.88-3.70 (m, 2H), 3.12-3.02 (m, 2H), 2.95-2.80 (m, 2H), 2.85 (s, 3H), 2.34 (s, 3H), 2.20-2.05 (m, 2H), 1.80-1.50 (m, 4H), 1.01 (t, J=7.2 Hz, 6H).

EXAMPLE 2(323)

8-(3-pentylamino)-2-methyl-3-(2-formyl-4-methoxyphenyl)-6,7-dihydro-5H-cyclopenta[d]pyrazolo[1,5-a]pyrimidine

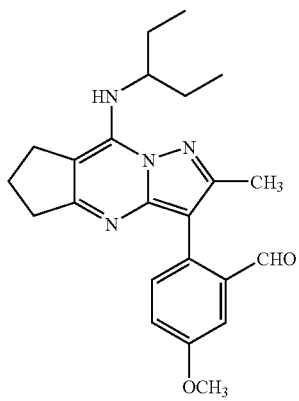

TLC: Rf 0.26 (hexane:ethyl acetate=3:1);

NMR (300 MHz, CDCl$_3$): δ 9.85 (s, 1H), 7.55 (d, J=2.7 Hz, 1H), 7.38 (d, J=8.4 Hz, 1H), 7.22 (dd, J=8.4, 2.7 Hz, 1H), 6.23 (d, J=9.6 Hz, 1H), 3.93-3.74 (m) and 3.89 (s) total 4H, 3.09 (t, J=7.5 Hz, 2H), 2.88 (t, J=7.5 Hz, 2H), 2.39 (s, 3H), 2.14 (quint, J=7.5 Hz, 2H), 1.83-1.50 (m, 4H), 1.02 (t, J=7.5 Hz, 6H).

EXAMPLE 2(324)

8-(3-pentylamino)-2-methyl-3-(2-cyano-4-methoxyphenyl)-6,7-dihydro-5H-cyclopenta[d]pyrazolo[1,5-a]pyrimidine

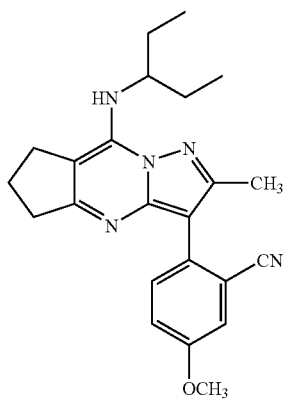

TLC: Rf 0.54 (hexane:ethyl acetate=1:1);

NMR (300 MHz, CDCl$_3$): δ 7.46 (d, J=9.0 Hz, 1H), 7.24 (d, J=2.4 Hz, 1H), 7.18 (dd, J=9.0, 2.4 Hz, 1H), 6.24 (d, J=10.5 Hz, 1H), 3.88-3.73 (m) and 3.86 (s) total 4H, 3.09 (t, J=7.2 Hz, 2H), 2.92 (t, J=7.2 Hz, 2H), 2.43 (s, 3H), 2.15 (quint, J=7.2 Hz, 2H), 1.80-1.50 (m, 4H), 1.02 (t, J=7.2 Hz, 6H).

EXAMPLE 2(325)

8-(3-pentylamino)-2-methyl-3-(2-ethyl-4-methoxyphenyl)-6,7-dihydro-5H-cyclopenta[d]pyrazolo[1,5-a]pyrimidine

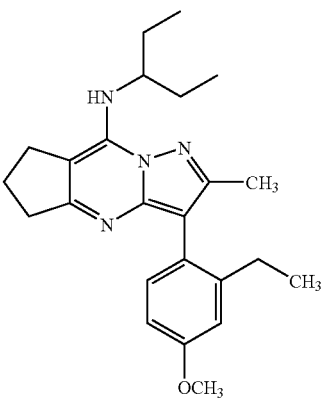

TLC: Rf 0.30 (hexane:ethyl acetate=3:1);

NMR (300 MHz, CDCl$_3$): δ 7.12 (d, J=8.4 Hz, 1H), 6.88 (d, J=2.4 Hz, 1H), 6.77 (dd, J=8.4, 2.4 Hz, 1H), 6.21 (d, J=10.5 Hz, 1H), 3.83-3.75 (m) and 3.83 (s) total 4H, 3.08 (t, J=7.2 Hz, 2H), 2.88 (t, J=7.2 Hz, 2H), 2.52 (q, J=7.8 Hz, 2H), 2.28 (s, 3H), 2.13 (quint, J=7.2 Hz, 2H), 1.83-1.50 (m, 4H), 1.10-0.98 (m, 9H).

EXAMPLE 2(326)

8-(4-heptylamino)-3-(2-chloro-4-methoxyphenyl)-6,7-dihydro-5H-cyclopenta[d]pyrazolo[1,5-a]pyrimidine hydrochloride

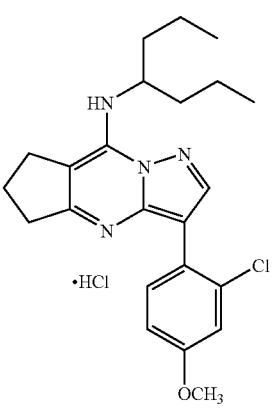

TLC: Rf 0.51 (hexane:ethyl acetate=3:1);

NMR (300 MHz, CDCl$_3$): δ 8.20 (s, 1H), 7.65 (d, J=8.4 Hz, 1H), 7.38 (d, J=10.2 Hz, 1H), 7.08-6.97 (m, 2H), 4.15 (m, 1H), 3.84 (s, 3H), 3.61 (m, 2H), 3.16 (m, 2H), 2.33 (m, 2H), 1.88-1.60 (m, 4H), 1.60-1.35 (m, 4H), 0.99 (t, J=7.5 Hz, 6H).

EXAMPLE 2(327)

8-(N,N-dipropylamino)-3-(2-chloro-4-methoxyphenyl)-6,7-dihydro-5H-cyclopenta[d]pyrazolo[1,5-a]pyrimidine

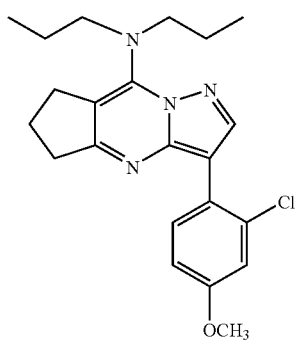

TLC: Rf 0.54 (hexane:ethyl acetate=3:1);

NMR (300 MHz, CDCl$_3$): δ 8.32 (s, 1H), 7.78 (d, J=8.7 Hz, 1H), 7.03 (d, J=2.7 Hz, 1H), 6.91 (dd, J=8.7, 2.7 Hz, 1H), 3.83 (s, 3H), 3.57 (m, 4H), 2.97 (m, 4H), 2.17 (m, 2H), 1.66-1.50 (m, 4H), 0.88 (t, J=7.5 Hz, 6H).

EXAMPLE 2(328)

8-(N,N-dipropylamino)-3-(2-chloro-4-methoxyphenyl)-5,7-dihydro-furo[3,4-d]pyrazolo[1,5-a]pyrimidine

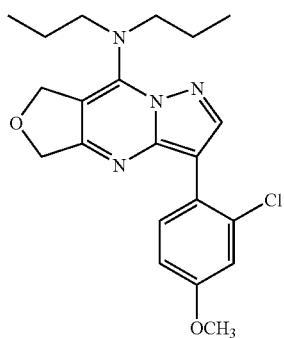

TLC: Rf 0.58 (hexane:ethyl acetate=2:1);

NMR (300 MHz, CDCl$_3$): δ 8.35 (s, 1H), 7.72 (d, J=9.0 Hz, 1H), 7.04 (d, J=2.4 Hz, 1H), 6.91 (dd, J=9.0, 2.4 Hz, 1H), 5.20 (s, 2H), 4.94 (s, 2H), 3.82 (s, 3H), 3.57 (t, J=7.5 Hz, 4H), 1.72-1.46 (m, 4H), 0.90 (t, J=7.2 Hz, 6H).

EXAMPLE 2(329)

8-(N-cyclopropylmethyl-N-propylamino)-3-(2-chloro-4-methoxyphenyl)-5,7-dihydro-furo[3,4-d]pyrazolo[1,5-a]pyrimidine

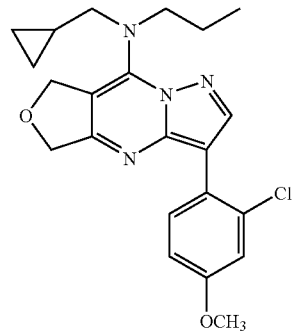

TLC: Rf 0.60 (hexane:ethyl acetate=2:1);

NMR (300 MHz, CDCl$_3$): δ 8.37 (s, 1H), 7.73 (d, J=8.4 Hz, 1H), 7.05 (d, J=2.7 Hz, 1H), 6.92 (dd, J=8.4, 2.7 Hz, 1H), 5.25 (s, 2H), 4.96 (s, 2H), 3.83 (s, 3H), 3.64-3.50 (m, 4H), 1.72-1.56 (m, 2H), 1.04 (m, 1H), 0.93 (t, J=7.5 Hz, 3H), 0.58-0.44 (m, 2H), 0.20-0.08 (m, 2H).

EXAMPLE 2(330)

8-(N-benzyl-N-cyclopropylmethylamino)-3-(2-chloro-4-methoxyphenyl)-5,7-dihydro-furo[3,4-d]pyrazolo[1,5-a]pyrimidine

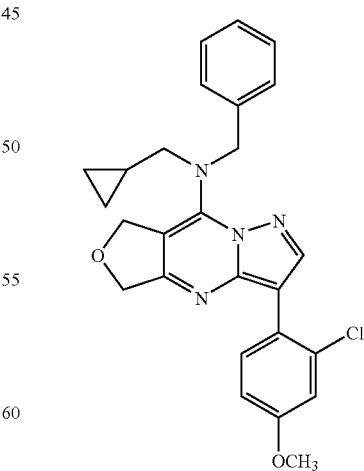

TLC: Rf 0.52 (hexane:ethyl acetate=2:1);

NMR (300 MHz, CDCl$_3$): δ 8.42 (s, 1H), 7.74 (d, J=8.4 Hz, 1H), 7.38-7.20 (m, 5H), 7.06 (d, J=2.7 Hz, 1H), 6.93 (dd,

J=8.4, 2.7 Hz, 1H), 5.25 (s, 2H), 4.96 (s, 2H), 4.95 (s, 2H), 3.84 (s, 3H), 3.43 (d, J=6.6 Hz, 2H), 1.04 (m, 1H), 0.58-0.46 (m, 2H), 0.16-0.04 (m, 2H).

EXAMPLE 2(331)

8-(N-cyclopropylmethyl-N-(4-methylphenyl)methylamino)-3-(2-chloro-4-methoxyphenyl)-5,7-dihydro-furo[3,4-d]pyrazolo[1,5-a]pyrimidine

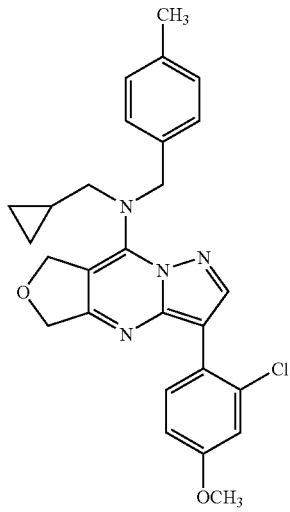

TLC: Rf 0.56 (hexane:ethyl acetate=2:1);

NMR (300 MHz, CDCl₃): δ 8.42 (s, 1H), 7.75 (d, J=8.4 Hz, 1H), 7.19 (d, J=7.8 Hz, 2H), 7.13 (d, J=7.8 Hz, 2H), 7.06 (d, J=2.4 Hz, 1H), 6.93 (dd, J=8.4, 2.4 Hz, 1H), 5.24 (s, 2H), 4.95 (s, 2H), 4.91 (s, 2H), 3.84 (s, 3H), 3.42 (d, J=6.3 Hz, 2H), 2.33 (s, 3H), 1.04 (m, 1H), 0.58-0.46 (m, 2H), 0.18-0.04 (m, 2H).

EXAMPLE 2(332)

8-(N-propyl-N-(2-butynyl)amino)-3-(2-chloro-4-methoxyphenyl)-5,7-dihydro-furo[3,4-d]pyrazolo[1,5-a]pyrimidine

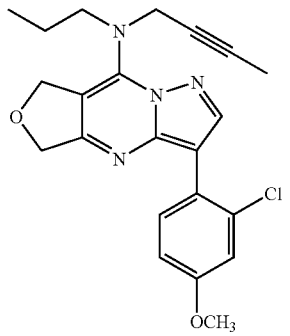

TLC: Rf 0.41 (hexane:ethyl acetate=2:1);

NMR (300 MHz, CDCl₃): δ 8.37 (s, 1H), 7.71 (d, J=8.7 Hz, 1H), 7.05 (d, J=2.7 Hz, 1H), 6.92 (dd, J=8.7, 2.7 Hz, 1H), 5.34 (s, 2H), 4.97 (s, 2H), 4.44 (q, J=2.4 Hz, 2H), 3.83 (s, 3H), 3.52 (m, 2H), 1.82 (t, J=2.4 Hz, 3H), 1.80-1.62 (m, 2H), 0.98 (t, J=7.2 Hz, 3H).

EXAMPLE 2(333)

8-(3-pentylamino)-2-methyl-3-(2-methoxycarbonyl-4-methoxyphenyl)-6,7-dihydro-5H-cyclopenta[d]pyrazolo[1,5-a]pyrimidine hydrochloride

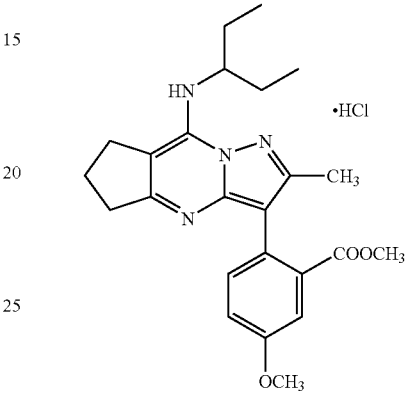

TLC: Rf 0.26 (hexane:ethyl acetate=2:1);

NMR (300 MHz, CDCl₃): δ 7.70 (d, J=2.7 Hz, 1H), 7.34 (d, J=8.4 Hz, 1H), 7.30-7.16 (m) and 7.19 (dd, J=8.4, 2.7 Hz) total 2H, 4.03-3.83 (m) and 3.89 (s) total 4H, 3.77 (s, 3H), 3.54-3.36 (m, 2H), 3.11 (t, J=7.5 Hz, 2H), 2.33-2.00 (m) and 2.25 (s) total 4H, 1.90-1.58 (m, 4H), 1.05 (t, J=7.5 Hz, 6H).

EXAMPLE 2(334)

8-(N-butyl-N-cyclopropylmethylamino)-3-(2-chloro-4-methoxyphenyl)-5,7-dihydro-furo[3,4-d]pyrazolo[1,5-a]pyrimidine

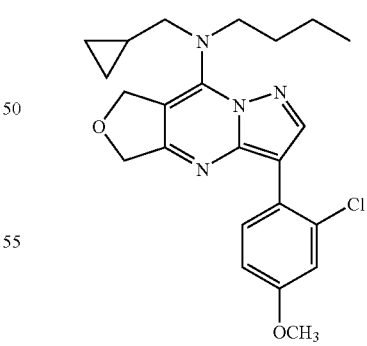

TLC: Rf 0.45 (hexane:ethyl acetate=2:1);

NMR (300 MHz, CDCl₃): δ 8.37 (s, 1H), 7.74 (d, J=9.0 Hz, 1H), 7.05 (d, J=2.7 Hz, 1H), 6.91 (dd, J=9.0, 2.7 Hz, 1H), 5.25 (s, 2H), 4.96 (s, 2H), 3.83 (s, 3H), 3.66-3.52 (m, 4H), 1.66-1.48 (m, 2H), 1.44-1.22 (m, 2H), 1.04 (m, 1H), 0.91 (t, J=7.2 Hz, 3H), 0.60-0.44 (m, 2H), 0.22-0.08 (m, 2H).

EXAMPLE 2(335)

8-(3-pentylamino)-3-(2-chloro-4-methoxyphenyl)-5,7-dihydro-furo[3,4-d]pyrazolo[1,5-a]pyrimidine

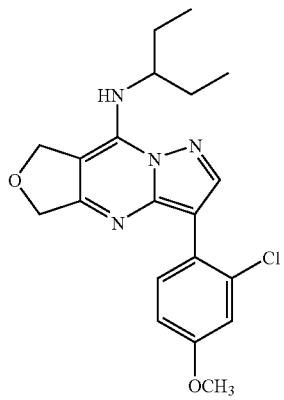

TLC: Rf 0.57 (hexane:ethyl acetate=2:1);

NMR (300 MHz, CDCl$_3$): δ 8.32 (s, 1H), 7.74 (d, J=8.7 Hz, 1H), 7.04 (d, J=2.7 Hz, 1H), 6.91 (dd, J=8.7, 2.7 Hz, 1H), 6.42 (d, J=10.8 Hz, 1H), 5.31 (s, 2H), 4.97 (s, 2H), 3.83 (s, 3H), 3.28 (m, 1H), 1.84-1.54 (m, 4H), 1.01 (t, J=7.2 Hz, 6H).

EXAMPLE 2(336)

8-(N-cyclopropylmethyl-N-(4-fluorophenyl)methylamino)-3-(2-chloro-4-methoxyphenyl)-5,7-dihydro-furo[3,4-d]pyrazolo[1,5-a]pyrimidine

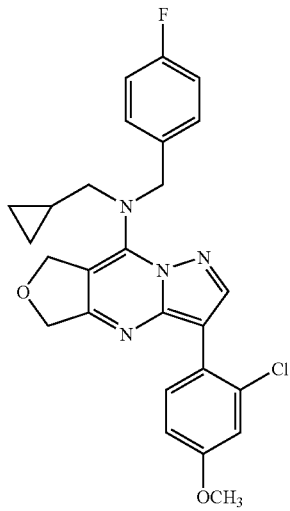

TLC: Rf 0.41 (hexane:ethyl acetate=2:1);

NMR (300 MHz, CDCl$_3$): δ 8.41 (s, 1H), 7.74 (d, J=9.0 Hz, 1H), 7.38-7.24 (m, 2H), 7.12-6.96 (m, 3H), 6.92 (dd, J=9.0, 2.7 Hz, 1H), 5.25 (s, 2H), 4.95 (s, 2H), 4.91 (s, 2H), 3.84 (s, 3H), 3.39 (d, J=6.9 Hz, 2H), 1.02 (m, 1H), 0.60-0.44 (m, 2H), 0.16-0.02 (m, 2H).

EXAMPLE 2(337)

8-(N-cyclopropyl-N-(2-fluorophenyl)methylamino)-2-methyl-3-(2-chloro-4-methoxyphenyl)-6,7-dihydro-5H-cyclopenta[d]pyrazolo[1,5-a]pyrimidine

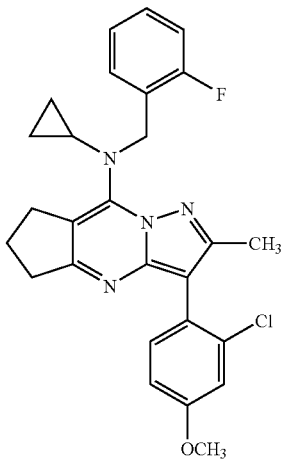

TLC: Rf 0.41 (toluene:ethyl acetate=10:1);

NMR (300 MHz, CDCl$_3$): δ 7.32 (d, J=8.4 Hz, 1H), 7.23 (m, 1H), 7.13-6.97 (m, 3H), 7.06 (d, J=2.7 Hz, 1H), 6.89 (dd, J=8.4, 2.7 Hz, 1H), 5.15 (brs, 2H), 3.84 (s, 3H), 2.98-2.86 (m, 4H), 2.83 (m, 1H), 2.40 (s, 3H), 2.02 (m, 2H), 0.84-0.72 (m, 4H).

EXAMPLE 2(338)

8-(N-cyclopropylmethyl-N-(2-fluorophenyl)methylamino)-2-methyl-3-(2-chloro-4-methoxyphenyl)-6,7-dihydro-5H-cyclopenta[d]pyrazolo[1,5-a]pyrimidine

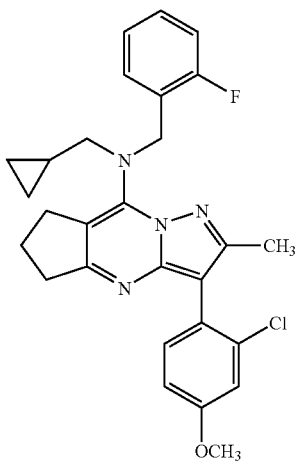

TLC: Rf 0.49 (toluene:ethyl acetate=10:1);

NMR (300 MHz, CDCl$_3$): δ 7.32 (d, J=8.7 Hz, 1H), 7.35-7.16 (m, 2H), 7.06 (d, J=2.4 Hz, 1H), 7.08-6.97 (m, 2H), 6.89 (dd, J=8.7 Hz, 2.4 Hz, 1H), 5.02 (s, 2H), 3.84 (s, 3H), 3.41 (d, J=6.9 Hz, 2H), 2.98-2.84 (m, 4H), 2.40 (s, 3H), 2.07 (m, 2H), 1.05 (m, 1H), 0.48 (m, 2H), 0.10 (m, 2H).

EXAMPLE 2(339)

8-(N-cyclopropylmethyl-N-propylamino)-3-(2-chloro-4-methoxyphenyl)-6,7-dihydro-5H-cyclopenta[d]pyrazolo[1,5-a]pyrimidine

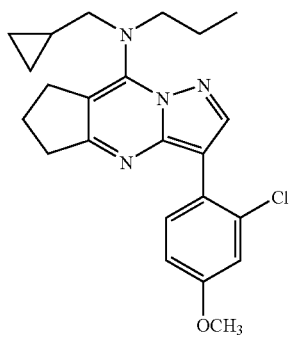

TLC: Rf 0.76 (hexane:ethyl acetate=2:1);

NMR (300 MHz, CDCl$_3$): δ 8.32 (s, 1H), 7.78 (d, J=8.7 Hz, 1H), 7.03 (d, J=2.7 Hz, 1H), 6.91 (dd, J=8.7, 2.7 Hz, 1H), 3.83 (s, 3H), 3.68-3.58 (m, 2H), 3.52 (d, J=6.9 Hz, 2H), 3.06-2.90 (m, 4H), 2.26-2.08 (m, 2H), 1.66-1.46 (m, 2H), 1.01 (m, 1H), 0.90 (t, J=7.2 Hz, 3H), 0.52-0.42 (m, 2H), 0.16-0.04 (m, 2H).

EXAMPLE 2(340)

8-(N-propyl-N-(4-methylphenyl)methylamino)-3-(2-chloro-4-methoxyphenyl)-6,7-dihydro-5H-cyclopenta[d]pyrazolo[1,5-a]pyrimidine

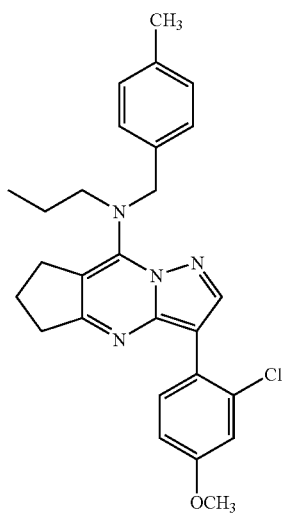

TLC: Rf 0.61 (hexane:ethyl acetate=2:1);

NMR (300 MHz, CDCl$_3$): δ 8.37 (s, 1H), 7.79 (d, J=9.0 Hz, 1H), 7.18-7.07 (m, 4H), 7.04 (d, J=2.7 Hz, 1H), 6.92 (dd, J=9.0, 2.7 Hz, 1H), 4.79 (s, 2H), 3.83 (s, 3H), 3.45-3.36 (m, 2H), 2.96 (t, J=7.8 Hz, 2H), 2.89 (t, J=7.8 Hz, 2H), 2.32 (s, 3H), 2.20-2.04 (m, 2H), 1.66-1.46 (m, 2H), 0.87 (t, J=7.2 Hz, 3H).

EXAMPLE 2(341)

8-(N-benzyl-N-cyclopropylmethylamino)-3-(2-chloro-4-methoxyphenyl)-6,7-dihydro-5H-cyclopenta[d]pyrazolo[1,5-a]pyrimidine

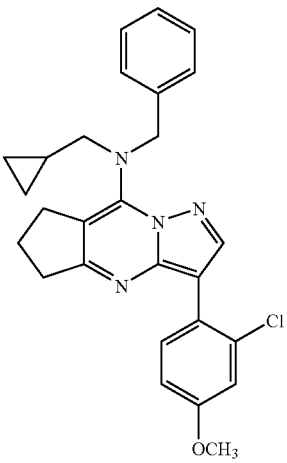

TLC: Rf 0.67 (hexane:ethyl acetate=2:1);

NMR (300 MHz, CDCl$_3$): δ 8.38 (s, 1H), 7.79 (d, J=8.7 Hz, 1H), 7.38-7.18 (m, 5H), 7.05 (d, J=2.4 Hz, 1H), 6.92 (dd, J=8.7, 2.4 Hz, 1H), 4.92 (s, 2H), 3.83 (s, 3H), 3.40 (d, J=6.9 Hz, 2H), 3.01 (t, J=7.2 Hz, 2H), 2.97 (t, J=7.8 Hz, 2H), 2.22-2.06 (m, 2H), 1.02 (m, 1H), 0.54-0.42 (m, 2H), 0.12-0.02 (m, 2H).

EXAMPLE 2(342)

8-(N-cyclopropylmethyl-N-(4-methylphenyl)methylamino)-3-(2-chloro-4-methoxyphenyl)-6,7-dihydro-5H-cyclopenta[d]pyrazolo[1,5-a]pyrimidine

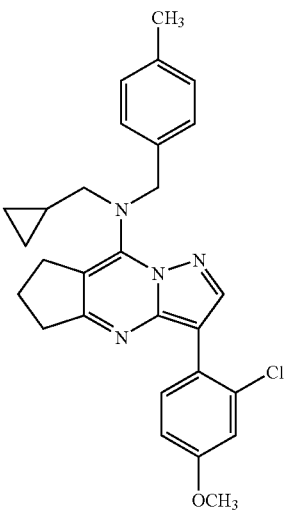

TLC: Rf 0.71 (hexane:ethyl acetate=2:1);

NMR (300 MHz, CDCl$_3$): δ 8.37 (s, 1H), 7.79 (d, J=8.4 Hz, 1H), 7.20 (d, J=8.1 Hz, 2H), 7.11 (d, J=8.1 Hz, 2H), 7.05 (d, J=2.7 Hz, 1H), 6.92 (dd, J=8.4, 2.7 Hz, 1H), 4.88 (s, 2H), 3.83

(s, 3H), 3.39 (d, J=6.6 Hz, 2H), 3.01 (t, J=7.2 Hz, 2H), 2.97 (t, J=7.8 Hz, 2H), 2.32 (s, 3H), 2.22-2.06 (m, 2H), 1.02 (m, 1H), 0.54-0.42 (m, 2H), 0.14-0.02 (m, 2H).

EXAMPLE 2(343)

8-(N-propyl-N-(4-fluorophenyl)methylamino)-3-(2-chloro-4-methoxyphenyl)-6,7-dihydro-5H-cyclopenta[d]pyrazolo[1,5-a]pyrimidine

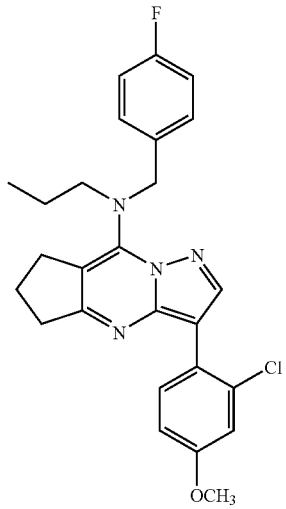

TLC: Rf 0.54 (hexane:ethyl acetate=2:1);
NMR (300 MHz, CDCl$_3$): δ 8.37 (s, 1H), 7.79 (d, J=8.7 Hz, 1H), 7.30-7.22 (m, 2H), 7.05 (d, J=2.4 Hz, 1H), 7.04-6.96 (m, 2H), 6.92 (dd, J=8.7, 2.4 Hz, 1H), 4.78 (s, 2H), 3.83 (s, 3H), 3.46-3.34 (m, 2H), 2.97 (t, J=7.8 Hz, 2H), 2.89 (t, J=7.2 Hz, 2H), 2.20-2.04 (m, 2H), 1.66-1.48 (m, 2H), 0.87 (t, J=7.5 Hz, 3H).

EXAMPLE 2(344)

8-dicyclopropylmethylamino-3-(2-chloro-4-methoxyphenyl)-6,7-dihydro-5H-cyclopenta[d]pyrazolo[1,5-a]pyrimidine

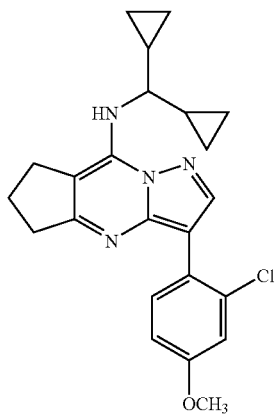

TLC: Rf 0.58 (hexane:ethyl acetate=2:1);
NMR (300 MHz, CDCl$_3$): δ 8.28 (s, 1H), 7.78 (d, J=8.7 Hz, 1H), 7.03 (d, J=2.4 Hz, 1H), 6.91 (dd, J=8.7, 2.4 Hz, 1H), 6.42 (d, J=9.6 Hz, 1H), 3.82 (s, 3H), 3.44 (m, 1H), 3.10-3.00 (m, 2H), 2.98-2.88 (m, 2H), 2.22-2.06 (m, 2H), 1.20-1.06 (m, 2H), 0.68-0.48 (m, 4H), 0.48-0.34 (m, 4H).

EXAMPLE 2(345)

8-(4-heptylamino)-3-(2-chloro-4-methoxyphenyl)-5,7-dihydro-furo[3,4-d]pyrazolo[1,5-a]pyrimidine

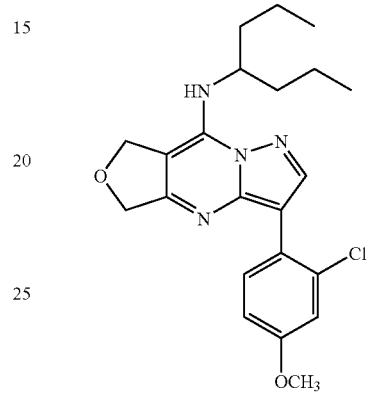

TLC: Rf 0.54 (hexane:ethyl acetate=2:1);
NMR (300 MHz, CDCl$_3$): δ 8.32 (s, 1H), 7.74 (d, J=8.7 Hz, 1H), 7.04 (d, J=2.7 Hz, 1H), 6.92 (dd, J=8.7, 2.7 Hz, 1H), 6.42 (d, J=10.8 Hz, 1H), 5.32 (s, 2H), 4.97 (s, 2H), 3.83 (s, 3H), 3.42 (m, 1H), 1.78-1.26 (m, 8H), 0.95 (t, J=7.2 Hz, 6H).

EXAMPLE 2(346)

8-(N-propyl-N-(4-methylphenyl)methylamino)-3-(2-chloro-4-methoxyphenyl)-5,7-dihydro-furo[3,4-d]pyrazolo[1,5-a]pyrimidine

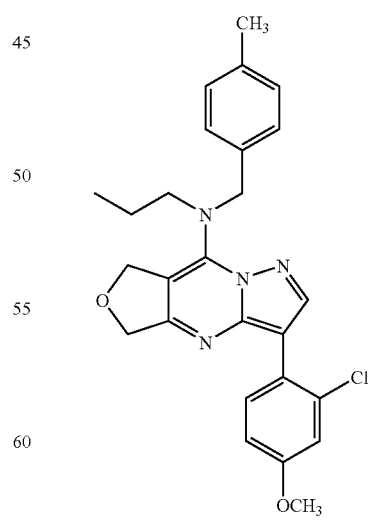

TLC: Rf 0.53 (hexane:ethyl acetate=2:1);
NMR (300 MHz, CDCl$_3$): δ 8.41 (s, 1H), 7.75 (d, J=8.7 Hz, 1H), 7.16-7.08 (m, 4H), 7.06 (d, J=2.4 Hz, 1H), 6.92 (dd, J=8.7, 2.4 Hz, 1H), 5.14 (s, 2H), 4.95 (s, 2H), 4.88 (s, 2H), 3.84 (s, 3H), 3.42-3.28 (m, 2H), 2.33 (s, 3H), 1.72-1.50 (m, 2H), 0.89 (t, J=7.5 Hz, 3H).

EXAMPLE 2(347)

8-(N-propyl-N-(4-fluorophenyl)methylamino)-3-(2-chloro-4-methoxyphenyl)-5,7-dihydro-furo[3,4-d]pyrazolo[1,5-a]pyrimidine

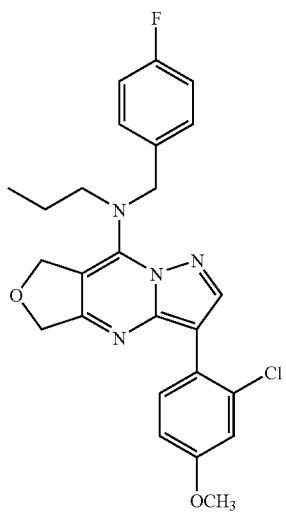

TLC: Rf 0.50 (hexane:ethyl acetate=2:1);
NMR (300 MHz, CDCl$_3$): δ 8.41 (s, 1H), 7.74 (d, J=8.4 Hz, 1H), 7.32-7.18 (m, 2H), 7.08-6.97 (m, 3H), 6.93 (dd, J=8.4, 2.4 Hz, 1H), 5.15 (s, 2H), 4.95 (s, 2H), 4.88 (s, 2H), 3.84 (s, 3H), 3.40-3.26 (m, 2H), 1.70-1.48 (m, 2H), 0.89 (t, J=7.2 Hz, 3H).

EXAMPLE 2(348)

8-dicyclopropylmethylamino-3-(2-chloro-4-methoxyphenyl)-5,7-dihydro-furo[3,4-d]pyrazolo[1,5-a]pyrimidine

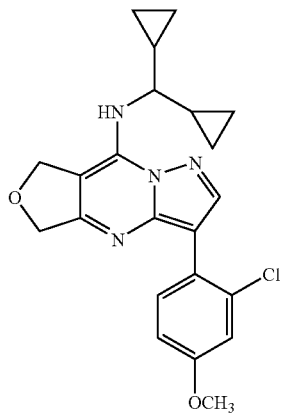

TLC: Rf 0.47 (hexane:ethyl acetate=2:1);
NMR (300 MHz, CDCl$_3$): δ 8.33 (s, 1H), 7.73 (d, J=8.7 Hz, 1H), 7.04 (d, J=2.7 Hz, 1H), 6.91 (dd, J=8.7, 2.7 Hz, 1H), 6.55 (d, J=9.6 Hz, 1H), 5.25 (s, 2H), 4.94 (s, 2H), 3.83 (s, 3H), 2.92 (m, 1H), 1.22-1.06 (m, 2H), 0.70-0.48 (m, 4H), 0.48-0.30 (m, 4H).

EXAMPLE 2(349)

8-(N-cyclopropylmethyl-N-(4-trifluoromethylphenyl)methylamino)-3-(2-chloro-4-methoxyphenyl)-5,7-dihydro-furo[3,4-d]pyrazolo[1,5-a]pyrimidine

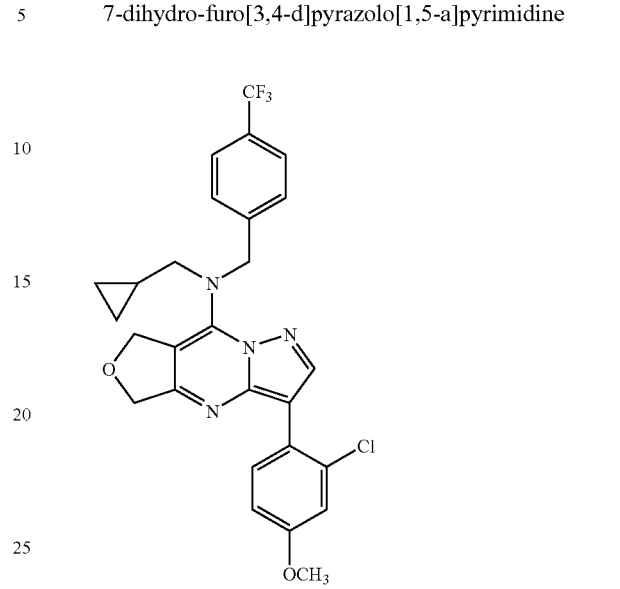

TLC: Rf 0.42 (hexane:ethyl acetate=2:1);
NMR (300 MHz, CDCl$_3$): δ 8.41 (s, 1H), 7.73 (d, J=8.4 Hz, 1H), 7.60 (d, J=8.1 Hz, 2H), 7.50 (d, J=8.1 Hz, 2H), 7.06 (d, J=2.7 Hz, 1H), 6.93 (dd, J=8.4, 2.7 Hz, 1H), 5.27 (s, 2H), 5.02 (s, 2H), 4.96 (s, 2H), 3.84 (s, 3H), 3.40 (d, J=6.6 Hz, 2H), 1.02 (m, 1H), 0.60-0.46 (m, 2H), 0.16-0.04 (m, 2H).

EXAMPLE 2(350)

8-(N-cyclopropyl-N-(4-methylphenyl)methylamino)-3-(2-chloro-4-methoxyphenyl)-6,7-dihydro-5H-cyclopenta[d]pyrazolo[1,5-a]pyrimidine

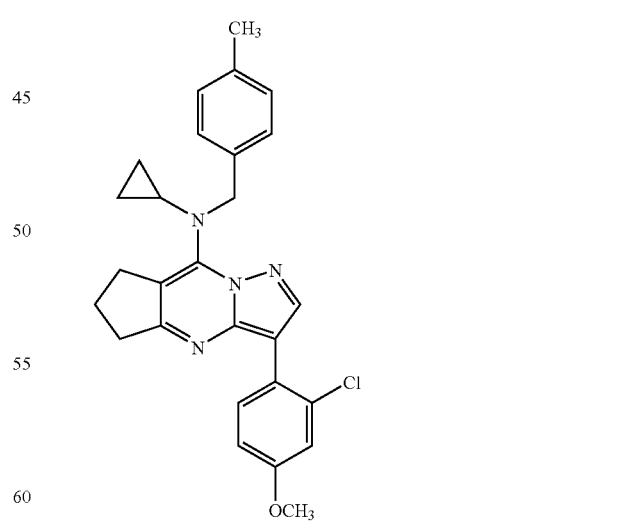

TLC: Rf 0.60 (hexane:ethyl acetate=2:1);
NMR (300 MHz, CDCl$_3$): δ 8.36 (s, 1H), 7.80 (d, J=8.4 Hz, 1H), 7.12-6.99 (m, 5H), 6.93 (dd, J=8.4, 2.7 Hz, 1H), 4.96 (s, 2H), 3.83 (s, 3H), 2.97 (t, J=7.8 Hz, 2H), 2.94 (t, J=7.5 Hz, 2H), 2.78 (m, 1H), 2.32 (s, 3H), 2.16-2.00 (m, 2H), 0.82-0.68 (m, 4H).

EXAMPLE 2(351)

8-(N-cyclopropylmethyl-N-(4-trifluoromethylphenyl)methylamino)-3-(2-chloro-4-methoxyphenyl)-6,7-dihydro-5H-cyclopenta[d]pyrazolo[1,5-a]pyrimidine

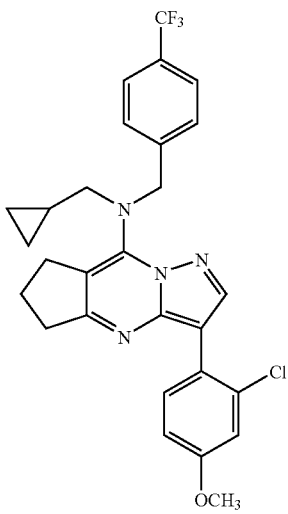

TLC: Rf 0.55 (hexane:ethyl acetate=2:1);

NMR (300 MHz, CDCl$_3$): δ 8.37 (s, 1H), 7.78 (d, J=8.7 Hz, 1H), 7.58 (d, J=8.1 Hz, 2H), 7.49 (d, J=8.1 Hz, 2H), 7.05 (d, J=2.7 Hz, 1H), 6.92 (dd, J=8.7, 2.7 Hz, 1H), 4.97 (s, 2H), 3.83 (s, 3H), 3.39 (d, J=6.6 Hz, 2H), 3.04 (t, J=7.2 Hz, 2H), 2.99 (t, J=7.8 Hz, 2H), 2.18 (m, 2H), 1.01 (m, 1H), 0.56-0.42 (m, 2H), 0.14-0.02 (m, 2H).

EXAMPLE 2(352)

8-(3-pentylamino)-3-(2-chloro-4-methoxyphenyl)-6,7-dihydro-5H-cyclopenta[d]pyrazolo[1,5-a]pyrimidine

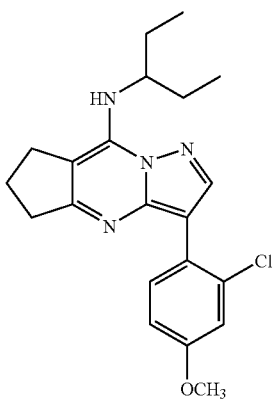

TLC: Rf 0.53 (hexane:ethyl acetate=2:1);

NMR (300 MHz, CDCl$_3$): δ 8.27 (s, 1H), 7.79 (d, J=8.7 Hz, 1H), 7.03 (d, J=2.4 Hz, 1H), 6.91 (dd, J=8.7, 2.4 Hz, 1H), 6.30 (d, J=10.2 Hz, 1H), 3.82 (s, 3H), 3.82 (m, 1H), 3.11 (t, J=7.2 Hz, 2H), 2.96 (t, J=7.8 Hz, 2H), 2.24-2.08 (m, 2H), 1.84-1.52 (m, 4H), 1.01 (t, J=7.5 Hz, 6H).

EXAMPLE 2(353)

8-(N-cyclopropylmethyl-N-(4-fluorophenyl)methylamino)-3-(2-chloro-4-methoxyphenyl)-6,7-dihydro-5H-cyclopenta[d]pyrazolo[1,5-a]pyrimidine

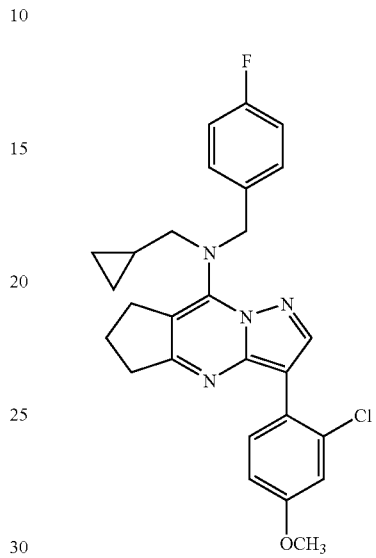

TLC: Rf 0.46 (hexane:ethyl acetate=2:1);

NMR (300 MHz, CDCl$_3$): δ 8.37 (s, 1H), 7.78 (d, J=8.7 Hz, 1H), 7.38-7.24 (m, 2H), 7.05 (d, J=2.7 Hz, 1H), 7.05-6.93 (m, 2H), 6.92 (dd, J=8.7, 2.7 Hz, 1H), 4.87 (s, 2H), 3.83 (s, 3H), 3.37 (d, J=6.9 Hz, 2H), 3.01 (t, J=7.5 Hz, 2H), 2.97 (t, J=7.5 Hz, 2H), 2.22-2.06 (m, 2H), 1.00 (m, 1H), 0.54-0.40 (m, 2H), 0.12-0.02 (m, 2H).

EXAMPLE 2(354)

8-(3-pentylamino)-2-methyl-3-(2-(1-methyl-1-hydroxyethyl)-4-methoxyphenyl)-6,7-dihydro-5H-cyclopenta[d]pyrazolo[1,5-a]pyrimidine

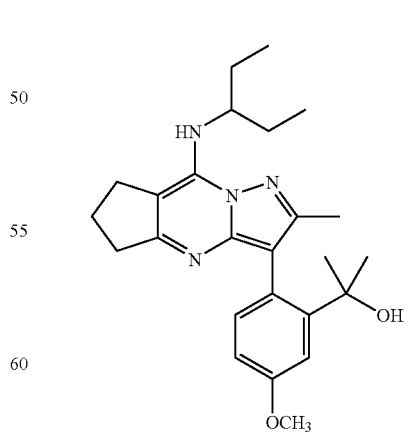

TLC: Rf 0.50 (hexane:ethyl acetate=1:2);

NMR (300 MHz, CDCl$_3$): δ 7.23 (d, J=2.7 Hz, 1H), 7.03 (d, J=8.7 Hz, 1H), 6.83 (dd, J=8.7, 2.7 Hz, 1H), 6.26 (d, J=10.2

Hz, 1H), 5.00-4.85 (m, 1H), 3.85-3.75 (m) and 3.84 (s) total 4H, 3.06 (t, J=6.9 Hz, 2H), 2.85 (t, J=6.9 Hz, 2H), 2.29 (s, 3H), 2.11 (quint, J=7.5 Hz, 2H), 1.80-1.50 (m) and 1.64 (s) total 7H, 1.30 (s, 3H), 1.03 (t, J=7.2 Hz) and 1.00 (t, J=7.2 Hz) total 6H.

EXAMPLE 2(355)

8-(N-propyl-N-(4-trifluoromethyloxyphenyl)methylamino)-2-methyl-3-(2-chloro-4-methoxyphenyl)-6,7-dihydro-5H-cyclopenta[d]pyrazolo[1,5-a]pyrimidine

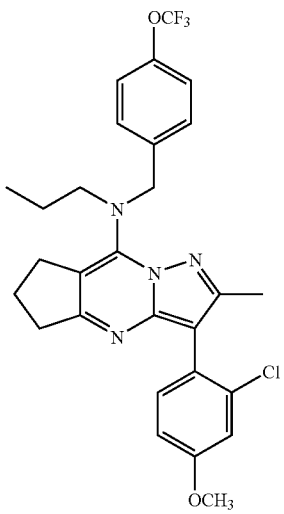

TLC: Rf 0.52 (hexane:ethyl acetate=2:1);
NMR (300 MHz, CDCl$_3$): δ 7.32 (d, J=9.0 Hz, 2H), 7.32 (d, J=8.4 Hz, 1H), 7.15 (d, J=9.0 Hz, 2H), 7.07 (d, J=2.7 Hz, 1H), 6.89 (dd, J=8.4, 2.7 Hz, 1H), 4.84 (s, 2H), 3.84 (s, 3H), 3.44-3.32 (m, 2H), 2.91 (t, J=7.5 Hz, 2H), 2.84 (t, J=7.8 Hz, 2H), 2.39 (s, 3H), 2.06-1.98 (m, 2H), 1.66-1.48 (m, 2H), 0.88 (t, J=7.2 Hz, 3H).

EXAMPLE 2(356)

8-(3-hexylamino)-2-methyl-3-(2-chloro-4-methoxyphenyl)-6,7-dihydro-5H-cyclopenta[d]pyrazolo[1,5-a]pyrimidine

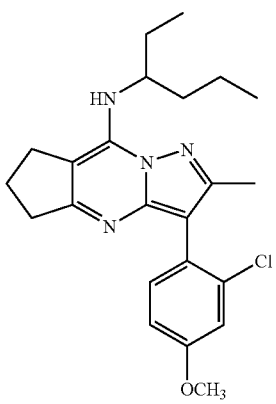

TLC: Rf 0.44 (hexane:ethyl acetate=2:1);
NMR (300 MHz, CDCl$_3$): δ 7.30 (d, J=8.7 Hz, 1H), 7.05 (d, J=2.4 Hz, 1H), 6.88 (dd, J=8.7, 2.4 Hz, 1H), 6.22 (d, J=10.8 Hz, 1H), 3.84 (m, 1H), 3.83 (s, 3H), 3.08 (t, J=7.5 Hz, 2H), 2.90 (t, J=7.8 Hz, 2H), 2.34 (s, 3H), 2.20-2.04 (m, 2H), 1.80-1.32 (m, 6H), 1.00 (t, J=6.9 Hz, 3H), 0.95 (t, J=6.9 Hz, 3H).

EXAMPLE 2(357)

8-(3-pentylamino)-2-methyl-3-(2-methoxy-4-methylpyridin-5-yl)-6,7-dihydro-5H-cyclopenta[d]pyrazolo[1,5-a]pyrimidine

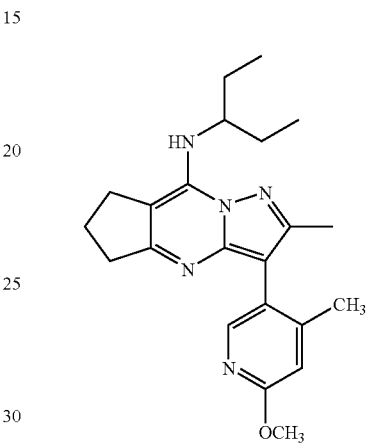

TLC: Rf 0.23 (hexane:ethyl acetate=2:1);
NMR (300 MHz, CDCl$_3$): δ 8.00 (s, 1H), 6.69 (s, 1H), 6.23 (d, J=10.5 Hz, 1H), 3.94 (s, 3H), 3.82 (m, 1H), 3.08 (t, J=7.5 Hz, 2H), 2.89 (t, J=7.8 Hz, 2H), 2.32 (s, 3H), 2.20-2.06 (m, 2H), 2.18 (s, 3H), 1.82-1.54 (m, 4H), 1.02 (t, J=7.2 Hz, 6H).

EXAMPLE 2(358)

8-(N-butyl-N-cyclopropylmethylamino)-3-(2-chloro-4-methoxyphenyl)-6,7-dihydro-5H-cyclopenta[d]pyrazolo[1,5-a]pyrimidine hydrochloride

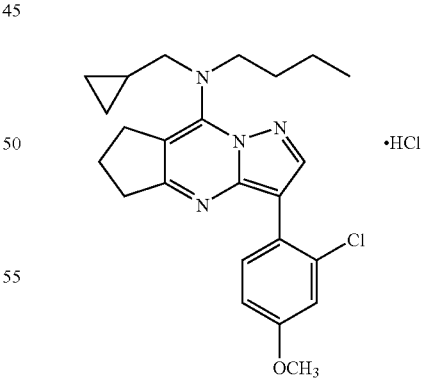

TLC: Rf 0.61 (hexane:ethyl acetate=2:1);
NMR (300 MHz, CDCl$_3$): δ 8.27 (s, 1H), 7.71 (d, J=8.4 Hz, 1H), 7.04 (d, J=2.4 Hz, 1H), 6.94 (m, 1H), 3.90-3.70 (m, 2H), 3.83 (s, 3H), 3.64 (d, J=6.6 Hz, 2H), 3.30-3.12 (m, 2H), 3.12-2.96 (m, 2H), 2.32-2.12 (m, 2H), 1.68-1.50 (m, 2H), 1.46-1.20 (m, 2H), 1.06 (m, 1H), 0.91 (t, J=7.2 Hz, 3H), 0.62-0.46 (m, 2H), 0.24-0.10 (m, 2H).

EXAMPLE 2(359)

8-(N-cyclopropyl-N-(4-methylphenyl)methylamino)-3-(2-chloro-4-methoxyphenyl)-5,7-dihydro-furo[3,4-d]pyrazolo[1,5-a]pyrimidine hydrochloride

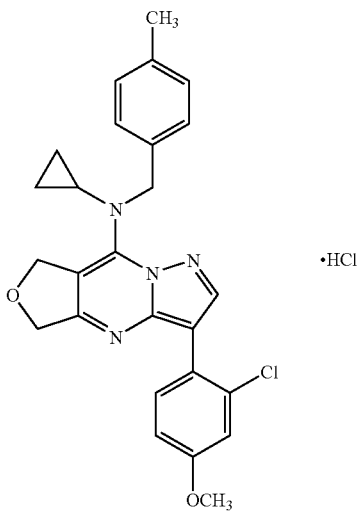

TLC: Rf 0.49 (hexane:ethyl acetate=2:1);
NMR (300 MHz, CDCl$_3$): δ 8.42 (s, 1H), 7.76 (d, J=8.7 Hz, 1H), 7.09 (d, J=8.1 Hz, 2H), 7.06 (d, J=2.7 Hz, 1H), 6.99 (d, J=8.1 Hz, 2H), 6.93 (dd, J=8.7, 2.7 Hz, 1H), 5.19 (s, 2H), 5.11 (s, 2H), 4.96 (s, 2H), 3.84 (s, 3H), 2.58 (m, 1H), 2.32 (s, 3H), 0.86-0.76 (m, 4H).

EXAMPLE 2(360)

8-(N-propyl-N-(4-methylphenyl)methylamino)-2-methyl-3-(2-chloro-4-methoxyphenyl)-6,7-dihydro-5H-cyclopenta[d]pyrazolo[1,5-a]pyrimidine

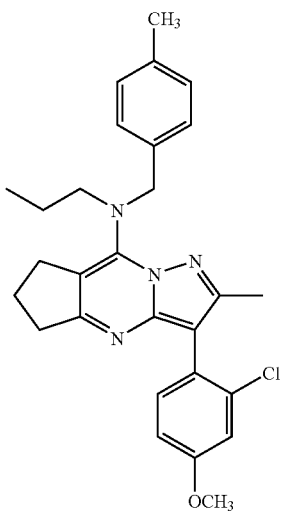

TLC: Rf 0.74 (hexane:ethyl acetate=2:1);
NMR (300 MHz, CDCl$_3$): δ 7.32 (d, J=8.7 Hz, 1H), 7.16-7.06 (m, 4H), 7.07 (d, J=3.0 Hz, 1H), 6.89 (dd, J=8.7, 3.0 Hz, 1H), 4.80 (s, 2H), 3.84 (s, 3H), 3.42-3.30 (m, 2H), 2.89 (t, J=7.8 Hz, 2H), 2.82 (t, J=7.2 Hz, 2H), 2.39 (s, 3H), 2.33 (s, 3H), 2.04-1.98 (m, 2H), 1.70-1.48 (m, 2H), 0.87 (t, J=7.2 Hz, 3H).

EXAMPLE 2(361)

8-(N-propyl-N-(4-cyanophenyl)methylamino)-2-methyl-3-(2-chloro-4-methoxyphenyl)-5,7-dihydro-furo[3,4-d]pyrazolo[1,5-a]pyrimidine

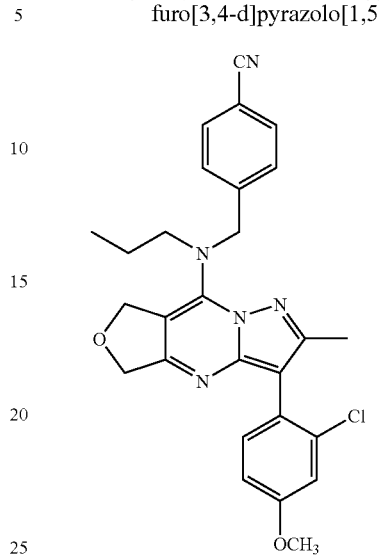

TLC: Rf 0.38 (hexane:ethyl acetate=2:1);
NMR (300 MHz, CDCl$_3$): δ 7.64 (d, J=8.1 Hz, 2H), 7.50 (d, J=8.1 Hz, 2H), 7.30 (d, J=8.4 Hz, 1H), 7.08 (d, J=2.7 Hz, 1H), 6.90 (d, J=8.4, 2.7 Hz, 1H), 5.14 (s, 2H), 5.01 (s, 2H), 4.91 (s, 2H), 3.84 (s, 3H), 3.36-3.22 (m, 2H), 2.38 (s, 3H), 1.70-1.50 (m, 2H), 0.89 (t, J=7.2 Hz, 3H).

EXAMPLE 2(362)

8-(N-propyl-N-(4-cyanophenyl)methylamino)-2-methyl-3-(2-chloro-4-methoxyphenyl)-6,7-dihydro-5H-cyclopenta[d]pyrazolo[1,5-a]pyrimidine

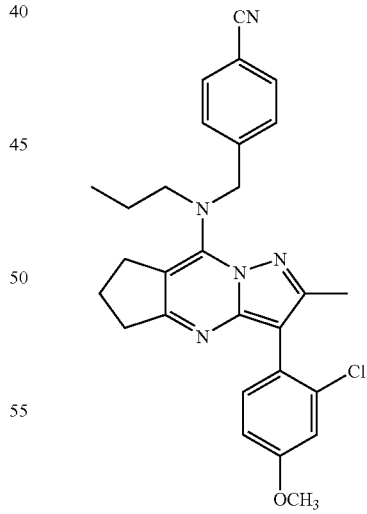

TLC: Rf 0.46 (hexane:ethyl acetate=2:1);
NMR (300 MHz, CDCl$_3$): δ 7.61 (d, J=7.8 Hz, 2H), 7.47 (d, J=7.8 Hz, 2H), 7.31 (d, J=8.4 Hz, 1H), 7.07 (d, J=2.7 Hz, 1H), 6.89 (dd, J=8.4, 2.7 Hz, 1H), 4.90 (s, 2H), 3.84 (s, 3H), 3.44-3.32 (m, 2H), 2.92 (t, J=7.8 Hz, 2H), 2.88 (t, J=7.5 Hz, 2H), 2.38 (s, 3H), 2.20-2.02 (m, 2H), 1.66-1.46 (m, 2H), 0.88 (t, J=7.2 Hz, 3H).

EXAMPLE 2(363)

8-(N-cyclopropylmethyl-N-methylamino)-2-methyl-3-(2-chloro-4-methoxyphenyl)-6,7-dihydro-5H-cyclopenta[d]pyrazolo[1,5-a]pyrimidine

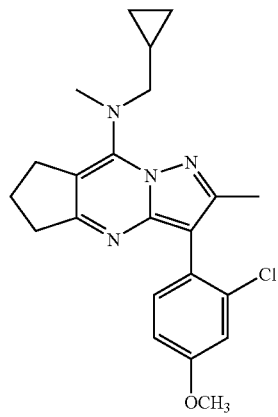

TLC: Rf 0.30 (hexane:ethyl acetate=2:1);

NMR (300 MHz, CDCl$_3$): δ 7.30 (d, J=8.4 Hz, 1H), 7.05 (d, J=3.0 Hz, 1H), 6.88 (dd, J=8.4, 3.0 Hz, 1H), 3.83 (s, 3H), 3.61 (d, J=6.9 Hz, 2H), 3.30 (s, 3H), 3.12 (t, J=7.2 Hz, 2H), 2.92 (t, J=7.5 Hz, 2H), 2.36 (s, 3H), 2.20-2.06 (m, 2H), 1.09 (m, 1H), 0.60-0.46 (m, 2H), 0.24-0.12 (m, 2H).

EXAMPLE 2(364)

8-(N-cyclopropylmethyl-N-methylamino)-2-methyl-3-(2-methyl-4-methoxyphenyl)-5,7-dihydro-furo[3,4-d]pyrazolo[1,5-a]pyrimidine

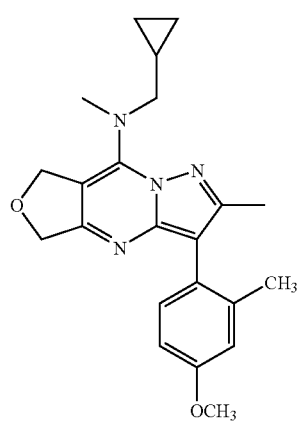

TLC: Rf 0.22 (hexane:ethyl acetate=2:1);

NMR (300 MHz, CDCl$_3$): δ 7.16 (d, J=8.4 Hz, 1H), 6.87 (d, J=3.0 Hz, 1H), 6.80 (dd, J=8.4, 3.0 Hz, 1H), 5.35 (s, 2H), 4.89 (s, 2H), 3.83 (s, 3H), 3.72 (dd, J=6.9, 1.5 Hz, 2H), 3.27 (s, 3H), 2.34 (s, 3H), 2.15 (s, 3H), 1.10 (m, 1H), 0.60-0.48 (m, 2H), 0.24-0.14 (m, 2H).

EXAMPLE 2(365)

8-(N-cyclopropylmethyl-N-methylamino)-2-methyl-3-(2-chloro-4-methoxyphenyl)-5,7-dihydro-furo[3,4-d]pyrazolo[1,5-a]pyrimidine

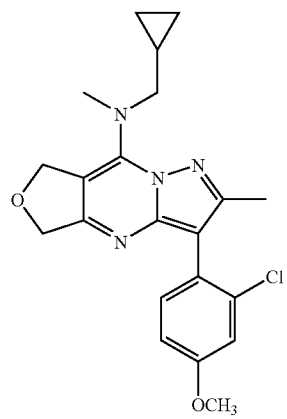

TLC: Rf 0.18 (hexane:ethyl acetate=2:1);

NMR (300 MHz, CDCl$_3$): δ 7.29 (d, J=8.7 Hz, 1H), 7.06 (d, J=2.7 Hz, 1H), 6.88 (dd, J=8.7, 2.7 Hz, 1H), 5.35 (s, 2H), 4.91 (s, 2H), 3.83 (s, 3H), 3.71 (d, J=6.9 Hz, 2H), 3.27 (s, 3H), 2.38 (s, 3H), 1.10 (m, 1H), 0.62-0.50 (m, 2H), 0.26-0.16 (m, 2H).

EXAMPLE 2(366)

8-(4-heptylamino)-3-(2,6-dimethyl-4-methoxyphenyl)-6,7-dihydro-5H-cyclopenta[d]pyrazolo[1,5-a]pyrimidine

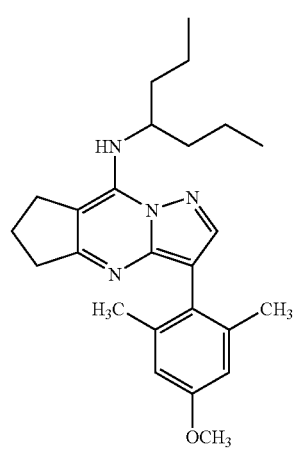

TLC: Rf 0.55 (hexane:ethyl acetate=2:1);

NMR (300 MHz, CDCl$_3$): δ 7.80 (s, 1H), 6.83 (s, 2H), 6.27 (d, J=11.1 Hz, 1H), 3.98 (m, 1H), 3.80 (s, 3H), 3.11 (t; J=7.5 Hz, 2H), 2.91 (t, J=7.8 Hz, 2H), 2.22-2.04 (m, 2H), 2.13 (s, 6H), 1.76-1.30 (m, 8H), 0.96 (t, J=7.2 Hz, 6H).

EXAMPLE 2(367)

8-dipropylamino-3-(2,6-dimethyl-4-methoxyphenyl)-6,7-dihydro-5H-cyclopenta[d]pyrazolo[1,5-a]pyrimidine

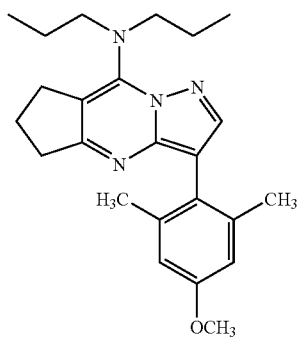

TLC: Rf 0.54 (hexane:ethyl acetate=2:1);

NMR (300 MHz, CDCl$_3$): δ 7.86 (s, 1H), 6.69 (s, 2H), 3.80 (s, 3H), 3.64-3.46 (m, 4H), 2.98 (t, J=7.2 Hz, 2H), 2.92 (t, J=7.5 Hz, 2H), 2.22-2.00 (m, 2H), 2.12 (s, 6H), 1.68-1.48 (m, 4H), 0.89 (t, J=7.5 Hz, 6H).

EXAMPLE 2(368)

8-(N-cyclopropylmethyl-N-propylamino)-3-(2,6-dimethyl-4-methoxyphenyl)-6,7-dihydro-5H-cyclopenta[d]pyrazolo[1,5-a]pyrimidine

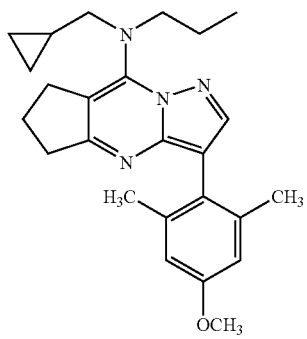

TLC: Rf 0.51 (hexane:ethyl acetate=2:1);
NMR (300 MHz, CDCl$_3$): δ 7.86 (s, 1H), 6.69 (s, 2H), 3.80 (s, 3H), 3.68-3.58 (m, 2H), 3.54 (d, J=6.6 Hz, 2H), 3.03 (t, J=7.5 Hz, 2H), 2.93 (t, J=7.5 Hz, 2H), 2.04-2.00 (m, 2H), 2.12 (s, 6H), 1.68-1.50 (m, 2H), 1.02 (m, 1H), 0.91 (t, J=7.5 Hz, 3H), 0.54-0.40 (m, 2H), 0.18-0.04 (m, 2H).

EXAMPLE 2(369)

8-(N-benzyl-N-cyclopropylmethylamino)-3-(2,6-dimethyl-4-methoxyphenyl)-6,7-dihydro-5H-cyclopenta[d]pyrazolo[1,5-a]pyrimidine

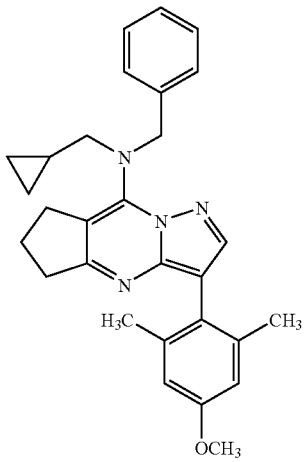

TLC: Rf 0.49 (hexane:ethyl acetate=2:1);
NMR (300 MHz, CDCl$_3$): δ 7.93 (s, 1H), 7.42-7.08 (m, 5H), 6.70 (s, 2H), 4.94 (s, 2H), 3.81 (s, 3H), 3.41 (d, J=6.6 Hz, 2H), 3.02 (t, J=7.5 Hz, 2H), 2.92 (t, J=7.8 Hz, 2H), 2.22-2.04 (m, 2H), 2.13 (s, 6H), 1.03 (m, 1H), 0.54-0.38 (m, 2H), 0.12-0.01 (m, 2H).

EXAMPLE 2(370)

8-(N-cyclopropylmethyl-N-(4-methylphenylmethyl)amino)-3-(2,6-dimethyl-4-methoxyphenyl)-6,7-dihydro-5H-cyclopenta[d]pyrazolo[1,5-a]pyrimidine

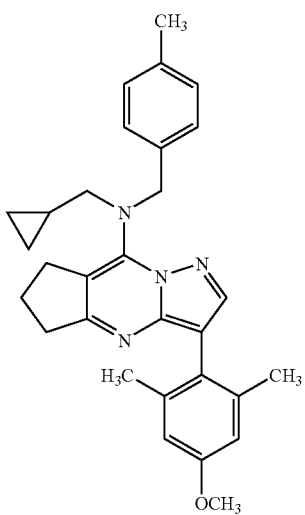

TLC: Rf 0.53 (hexane:ethyl acetate=2:1);
NMR (300 MHz, CDCl$_3$): δ 7.92 (s, 1H), 7.21 (d, J=8.1 Hz, 2H), 7.11 (d, J=8.1 Hz, 2H), 6.70 (s, 2H), 4.89 (s, 2H), 3.81 (s, 3H), 3.40 (d, J=6.9 Hz, 2H), 3.02 (t, J=7.2 Hz, 2H), 2.92 (t, J=7.5 Hz, 2H), 2.32 (s, 3H), 2.22-2.04 (m, 2H), 2.13 (s, 6H), 1.03 (m, 1H), 0.54-0.40 (m, 2H), 0.10-0.01 (m, 2H).

EXAMPLE 2(371)

8-(N-propyl-N-(4-fluorophenylmethyl)amino)-3-(2,6-dimethyl-4-methoxyphenyl)-6,7-dihydro-5H-cyclopenta[d]pyrazolo[1,5-a]pyrimidine

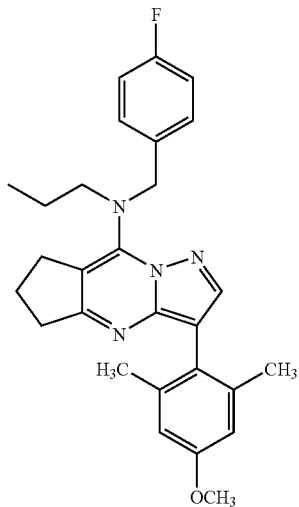

TLC: Rf 0.46 (hexane:ethyl acetate=2:1);

NMR (300 MHz, CDCl$_3$): δ 7.92 (s, 1H), 7.36-7.18 (m, 2H), 7.06-6.88 (m, 2H), 6.70 (s, 2H), 4.80 (s, 2H), 3.81 (s, 3H), 3.46-3.32 (m, 2H), 3.00-2.80 (m, 4H), 2.22-2.00 (m, 2H), 2.13 (s, 6H), 1.70-1.48 (m, 2H), 0.88 (t, J=7.2 Hz, 3H).

EXAMPLE 2(372)

8-dicyclopropylmethylamino-3-(2,6-dimethyl-4-methoxyphenyl)-6,7-dihydro-5H-cyclopenta[d]pyrazolo[1,5-a]pyrimidine

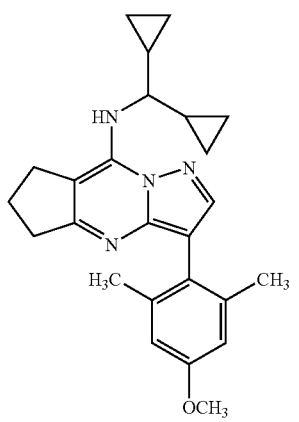

TLC: Rf 0.45 (hexane:ethyl acetate=2:1);

NMR (300 MHz, CDCl$_3$): δ 7.81 (s, 1H), 6.68 (s, 2H), 6.40 (d, J=9.9 Hz, 1H), 3.80 (s, 3H), 3.46 (m, 1H), 3.05 (t, J=7.5 Hz, 2H), 2.89 (t, J=7.8 Hz, 2H), 2.22-2.02 (m, 2H), 2.13 (s, 6H), 1.20-1.06 (m, 2H), 0.68-0.36 (m, 8H).

EXAMPLE 2(373)

8-(N-butyl-N-cyclopropylmethylamino)-3-(2,6-dimethyl-4-methoxyphenyl)-6,7-dihydro-5H-cyclopenta[d]pyrazolo[1,5-a]pyrimidine

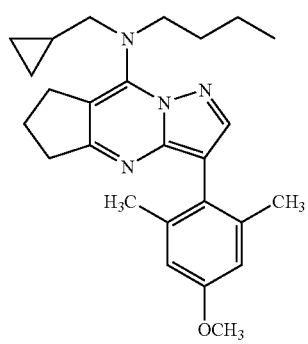

TLC: Rf 0.61 (hexane:ethyl acetate=2:1)

NMR (300 MHz, CDCl$_3$): δ 7.87 (s, 1H), 6.69 (s, 2H), 3.80 (s, 3H), 3.76-3.60 (m, 2H), 3.53 (d, J=6.9 Hz, 2H), 3.03 (t, J=7.2 Hz, 2H), 2.93 (t, J=7.5 Hz, 2H), 2.22-2.00 (m, 2H), 2.12 (s, 6H), 1.64-1.46 (m, 2H), 1.42-1.22 (m, 2H), 1.02 (m, 1H), 0.90 (t, J=7.2 Hz, 3H), 0.56-0.38 (m, 2H), 0.18-0.02 (m, 2H).

EXAMPLE 2(374)

8-(N-cyclopropylmethyl-N-(4-fluorophenyl)methylamino)-3-(2,6-dimethyl-4-methoxyphenyl)-6,7-dihydro-5H-cyclopenta[d]pyrazolo[1,5-a]pyrimidine

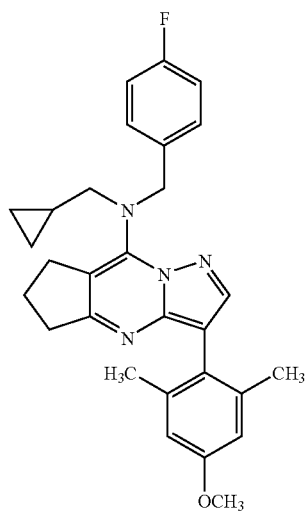

TLC: Rf 0.51 (hexane:ethyl acetate=2:1);

NMR (300 MHz, CDCl$_3$): δ 7.92 (s, 1H), 7.38-7.26 (m, 2H), 7.06-6.94 (m, 2H), 6.71 (s, 2H), 4.89 (s, 2H), 3.81 (s, 3H), 3.39 (d, J=6.6 Hz, 2H), 3.02 (t, J=7.2 Hz, 2H), 2.93 (t, J=7.2 Hz, 2H), 2.22-2.00 (m, 2H), 2.13 (s, 6H), 1.01 (m, 1H), 0.54-0.40 (m, 2H), 0.10-0.01 (m, 2H).

EXAMPLE 3

8-(N-ethyl-N-n-butylamino)-2-hydroxymethyl-3-(2-methyl-4-hydroxyphenyl)-6,7-dihydro-5H-cyclopenta[d]pyrazolo[1,5-a]pyrimidine

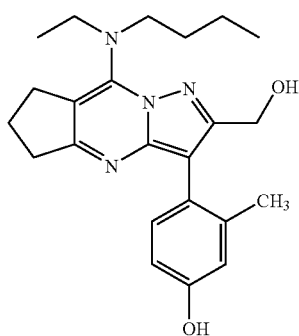

To a solution of the compound prepared in Example 2(1) (506 mg) in methylene chloride (14 ml) which was cooled to −78° C., 1M boron tribromide in methylene chloride (12 ml) was added. The mixture was stirred for 30 minutes at −78° C. and for 5 hours at −30° C. The reaction mixture was poured into a saturated aqueous solution of sodium bicarbonate and the resultant solution was extracted with ethyl acetate. The organic layer was washed with a saturated aqueous solution of sodium chloride, dried over anhydrous sodium sulfate and concentrated. The residue was purified by column chromatography on silica gel (n-hexane:ethyl acetate=1:1→2:3) to give the title compound (303 mg) having the following physical data TLC: Rf 0.14 (n-hexane:ethyl acetate=1:1);

NMR (300 MHz, CDCl$_3$): δ 9.41 (brs, 1H), 6.90 (d, J=9.0 Hz, 1H), 6.42 (m, 2H), 4.71 (brs, 2H), 3.70 (q, J=7.5 Hz, 2H), 3.64 (t, J=7.5 Hz, 2H), 3.01 (t, J=7.8 Hz, 4H), 2.39 (brs, 1H), 2.18 (m, 2H), 2.01 (s, 3H), 1.58 (m, 2H), 1.35 (m, 2H), 1.21 (t, J=7.5 Hz, 3H), 0.91 (t, J=7.5 Hz, 3H).

EXAMPLE 4

8-(N-ethyl-N-n-butylamino)-2-hydroxymethyl-3-(2-methyl-4-methoxyphenyl)-6,7-dihydro-5H-cyclopenta[d]pyrazolo[1,5-a]pyrimidine

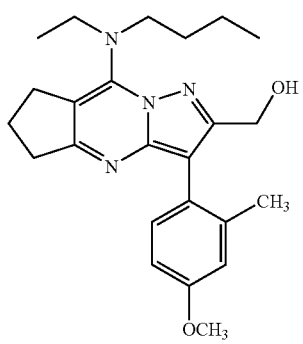

To a solution of the compound prepared in Example 3 (985 mg) in methylene chloride (10 ml) which was cooled to 0° C., sodium hydride (95 mg; 63.1% dispersion in oil) was added. The mixture was stirred for 30 minutes. Methyl iodide (0.18 ml) was added to the reaction mixture, and the resultant mixture was stirred for 2 hours at 0° C. A saturated aqueous solution of ammonium chloride was added to the reaction mixture, and the resultant solution was extracted with ethyl acetate. The organic layer was washed with 1M aqueous solution of sodium hydroxide and a saturated aqueous solution of sodium chloride, successively, dried over anhydrous sodium sulfate and concentrated. The residue was purified by column chromatography on silica gel (toluene:ethyl acetate=5:1→4:1→7:2) to give the title compound (947 mg) having the following physical data.

TLC: Rf 0.35 (n-hexane:ethyl acetate=1:1);

NMR (300 MHz, CDCl$_3$): δ 57.19 (d, J=8.4 Hz, 1H), 6.85 (d, J=2.7 Hz, 1H), 6.78 (dd, J=8.4, 2.7 Hz, 1H), 4.73 (d, J=5.7 Hz, 2H), 3.82 (s, 3H), 3.65 (q, J=7.2 Hz, 2H), 3.59 (t, J=7.2 Hz, 2H), 2.98 (t, J=6.9 Hz, 2H), 2.92 (t, J=7.8 Hz, 2H), 2.35 (m, 1H), 2.19 (s, 3H), 2.15 (m, 2H), 1.55 (m, 2H), 1.35 (m, 2H), 1.18 (t, J=7.2 Hz, 3H), 0.90 (t, J=7.2 Hz, 3H).

EXAMPLE 5

8-(N-propyl-N-(2-methoxyiminoethyl)amino)-2-methyl-3-(2-methyl-4-methoxyphenyl)-6,7-dihydro-5H-cyclopenta[d]pyrazolo[1,5-a]pyrimidine

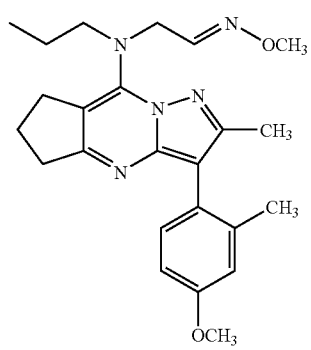

To a solution of the compound prepared in Example 2(2) (186 mg) in dimethylsulfoxide (5 ml), triethylamine (0.39 ml) and sulfur trioxide pyridine complex (225 mg) were added. The mixture was stirred for 2 hours at room temperature. The reaction mixture was poured into water and extracted with ethyl acetate. The organic layer was washed with a saturated aqueous solution of sodium chloride, dried over anhydrous sodium sulfate and concentrated. To a solution of the residue in pyridine (5 ml), o-methylhydroxylamine hydrochloride (28 mg) was added. The mixture was stirred for 15 hours at room temperature. The reaction mixture was concentrated and diluted with ethyl acetate. The diluted solution was washed with a saturated aqueous solution of sodium bicarbonate and a saturated aqueous solution of sodium chloride, successively, dried over anhydrous sodium sulfate and concentrated. The residue was purified by column chromatography on silica gel (n-hexane:ethyl acetate=4:1→3:1) to give the title compound (16 mg) having the following physical data.

TLC: Rf 0.78 (n-hexane:ethyl acetate=1:1);

NMR (300 MHz, CDCl$_3$):

major isomer

δ 7.57 (t, J=5.7 Hz, 1H), 7.15 (d, J=8.4 Hz, 1H), 6.86 (d, J=2.4 Hz, 1H), 6.79 (dd, J=8.4, 2.4 Hz, 1H), 4.35 (d, J=6.0 Hz, 2H), 3.86 (s, 3H), 3.82 (s, 3H), 3.49 (t, J=7.8 Hz, 2H), 2.99 (t, J=7.2 Hz, 2H), 2.91 (t, J=7.5 Hz, 2H), 2.32 (s, 3H), 2.18 (s, 3H), 2.14 (m, 2H), 1.58 (m, 2H), 0.90 (t, J=7.2 Hz, 3H)

minor isomer

δ 7.15 (d, J=8.4 Hz, 1H), 6.95 (t, J=3.9 Hz, 1H), 6.86 (d, J=2.4 Hz, 1H), 6.79 (dd, J=8.4, 2.4 Hz, 1H), 4.47 (d, J=4.2 Hz, 2H), 3.90 (s, 3H), 3.82 (s, 3H), 3.54 (t, J=7.8 Hz, 2H), 2.99 (t, J=7.2 Hz, 2H), 2.91 (t, J=7.5 Hz, 2H), 2.32 (s, 3H), 2.18 (s, 3H), 2.14 (m, 2H), 1.58 (m, 2H), 0.92 (t, J=7.2 Hz, 3H).

EXAMPLE 5(1)-5(2)

The following compounds were obtained by the same procedure as a reaction of Example 5, using the compound prepared in Example 2(26), or the compound prepared in Example 4 and hydroxylamine hydrochloride instead of o-methylhydroxylamine hydrochloride.

EXAMPLE 5(1)

8-(N-propyl-N-(2-methoxyiminoethyl)amino)-2-methyl-3-(2-methyl-4-methoxyphenyl)-5,7-dihydro-furo[3,4-d]pyrazolo[1,5-a]pyrimidine hydrochloride

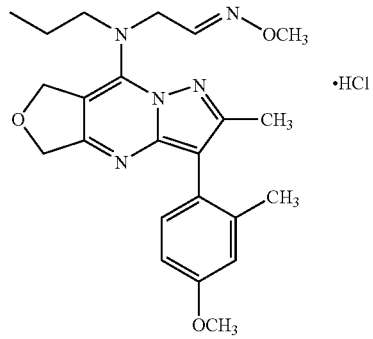

TLC: Rf 0.22 (n-hexane:ethyl acetate=3:1);

NMR (300 MHz, pyridine-d$_6$ 0.5 ml+CDCl$_3$ 0.1 ml):

major isomer

δ 7.87 (t, J=5.4 Hz, 1H), 7.38 (d, J=8.4 Hz, 1H), 7.03 (d, J=2.7 Hz, 1H), 6.95 (dd, J=8.4, 2.7 Hz, 1H), 5.27 (s, 2H), 4.97 (s, 2H), 4.59 (d, J=5.4 Hz, 2H), 3.86 (s, 3H), 3.74 (s, 3H), 3.38 (t, J=7.5 Hz, 2H), 2.44 (s, 3H), 2.31 (s, 3H), 1.65-1.50 (m, 2H), 0.81 (t, J=7.5 Hz, 3H).

minor isomer

δ 7.38 (d, J=8.4 Hz, 1H), 7.31 (t, J=4.2 Hz, 1H), 7.03 (d, J=2.7 Hz, 1H), 6.95 (dd, J=8.4, 2.7 Hz, 1H), 5.25 (s, 2H), 4.95 (s, 2H), 4.71 (d, J=4.2 Hz, 2H), 3.92 (s, 3H), 3.74 (s, 3H), 3.43 (t, J=7.2 Hz, 2H), 2.43 (s, 3H), 2.31 (s, 3H), 1.65-1.50 (m, 2H), 0.84 (t, J=7.2 Hz, 3H).

EXAMPLE 5(2)

8-(N-ethyl-N-n-butylamino)-2-hydroxyiminomethyl-3-(2-methyl-4-methoxyphenyl)-6,7-dihydro-5H-cyclopenta[d]pyrazolo[1,5-a]pyrimidine

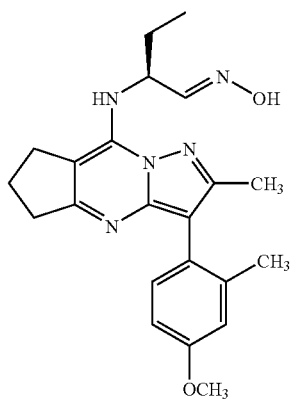

TLC: Rf 0.19 (n-hexane:ethyl acetate=3:1);

NMR (300 MHz, CDCl$_3$): δ 8.15 (s, 1H), 7.96 (brs, 1H), 7.18 (d, J=8.1 Hz, 1H), 6.85 (d, J=2.7 Hz, 1H), 6.79 (dd, J=8.1, 2.7 Hz, 1H), 3.82 (s, 3H), 3.67 (q, J=7.2 Hz, 2H), 3.61 (t, J=7.5 Hz, 2H), 2.99 (t, J=7.2 Hz, 2H), 2.92 (t, J=7.8 Hz, 2H), 2.18 (s, 3H), 2.16 (m, 2H), 1.55 (m, 2H), 1.33 (m, 2H), 1.18 (t, J=7.2 Hz, 3H), 0.89 (t, J=7.5 Hz, 3H).

EXAMPLE 6

8-[(2S)-1-hydroxyiminobutan-2-yl]amino-2-methyl-3-(2-methyl-4-methoxyphenyl)-6,7-dihydro-5H-cyclopenta[d]pyrazolo[1,5-a]pyrimidine To a solution of the compound prepared in Example 2(15) (290 mg) in acetic acid (4 ml), 1M hydrochloric acid (1.4 ml) was added, and the mixture was stirred for 1 hour at 80° C. The reaction mixture was poured into a saturated aqueous solution of sodium bicarbonate (100 ml) under ice-bath, the resultant mixture was extracted with ethyl acetate. The organic layer was washed with a saturated aqueous solution of sodium chloride, dried over anhydrous sodium sulfate and concentrated. Hydroxylamine hydrochloride (52 mg) was added to a solution of the residue in pyridine (3 ml), and the mixture was stirred for 15 hours at room temperature. The reaction mixture was concentrated, and diluted with ethyl acetate. The diluted solution was washed with a saturated aqueous solution of sodium bicarbonate and a saturated aqueous solution of sodium chloride, successively, dried over anhydrous sodium sulfate and concentrated. The residue was purified by column chromatography on silica gel (n-hexane: ethyl acetate=1:1) to give the title compound (143 mg) having the following physical data as isomeric mixtures.

TLC: Rf 0.32 (n-hexane:ethyl acetate=1:1);
NMR (300 MHz, CDCl$_3$):

major isomer

δ 7.80 (brs, 1H), 7.47 (d, J=6.0 Hz, 1H), 7.14 (d, J=8.4 Hz, 1H), 6.84 (d, J=2.7 Hz, 1H), 6.78 (dd, J=8.4, 2.7 Hz, 1H), 6.53 (d, J=9.6 Hz, 1H), 4.60 (m, 1H), 3.82 (s, 3H), 3.25-3.00 (m, 2H), 2.88 (t, J=7.5 Hz, 2H), 2.31 (s, 3H), 2.17 (s, 3H), 2.10 (m, 2H), 1.90 (m, 2H), 1.11 (t, J=7.2 Hz, 3H).

minor isomer

δ 8.52 (brs, 1H), 7.14 (d, J=8.4 Hz, 1H), 6.84 (d, J=2.7 Hz, 1H), 6.80 (m, 1H), 6.78 (dd, J=8.4, 2.7 Hz, 1H), 6.44 (d, J=9.6 Hz, 1H), 5.23 (m, 1H), 3.82 (s, 3H), 3.25-3.00 (m, 2H), 2.88 (t, J=7.5 Hz, 2H), 2.31 (s, 3H), 2.17 (s, 3H), 2.10 (m, 2H), 1.90 (m, 2H), 1.11 (t, J=7.2 Hz, 3H).

EXAMPLE 6(1)

8-[(2S)-1-methoxyiminobutan-2-yl]amino-2-methyl-3-(2-methyl-4-methoxyphenyl)-5,7-dihydro-furo[3,4-d]pyrazolo[1,5-a]pyrimidine

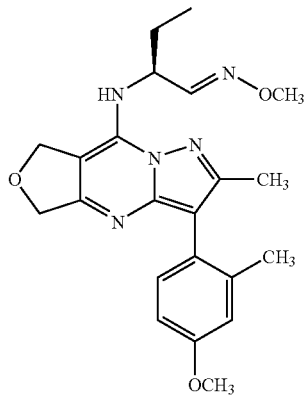

The title compound (128 mg) having the following physical data was obtained by the same procedure as a reaction of Example 5, using the compound prepared in Example 2(14) (365 mg) and o-methylhydroxylamine hydrochloride instead of hydroxylamine hydrochloride.

TLC: Rf 0.20 (n-hexane:ethyl acetate=3:1);
NMR (300 MHz, CDCl$_3$):

major isomer

δ 7.36 (d, J=6.0 Hz, 1H), 7.14 (d, J=8.4 Hz, 1H), 6.86 (d, J=2.7 Hz, 1H), 6.79 (dd, J=8.4, 2.7 Hz, 1H), 6.60 (d, J=9.9 Hz, 1H), 5.47 (d, J=10.5 Hz, 1H), 5.31 (d, J=10.5 Hz, 1H), 4.89 (s, 2H), 4.07 (m, 1H), 3.86 (s, 3H), 3.82 (s, 3H), 2.33 (s, 3H), 2.16 (s, 3H), 1.96-1.87 (m, 2H), 1.10 (t, J=7.5 Hz, 3H).

minor isomer

δ 7.14 (d, J=8.4 Hz, 1H), 6.86 (d, J=2.7 Hz, 1H), 6.79 (dd, J=8.4, 2.7 Hz, 1H), 6.76 (m, 1H), 6.53 (d, J=9.9 Hz, 1H), 5.30 (m, 2H), 4.89 (s, 2H), 4.72 (m, 1H), 3.96 (s, 3H), 3.82 (s, 3H), 2.33 (s, 3H), 2.16 (s, 3H), 1.96-1.87 (m, 2H), 1.10 (t, J=7.5 Hz, 3H).

EXAMPLE 7

8-[(1S)-1-cyanopropylamino]-2-methyl-3-(2-methyl-4-methoxyphenyl)-6,7-dihydro-5H-cyclopenta[d]pyrazolo[1,5-a]pyrimidine

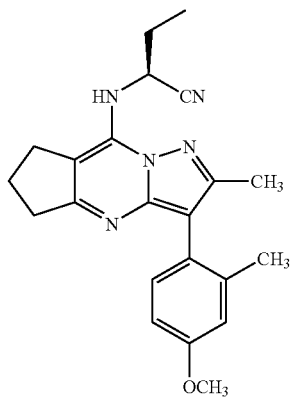

To a solution of the compound prepared in Example 6 (137 mg) in methylene chloride (1 ml) which was cooled to −78° C., triethylamine (0.32 ml) and trifluoromethanesulfonic anhydride (0.13 ml) were added. The mixture was stirred for 2 hours at room temperature. A saturated aqueous solution of sodium bicarbonate was added to the reaction mixture, and the resultant solution was extracted with ethyl acetate. The organic layer was washed with a saturated aqueous solution of sodium chloride, dried over anhydrous sodium sulfate and concentrated. The residue was purified by column chromatography on silica gel (n-hexane:ethyl acetate=3:1→2:1) to give the title compound (100 mg) having the following physical data.

TLC: Rf 0.27 (n-hexane:ethyl acetate=2:1);
NMR (300 MHz, CDCl$_3$): δ 7.15 (d, J=8.1 Hz, 1H), 6.86 (d, J=2.7 Hz, 1H), 6.79 (dd, J=8.1, 2.7 Hz, 1H), 6.50 (d, J=9.6 Hz, 1H), 4.78 (m, 1H), 3.82 (s, 3H), 3.33 (ddd, J=14.4, 7.5, 6.3 Hz, 1H), 3.11 (ddd, J=14.4, 8.1, 6.3 Hz, 1H), 2.93 (m, 2H), 2.31 (s, 3H), 2.25-2.10 (m, 7H), 1.29 (t, J=7.5 Hz, 3H).

EXAMPLE 7(1)

8-(N-ethyl-N-n-butylamino)-2-cyano-3-(2-methyl-4-methoxyphenyl)-6,7-dihydro-5H-cyclopenta[d]pyrazolo[1,5-a]pyrimidine

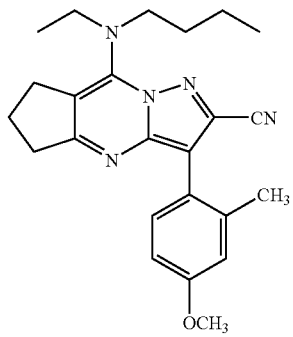

The title compound (195 mg) having the following physical data was obtained by the same procedure as a reaction of Example 7, using the compound prepared in Example 5(2) (211 mg).

TLC: Rf 0.34 (n-hexane:ethyl acetate=3:1);

NMR (300 MHz, CDCl$_3$): δ 7.28 (d, J=8.4 Hz, 1H), 6.88 (d, J=2.7 Hz, 1H), 6.83 (dd, J=8.4, 2.7 Hz, 1H), 3.83 (s, 3H), 3.65 (q, J=6.9 Hz, 2H), 3.58 (t, J=7.5 Hz, 2H), 3.00 (t, J=7.2 Hz, 2H), 2.96 (t, J=7.8 Hz, 2H), 2.29 (s, 3H), 2.18 (m, 2H), 1.57 (m, 2H), 1.33 (m, 2H), 1.20 (t, J=6.9 Hz, 3H), 0.91 (t, J=7.2 Hz, 3H).

EXAMPLE 8

9-(3-pentylamino)-6-methyl-5-(2-methyl-4-methoxyphenyl)-furo[3,2-d]pyrazolo[1,5-a]pyrimidine

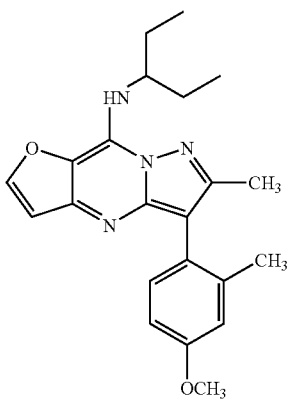

To a solution of the compound prepared in Example 2(6) (215 mg) in diphenyl ether (3 ml), 10% palladium carbon (150 mg) was added, and the mixture was stirred for 4 hours at 250° C. After the reaction mixture was cooled to room temperature, it was diluted with methanol (10 ml). The diluted solution was filtered though celite (registered trademark). The filtrate was concentrated, and the residue was purified by column chromatography on silica gel (n-hexane:acetone=9:1) to give the title compound (150 mg) having the following physical data.

TLC: Rf 0.42 (n-hexane:ethyl acetate=2:1);

NMR (300 MHz, CDCl$_3$): δ 7.76 (d, J=2.4 Hz, 1H), 7.20 (d, J=8.1 Hz, 1H), 6.88 (d, J=2.7 Hz, 1H), 6.80 (dd, J=8.1, 2.7 Hz, 1H), 6.78 (d, J=2.4 Hz, 1H), 6.28 (brd, J=10.2 Hz, 1H), 4.30 (m, 1H), 3.83 (s, 3H), 2.37 (s, 3H), 2.21 (s, 3H), 1.92-1.65 (m, 4H), 1.05 (m, 6H).

EXAMPLE 9

8-(3-pentyloxy)-2-methyl-3-(2-methyl-4-methoxyphenyl)-6,7-dihydro-5H-cyclopenta[d]pyrazolo[1,5-a]pyrimidine

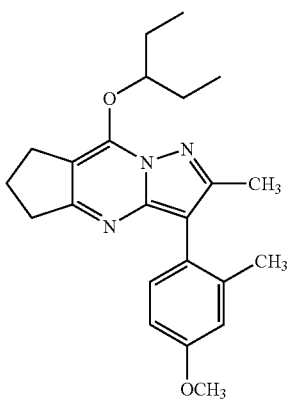

3-Pentanol (202 mg) was dropped into a solution of sodium hydride (92.0 mg; 60% in oil) in toluene, and the mixture was stirred for 2 minutes at 80° C. The compound prepared in Reference example 7 (250 mg) was added to this mixture, and the resultant mixture was stirred for 5 hours. Water and ethyl acetate were added to the reaction mixture and stirred. The organic layer was separated. Meanwhile, the water layer was extracted with ethyl acetate. A combined organic layer was washed with a saturated aqueous solution of sodium chloride, dried over anhydrous sodium sulfate and concentrated. The residue was purified by column chromatography on silica gel (hexane:ethyl acetate=5:1) to give the title compound (128 mg) having the following physical data.

TLC: Rf 0.58 (toluene:acetone=5:1);

NMR (300 MHz, CDCl$_3$): δ 7.16 (d, J=8.4 Hz, 1H), 6.86 (d, J=2.4 Hz, 1H), 6.79 (dd, J=8.4, 2.4 Hz, 1H), 5.05 (quint, J=6.0 Hz, 1H), 3.82 (s, 3H), 3.05 (t, J=7.5 Hz, 2H), 2.94 (t, J=7.5 Hz, 2H), 2.34 (s, 3H), 2.22-2.10 (m, 2H), 2.16 (s, 3H), 1.92-1.78 (m, 4H), 1.05 (t, J=7.5 Hz, 6H).

EXAMPLE 9(1)-9(5)

The following compounds were obtained by the same procedure as a reaction of Example 9, using a corresponding compound.

EXAMPLE 9(1)

8-(3-pentyloxy)-2-methyl-3-(2-chloro-4-methoxyphenyl)-6,7-dihydro-5H-cyclopenta[d]pyrazolo[1,5-a]pyrimidine

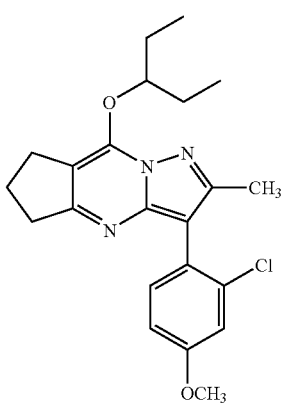

TLC: Rf 0.50 (hexane:ethyl acetate=3:1);

NMR (300 MHz, CDCl$_3$): δ 7.29 (d, J=8.4 Hz, 1H), 7.06 (d, J=2.4 Hz, 1H), 6.89 (dd, J=8.4, 2.4 Hz, 1H), 5.06 (quint, J=6.0 Hz, 1H), 3.83 (s, 3H), 3.05 (t, J=7.2 Hz, 2H), 2.95 (t, J=7.2 Hz, 2H), 2.38 (s, 3H), 2.16 (quint, J=7.2 Hz, 2H), 1.94-1.74 (m, 4H), 1.04 (t, J=7.5 Hz, 6H).

EXAMPLE 9(2)

8-(3-pentyloxy)-2-methyl-3-(2-chloro-4-methoxyphenyl)-5,7-dihydro-furo[3,4-d]pyrazolo[1,5-a]pyrimidine

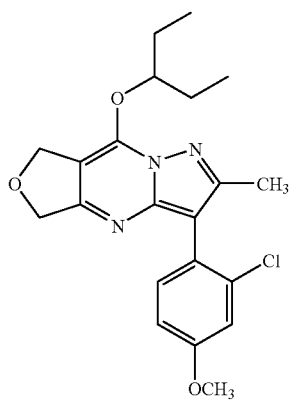

TLC: Rf 0.25 (hexane:ethyl acetate=3:1);
NMR (300 MHz, CDCl$_3$): δ 7.28 (d, J=8.4 Hz, 1H), 7.07 (d, J=2.7 Hz, 1H), 6.90 (dd, J=8.4, 2.7 Hz, 1H), 5.29 (s, 2H), 4.93 (s, 2H), 4.56 (m, 1H), 3.84 (s, 3H), 2.41 (s, 3H), 1.99-1.80 (m, 4H), 1.05 (t, J=7.5 Hz, 6H).

EXAMPLE 9(3)

8-(4-heptyloxy)-2-methyl-3-(2-chloro-5-methoxyphenyl)-6,7-dihydro-5H-cyclopenta[d]pyrazolo[1,5-a]pyrimidine

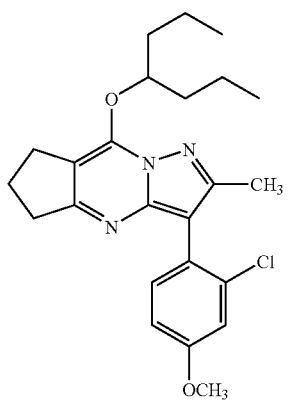

TLC: Rf 0.85 (hexane:ethyl acetate=1:1);
NMR (300 MHz, CDCl$_3$): δ 7.29 (d, J=8.7 Hz, 1H), 7.06 (d, J=2.7 Hz, 1H), 6.89 (dd, J=8.7, 2.7 Hz, 1H), 5.22 (quint, J=6.0 Hz, 1H), 3.83 (s, 3H), 3.05 (t, J=7.5 Hz, 2H), 2.95 (t, J=7.5 Hz, 2H), 2.37 (s, 3H), 2.16 (quint, J=7.5 Hz, 2H), 1.90-1.66 (m, 4H), 1.58-1.42 (m, 4H), 0.95 (t, J=7.2 Hz, 6H).

EXAMPLE 9(4)

8-isopropyloxy-2-methyl-3-(2-chloro-5-methoxyphenyl)-6,7-dihydro-5H-cyclopenta[d]pyrazolo[1,5-a]pyrimidine

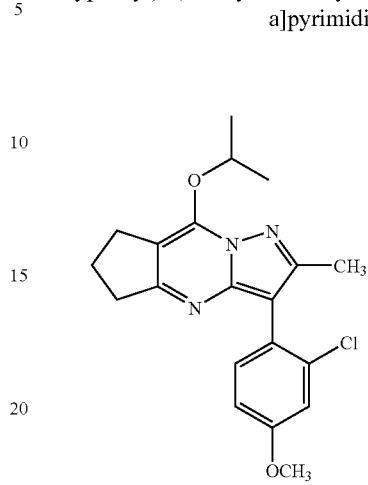

TLC: Rf 0.36 (hexane:ethyl acetate=2:1);
NMR (300 MHz, CDCl$_3$): δ 7.29 (d, J=8.4 Hz, 1H), 7.06 (d, J=2.4 Hz, 1H), 6.89 (dd, J=8.4, 2.4 Hz, 1H), 5.43 (sept, J=6.3 Hz, 1H), 3.83 (s, 3H), 3.06 (t, J=7.5 Hz, 2H), 2.96 (t, J=7.5 Hz, 2H), 2.38 (s, 3H), 2.16 (quint, J=7.5 Hz, 2H), 1.51 (d, J=6.3 Hz, 6H).

EXAMPLE 9(5)

8-(1,6-heptadien-4-yl)oxy-2-methyl-3-(2-chloro-4-methoxyphenyl)-6,7-dihydro-5H-cyclopenta[d]pyrazolo[1,5-a]pyrimidine

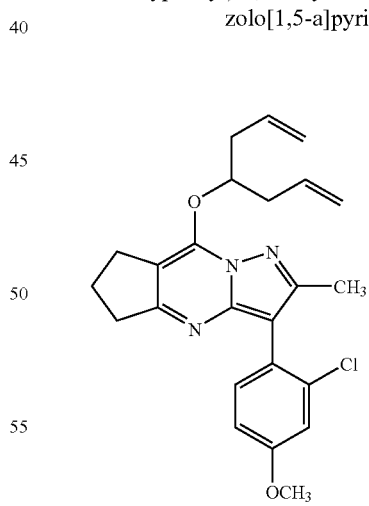

TLC: Rf 0.58 (hexane:ethyl acetate=2:1);
NMR (300 MHz, CDCl$_3$): δ 7.29 (d, J=8.4 Hz, 1H), 7.06 (d, J=2.7 Hz, 1H), 6.89 (dd, J=8.4, 2.7 Hz, 1H), 5.90 (ddt, J=17.1, 10.2, 6.9 Hz, 2H), 5.34 (quint, J=6.3 Hz, 1H), 5.17 (m, 2H), 5.11 (dd, m, 2H), 3.83 (s, 3H), 3.01 (t, J=7.5 Hz, 2H), 2.95 (t, J=7.5 Hz, 2H), 2.70-2.50 (m, 4H), 2.38 (s, 3H), 2.15 (quint, J=7.5 Hz, 2H).

EXAMPLE 10

8-(3-pentylthio)-2-methyl-3-(2-chloro-5-methoxyphenyl)-6,7-dihydro-5H-cyclopenta[d]pyrazolo[1,5-a]pyrimidine hydrochloride

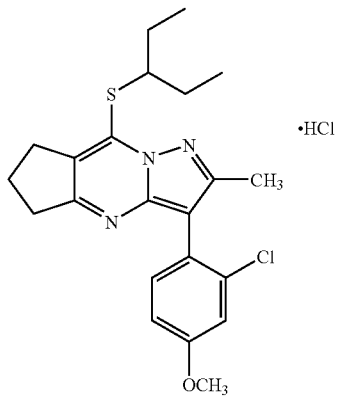

3-Acetylthiopentane (252 mg) and the compound prepared in Reference example 7 (300 mg) were added to a solution of sodium hydride (68.9 mg; 60% in oil) in ethanol (17 ml) at 0° C. After the mixture was stirred for 1 hour, the reaction mixture was concentrated. Water and ethyl acetate were added to the residue and stirred. The organic layer was separated. Meanwhile, the water layer was extracted with ethyl acetate. A combined organic layer was washed with a saturated aqueous solution of sodium chloride, dried over anhydrous sodium sulfate and concentrated. The residue was purified by column chromatography on silica gel (hexane:ethyl acetate=5:1) 4N hydrochloric acid—ethyl acetate (0.2 ml) was added to the purified matter, and the solution was stirred for 10 minutes and concentrated to give the title compound (271.1 mg) having the following physical data.

TLC: Rf 0.57 (hexane:ethyl acetate=2:1);

NMR (300 MHz, CDCl$_3$): δ 7.29 (d, J=8.7 Hz, 1H), 7.07 (d, J=2.4 Hz, 1H), 6.89 (dd, J=8.7, 2.4 Hz, 1H), 4.27 (quint. J=6.3 Hz, 1H), 3.84 (s, 3H), 3.05 (t, J=7.5 Hz, 2H), 3.00 (t, J=7.5 Hz, 2H), 2.40 (s, 3H), 2.17 (quint, J=7.5 Hz, 2H), 1.72-1.64 (m, 4H), 1.02 (t, J=7.5 Hz, 6H).

EXAMPLE 11

8-(4-methylphenyl)-2-methyl-3-(2-methyl-4-methoxyphenyl)-6,7-dihydro-5H-cyclopenta[d]pyrazolo[1,5-a]pyrimidine

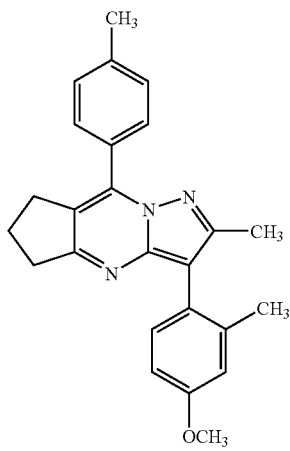

To the compound prepared in Reference example 7 (300 mg) in dimethoxyethane (3 ml), 4-methylphenylboronic acid (131 mg), palladium acetate (11 mg), triphenylphosphine (48 mg) and a saturated aqueous solution of sodium carbonate (2 ml) were added, and the mixture was refluxed with heating for 5 hours. After the reaction mixture was cooled, it was diluted with ethyl acetate. The diluted solution was washed with a saturated aqueous solution of sodium chloride and water, dried over anhydrous magnesium sulfate and concentrated. The residue was purified by column chromatography on silica gel (hexane:ethyl acetate=5:1) to give the title compound (222 mg) having the following physical data.

TLC: Rf 0.41 (hexane:ethyl acetate=3:1);

NMR (300 MHz, CDCl$_3$): δ 7.72 (d, J=8.1 Hz, 2H), 7.36 (d, J=8.1 Hz, 2H), 7.19 (d, J=8.4 Hz, 1H), 6.88 (d, J=2.7 Hz, 1H), 6.81 (dd, J=2.7, 8.4 Hz, 1H), 3.84 (s, 3H), 3.01 (t, J=7.5 Hz, 2H), 2.94 (t, J=6.6 Hz, 2H), 2.45 (s, 3H), 2.30 (s, 3H), 2.20 (s, 3H), 2.14 (m, 2H).

EXAMPLE 11(1)-11(5)

The following compounds were obtained by the same procedure as a reaction of Example 11, using a corresponding compound.

EXAMPLE 11(1)

8-(2,4-dichlorophenyl)-2-methyl-3-(2-methyl-4-methoxyphenyl)-6,7-dihydro-5H-cyclopenta[d]pyrazolo[1,5-a]pyrimidine hydrochloride

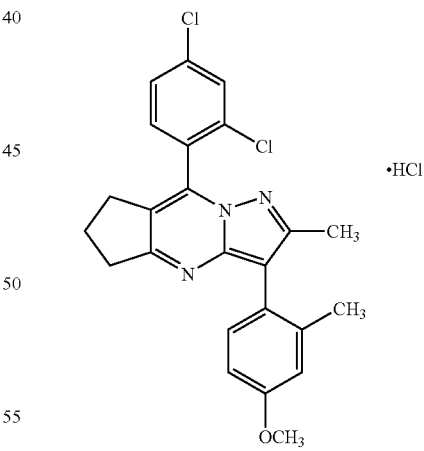

TLC: Rf TLC: Rf 0.38 (hexane:ethyl acetate=3:1);

NMR (300 MHz, DMSO-d$_6$): δ 7.91 (d, J=1.8 Hz, 1H), 7.70 (d, J=8.4 Hz, 1H), 7.64 (dd, J=1.8, 8.4 Hz, 1H), 7.11 (br d, J=8.1 Hz, 1H), 6.90 (d, J=2.7 Hz, 1H), 6.81 (dd, J=2.7, 8.4 Hz, 1H), 3.77 (s, 3H), 2.94 (m, 2H), 2.68 (m, 2H), 2.14 (s, 3H), 2.12 (m, 2H), 2.09 (s, 3H).

EXAMPLE 11(2)

8-(3-trifluoromethylphenyl)-2-methyl-3-(2-methyl-4-methoxyphenyl)-6,7-dihydro-5H-cyclopenta[d]pyrazolo[1,5-a]pyrimidine

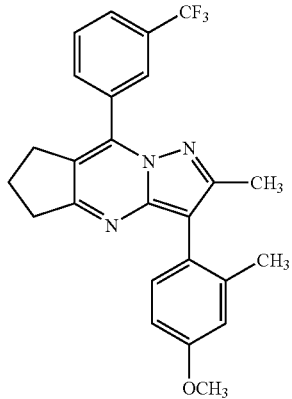

TLC: Rf 0.27 (hexane:ethyl acetate=3:1);

NMR (300 MHz, CDCl$_3$): δ 8.08 (brs, 1H), 8.06 (brd, J=8.1 Hz, 1H), 7.79 (brd, J=7.8 Hz, 1H), 7.70 (brdd, J=8.1, 7.8 Hz, 1H), 7.19 (d, J=8.1 Hz, 1H), 6.89 (d, J=2.7 Hz, 1H), 6.82 (dd, J=8.1, 2.7 Hz, 1H), 3.84 (s, 3H), 3.04 (t, J=7.5 Hz, 2H), 2.94 (t, J=7.5 Hz, 2H), 2.31 (s, 3H), 2.20 (s, 3H), 2.18 (m, 2H).

EXAMPLE 11(3)

8-(4-methoxyphenyl)-2-methyl-3-(2-methyl-4-methoxyphenyl)-6,7-dihydro-5H-cyclopenta[d]pyrazolo[1,5-a]pyrimidine hydrochloride

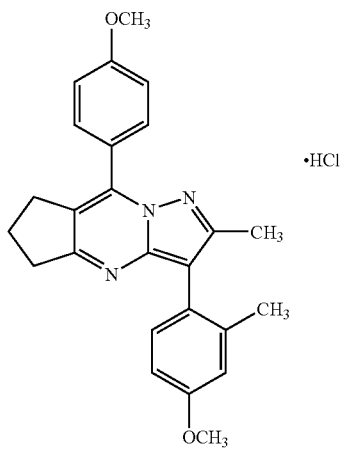

TLC: Rf 0.23 (hexane:ethyl acetate=3:1);

NMR (300 MHz, CDCl$_3$): δ 7.92 (d, J=9.0 Hz, 2H), 7.16 (d, J=9.0 Hz, 2H), 7.16 (d, J=9.0 Hz, 1H), 6.92 (d, J=2.7 Hz, 1H), 6.86 (dd, J=9.0, 2.7 Hz, 1H), 3.95 (s, 3H), 3.85 (s, 3 H), 3.61 (t, J=7.5 Hz, 2H), 3.09 (t, J=7.5 Hz, 2H), 2.38 (s, 3H), 2.30 (m, 2H), 2.20 (s, 3 H).

EXAMPLE 11(4)

8-(3,5-dichlorophenyl)-2-methyl-3-(2-methyl-4-methoxyphenyl)-6,7-dihydro-5H-cyclopenta[d]pyrazolo[1,5-a]pyrimidine

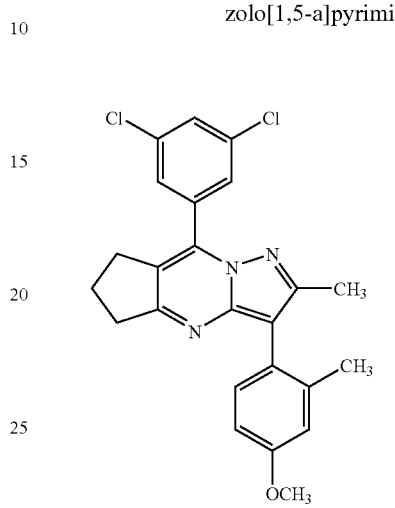

TLC: Rf 0.50 (hexane:ethyl acetate=3:1);

NMR (300 MHz, CDCl$_3$): δ 7.69 (d, J=1.8 Hz, 2H), 7.52 (t, J=1.8 Hz, 1H), 7.17 (d, J=8.4 Hz, 1H), 6.88 (d, J=2.7 Hz, 1H), 6.82 (dd, J=2.7, 8.4 Hz, 1H), 3.84 (s, 3H), 3.02 (t, J=7.5 Hz, 2H), 2.93 (t, J=6.9 Hz, 2H), 2.32 (s, 3H), 2.19 (s, 3H), 2.17 (m, 2H).

EXAMPLE 11(5)

8-(2-methylphenyl)-2-methyl-3-(2-methyl-4-methoxyphenyl)-6,7-dihydro-5H-cyclopenta[d]pyrazolo[1,5-a]pyrimidine

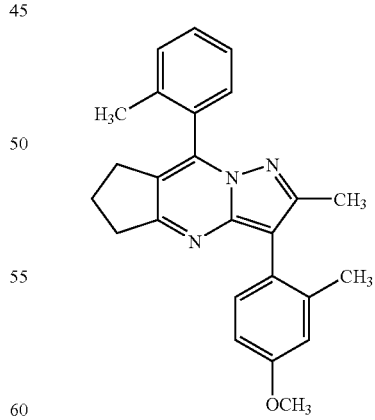

TLC: Rf 0.38 (hexane:ethyl acetate=3:1);

NMR (300 MHz, CDCl$_3$): δ 7.34-7.48 (m, 4H), 7.20 (m, 1H), 6.89 (d, J=2.7 Hz, 1H), 6.82 (dd, J=2.7, 8.1 Hz, 1H), 3.84 (s, 3H), 3.04 (m, 2H), 2.81 (m, 1H), 2.62 (m, 1H), 2.27 (s, 3H), 2.20 (m, 3H), 2.17 (s, 3H), 2.15 (m, 2H).

EXAMPLE 12

8-bis(ethoxycarbonyl)methyl-2-methyl-3-(2-methyl-4-methoxyphenyl)-6,7-dihydro-5H-cyclopenta[d]pyrazolo[1,5-a]pyrimidine

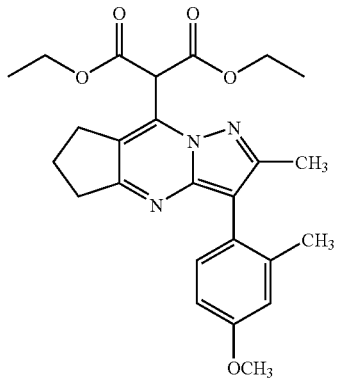

Diethyl malonate (880 mg) was added to a suspension of sodium hydride (210 mg; 63.1% in oil) in tetrahydrofuran (10 ml), and the mixture was stirred for 30 minutes at room temperature. The compound prepared in Reference example 7 (820 mg) was added to the reaction mixture, and the resultant mixture was refluxed with heating for 4 hours. A saturated aqueous solution of ammonium chloride (10 ml) was added to the reaction mixture, and it was extracted with ethyl acetate. The organic layer was washed with a saturated aqueous solution of sodium chloride, dried over anhydrous sodium sulfate and concentrated. The residue was purified by column chromatography on silica gel (hexane:ethyl acetate=8:1→7:1) to give the title compound (1.10 g) having the following physical data.

TLC: Rf 0.48 (hexane:ethyl acetate=2:1);

NMR (300 MHz, CDCl$_3$): δ 7.15 (d, J=8.1 Hz, 1H), 6.87 (d, J=3.0 Hz, 1H), 6.80 (dd, J=8.1, 3.0 Hz, 1H), 6.02 (s, 1H), 4.32 (m, 4H), 3.82 (s, 3H), 2.96 (t, J=7.8 Hz, 2H), 2.91 (t, J=7.8 Hz, 2H), 2.32 (s, 3H), 2.21-2.09 (m, 2H), 2.17 (s, 3H), 1.32 (t, J=7.2 Hz, 6H).

EXAMPLE 12(1)-12(4)

The following compounds were obtained by the same procedure as a reaction of Example 12, using a corresponding compound.

EXAMPLE 12(1)

8-(1-dimethylamino-1,3-dioxo-2-butyl)-2-methyl-3-(2-methyl-4-methoxyphenyl)-6,7-dihydro-5H-cyclopenta[d]pyrazolo[1,5-a]pyrimidine

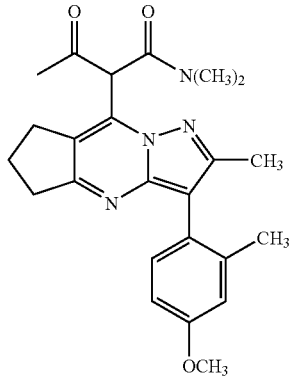

TLC: Rf 0.55 (ethyl acetate);

NMR (300 MHz, CDCl$_3$): δ 7.14 (d, J=8.1 Hz, 1H), 6.87 (d, J=1.8 Hz, 1H), 6.83-6.74 (m, 1H), 6.29 (s, 1H), 3.83 (s, 3H), 3.05 (s, 3H), 3.05-2.60 (m, 6H), 2.41 (s, 3H), 2.30 (s, 3H), 2.16 (brs, 6H).

EXAMPLE 12(2)

8-(2,4-dioxo-3-pentyl)-2-methyl-3-(2-methyl-4-methoxyphenyl)-6,7-dihydro-5H-cyclopenta[d]pyrazolo[1,5-a]pyrimidine

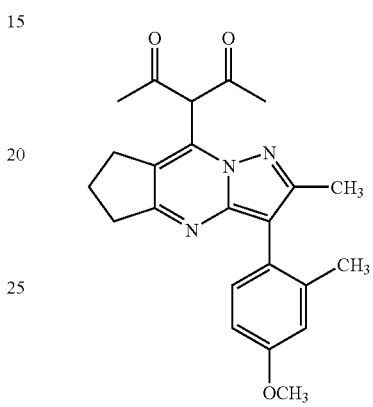

TLC: Rf 0.34 (hexane:ethyl acetate=3:1);

NMR (300 MHz, CDCl$_3$): δ 16.93 (s, 1H), 7.19 (d, J=8.4 Hz, 1H), 6.89 (d, J=3.0 Hz, 1H), 6.83 (dd, J=8.4, 3.0 Hz, 1H), 3.84 (s, 3H), 3.04 (t, J=7.2 Hz, 2H), 2.81 (t, J=7.2 Hz, 2H), 2.33 (s, 3H), 2.20 (quint, J=7.2 Hz, 2H), 2.18 (s, 3H), 1.95 (s, 6H).

EXAMPLE 12(3)

8-bis(ethoxycarbonyl)methyl-2-methyl-3-(2-chloro-4-methoxyphenyl)-6,7-dihydro-5H-cyclopenta[d]pyrazolo[1,5-a]pyrimidine

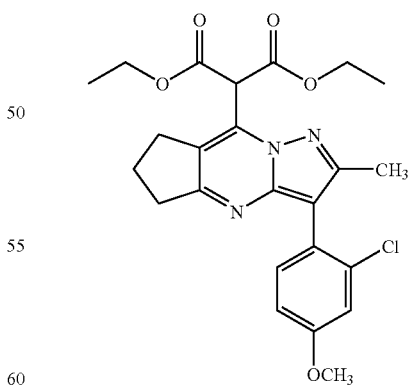

TLC: Rf 0.18 (hexane:ethyl acetate=3:1);

NMR (300 MHz, CDCl$_3$): δ 7.28 (d, J=8.4 Hz, 1H), 7.07 (d, J=2.4 Hz, 1H), 6.89 (dd, J=8.4, 2.4 Hz, 1H), 6.02 (s, 1H), 4.40-4.20 (m, 4H), 3.84 (s, 3H), 2.98 (t, J=7.5 Hz, 2H), 2.92 (t, J=7.5 Hz, 2H), 2.35 (s, 3H), 2.17 (quint, J=7.5 Hz, 2H), 1.31 (t, J=7.2 Hz, 6H).

EXAMPLE 12(4)

8-bis(ethoxycarbonyl)methyl-2-methyl-3-(2-chloro-4-methoxyphenyl)-5,7-dihydro-furo[3,4-d]pyrazolo[1,5-a]pyrimidine

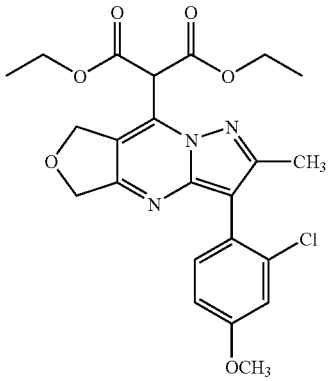

TLC: Rf 0.28 (hexane:ethyl acetate=3:1);
NMR (300 MHz, CDCl$_3$): δ 7.28 (d, J=8.4 Hz, 1H), 7.08 (d, J=2.4 Hz, 1H), 6.91 (dd, J=8.4, 2.4 Hz, 1H), 6.12 (s, 1H), 5.11 (s, 2H), 4.95 (s, 2H), 4.41-4.20 (m, 4H), 3.84 (s, 3H), 2.39 (s, 3H), 1.33 (t, J=7.2 Hz, 6H).

EXAMPLE 13

8-(1,3-hydroxy-2-propyl)-2-methyl-3-(2-methyl-4-methoxyphenyl)-6,7-dihydro-5H-cyclopenta[d]pyrazolo[1,5-a]pyrimidine

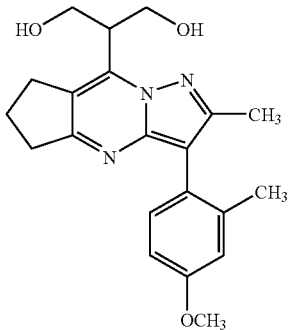

Under argon atmosphere, 1M diisopropyl aluminium hydride (3.94 ml; in hexane) was dropped into a solution of the compound prepared in Example 12 (355 mg) in anhydrous diethyl ether (7 ml) at −78° C. The mixture was warmed at 0° C. and stirred for 4.5 hours. Methanol was dropped into the mixture and then it was warmed at room temperature. 1N hydrochloric acid was added to the reaction mixture, and the mixture was extracted with ethyl acetate. The organic layer was washed with a saturated aqueous solution of sodium chloride, dried over anhydrous sodium sulfate and concentrated. The residue was purified by column chromatography on silica gel (hexane:ethyl acetate=3:1) to give the title compound (260 mg) having the following physical data.

TLC: Rf 0.50 (chloroform:methanol=9:1);
NMR (300 MHz, CDCl$_3$): δ 7.13 (brd, J=8.7 Hz, 1H), 6.87 (s, 1H), 6.80 (brd, J=8.7 Hz, 1H), 4.97 (m, 1H), 4.90 (m, 1H), 4.24 (m, 2H), 4.13 (m, 2H), 3.83 (s, 3H), 3.59 (m, 1H), 2.98 (brt, J=7.2 Hz, 4H), 2.31 (s, 3H), 2.28-2.00 (m, 5H).

EXAMPLE 14

8-(1,3-dimethoxy-2-propyl)-2-methyl-3-(2-methyl-4-methoxyphenyl)-6,7-dihydro-5H-cyclopenta[d]pyrazolo[1,5-a]pyrimidine

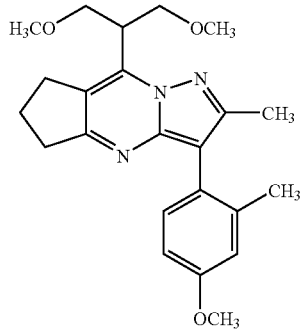

A solution of the compound prepared in Example 13 (120 mg) in DMF (2 ml) was dropped into a solution of sodium hydride (26.0 mg; 60% in oil) in DMF at 0° C. methyl iodide (81.0 µl) was dropped into the mixture, and then stirred for 1 hour. Water and ethyl acetate were added to the reaction mixture, and the organic layer was separated. Besides, the water layer was extracted with ethyl acetate. A combined organic layer was washed with a saturated aqueous solution of sodium chloride, dried over anhydrous sodium sulfate and concentrated after benzene (5 ml) was added. The residue was purified by column chromatography on silica gel (hexane:ethyl acetate=3:1) to give the title compound (58.7 mg) having the following physical data.

TLC: Rf 0.80 (ethyl acetate);
NMR (300 MHz, CDCl$_3$): δ 7.15 (d, J=8.4 Hz, 1H), 6.86 (d, J=2.4 Hz, 1H), 6.79 (dd, J=8.4, 2.4 Hz, 1H), 4.28-4.16 (m, 1H), 4.14-4.06 (m, 2H), 3.96-3.86 (m, 2H), 3.83 (s, 3H), 3.35 (s, 6H), 3.06 (t, J=7.5 Hz, 2H), 2.94 (t, J=7.5 Hz, 2H), 2.31 (s, 3H), 2.17 (s, 3H), 2.17-2.08 (m, 2H).

EXAMPLE 15

8-(N,N-dimethylcarbamoylmethyl)-2-methyl-3-(2-methyl-4-methoxyphenyl)-6,7-dihydro-5H-cyclopenta[d]pyrazolo[1,5-a]pyrimidine

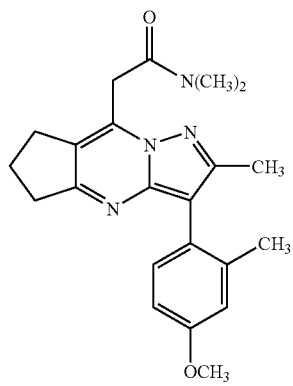

To a solution of the compound prepared in Example 12 (410 mg) in methanol (1 ml), 50% aqueous solution of dimethylamino (491 mg) was added at 24° C., and the mixture was stirred for 20 hours at 90° C. The reaction mixture was cooled to room temperature, and water and ethyl acetate were added to the mixture and stirred. The organic layer was separated. Besides, the water layer was extracted with ethyl acetate. The combined organic layer was washed with a saturated aqueous solution of sodium chloride, dried over anhydrous sodium sulfate and concentrated. The residue was purified by column chromatography on silica gel (hexane:ethyl acetate=5:1) to give the title compound (102.7 mg) having the following physical data.

TLC: Rf 0.55 (hexane:ethyl acetate=1:1);

NMR (300 MHz, CDCl$_3$): δ 7.16 (d, J=8.4 Hz, 1H), 6.87 (d, J=2.7 Hz, 1H), 6.80 (dd, J=8.4, 2.7 Hz, 1H), 3.83 (s, 3H), 3.27 (d, J=1.2 Hz, 1H), 3.04-2.94 (m, 5H), 2.72 (s, 3H), 2.36 (s, 3H), 2.24-2.10 (m, 8H).

REFERENCE EXAMPLE 8

2-chloro-4-methoxybenzaldehyde

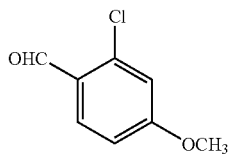

To suspension of sodium hydride (2.6 g; 62.6% in oil) in dimethylformamide (80 ml), a solution of 2-chloro-4-hydroxybenzaldehyde (10.0 g) in dimethylformamide (50 ml) was dropped over 15 minutes. The mixture was stirred for 30 minutes. Methyl iodide (4.2 ml) was dropped into the reaction mixture over 10 minutes at 0° C., and stirred for 1 hour. The reaction mixture was poured into water and extracted with hexane/ethyl acetate (1:1) The organic layer was washed with water and a saturated aqueous solution of sodium chloride, dried over anhydrous magnesium sulfate and concentrated to give the title compound (10.7 g) having the following physical data.

TLC: Rf 0.61 (hexane:ethyl acetate=3:1);

NMR (300 MHz, CDCl$_3$): δ 10.33 (d, J=0.6 Hz, 1H), 7.90 (d, J=9.0 Hz, 1H), 6.94 (d, J=2.4 Hz, 1H), 6.89 (ddd, J=9.0, 2.4, 0.6 Hz, 1H), 3.89 (s, 3H).

REFERENCE EXAMPLE 9

1-(2,2-dibromoethenyl)-2-chloro-4-methoxybenzene

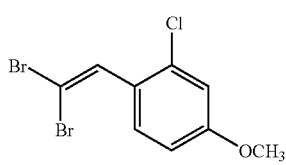

Carbon tetrabromide (10.7 g) was added to a solution of the compound prepared in Reference example 8 (5.0 g) in methylene chloride. Triphenylphosphine (16.9 g) was added by portions to the mixture maintaining inside temperature of 5 degree or less. The mixture was stirred for 30 minutes at 0° C. A suspension of the reaction mixture in hexane (500 ml) was poured into silica gel (30 g) and then filtered. The silica gel was washed with hexane/ethyl acetate (10:1) The filtrate and washings were combined and it was concentrated. The residue was purified by column chromatography on silica gel (hexane:ethyl acetate=10:1) to give the title compound (6.6 g) having the following physical data.

TLC: Rf 0.82 (hexane:ethyl acetate=3:1);

NMR (300 MHz, CDCl$_3$): δ 7.62 (d, J=9.0 Hz, 1H), 7.51 (s, 1H), 6.94 (d, J=2.1 Hz, 1H), 6.83 (dd, J=9.0, 2.1 Hz, 1H), 3.81 (s, 3H).

REFERENCE EXAMPLE 10

1-(1-propynyl)-2-chloro-5-methoxybenzene

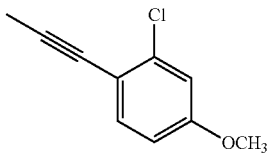

To a solution of the compound prepared in Reference Example 9 (1.98 g) in tetrahydrofuran (20 ml), 1.57M solution of n-butyl lithium in hexane (8.2 ml) was added at −78° C. The mixture was stirred for 30 minutes and 1 hour at 0° C. The reaction mixture was cooled to −78° C., and methyl iodide (0.46 ml) was added and stirred for 1 hour at 0° C. The reaction mixture was poured into water and extracted with ethyl acetate. The organic layer was washed with a saturated aqueous solution of sodium chloride, dried over anhydrous magnesium sulfate and concentrated. The residue was purified by column chromatography on silica gel (hexane:ethyl acetate=10:1) to give the title compound (0.89 g) having the following physical data.

TLC: Rf 0.69 (hexane:ethyl acetate=5:1);

NMR (300 MHz, CDCl$_3$): δ 7.34 (d, J=8.7 Hz, 1H), 6.91 (d, J=2.7 Hz, 1H), 6.73 (d, J=8.7 Hz, 2.7 Hz, 1H), 3.79 (s, 3H), 2.10 (s, 3H).

REFERENCE EXAMPLE 11

5-bis(trimethylsilyl)amino-2-cyano-3-methyl-4-(2-chloro-4-methoxyphenyl)pyrrole

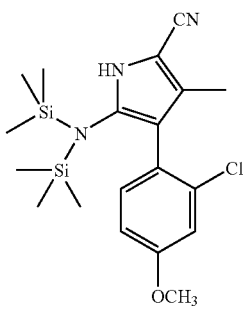

Under argon atmosphere, diisobutyl aluminum hydride (13.8 ml) was added slowly to nickel chloride (832 g), which was dried with heating for 30 minutes, and then the mixture was stirred for 15 minutes. After a color of the mixture was changed to black, the compound prepared in Reference example 10 (11.6 g) in trimethylsilyl cyanide (46 ml) was added over 25 minutes to the reaction mixture. The mixture was heated, and hexane was distilled off. The solution was stirred for 2.5 hours at 130° C. The reaction mixture was cooled at room temperature, and diluted with methylene chloride. The diluted solution was purified by column chromatography on silica gel (hexane:ethyl acetate=10:1) to give the title compound (9.5 g) having the following physical data and 2-bis(trimethylsilyl)amino-5-cyano-3-methyl-4-(2-chloro-4-methoxyphenyl)pyrrole (5.2 g) as by-product.

TLC: Rf 0.34 (hexane:ethyl acetate=10:1);

NMR (300 MHz, CDCl$_3$): δ 7.76 (brs, 1H), 7.10 (d, J=8.4 Hz, 1H), 7.00 (d, J=2.7 Hz, 1H), 6.82 (dd, J=8.4, 2.7 Hz, 1H), 3.83 (s, 3H), 2.06 (s, 3H), 0.14 (s, 9H), −0.14 (s, 9H).

REFERENCE EXAMPLE 12

5-amino-2-cyano-3-methyl-4-(2-chloro-4-methoxyphenyl)pyrrole

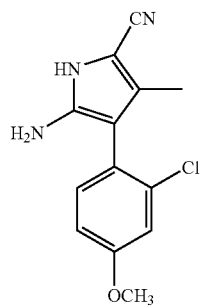

To a solution of the compound prepared in Reference Example 11 (6.27 g) in methanol (50 ml), 1N aqueous solution of sodium hydroxide (15.4 ml) was added at room temperature. The mixture was refluxed with heating for 1.5 hours. After the reaction mixture was cooled to room temperature, the reaction mixture was poured into an aqueous solution of sodium carbonate, and extracted with ethyl acetate. The organic layer was washed with a saturated aqueous solution of sodium chloride, dried over anhydrous magnesium sulfate and concentrated to give the title compound (4.78 g) having the following physical data.

TLC: Rf 0.20 (hexane:ethyl acetate=3:1);

NMR (300 MHz, CDCl$_3$): δ 8.61 (brs, 1H), 7.14 (d, J=8.7 Hz, 1H), 7.03 (d, J=2.4 Hz, 1H), 6.86 (dd, J=8.7, 2.4 Hz, 1H), 3.83 (s, 3H), 3.71 (brs, 2H), 2.04 (s, 3H).

EXAMPLE 16

1-cyano-2-methyl-8-hydroxy-3-(2-chloro-4-methoxyphenyl)-6,7-dihydro-5H-cyclopenta[d]pyrazolo[1,2-a]pyrimidine

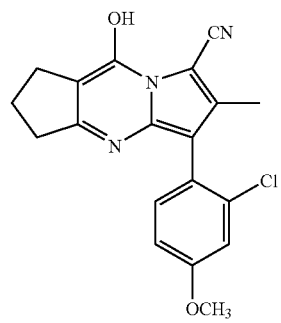

The title compound (1.35 g) was obtained by the same procedure as a reaction of Example 1, using the compound prepared in Reference Example 12 (4.15 g).

TLC: Rf 0.15 (hexane:ethyl acetate=1:1);

NMR (300 MHz, DMSO-d): δ 12.25 (brs, 1H), 7.31 (d, J=7.8 Hz, 1H), 7.20 (d, J=2.7 Hz, 1H), 7.02 (dd, J=7.8, 2.7 Hz, 1H), 3.83 (s, 3H), 2.83 (m, 2H), 2.66 (m, 2H), 2.06 (s, 3H), 2.03 (m, 2H).

EXAMPLE 17

1-cyano-2-methyl-8-(3-pentylamino)-3-(2-chloro-4-methoxyphenyl)-6,7-dihydro-5H-cyclopenta[d]pyrazolo[1,2-a]pyrimidine

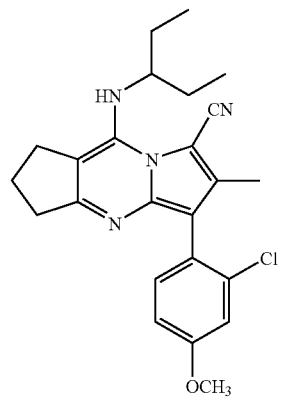

The title compound (112 mg) was obtained by the same procedure as a reaction of Example 2, using 1-cyano-2-methyl-8-chloro-3-(2-chloro-4-methoxyphenyl)-6,7-dihydro-5H-cyclopenta[d]pyrrolo[1,2-a]pyrimidine (180 mg) which was prepared by the same procedure as a reaction of Reference Example 7 using the compound prepared in Reference example 16.

TLC: Rf 0.36 (toluene:ethyl acetate=9:1);

NMR (300 MHz, CDCl$_3$): δ 7.25 (d, J=8.4 Hz, 1H), 7.05 (d, J=2.4 Hz, 1H), 6.88 (dd, J=8.4, 2.4 Hz, 1H), 5.94 (d, J=9.0 Hz, 1H), 3.83 (s, 3H), 3.82 (m, 1H), 3.04 (m, 2H), 2.87 (m, 2H), 2.29 (s, 3H), 2.11 (m, 2H), 1.82-1.60 (m, 4H), 1.04 (t, J=7.5 Hz, 3H), 1.03 (t, J=7.5 Hz, 3H).

EXAMPLE 17(1)

1-cyano-2-methyl-8-dipropylamino-3-(2-chloro-4-methoxyphenyl)-6,7-dihydro-5H-cyclopenta[d]pyrazolo[1,2-a]pyrimidine

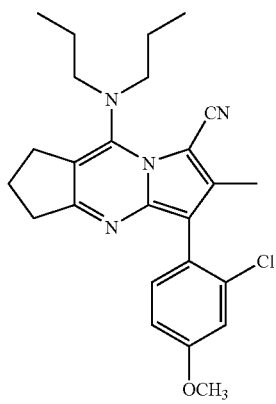

The title compound having the following physical data was obtained by the same procedure as a series of reactions of Reference Example 8→Reference Example 9→Reference Example 10→Reference Example 11→Reference Example 12→Example 16→Example 17, using a corresponding compound.

TLC: Rf 0.39 (hexane:ethyl acetate=3:1);

NMR (300 MHz, CDCl$_3$): δ 7.26 (d, J=8.1 Hz, 1H), 7.06 (d, J=2.4 Hz, 1H), 6.89 (dd, J=8.1, 2.4 Hz, 1H), 3.84 (s, 3H), 3.35-3.13 (m, 4H), 3.00-2.80 (m, 4H), 2.32 (s, 3H), 2.14 (m, 2H), 1.81-1.38 (m, 4H), 0.91 (t, J=7.5 Hz, 6H).

REFERENCE EXAMPLE 13

5-amino-4-cyano-2,3-dimethyl-1-(2-methyl-4-methoxyphenyl)pyrrole

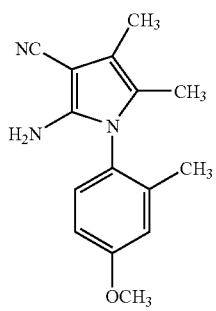

To a solution of 2-methyl-4-methoxyaniline (10 g) in toluene (120 ml), acetoin and p-toluenesulfonic acid hydrate (44 mg) were added. The mixture was refluxed with heating for 2 hours. After the reaction mixture was cooled to room temperature, malononitrile (4.6 ml) was added to the reaction mixture, and it was refluxed with heating for 12 hours. The cooled reaction mixture was concentrated. The residue was diluted with ether, and filtered to give the title compound (5.73 g) having the following physical data TLC: Rf 0.65 (hexane:ethyl acetate=1:1);

NMR (300 MHz, CDCl$_3$): δ 7.07 (d, J=8.4 Hz, 1H), 6.87 (d, J=3.0 Hz, 1H), 6.82 (dd, J=3.0, 8.4 Hz, 1H), 3.84 (s, 3H), 3.71 (brs, 2H), 2.06 (s, 3H), 1.99 (s, 3H), 1.73 (s, 3H).

EXAMPLE 18

2,3-dimethyl-4-amino-1-(2-methyl-4-methoxyphenyl)-6,7-dihydro-5H-cyclopenta[e]pyrrolo[2,3-b]pyridine

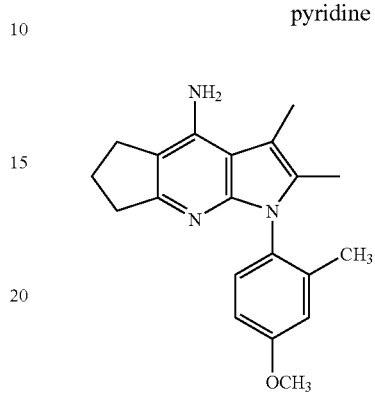

To a solution of the compound prepared in Reference Example 13 (4.0 g) in benzene (40 ml), cyclopentanone (1.46 ml) and p-toluenesulfonic acid hydrate (40 mg) were added. The mixture was refluxed with heating and dehydrating for 12 hours. An insoluble matter was removed by filtration through celite, and the filtrate was concentrated. Under an argon atmosphere, 2M lithium diisopropylamide (15.7 ml; in THF) was added to a solution of the residue in anhydrous tetrahydrofuran (80 ml) at 0° C., and then the mixture was warmed to room temperature and stirred for 5 days. Water was added to the reaction mixture, and the mixture was extracted with ethyl acetate. The extract was washed with water and a saturated aqueous solution of sodium chloride, successively, dried over anhydrous magnesium sulfate and concentrated. The residue was purified by column chromatography on silica gel (ethyl acetate) to give the title compound (2.85 g) having the following physical data TLC: Rf 0.51 (chloroform:methanol=10:1);

NMR (300 MHz, CDCl$_3$): δ 7.10 (d, J=8.4 Hz, 1H), 6.85 (d, J=3.0 Hz, 1H), 6.80 (dd, J=3.0, 8.4 Hz, 1H), 4.31 (s, 2H), 3.83 (s, 3H), 2.90 (m, 2H), 2.74 (m, 2H), 2.48 (s, 3H), 2.10 (m, 2H), 1.97 (s, 3H), 1.90 (s, 3H).

EXAMPLE 19

2,3-dimethyl-4-ethylcarbonylamino-1-(2-methyl-4-methoxyphenyl)-6,7-dihydro-5H-cyclopenta[e]pyrrolo[2,3-b]pyridine

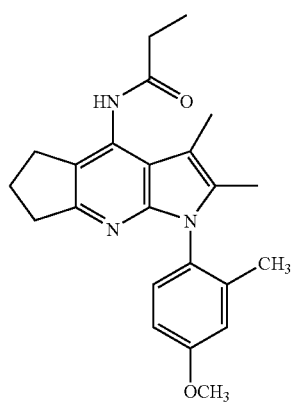

To a solution of the compound prepared in Example 18 (600 mg) in THF (60 ml), triethylamine (520 µl) and propionyl chloride (180 µl) were added. The mixture was stirred for 2 hours. The reaction mixture was diluted with ethyl acetate, and the diluted solution was washed with a saturated aqueous solution of sodium bicarbonate and with a saturated aqueous solution of sodium chloride, successively, dried over anhydrous magnesium sulfate and concentrated. The residue was washed with hexane to give the title compound (451 mg) having the following physical data.

TLC: Rf 0.60 (chloroform:methanol=10:1);

NMR (300 MHz, CDCl$_3$): δ 7.30 (m, 1H), 7.08 (d, J=8.4 Hz, 1H), 6.87 (d, J=2.7 Hz, 1H), 6.83 (dd, J=2.7, 8.4 Hz, 1H), 3.84 (s, 3H), 2.98 (t, J=7.2 Hz, 2H), 2.87 (m, 2H), 2.51 (m, 2H), 2.37 (s, 3H), 2.09 (m, 2H), 2.02 (s, 3H), 1.88 (s, 3H), 1.33 (m, 3H).

EXAMPLE 20

2,3-dimethyl-4-propylamino-1-(2-methyl-4-methoxyphenyl)-6,7-dihydro-5H-cyclopenta[e]pyrrolo[2,3-b]pyridine

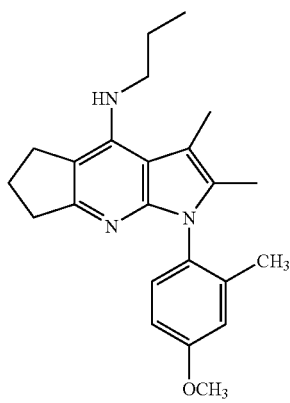

To a solution of the compound prepared in Example 19 (451 mg) in THF (5.0 ml), 2M borane dimethylsulfide complex (4.8 ml; in THF) was added, and the mixture was refluxed with heating for 5 hours. Methanol was added to the reaction mixture, and then the mixture was refluxed with heating for 2 hours. After the reaction mixture was cooled, the mixture was diluted with ethyl acetate. The diluted solution was washed with water and a saturated aqueous solution of sodium chloride, dried over anhydrous magnesium sulfate and concentrated. The residue was purified by column chromatography on silica gel (hexane:ethyl acetate=1:1) to give the title compound (268 mg) having the following physical data.

TLC: Rf 0.47 (hexane:ethyl acetate=1:1);

NMR (300 MHz, CDCl$_3$): δ 7.09 (d, J=8.7 Hz, 1H), 6.85 (d, J=2.7 Hz, 1H), 6.80 (dd, J=2.7, 8.7 Hz, 1H), 3.83 (s, 3H), 3.43 (m, 2H), 3.05 (m, 2H), 2.84 (m, 2H), 2.48 (s, 3H), 2.04 (m, 2H), 1.97 (s, 3H), 1.90 (s, 3H), 1.65 (m, 21-1), 1.02 (t, J=7.5 Hz, 3H).

EXAMPLE 21

2,3-dimethyl-4-(N-ethylcarbonyl-N-propylamino)-1-(2-methyl-4-methoxyphenyl)-6,7-dihydro-5H-cyclopenta[e]pyrrolo[2,3-b]pyridine

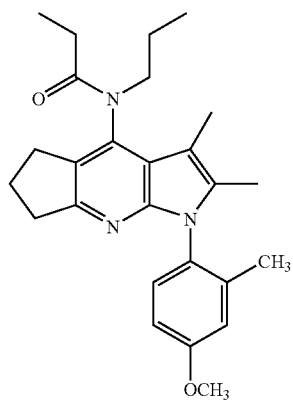

Under argon atmosphere, triethylamine (360 µl) and propionyl chloride (134 µl) were added to a solution of the compound prepared in Example 20 (234 mg) in methylene chloride (3.0 ml) at 0° C. The mixture was stirred for 1 hour. The reaction mixture was diluted with ethyl acetate, and the diluted solution was washed with a saturated aqueous solution of sodium bicarbonate, water and a saturated aqueous solution of sodium chloride, successively, dried over anhydrous magnesium sulfate and concentrated. The residue was purified by column chromatography on silica gel (hexane:ethyl acetate=2:1) to give the title compound (242 g) having the following physical data.

TLC: Rf 0.57 (hexane:ethyl acetate=1:1);

NMR (300 MHz, CDCl$_3$): δ7.11 (m, 1H), 6.90 (d, J=2.4 Hz, 1H), 6.85 (dd, J=2.4, 8.4 Hz, 1H), 3.92 (m, 1H), 3.86 (s, 3H), 3.42 (m, 1H), 3.01 (t, J=7.8 Hz, 2H), 2.87 (m, 2H), 2.20 (s, 3H), 1.94-2.20 (m, 4H), 2.05 (s, 3H), 1.92 and 1.90 (s, total 3H), 1.63 (m, 2H), 0.99-1.10 (m, 3H), 0.85-0.94 (m, 3H).

EXAMPLE 22

2,3-dimethyl-4-dipropylamino-1-(2-methyl-4-methoxyphenyl)-6,7-dihydro-5H-cyclopenta[e]pyrrolo[2,3-b]pyridine

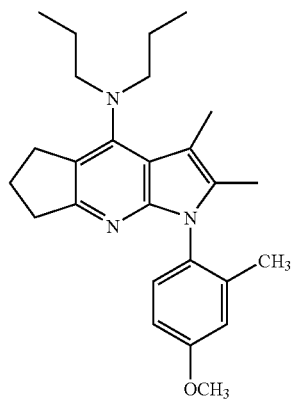

The title compound (182 mg) having the following physical data was obtained by the same procedure as a reaction of Example 20, using the compound prepared in Example 21 (242 mg).

TLC: Rf 0.45 (hexane:ethyl acetate=3:1);

NMR (300 MHz, CDCl$_3$): δ 7.10 (d, J=8.4 Hz, 1H), 6.87 (d, J=2.7 Hz, 1H), 6.81 (dd, J=8.4, 2.7 Hz, 1H), 3.84 (s, 3H), 3.17 (m, 4H), 2.95 (t, J=7.5 Hz, 2H), 2.88 (t, J=7.5 Hz, 2H), 2.44 (s, 3H), 2.05 (m, 2H), 2.01 (s, 3H), 1.92 (s, 3H), 1.52 (m, 4H), 0.85 (t, J=7.2 Hz, 6H).

EXAMPLE 22(1)

2,3-dimethyl-4-(N-ethyl-N-pentylamino)-1-(2-methyl-4-methoxyphenyl)-6,7-dihydro-5H-cyclopenta[e]pyrrolo[2,3-b]pyridine

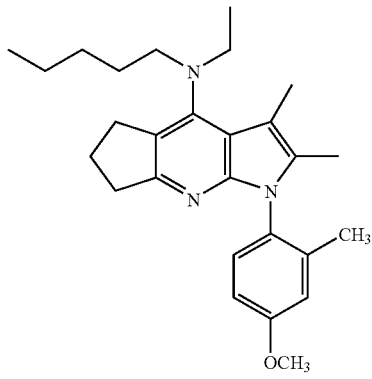

The title compound having the following physical data was obtained by the same procedure as a series of reactions of Example 19→Example 20→Example 21→Example 22, using a compound prepared in Example 18 and a corresponding compound.

TLC: Rf 0.41 (hexane:ethyl acetate=3:1);

NMR (300 MHz, CDCl$_3$): δ 7.10 (d, J=8.4 Hz, 1H), 6.86 (d, J=2.7 Hz, 1H), 6.81 (dd, J=8.4, 2.7 Hz, 1H), 3.84 (s, 3H), 3.27 (q, J=6.9 Hz, 2H), 3.18 (m, 2H), 2.95 (t, J=7.2 Hz, 2H), 2.88 (t, J=7.8 Hz, 2H), 2.44 (s, 3H), 2.05 (m, 2H), 2.00 (s, 3H), 1.91 (s, 3H), 1.50 (m, 2H), 1.38-1.20 (m, 4H), 1.05 (t, J=6.9 Hz, 3H), 0.86 (t, J=6.9 Hz, 3H).

Formulation Example

Formulation Example 1

The following components were admixed in conventional method and punched out to obtain 100 tablets each containing 50 mg of active ingredient.

| | |
|---|---|
| 8-(3-pentylamino)-2-methyl-3-(2-methyl-4-methoxyphenyl)-6,7-dihydro-5H-cyclopenta[d]pyrazolo[1,5-a]pyrimidine | 5.0 g |
| Carboxymethylcellulose calcium (disintegrating agent) | 0.2 g |
| Magnesium stearate (lubricating agent) | 0.1 g |
| Microcrystalline cellulose | 4.7 g |

Formulation Example 2

The following components were admixed in conventional method. The solution was sterilized in conventional manner, placed 5 ml portions into ampoules and freeze-dried to obtain 100 ampoules each containing 20 mg of the active ingredient.

| | |
|---|---|
| 8-(3-pentylamino)-2-methyl-3-(2-methyl-4-methoxyphenyl)-6,7-dihydro-5H-cyclopenta[d]pyrazolo[1,5-a]pyrimidine | 2.0 g |
| mannitol | 20 g |
| distilled water | 500 ml |

The invention claimed is:
1. A compound of formula (I)

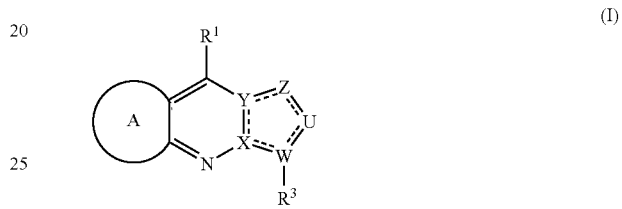

wherein X is carbon;
Y is nitrogen;
W is carbon or nitrogen;
U and Z each independently, is CR$^2$, NR$^{13}$, nitrogen, oxygen, sulfur, C═O or C═S;
R$^2$ is
(i) hydrogen,
(ii) C1-8 alkyl,
(iii) C2-8 alkenyl,
(iv) C2-8 alkynyl,
(v) halogen atom,
(vi) CF$_3$,
(vii) cyano,
(viii) nitro,
(ix) NR$^9$R$^{10}$ in which R$^9$ and R$^{10}$ each independently,
  (i) hydrogen,
  (ii) C1-4 alkyl,
  (iii) C3-10 mono- or bi-carbocyclic ring,
  (iv) 3-10 membered mono- or bi-heterocyclic ring containing 1-4 of nitrogen(s), 1-2 of oxygen(s) and/or 1-2 of sulfur(s) or
  (v) C1-4 alkyl substituted by C3-10 mono- or bi-carbocyclic ring or 3-10 membered mono- or bi-heterocyclic ring containing 1-4 of nitrogen(s), 1-2 of oxygen(s) and/or 1-2 of sulfur(s),
(x) OR$^{11}$ in which R$^{11}$ is
  (i) hydrogen,
  (ii) C1-4 alkyl,
  (iii) C5-6 carbocyclic ring,
  (iv) 5 or 6 membered heterocyclic ring containing 1-2 of nitrogen(s), 1 of oxygen and/or 1 of sulfur or
  (v) C1-4 alkyl substituted by C5-6 carbocyclic ring or 5 or 6 membered heterocyclic ring containing 1-2 of nitrogen(s), 1 of oxygen and/or 1 of sulfur,
(xi) SH,
(xii) S(O)$_n$R$^{12}$ in which n is 0, 1 or 2, R$^{12}$ is
  (i) C1-4 alkyl,
  (ii) C5-6 carbocyclic ring, (iii) 5 or 6 membered heterocyclic ring containing 1-2 of nitrogen(s), 1 of oxygen and/or 1 of sulfur or
(iv) C1-4 alkyl substituted by C5-6 carbocyclic ring or 5 or 6 membered heterocyclic ring containing 1-2 of nitrogen(s), 1 of oxygen and/or 1 of sulfur,
(xiii) $COR^{11}$,
(xiv) $COOR^{11}$,
(xv) $CONR^9R^{10}$,
(xvi) C3-10 mono- or bi-carbocyclic ring,
(xvii) 3-10 membered mono- or bi-heterocyclic ring containing 1-4 of nitrogen(s), 1-2 of oxygen(s) and/or 1-2 of sulfur(s) or
(xviii) C1-4 alkyl substituted by 1-2 of substitutes selected from halogen atom, $CF_3$, $OCF_3$, cyano, nitro, $NR^9R^{10}$, $OR^{11}$, $=N-OR^{11}$, SH, $S(O)_nR^{12}$, $COR^{11}$, $COOR^{11}$, $CONR^9R^{10}$, C3-10mono- or bi- carbocyclic ring and 3-10 membered mono- or bi-heterocyclic ring containing 1-4 of nitrogen(s), 1-2 of oxygen(s) and/or 1-2 of sulfur(s),
$R^{13}$ is
(i) hydrogen,
(ii) C1-4 alkyl,
(iii) C2-4 alkenyl,
(iv) C2-4 alkynyl,
(v) C3-10 mono- or bi-carbocyclic ring,
(vi) 3-10 membered mono- or bi-heterocyclic ring containing 1-4 of nitrogen(s), 1-2 of oxygen(s) and/or 1-2 of sulfur(s) or
(vii) C1-4 alkyl substituted by C3-10 mono- or bi-carbocyclic ring or 3-10 membered mono- or bi-heterocyclic ring containing 1-4 of nitrogen(s), 1-2 of oxygen(s) and/or 1-2 of sulfur(s),
═══ is a single bond or a double bond,

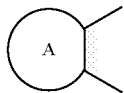

is C4-6 carbocyclic ring which is unsubstituted or substituted by 1-3 of substitutes selected from C1-4 alkyl, C1-4 alkoxy, halogen atom and $CF_3$,
$R^1$ is
(i) C1-8 alkyl which is unsubstituted or substituted by 1-5 of $R^{14}$,
(ii) C2-8 alkenyl which is unsubstituted or substituted by 1-5 of $R^{14}$,
(iii) C2-8 alkynyl which is unsubstituted or substituted by 1-5 of $R^{14}$,
(iv) $NR^4R^5$ in which $R^4$ and $R^5$ each independently,
  (i) hydrogen,
  (ii) C1-15 alkyl which is unsubstituted or substituted by 1-5 of $R^{17}$,
  (iii) C2-15 alkenyl which is unsubstituted or substituted by 1-5 of $R^{17}$,
  (iv) C2-15 alkynyl which is unsubstituted or substituted by 1-5 of $R^{17}$,
  (v) C3-15 mono- or bi-carbocyclic ring which is unsubstituted or substituted by 1-5 of $R^{18}$,
  (vi) 3-15 membered mono- or bi-heterocyclic ring containing 1-4 of nitrogen(s), 1-2 of oxygen(s) and/or 1-2 of sulfur(s) which is unsubstituted or substituted by 1-5 of $R^{18}$,
(v) $OR^6$ in which $R^6$ is
  (i) hydrogen,
  (ii) C1-10 alkyl,
  (iii) C2-10 alkenyl,
  (iv) C2-10 alkynyl,
  (v) C3-15 mono- or bi-carbocyclic ring which is unsubstituted or substituted by 1-5 of $R^{18}$,
  (vi) 3-15 membered mono- or bi-heterocyclic ring containing 1-4 of nitrogen(s), 1-2 of oxygen(s) and/or 1-2 of sulfur(s) which is unsubstituted or substituted by 1-5 of $R^{18}$,
  (vii) C1-4 alkyl substituted by 1-2 of substitutes selected from halogen atom, $CF_3$, $OCF_3$, cyano, nitro, $NR^9R^{10}$, $OR^{11}$, $=N-OR^{11}$, SH, $S(O)nR^{12}$, $COR^{11}$, $COOR^{11}$, $CONR^9R^{10}$, C3-10 mono- or bi-carbocyclic ring which is unsubstituted or substituted by 1-5 of $R^{18}$, and 3-10 membered mono- or bi-heterocyclic ring containing 1-4 of nitrogen(s), 1-2 of oxygen(s) and/or 1-2 of sulfur(s) which is unsubstituted or substituted by 1-5 of $R^{18}$,
(vi) SH,
(vii) $S(O)nR^7$ in which n is as hereinbefore defined, $R^7$ is
  (i) C1-8 alkyl,
  (ii) C3-10 mono- or bi-carbocyclic ring which is unsubstituted or substituted by 1-5 of $R^{18}$,
  (iii) 3-10 membered mono- or bi-heterocyclic ring containing 1-4 of nitrogen(s), 1-2 of oxygen(s) and/or 1-2 of sulfur(s) which is unsubstituted or substituted by 1-5 of $R^{18}$,
  (iv) C1-4 alkyl substituted by C3-10 mono- or bi-carbocyclic ring, which is unsubstituted or substituted by 1-5 of $R^{18}$ or 3-10 membered mono- or bi-heterocyclic ring containing 1-4 of nitrogen(s), 1-2 of oxygen (s) and/or 1-2 of sulfur(s) which is unsubstituted or substituted by 1-5 of $R^{18}$,
(viii) $COR^6$,
(ix) $COOR^6$,
(x) $CONR^4R^5$,
(xi) $NR^8COR^{6a}$ in which $R^{6a}$ is
  (i) hydrogen,
  (ii) C1-10 alkyl,
  (iii) C2-10 alkenyl,
  (iv) C2-10 alkynyl or
  (v) C1-4 alkyl substituted by 1-2 of substitutes selected from halogen atom, $CF_3$, $OCF_3$, cyano, nitro, $NR^9R^{10}$, $OR^{11a}$, $=N-R^{11}$, SH, $S(O)nR^{12}$, $COR^{11}$, $COOR^{11}$ and $CONR^9R^{10}$,
(xii) $NR^8COOR^6$ in which $R^6$ is as hereinbefore defined, $R^8$ is
  (i) hydrogen,
  (ii) C1-8 alkyl,
  (iii) C2-8 alkenyl,
  (iv) C2-8 alkynyl,
  (v) C3-10 mono- or bi-carbocycic ring which is unsubstituted or substituted by 1-5 of $R^{18}$,
  (vi) 3-10 membered mono- or bi-heterocyclic ring containing 1-4 of nitrogen(s), 1-2 of oxygen(s) and/or 1-2 of sulfur(s) which is unsubstituted or substituted by 1-5 of $R^{18}$ or
  (vii) C1-4 alkyl substituted by 1-2 of substitutes selected from halogen atom, $CF_3$, $OCF_3$, cyano, nitro, $NR^9R^{10}$, $=N-OR^{11}$, SH, $S(O)nR^{12}$, $COR^{11}$, COOR$^{11}$, CONR$^9$R$^{10}$, C3-10 mono- or bi-carbocyclic ring which is unsubstituted or substituted by 1-5 of R$^{18}$, and 3-10 membered mono- or bi-heterocyclic ring containing 1-4 of nitrogen(s), 1-2 of oxygen(s) and/or 1-2 of sulfur(s) which is unsubstituted or substituted by 1-5 of R$^{18}$, (xiii) NR$^8$CONR$^4$R$^5$, (xiv) C3-15 mono- or bi-carbocyclic ring which is unsubstituted or substituted by 1-5 of R$^{15}$ or (xv) 3-15 membered mono- or bi-heterocyclic ring containing 1-4 of nitrogen(s), 1-2 of oxygen(s) and/or 1-2 of sulfur(s) which is unsubstituted or substituted by 1-5 of R$^{15}$, R$^{11a}$ is (i) hydrogen, (ii) C1-4 alkyl or (iii) C1-4 alkyl substituted by C5-6 carbocyclic ring or 5 or 6 membered heterocyclic ring containing 1-2 of nitrogen(s), 1 of oxygen and/or 1 of sulfur, R$^{14}$ is (a) halogen atom, (b) CF$_3$, (c) OCF$_3$, (d) cyano, (e) nitro, (f) NR$^4$R$^5$, (g) OR$^6$, (h) =N—OR$^6$, (j) SH, (k) S(O)$^n$R$^7$, (l) COR$^6$, (m) COOR$^6$, (n) CONR$^{45}$, (o) NR$^8$COR$^6$, (p) NR$^8$COOR$^6$, (q) NR$^8$CONR$^4$R$^5$, (r) C3-15 mono- or bi-carbocyclic ring which is unsubstituted or substituted by 1-5 of R$^{15}$ or (s) 3-15 membered mono- or bi-heterocyclic ring containing 1-4 of nitrogen(s), 1-2 of oxygen(s) and/or 1-2 of sulfur(s) which is unsubstituted or substituted by 1-5 of R$^{15}$, R$^{15}$ is (a) C1-8 alkyl, (b) C2-8 alkenyl, (c) C2-8 alkynyl, (d) C1-4 alkoxy(C1-4)alkyl, (e) halogen atom, (f) CF$_3$, (g) OCF$_3$, (h) cyano, (j) nitro, (k) NR$^4$R$^5$, (l) OR$^6$, (m) SH, (n) S(O)$_{nR}$$^7$, (o) COR$^6$, (p) COOR$^6$, (q) CONR$^4$R$^5$, (r) NR$^8$COR$^6$, (s) NR$^8$COOR$^6$, (t) NR$^8$CONR$^4$R$^5$, (u) C3-10 mono- or bi-carbocyclic ring which is unsubstituted or substituted by 1-5 of R$^{20}$, (v) 3-10 membered mono- or bi-heterocyclic ring containing 1-4 of nitrogen(s), 1-2 of oxygen(s) and/or 1-2 of sulfur(s) which is unsubstituted or substituted by 1-5 of R$^{20}$ or (w) C1-4 alkyl substituted by 1-2 of substitutes selected from halogen atom, CF$_3$, OCF$_3$, cyano, nitro, NR$^4$R$^5$, OR$^6$, =N—OR$^6$, SH, S(O)$_n$R$^7$, COR$^6$,COOR$^6$, CONR$^4$R$^5$,NR$^8$COR$^6$,NR$^8$COOR$^6$, NR$^8$CONR$^4$R$^5$, C3-10 mono- or bi-carbocyclic ring which is unsubstituted or substituted by 1-5 of R$^{20}$, and 3-10 membered mono- or bi-heterocyclic ring containing 1-4 of nitrogen(s), 1-2 of oxygen(s) and/or 1-2 of sulfur(s) which is unsubstituted or substituted by 1-5 of R$^{20}$, R$^{17}$ is (a) halogen atom, (b) CF$_3$, (c) OCF$_3$, (d) cyano, (e) nitro, (f) NR$^9$R$^{10}$, (g) OR$^{11a}$, (h) =N—OR$^{11}$, (j) SH, (k) S(O)$_n$R$^{12}$, (l) COR$^{11}$, (m) COOR$^{11}$, (n) CONR$^9$R$^{10}$, (o) NR$^8$COR$^{11}$, (p) NR$^8$COOR$^{11}$, (q) NR$^8$CONR$^9$R$^{10}$, (r) C3-15 mono- or bi-carbocyclic ring which is unsubstituted or substituted by 1-5 of R$^{18a}$ or (s) 3-15 membered mono- or bi-heterocyclic ring containing 1-4 of nitrogen(s), 1-2 of oxygen(s) and/or 1-2 of sulfur(s) which is unsubstituted or substituted by 1-5 of R$^{18a}$, R$^{18}$ is (a) C1-4 alkyl, (b) C2-4 alkenyl, (c) C2-4 alkynyl, (d) halogen atom, (e) CF$_3$, (f) OCF$_3$, (g) cyano, (h) nitro, (j) SH, (k) S(O)$_n$R$^{12}$, (l) NR$^9$R$^{10}$, (m) OR$^{11}$, (n) COR$^{11}$, (o) COOR$^{11}$, (p) CONR$^9$R$^{10}$, (q) C5-6 carbocyclic ring, (r) 5 or 6 membered heterocyclic ring containing 1-2 of nitrogen(s), 1 of oxygen and/or 1 of sulfur or (s) C1-4 alkyl substituted by C5-6 carbocyclic ring or 5 or 6 membered heterocyclic ring containing 1-2 of nitrogen(s), 1 of oxygen and/or 1 of sulfur, R$^{18a}$ is (a) C1-4 alkyl, (b) C2-4 alkenyl, (c) C2-4 alkynyl, (d) halogen atom, (e) CF$_3$, (f) OCF$_3$, (g) cyano, (h) nitro, (j) SH, (k) S(O)$_n$R$^{12}$, (l) NR$^9$R$^{10}$, (m) OR$^{11a}$, (n) COR$^{11}$, (o) COOR$^{11}$ or (p) CONR$^9$R$^{10}$, R$^{19}$ is C1-4 alkyl, C1-4 alkoxy, halogen atom, CF$_3$, OCF$_3$, cyano, nitro, amino, NH(C1-4 alkyl) or N(C1-4 alkyl)$_2$, R$^3$ is (i) C5-10 mono- or bi-carbocyclic ring substituted by 1-5 of R$^{16}$ or (ii) 5-10 membered mono- or bi-heterocyclic ring containing 1-4 of nitrogen(s), 1-2 of oxygen(s) and/or 1-2 of sulfur(s) substituted by 1-5 of R$^{16}$, R$^{16}$ is (a) C1-8 alkyl, (b) C2-8 alkenyl, (c) C2-8 alkynyl, (d) halogen atom, (e) CF$_3$, (f) OCF$_3$, (g) cyano, (h) nitro, (j) NR$^9$R$^{10}$, (k) OR$^{11}$, (l) SH, (m) S(O)$_n$R$^{12}$, (n) COR$^{11}$, (o) COOR$^{11}$, (p) CONR$^9$R$^{10}$, (q) NR$^8$COR$^{11}$, (r) NR$^8$COOR$^{11}$, (s) NR$^8$CONR$^9$R$^{10}$, (t) C3-10 mono- or bi-carbocyclic ring, (u) 3-10 membered mono- or bi-heterocyclic ring containing 1-4 of nitrogen(s), 1-2 of oxygen(s) and/or 1-2 of sulfur(s)

(v) C1-4 alkyl substituted by 1-2 of substitutes selected from halogen atom, CF$_3$, OCF$_3$, cyano, nitro, NR$^9$R$^{10}$, OR$^{11}$, =N-OR$^{11}$, SH, S(O)$_n$R$^{12}$, COR$^{11}$, COOR$^{11}$, CONR$^9$R$^{10}$, NR$^8$COR$^{11}$, NR$^8$COOR$^{11}$, NR$^8$CONR$^9$R$^{10}$, C3-10 mono- or bi-carbocyclic ring, and 3-10 membered mono-or bi-heterocyclic ring containing 1-4 of nitrogen(s), 1-2 of oxygen(s) and/or 1-2 of sulfur(s), with the proviso that (1) when each of X and W is carbon, each of Y and Z is nitrogen, U is CR$^2$ and R$^1$ is OR$^6$, then R$^3$ is not phenyl substituted by 1 of halogen atom, phenyl substituted by 1 of trifluoromethyl and phenyl substituted by trifluoromethyl and nitro, (2) when each of X and Z is carbon and each of U and W is nitrogen, then R$^3$ is C5-10 mono- or bi-carbocyclic ring substituted by 1-5 of R$^{16}$; and (3) when R$^{16}$ is S(O)$_n$R$^{12}$ and R$^{12}$ is (iii), R$^{12}$ is a 5 or 6 membered heterocyclic ring containing 1-2 nitrogen, a 5 or 6 membered heterocyclic ring containing 1 of oxygen and/or a 5 membered heterocyclic ring containing 1 of sulfur;

a pharmaceutically acceptable salt thereof or a hydrate thereof.

2. The compound according to claim 1, wherein X is carbon, Y is nitrogen, each of U and Z is carbon or nitrogen and W is carbon, a pharmaceutically acceptable salt thereof or a hydrate thereof.

3. The compound according to claim 2, wherein each of X, U and W is carbon, each of Y and Z is nitrogen, a pharmaceutically acceptable salt thereof or a hydrate thereof.

4. The compound according to claim 2, wherein each of X, Z, U and W is carbon, Y is nitrogen, a pharmaceutically acceptable salt thereof or a hydrate thereof.

5. The compound according to claim 1, wherein R$^1$ is (i) C1-8 alkyl which is unsubstituted or substituted by 1-5 of R$^{14}$, (ii) C2-8 alkenyl which is unsubstituted or substituted by 1-5 of R$^{14}$, (iii) C2-8 alkynyl which is unsubstituted or substituted by 1-5 of $R^{14}$, (iv) $NR^4R^5$, (v) $OR^6$, (vi) C3-15 mono- or bi-carbocyclic ring which is unsubstituted or substituted by 1-5 of $R^{15}$, or (vii) 3-15 membered mono- or bi-heterocyclic ring containing 1-4 of nitrogen(s), 1-2 of oxygen(s) and/or 1-2 of sulfur(s) which is unsubstituted or substituted by 1-5 of $R^{15}$, in which $R^{14}$ and $R^{15}$ have the same meanings as those defined in claim 1, a pharmaceutically acceptable salt thereof or a hydrate thereof.

6. The compound according to claim 1, which is represented by formula (I-i)

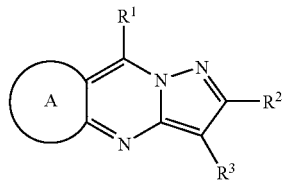

(I-i)

wherein all symbols have the same meanings as those defined in claim 1, a pharmaceutically acceptable salt thereof or a hydrate thereof.

7. The compound according to claim 6, wherein $R^1$ is $NR^4R^5$, and $R^1 NR^4R^5$, and (a) $R^4$ is (i) hydrogen atom, and $R^5$ is (ii) C1-15 alkyl which is unsubstituted or substituted by 1-5 of $R^{17}$, (iii) C2-15 alkenyl which is unsubstituted or substituted by 1-5 of $R^{17}$, (iv) C2-15 alkynyl which is unsubstituted or substituted by 1-5 of $R^{17}$, (v) C3-15 mono- or bi-carbocyclic ring which is unsubstituted or substituted by 1-5 of $R^{18}$ or (vi) 3-15 membered mono- or bi-heterocyclic ring containing 1-4 of nitrogen(s), 1-2 of oxygen(s) and/or 1-2 of sulfur(s) which is unsubstituted or substituted by 1-5 of $R^{18}$ or (b) $R^4$ is (ii) C1-15 alkyl which is unsubstituted or substituted by 1-5 of $R^{17}$, (iii) C2-15 alkenyl which is unsubstituted or substituted by 1-5 of $R^{17}$, (iv) C2-15 alkynyl which is unsubstituted or substituted by 1-5 of $R^{17}$ or (v-1) C3-6 mono-carbocyclic ring and $R^5$ is (ii) C1-15 alkyl which is unsubstituted or substituted by 1-5 of $R^{17}$, (iii) C2-15 alkenyl which is unsubstituted or substituted by 1-5 of $R^{17}$, (iv) C2-15 alkynyl which is unsubstituted or substituted by 1-5 of $R^{17}$, (v) C3-15 mono- or bi-carbocyclic ring which is unsubstituted or substituted by 1-5 of $R^{18}$ or (vi) 3-15 membered mono- or bi-heterocyclic ring containing 1-4 of nitrogen(s), 1-2 of oxygen(s) and/or 1-2 of sulfur(s) which is unsubstituted or substituted by 1-5 of $R^{18}$, a pharmaceutically acceptable salt thereof or a hydrate thereof.

8. The compound according to claim 1 which is represented by formula (I-ii)

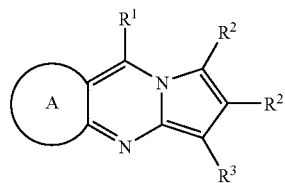

(I-ii)

wherein all symbols have the same meanings as those defined in claim 1, a pharmaceutically acceptable salt thereof or a hydrate thereof.

9. The compound according to claim 8, wherein $R^1$ is $NR^4R^5$, and (a) $R^4$ is (i) hydrogen atom, (ii) C1-15 alkyl which is unsubstituted or substituted by 1-5 of $R^{17}$, (iii) C2-15 alkenyl which is unsubstituted or substituted by 1-5 of $R^{17}$, (iv) C2-15 alkynyl which is unsubstituted or substituted by 1-5 of $R^{17}$, (v) C3-15 mono- or bi-carbocyclic ring which is unsubstituted or substituted by 1-5 of $R^{18}$ or (vi) 3-15 membered mono- or bi-heterocyclic ring containing 1-4 of nitrogen(s), 1-2 of oxygen(s) and/or 1-2 of sulfur(s) which is unsubstituted or substituted by 1-5 of $R^{18}$ or (b) $R^4$ is (ii) C1-15 alkyl which is unsubstituted or substituted by 1-5 of $R^{17}$, (iii) C2-15 alkenyl which is unsubstituted or substituted by 1-5 of $R^{17}$, (iv) C2-15 alkynyl which is unsubstituted or substituted by 1-5 of $R^{17}$ or (v-1) C3-6 mono-carbocyclic ring and $R^5$ is (ii) C1-15 alkyl which is unsubstituted or substituted by 1-5 of $R^{17}$, (iii) C2-15 alkenyl which is unsubstituted or substituted by 1-5 of $R^{17}$, (iv) C2-15 alkynyl which is unsubstituted or substituted by 1-5 of $R^{17}$, (v) C3-15 mono- or bi-carbocyclic ring which is unsubstituted or substituted by 1-5 of $R^{18}$ or (vi) 3-15 membered mono- or bi-heterocyclic ring containing 1-4 of nitrogen(s), 1-2 of oxygen(s) and/or 1-2 of sulfur(s) which is unsubstituted or substituted by 1-5 of $R^{18}$, a pharmaceutically acceptable salt thereof or a hydrate thereof.

10. The compound according to claim 1, which is selected from (1) 8-(3-pentylamino)-2-methyl-3-(2-methyl-4-methoxyphenyl)-6,7-dihydro-5H-cyclopenta [d]pyrazolo[1,5-a]pyrimidine, (2) 8-(N-ethyl-N-n-butylamino)-2-methoxymethyl-3-(2-methyl-4-methoxyphenyl)-6,7-dihydro-5H-cyclopenta [d]pyrazolo[1,5-a]pyrimidine, (3) 8-(N-propyl-N-(2-hydroxyethyl)amino)-2-methyl-3-(2-methyl-4-methoxyphenyl)-6,7-dihydro-5H-cyclopenta[d]pyrazolo[1,5-a]pyrimidine, (4) 9-(3-pentylamino)-2-methyl-3-(2-methyl-4-methoxyphenyl)-5,6,7,8-tetrahydro-pyrazolo[3,2-b]quinazoline, (5) 8-[(2S)-1,1-dimethoxybutan-2-yl]amino-2-methyl-3-(2-methyl-4-methoxyphenyl)-6,7-dihydro-5H-cyclopenta[d]pyrazolo[1,5-a]pyrimidine, (6) 8-(1,3-dimethoxypropan-2-yl)amino-2-methyl-3-(2-methyl-4-methoxyphenyl)-6,7-dihydro-5H-cyclopenta[d]pyrazolo[1,5-a]pyrimidine, (7) 8-bis(2-methoxyethyl)amino-2-methyl-3-(2-methyl-4-methoxyphenyl)-6,7-dihydro-5H-cyclopenta[d]pyrazolo[1,5-a]pyrimidine,
(8) 8-(3-pentylamino)-2-methyl-3-(2,4-dichlorophenyl)-6,7-dihydro-5H-cyclopenta[d]pyrazolo[1,5-a]pyrimidine,
(9) 8-diethylamino-2-methyl-3-(2-methyl-4-methoxyphenyl)-6,7-dihydro-5H-cyclopenta[d]pyrazolo[1,5-a]pyrimidine,
(10) 8-(N-ethyl-N-n-butylamino)-2-methyl-3-(2,4-dichlorophenyl)-6,7-dihydro-5H-cyclopenta[d]pyrazolo[1,5-a]pyrimidine,
(11) 8-dicyclopropylmethylamino-2-methyl-3-(2-methyl-4-methoxyphenyl)-6,7-dihydro-5H-cyclopenta[d]pyrazolo[1,5-a]pyrimidine,
(12) 8-(3-pentylamino)-2-methoxymethyl-3-(2-methyl-4-methoxyphenyl)-6,7-dihydro-5H-cyclopenta[d]pyrazolo[1,5-a]pyrimidine,
(13) 8-(3-pentylamino)-2-methyl-3-(1,3-dioxaindan-5-yl)-6,7-dihydro-5H-cyclopenta[d]pyrazolo[1,5-a]pyrimidine,
(14) 8-(3-pentylamino)-2-methyl-3-(3,4-dimethoxyphenyl)-6,7-dihydro-5H-cyclopenta[d]pyrazolo[1,5-a]pyrimidine,
(15) 8-(3-pentylamino)-2-cyclobutyl-3-(2-methyl-4-methoxyphenyl)-6,7-dihydro-5H-cyclopenta[d]pyrazolo[1,5-a]pyrimidine,
(16) 8-(3-pentylamino)-2-ethyl-3-(2-methyl-4-methoxyphenyl)-6,7-dihydro-5H-cyclopenta[d]pyrazolo[1,5-a]pyrimidine,
(17) 8-(3-pentylamino)-2-isopropyl-3-(2-methyl-4-methoxyphenyl)-6,7-dihydro-5H-cyclopenta[d]pyrazolo[1,5-a]pyrimidine,
(18) 8-(2-ethylbutylamino)-2-methyl-3-(2-methyl-4-methoxyphenyl)-6,7-dihydro-5H-cyclopenta[d]pyrazolo[1,5-a]pyrimidine,
(19) 8-(3-pentylamino)-2-methylthiomethyl-3-(2-methyl-4-methoxyphenyl)-6,7-dihydro-5H-cyclopenta[d]pyrazolo[1,5-a]pyrimidine,
(20) 8-(3-pentylamino)-2-methyl-3-(2,4-dimethylphenyl)-6,7-dihydro-5H-cyclopenta[d]pyrazolo[1,5-a]pyrimidine,
(21) 8-(3-pentylamino)-2-methyl-3-(2,5-dimethylphenyl)-6,7-dihydro-5H-cyclopenta[d]pyrazolo[1,5-a]pyrimidine,
(22) 8-cyclobutylamino-2-methyl-3-(2-methyl-4-methoxyphenyl)-6,7-dihydro-5H-cyclopenta[d]pyrazolo[1,5-a]pyrimidine,
(23) 8-(N-ethyl-N-cyclobutylamino)-2-methyl-3-(2-methyl-4-methoxyphenyl)-6,7-dihydro-5H-cyclopenta[d]pyrazolo[1,5-a]pyrimidine,
(24) 8-(propan-1,3-diol-2-yl)amino-2-methyl-3-(2-methyl-4-methoxyphenyl)-6,7-dihydro-5H-cyclopenta[d]pyrazolo[1,5-a]pyrimidine,
(25) 8-(3-pentylamino)-2-(2-furyl)-3-(2-methyl-4-methoxyphenyl)-6,7-dihydro-5H-cyclopenta[1,5-a]pyrimidine,
(26) 8-(3-pentylamino)-2-phenyl-3-(2-methyl-4-methoxyphenyl)-6,7-dihydro-5H-cyclopenta[d]pyrazolo[1,5-a]pyrimidine,
(27) 8-(2-dimethylaminoethyl)amino-2-methyl-3-(2-methyl-4-methoxyphenyl)-6,7-dihydro-5H-cyclopenta[d]pyrazolo[1,5-a]pyrimidine,
(28) 8-(N-methyl-N-(2-dimethylaminoethyl)amino)-2-methyl-3-(2-methyl-4-methoxyphenyl)-6,7-dihydro-5H-cyclopenta[d]pyrazolo[1,5-a]pyrimidine,
(29) 8-(N-ethyl-N-(2-dimethylaminoethyl)amino)-2-methyl-3-(2-methyl-4-methoxyphenyl)-6,7-dihydro-5H-cyclopenta[d]pyrazolo[1,5-a]pyrimidine,
(30) 8-(4-heptylamino)-2-methyl-3-(2-methyl-4-methoxyphenyl)-6,7-dihydro-5H-cyclopenta[d]pyrazolo[1,5-a]pyrimidine,
(31) 8-(2-butylamino)-2-methyl-3-(2-methyl-4-methoxyphenyl)-6,7-dihydro-5H-cyclopenta[d]pyrazolo[1,5-a]pyrimidine,
(32) 8-(N-propyl-N-cyclopropylmethylamino)-2-methyl-3-(2-methyl-4-methoxyphenyl)-6,7-dihydro-5H-cyclopenta[d]pyrazolo[1,5-a]pyrimidine,
(33) 8-(3-pentylamino)-3-(2-methyl-4-methoxyphenyl)-6,7-dihydro-5H-cyclopenta[d]pyrazolo[1,5-a]pyrimidine,
(34) 8-[(2R)-1-methoxybutan-2-yl]amino-2-methyl-3-(2-methyl-4-methoxyphenyl)-6,7-dihydro-5H-cyclopenta[d]pyrazolo[1,5-a]pyrimidine,
(35) 8-[(2S)-1-methoxybutan-2-yl]amino-2-methyl-3-(2-methyl-4-methoxyphenyl)-6,7-dihydro-5H-cyclopenta[d]pyrazolo[1,5-a]pyrimidine,
(36) 8-cyclopentylamino-2-methyl-3-(2-methyl-4-methoxyphenyl)-6,7-dihydro-5H-cyclopenta[1,5-a]pyrimidine,
(37) 8-(3-pentylamino)-2-methyl-3-(2,4-difluorophenyl)-6,7-dihydro-5H-cyclopenta[d]pyrazolo[1,5-a]pyrimidine,
(38) 8-(3-pentylamino)-2-trifluoromethyl-3-(2-methyl-4-methoxyphenyl)-6,7-dihydro-5H-cyclopenta[d]pyrazolo[1,5-a]pyrimidine,
(39) 8-(N-ethyl-N-(2-methoxyethyl)amino)-2-methyl-3-(2-methyl-4-methoxyphenyl)-6,7-dihydro-5H-cyclopenta[d]pyrazolo[1,5-a]pyrimidine,
(40) 8-cyclohexylamino-2-methyl-3-(2-methyl-4-methoxyphenyl)-6,7-dihydro-5H-cyclopenta[1,5-a]pyrimidine,
(41) 8-(N-propyl-N-(3-pentyl)amino)-2-methyl-3-(2-methyl-4-methoxyphenyl)-6,7-dihydro-5H-cyclopenta[d]pyrazolo[1,5-a]pyrimidine,
(42) 8-(3-pentylamino)-2-methyl-2-(4-methoxyphenyl)-6,7-dihydro-5H-cyclopenta[d]pyrazolo[1,5-a]pyrimidine,
(43) 8-(3-pentylamino)-2-isopropyl-3-(4-methoxyphenyl)-6,7-dihydro-5H-cyclopenta[d]pyrazolo[1,5-a]pyrimidine,
(44) 8-t-butylamino-2-methyl-3-(2-methyl-4-methoxyphenyl)-6,7-dihydro-5H-cyclopenta[d]pyrazolo[1,5-a]pyrimidine,
(45) 8-(3-pentylamino)-3-(2,4,6-trimethylphenyl)-6,7-dihydro-5H-cyclopenta[d]pyrazolo[1,5-a]pyrimidine,
(46) 8-(1-cyclobutylethyl)amino-2-methyl-3-(2-methyl-4-methoxyphenyl)-6,7-dihydro-5H-cyclopenta[d]pyrazolo[1,5-a]pyrimidine,
(47) 8-(3-pentylamino)-2-methyl-3-(2,3-dimethyl-4-methoxyphenyl)-6,7-dihydro-5H-cyclopenta[d]pyrazolo[1,5-a]pyrimidine,
(48) 8-(3-pentylamino)-2-methyl-3-(2,5-dimethyl-4-methoxyphenyl)-6,7-dihydro-5H-cyclopenta[d]pyrazolo[1,5-a]pyrimidine,
(49) 8-(N-(2,2,2-trifluoroethyl)-N-cyclopropylmethylamino)-2-methyl-3-(2-methyl-4-methoxyphenyl)-6,7-dihydro-5H-cyclopenta[d]pyrazolo[1,5-a]pyrimidine,
(50) 8-(2,2,2-trifluoroethyl)amino-2-methyl-3-(2-methyl-4-methoxyphenyl)-6,7-dihydro-5H-cyclopenta[d]pyrazolo[1,5-a]pyrimidine,

(51) 8-(3-pentylamino)-3-(2,6-dimethyl-4-methoxyphenyl)-6,7-dihydro-5H-cyclopenta[d]pyrazolo[1,5-a]pyrimidine,
(52) 8-(3-pentylamino)-3-(4,6-dimethyl-2-methoxyphenyl)-6,7-dihydro-5H-cyclopenta[d]pyrazolo[1,5-a]pyrimidine,
(53) 8-(3-pentylamino)-2-methyl-3-(2,6-dimethyl-4-methoxyphenyl)-6,7-dihydro-5H-cyclopenta[d]pyrazolo[1,5-a]pyrimidine,
(54) 8-(3-pentylamino)-2-methyl-3-(4,6-dimethyl-2-methoxyphenyl)-6,7-dihydro-5H-cyclopenta[d]pyrazolo[1,5-a]pyrimidine,
(55) 8-(3-methylpentan-3-yl)amino-2-methyl-3-(2-methyl-4-methoxyphenyl)-6,7-dihydro-5H-cyclopenta[d]pyrazolo[1,5-a]pyrimidine,
(56) 8-(3-pentylamino)-2-methyl-3-(5-chioro-1,3-dioxaindan-6-yl)-6,7-dihydro-5H-cyclopenta[d]pyrazolo[1,5-a]pyrimidine,
(57) 8-(N-ethyl-N-benzylamino)-2-methyl-3-(2-methyl-4-methoxyphenyl)-6,7-dihydro-5H-cyclopenta[d]pyrazolo[1,5-a]pyrimidine,
(58) 8-(3-pentylamino)-2-methyl-3-(2-chloro-4-trifluoromethoxyphenyl)-6,7-dihydro-5H-cyclopenta[d]pyrazolo[1,5-a]pyrimidine,
(59) 8-(3-pentylamino)-2-methyl-3-(2-chloro-4-methoxyphenyl)-6,7-dihydro-5H-cyclopenta[d]pyrazolo[1,5-a]pyrimidine,
(60) 8-(N-benzyl-N-(2-methoxyethyl)amino)-2-methyl-3-(2-methyl-4-methoxyphenyl)-6,7-dihydro-5H-cyclopenta[d]pyrazolo[1,5-a]pyrimidine,
(61) 8-(3-pentylamino)-2-methyl-3-(2-methoxy-4,5-dimethylphenyl)-6,7-dihydro-5H-cyclopenta[d]pyrazolo[1,5-a]pyrimidine,
(62) 8-phenylamino-2-methyl-3-(2-methyl-4-methoxyphenyl)-6,7-dihydro-5H-cyclopenta[d]pyrazolo[1,5-a]pyrimidine,
(63) 8-(2-methylphenyl)amino-2-methyl-3-(2-methyl-4-methoxyphenyl)-6,7-dihydro-5H-cyclopenta[d]pyrazolo[1,5-a]pyrimidine,
(64) 8-(3-methylphenyl)amino-2-methyl-3-(2-methyl-4-methoxyphenyl)-6,7-dihydro-5H-cyclopenta[d]pyrazolo[1,5-a]pyrimidine,
(65) 8-(4-methylphenyl)amino-2-methyl-3-(2-methyl-4-methoxyphenyl)-6,7-dihydro-5H-cyclopenta[d]pyrazolo[1,5-a]pyrimidine,
(66) 8-(N-phenyl-N-propylamino)-2-methyl-3-(2-methyl-4-methoxyphenyl)-6,7-dihydro-5H-cyclopenta[d]pyrazolo[1,5-a]pyrimidine,
(67) 8-(N-benzyl-N-propylamino)-2-methyl-3-(2-methyl-4-methoxyphenyl)-6,7-dihydro-5H-cyclopenta[d]pyrazolo[1,5-a]pyrimidine,
(68) 8-(N, N-diallylamino)-2-methyl-3-(2-methyl-4-methoxyphenyl)-6,7-dihydro-5H-cyclopenta[d]pyrazolo[1,5-a]pyrimidine,
(69) 8-(3-pentylamino)-2-methyl-3-(2-methyl-4-dimethylaminophenyl)-6,7-dihydro-5H-cyclopenta[d]pyrazolo[1,5-a]pyrimidine,
(70) 8-(1-phenylpropylamino)-2-methyl-3-(2-methyl-4-methoxyphenyl)-6,7-dihydro-5H-cyclopenta[d]pyrazolo[1,5-a]pyrimidine,
(71) 8-(N-(2-phenylethyl)-N-propylamino)-2-methyl-3-(2-methyl-4-methoxyphenyl)-6,7-dihydro-5H-cyclopenta[d]pyrazolo[1,5-a]pyrimidine,
(72) 8-(N-(3-phenylpropyl)-N-propylamino)-2-methyl-3-(2-methyl-4-methoxyphenyl)-6,7-dihydro-5H-cyclopenta[d]pyrazolo[1,5-a]pyrimidine,
(73) 8-(N-(4-phenylbutyl)-N-propylamino)-2-methyl-3-(2-methyl-4-methoxyphenyl)-6,7-dihydro-5H-cyclopenta[d]pyrazolo[1,5-a]pyrimidine,
(74) 8-(1-phenyl-2-butyl)amino-2-methyl-3-(2-methyl-4-methoxyphenyl)-6,7-dihydro-5H-cyclopenta[d]pyrazolo[1,5-a]pyrimidine,
(75) 8-(1-phenyl-3-pentyl)amino-2-methyl-3-(2-methyl-4-methoxyphenyl)-6,7-dihydro-5H-cyclopenta[d]pyrazolo[1,5-a]pyrimidine,
(76) 8-(N-(4-methylphenyl)-N-propylamino)-2-methyl-3-(2-methyl-4-methoxyphenyl)-6,7-dihydro-5H-cyclopenta[d]pyrazolo[1,5-a]pyrimidine,
(77) 8-(N-(4-methylphenyl)methyl-N-propylamino)-2-methyl-3-(2-methyl-4-methoxyphenyl)-6,7-dihydro-5H-cyclopenta[d]pyrazolo[1,5-a]pyrimidine,
(78) 8-(N-(3-methylphenyl)-N-propylamino)-2-methyl-3-(2-methyl-4-methoxyphenyl)-6,7-dihydro-5H-cyclopenta[d]pyrazolo[1,5-a]pyrimidine,
(79) 8-(N-(4-methoxyphenyl)methyl-N-propylamino)-2-methyl-3-(2-methyl-4-methoxyphenyl)-6,7-dihydro-5H-cyclopenta[d]pyrazolo[1,5-a]pyrimidine,
(80) 8-(N-(4-chlorophenyl)methyl-N-propylamino)-2-methyl-3-(2-methyl-4-methoxyphenyl)-6,7-dihydro-5H-cyclopenta[d]pyrazolo[1,5-a]pyrimidine,
(81) 8-(N-(2-methylphenyl)-N-propylamino)-2-methyl-3-(2-methyl-4-methoxyphenyl)-6,7-dihydro-5H-cyclopenta[d]pyrazolo[1,5-a]pyrimidine,
(82) 8-(3-pentylamino)-2-methyl-3-(2-dimethylamino-4-methylpyridin-5-yl)-6,7-dihydro-5H-cyclopenta[d]pyrazolo[1,5-a]pyrimidine,
(83) 8-((2S)-1-methoxy-3-phenyl-2-propyl)amino-2-methyl-3-(2-methyl-4-methoxyphenyl)-6,7-dihydro-5H-cyclopenta[d]pyrazolo[1,5-a]pyrimidine,
(84) 8-(N-(4-methylthiophenyl)methyl-N-propylamino)-2-methyl-3-(2-methyl-4-methoxyphenyl)-6,7-dihydro-5H-cyclopenta[d]pyrazolo[1,5-a]pyrimidine,
(85) 8-(N, N-dibutylamino)-2-methyl-3-(2-methyl-4-methoxyphenyl)-6,7-dihydro-5H-cyclopenta[d]pyrazolo[1,5-a]pyrimidine,
(86) 8-(N-methyl-N-butylamino)-2-methyl-3-(2-methyl-4-methoxyphenyl)-6,7-dihydro-5H-cyclopenta[d]pyrazolo[1,5-a]pyrimidine,
(87) 8-(N-(4-methylphenyl)methyl-N-butylamino)-2-methyl-3-(2-methyl-4-methoxyphenyl)-6,7-dihydro-5H-cyclopenta[d]pyrazolo[1,5-a]pyrimidine,
(88) 8-(N-(4-methylphenyl)methyl-N-(2-methoxyethyl)amino)-2-methyl-3-(2-methyl-4-methoxyphenyl)-6,7-dihydro-5H-cyclopenta[d]pyrazolo[1,5-a]pyrimidine,
(89) 8-(N-cyclopropyl-N-(4-methylphenyl)methylamino)-2-methyl-3-(2-methyl-4-methoxyphenyl)-6,7-dihydro-5H-cyclopenta[d]pyrazolo[1,5-a]pyrimidine,
(90) 8-(N-cyclopropylmethyl-N-(4-methylphenyl)methylamino)-2-methyl-3-(2-methyl-4-methoxyphenyl)-6,7-dihydro-5H-cyclopenta[d]pyrazolo[1,5-a]pyrimidine,
(91) 8-(N, N-dipropylamino)-2-methyl-3-(2-methyl-4-methoxyphenyl)-6,7-dihydro-5H-cyclopenta[d]pyrazolo[1,5-a]pyrimidine,
(92) 8-(N-(4-methylphenyl)methyl-N-(2-butynyl)amino)-2-methyl-3-(2-methyl-4-methoxyphenyl)-6,7-dihydro-5H-cyclopenta[d]pyrazolo[1,5-a]pyrimidine,
(93) 8-(N-propyl-N-(2-butynyl)amino)-2-methyl-3-(2-methyl-4-methoxyphenyl)-6,7-dihydro-5H-cyclopenta[d]pyrazolo[1,5-a]pyrimidine,
(94) 8-(5-nonylamino)-2-methyl-3-(2-methyl-4-methoxyphenyl)-6,7-dihydro-5H-cyclopenta[d]pyrazolo[1,5-a]pyrimidine,

(95) 8-(N-cyclopentyl-N-(4-methylphenyl)methylamino)-2-methyl-3-(2-methyl-4-methoxyphenyl)-6,7-dihydro-5H-cyclopenta[d]pyrazolo[1,5-a]pyrimidine,

(96) 8-(N-cyclopropylmethyl-N-(4-methylthiophenyl)methylamino)-2-methyl-3-(2-methyl-4-methoxyphenyl)-6,7-dihydro-5H-cyclopenta[d]pyrazolo[1,5-a]pyrimidine,

(97) 8-(N-(4-fluorophenyl)methyl-N-propylamino)-2-methyl-3-(2-methyl-4-methoxyphenyl)-6,7-dihydro-5H-cyclopenta[d]pyrazolo[1,5-a]pyrimidine,

(98) 8-(N-cyclobutyl-N-(4-methylphenyl)methylamino)-2-methyl-3-(2-methyl-4-methoxyphenyl)-6,7-dihydro-5H-cyclopenta[d]pyrazolo[1,5-a]pyrimidine,

(99) 8-(N-ethyl-N-(4-methylphenyl)methylamino)-2-methyl-3-(2-methyl-4-methoxyphenyl)-6,7-dihydro-5H-cyclopenta[d]pyrazolo[1,5-a]pyrimidine, (100) 8-(N-propyl-N-(4-trifluoromethylphenyl)methylamino)-2-methyl-3-(2-methyl-4-methoxyphenyl)-6,7-dihydro-5H-cyclopenta[d]pyrazolo[1,5-a]pyrimidine, (101) 8-(N-propyl-N-(tetrahydrofuran-2-yl)methylamino)-2-methyl-3-(2-methyl-4-methoxyphenyl)-6,7-dihydro-5H-cyclopenta[d]pyrazolo[1,5-a]pyrimidine, (102) 8-(N-butyl-N-(2-methoxyethyl)amino)-2-methyl-3-(2-methyl-4-methoxyphenyl)-6,7-dihydro-5H-cyclopenta[d]pyrazolo[1,5-a]pyrimidine, (103) 8-(N-propyl-N-cyclopropylamino)-2-methyl-3-(2-methyl-4-methoxyphenyl)-6,7-dihydro-5H-cyclopenta[d]pyrazolo[1,5-a]pyrimidine, (104) 8-(N-cyclobutylmethyl-N-(2-methoxyethyl)amino)-2-methyl-3-(2-methyl-4-methoxyphenyl)-6,7-dihydro-5H-cyclopenta[d]pyrazolo[1,5-a]pyrimidine, (105) 8-(4-heptylamino)-2-methyl-3-(2-chloro-4-methoxyphenyl)-6,7-dihydro-5H-cyclopenta[d]pyrazolo[1,5-a]pyrimidine, (106) 8-(N-cyclopropylmethyl-N-(2-butyryl)amino)-2-methyl-3-(2-methyl-4-methoxyphenyl)-6,7-dihydro-5H-cyclopenta[d]pyrazolo[1,5-a]pyrimidine, (107) 8-(N-(2-methoxyethyl)-N-(2-butyryl)amino)-2-methyl-3-(2-methyl-4-methoxyphenyl)-6,7-dihydro-5H-cyclopenta[d]pyrazolo[1,5-a]pyrimidine, (108) 8-(2-butyrylamino)-2-methyl-3-(2-methyl-4-methoxyphenyl)-6,7-dihydro-5H-cyclopenta[d]pyrazolo[1,5-a]pyrimidine, (109) 8-(N-cyclopropylmethyl-N-(4-methylphenyl)methylamino)-2-methyl-3-(2-methyl-4-methoxyphenyl)-6,7-dihydro-5H-cyclopenta[d]pyrazolo[1,5-a]pyrimidine, (110) 8-(N-propyl-N-(4-trifluoromethyloxyphenyl)methylamino)-2-methyl-3-(2-methyl-4-methoxyphenyl)-6,7-dihydro-5H-cyclopenta[d]pyrazolo[1,5-a]pyrimidine, (111) 8-(N-(2-butyryl)-N-cyclopropylmethylamino)-2-methyl-3-(2-chloro-4-methoxyphenyl)-6,7-dihydro-5H-cyclopenta[d]pyrazolo[1,5-a]pyrimidine, (112) 8-(N-propyl-N-(3-methylphenyl)methylamino)-2-methyl-3-(2-methyl-4-methoxyphenyl)-6,7-dihydro-5H-cyclopenta[d]pyrazolo[1,5-a]pyrimidine, (113) 8-(N-propyl-N-(2-methylphenyl)methylamino)-2-methyl-3-(2-methyl-4-methoxyphenyl)-6,7-dihydro-5H-cyclopenta[d]pyrazolo[1,5-a]pyrimidine, (114) 8-(3-pentylamino)-2-methyl-3-(2-chloro-4-ethoxyphenyl)-6,7-dihydro-5H-cyclopenta[d]pyrazolo[1,5-a]pyrimidine, (115) 8-(N-methyl-N-hexylamino)-2-methyl-3-(2-methyl-4-methoxyphenyl)-6,7-dihydro-5H-cyclopenta[d]pyrazolo[1,5-a]pyrimidine, (116) 8-(N-methyl-N-(3-pentyl)amino)-2-methyl-3-(2-methyl-4-methoxyphenyl)-6,7-dihydro-5H-cyclopenta[d]pyrazolo[1,5-a]pyrimidine, (117) 8-(N-methyl-N-(4-heptyl)amino)-2-methyl-3-(2-methyl-4-methoxyphenyl)-6,7-dihydro-5H-cyclopenta[d]pyrazolo[1,5-a]pyrimidine, (118) 8-(N-cyclobutyl-N-propylamino)-2-methyl-3-(2-methyl-4-methoxyphenyl)-6,7-dihydro-5H-cyclopenta[d]pyrazolo[1,5-a]pyrimidine, (119) 8-(N-isobutyl-N-(2-dimethylaminoethyl)amino)-2-methyl-3-(2-methyl-4-methoxyphenyl)-6,7-dihydro-5H-cyclopenta[d]pyrazolo[1,5-a]pyrimidine, (120) 8-(N-propyl-N-(4-fluorophenyl)methylamino)-2-methyl-3-(2-chloro-4-methoxyphenyl)-6,7-dihydro-5H-cyclopenta[d]pyrazolo[1,5-a]pyrimidine, (121) 8-(N-cyclopropylmethyl-N-(4-fluorophenyl)methylamino)-2-methyl-3-(2-chloro-4-methoxyphenyl)-6,7-dihydro-5H-cyclopenta[d]pyrazolo[1,5-a]pyrimidine, (122) 8-(3-pentylamino)-2-methyl-3-(3-chloro-5-trifluoromethylpyridin-2-yl)-6,7-dihydro-5H-cyclopenta[d]pyrazolo[1,5-a]pyrimidine, (123) 8-(n-butyl-N-propylamino)-2-methyl-3-(2-methyl-4-methoxyphenyl)-6,7-dihydro-5H-cyclopenta[d]pyrazolo[1,5-a]pyrimidine, (124) 8-(N-cyclopropyl-N-(4-fluorophenyl)methylamino)-2-methyl-3-(2-chloro-4-methoxyphenyl)-6,7-dihydro-5H-cyclopenta[d]pyrazolo[1,5-a]pyrimidine, (125) 8-(N-propyl-N-(2-fluorophenyl)methylamino)-2-methyl-3-(2-methyl-4-methoxyphenyl)-6,7-dihydro-5H-cyclopenta[d]pyrazolo[1,5-a]pyrimidine, (126) 8-(N-propyl-N-(3-fluorophenyl)methylamino)-2-methyl-3-(2-methyl-4-methoxyphenyl)-6,7-dihydro-5H-cyclopenta[d]pyrazolo[1,5-a]pyrimidine, (127) 8-dicyclopropylmethylamino-2-methyl-3-(2-chloro-4-methoxyphenyl)-6,7-dihydro-5H-cyclopenta[d]pyrazolo[1,5-a]pyrimidine, (128) 8-(N-butyl-N-propylamino)-2-methyl-3-(2-chloro-4-methoxyphenyl)-6,7-dihydro-5H-cyclopenta[d]pyrazolo[1,5-a]pyrimidine, (129) 8-(N-cyclopropylmethyl-N-propylamino)-2-methyl-3-(2-chloro-4-methoxyphenyl)-6,7-dihydro-5H-cyclopenta[d]pyrazolo[1,5-a]pyrimidine, (130) 8-(N-(2-butynyl)-N-propylamino)-2-methyl-3-(2-chloro-4-methoxyphenyl)-6,7-dihydro-5H-cyclopenta[d]pyrazolo[1,5-a]pyrimidine, (131) 8-(N-butyl-N-(2-methoxyethyl)amino)-2-methyl-3-(2-chloro-4-methoxyphenyl)-6,7-dihydro-5H-cyclopenta[d]pyrazolo[1,5-a]pyrimidine, (132) 8-(N-cyclopropylmethyl-N-(4-fluorophenyl)methylamino)-2-methyl-3-(2-methyl-4-methoxyphenyl)-6,7-dihydro-5H-cyclopenta[d]pyrazolo[1,5-a]pyrimidine, (133) 8-(3-pentylamino)-2-methyl-3-(3, 5-dichloropyridin-2-yl)-6,7-dihydro-5H-cyclopenta[d]pyrazolo[1,5-a]pyrimidine, (134) 8-(N-butyl-N-ethylamino)-2-methyl-3-(2-chloro-4-methoxyphenyl)-6,7-dihydro-5H-cyclopenta[d]pyrazolo[1,5-a]pyrimidine, (135) 8-(N-cyclopropylmethyl-N-(4-trifluoromethylphenyl)methylamino)-2-methyl-3-(2-methyl-4-methoxyphenyl)-6,7-dihydro-5H-cyclopenta[d]pyrazolo[1,5-a]pyrimidine, (136) 8-(N-benzyl-N-(2-dimethylaminoethyl)amino)-2-methyl-3-(2-methyl-4-methoxyphenyl)-6,7-dihydro-5H-cyclopenta[d]pyrazolo[1,5-a]pyrimidine, (137) 8-(N-benzyl-N-(2-dimethylaminoethyl)amino)-2-methyl-3-(2-chloro-4-methoxyphenyl)-6,7-dihydro-5H-cyclopenta[d]pyrazolo[1,5-a]pyrimidine, (138) 8-(N-(2-butynyl)-N-ethylamino)-2-methyl-3-(2-methyl-4-methoxyphenyl)-6,7-dihydro-5H-cyclopenta[d]pyrazolo[1,5-a]pyrimidine, (139) 8-(N-(2-butynyl)-N-ethylamino)-2-methyl-3-(2-chloro-4-methoxyphenyl)-6,7-dihydro-5H-cyclopenta[d]pyrazolo[1,5-a]pyrimidine, (140) 8-(N, N-dipropylamino)-2-methyl-3-(2-chloro-4-methoxyphenyl)-6,7-dihydro-5H-cyclopenta[d]pyrazolo[1,5-a]pyrimidine, (141) 8-(N-propyl-N-(4-cyanophenyl)methylamino)-2-methyl-3-(2-methyl-4-methoxyphenyl)-6,7-dihydro-5H-cyclopenta[d]pyrazolo[1,5-a]pyrimidine, (142) 8-(N-propyl-N-(3-fluorophenyl)methylamino)-2-methyl-3-(2-chloro-4-methoxyphenyl)-6,7-dihydro-5H-cyclopenta[d]pyrazolo[1,5-a]pyrimidine, (143) 8-dipropylamino-2-methyl-3-(2,5-dichlorophenyl)-6,7-dihydro-5H-cyclopenta[d]pyrazolo[1,5-a]pyrimidine, (144) 8-dipropylamino-2-methyl-3-(2,4-dichlorophenyl)-6,7-dihydro-5H-cyclopenta[d]pyrazolo[1,5-a]pyrimidine, (145) 8-dipropylamino-2-methyl-3-(4-methylphenyl)-6,7-dihydro-5H-cyclopenta[d]pyrazolo[1,5-a]pyrimidine, (146) 8-dipropylamino-2-methyl-3-(3-methylphenyl)-6,7-dihydro-5H-cyclopenta[d]pyrazolo[1,5-a]pyrimidine, (147) 8-dipropylamino-2-methyl-3-(2-methylphenyl)-6,7-dihydro-5H-cyclopenta[d]pyrazolo[1,5-a]pyrimidine, (148) 8-(N-propyl-N-(benz[d]1,3-dioxolan-5-yl)methylamino)-2-methyl-3-(2-methyl-4-methoxyphenyl)-6,7-dihydro-5H-cyclopenta[d]pyrazolo[1,5-a]pyrimidine, (149) 8-(N-propyl-N-(benz[d]1,3-dioxolan-5-yl)methylamino)-2-methyl-3-(2-chloro-4-methoxyphenyl)-6,7-dihydro-5H-cyclopenta[d]pyrazolo[1,5-a]pyrimidine, (150) 8-(3-pentylamino)-2-methyl-3-(2-methylphenyl)-6,7-dihydro-5H-cyclopenta[d]pyrazolo[1,5-a]pyrimidine, (151) 8-(3-pentylamino)-2-methyl-3-(3-methylphenyl)-6,7-dihydro-5H-cyclopenta[d]pyrazolo[1,5-a]pyrimidine, (152) 8-(3-pentylamino)-2-methyl-3-(4-methylphenyl)-6,7-dihydro-5H-cyclopenta[d]pyrazolo[1,5-a]pyrimidine, (153) 8-(3-pentylamino)-2-methyl-3-(2-methylthio-4-methoxyphenyl)-6,7-dihydro-5H-cyclopenta[d]pyrazolo[1,5-a]pyrimidine, (154) 8-(N-benzyl-N-cyclopropylmethylamino)-2-methyl-3-(2-methyl-4-methoxyphenyl)-6,7-dihydro-5H-cyclopenta[d]pyrazolo[1,5-a]pyrimidine, (155) 8-(N-benzyl-N-cyclopropylmethylamino)-2-methyl-3-(2-chloro-4-methoxyphenyl)-6,7-dihydro-5H-cyclopenta[d]pyrazolo[1,5-a]pyrimidine, (156) 8-(N-butyl-N-(2-butynyl)amino)-2-methyl-3-(2-methyl-4-methoxyphenyl)-6,7-dihydro-5H-cyclopenta[d]pyrazolo[1,5-a]pyrimidine, (157) 8-(3-pentylamino)-2-methyl-3-(2-methyl-4-fluorophenyl)-6,7-dihydro-5H-cyclopenta[d]pyrazolo[1,5-a]pyrimidine, (158) 8-(3-pentylamino)-2-methyl-3-(2,5-dichlorophenyl)-6,7-dihydro-5H-cyclopenta[d]pyrazolo[1,5-a]pyrimidine, (159) 8-(3-pentylamino)-2-methyl-3-(2,4-dimethoxyphenyl)-6,7-dihydro-5H-cyclopenta[d]pyrazolo[1,5-a]pyrimidine, (160) 8-(3-pentylamino)-2-methyl-3-(2-fluoro-4-methylphenyl)-6,7-dihydro-5H-cyclopenta[d]pyrazolo[1,5-a]pyrimidine, (161) 8-(N-butyl-N-(2-butynyl)amino)-2-methyl-3-(2-chloro-4-methoxyphenyl)-6,7-dihydro-5H-cyclopenta[d]pyrazolo[1,5-a]pyrimidine, (162) 8-(3-methyl-2-butylamino)-2-methyl-3-(2-methyl-4-methoxyphenyl)-6,7-dihydro-5H-cyclopenta[d]pyrazolo[1,5-a]pyrimidine, (163) 8-(1-cyclohexylethylamino)-2-methyl-3-(2-methyl-4-methoxyphenyl)-6,7-dihydro-5H-cyclopenta[d]pyrazolo[1,5-a]pyrimidine, (164) 8-(2-pentylamino)-2-methyl-3-(2-methyl-4-methoxyphenyl)-6,7-dihydro-5H-cyclopenta[d]pyrazolo[1,5-a]pyrimidine, (165) 8-(2-heptylamino)-2-methyl-3-(2-methyl-4-methoxyphenyl)-6,7-dihydro-5H-cyclopenta[d]pyrazolo[1,5-a]pyrimidine, (166) 8-(1-methoxy-2-propylamino)-2-methyl-3-(2-methyl-4-methoxyphenyl)-6,7-dihydro-5H-cyclopenta[d]pyrazolo[1,5-a]pyrimidine, (167) 8-(2-octylamino)-2-methyl-3-(2-methyl-4-methoxyphenyl)-6,7-dihydro-5H-cyclopenta[d]pyrazolo[1,5-a]pyrimidine, (168) 8-(1,2,3,4-tetrahydronaphthalen-1-yl)amino-2-methyl-3-(2-methyl-4-methoxyphenyl)-6,7-dihydro-5H-cyclopenta[d]pyrazolo[1,5-a]pyrimidine, (169) 8-((1S, 2S, 3S, 5R)-2,6, 6-trimethylbicyclo[3.1.1]-3-heptyl)amino-2-methyl-3-(2-methyl-4-methoxyphenyl)-6,7-dihydro-5H-cyclopenta[d]pyrazolo[1,5-a]pyrimidine, (170) 8-(3-pentylamino)-2-methyl-3-(2-methyl-4-chlorophenyl)-6,7-dihydro-5H-cyclopenta[d]pyrazolo[1,5-a]pyrimidine, (171) 8-(3-pentylamino)-2-methyl-3-(2,5-dimethoxyphenyl)-6,7-dihydro-5H-cyclopenta[d]pyrazolo[1,5-a]pyrimidine, (172) 8-(3-pentylamino)-2-methyl-3-(2-methoxyphenyl)-6,7-dihydro-5H-cyclopenta[d]pyrazolo[1,5-a]pyrimidine, (173) 8-(N-ethyl-N-(4-hydroxybutyl)amino)-2-methyl-3-(2-methyl-4-methoxyphenyl)-6,7-dihydro-5H-cyclopenta[d]pyrazolo[1,5-a]pyrimidine, (174) 8-(3-pentylamino)-2-methyl-3-(2-methoxy-5-isopropylphenyl)-6,7-dihydro-5H-cyclopenta[d]pyrazolo[1,5-a]pyrimidine, (175) 8-(3-pentylamino)-2-methyl-3-(2-methoxy-5-fluorophenyl)-6,7-dihydro-5H-cyclopenta[d]pyrazolo[1,5-a]pyrimidine, (176) 8-(N-butyl-N-(4-fluorophenyl)methylamino)-2-methyl-3-(2-chloro-5-methoxyphenyl)-6,7-dihydro-5H-cyclopenta[d]pyrazolo[1,5-a]pyrimidine, (177) 8-(3-pentylamino)-2-methyl-3-(2-methoxy-5-chlorophenyl)-6,7-dihydro-5H-cyclopenta[d]pyrazolo[1,5-a]pyrimidine, (178) 8-(N-cyclopropylmethyl-N-(4-trifluoromethylphenyl)methylamino)-2-methyl-3-(2-chloro-5-methoxyphenyl)-6,7-dihydro-5H-cyclopenta[d]pyrazolo[1,5-a]pyrimidine, (179) 8-(3-pentylamino)-2-methyl-3-(2-methyl-4-cyanophenyl)-6,7-dihydro-5H-cyclopenta[d]pyrazolo[1,5-a]pyrimidine, (180) 8-(N-propyl-N-(2-methoxyethyl)amino)-2-methyl-3-(2-chloro-5-methoxyphenyl)-6,7-dihydro-5H-cyclopenta[d]pyrazolo[1,5-a]pyrimidine, (181) 8-(N-ethyl-N-(4-methylthiophenyl)methylamino)-2-methyl-3-(2-chloro-4-methoxyphenyl)-6,7-dihydro-5H-cyclopenta[d]pyrazolo[1,5-a]pyrimidine,
(182) 8-(3-pentylamino)-2-methyl-3-(4-methylthiophenyl)-6,7-dihydro-5H-cyclopenta[d]pyrazolo[1,5-a]pyrimidine,
(183) 8-(3-pentylamino)-2-methyl-3-(4-dimethylaminophenyl)-6,7-dihydro-5H-cyclopenta[d]pyrazolo[1,5-a]pyrimidine,
(184) 8-(3-pentylamino)-2-methyl-3-(2-chloro-4-methylthiophenyl)-6,7-dihydro-5H-cyclopenta[d]pyrazolo[1,5-a]pyrimidine,
(185) 8-(N-(2-methoxyethyl)-N-(2-butynyl)amino)-2-methyl-3-(2-chloro-4-methoxyphenyl)-6,7-dihydro-5H-cyclopenta[d]pyrazolo[1,5-a]pyrimidine,
(186) 8-(N-propyl-N-(5-methylfuran-2-yl)methylamino)-2-methyl-3-(2-chloro-4-methoxyphenyl)-6,7-dihydro-5H-cyclopenta[d]pyrazolo[1,5-a]pyrimidine,
(187) 8-(N-benzyl-N-cyclopropylamino)-2-methyl-3-(2-chloro-4-methoxyphenyl)-6,7-dihydro-5H-cyclopenta[d]pyrazolo[1,5-a]pyrimidine,
(188) 8-(N-cyclopropylmethyl-N-(2-methoxyethyl)amino)-2-methyl-3-(2-chloro-4-methoxyphenyl)-6,7-dihydro-5H-cyclopenta[d]pyrazolo[1,5-a]pyrimidine,
(189) 8-(3-pentylamino)-2-methyl-3-(2-chloro-4-bromophenyl)-6,7-dihydro-5H-cyclopenta[d]pyrazolo[1,5-a]pyrimidine,
(190) 8-(3-pentylamino)-2-methyl-3-(2,5-dichloro-4-methoxyphenyl)-6,7-dihydro-5H-cyclopenta[d]pyrazolo[1,5-a]pyrimidine,
(191) 8-dibutylamino-2-methyl-3-(2-chloro-4-methoxyphenyl)-6,7-dihydro-5H-cyclopenta[d]pyrazolo[1,5-a]pyrimidine,
(192) 8-bis(2-methoxyethyl)amino-2-methyl-3-(2-chloro-4-methoxyphenyl)-6,7-dihydro-5H-cyclopenta[d]pyrazolo[1,5-a]pyrimidine,
(193) 8-(N-ethyl-N-cyclopropylmethylamino)-2-methyl-3-(2-chloro-4-methoxyphenyl)-6,7-dihydro-5H-cyclopenta[d]pyrazolo[1,5-a]pyrimidine,
(194) 8-(N-cyclopropyl-N-(4-cyanophenyl)methylamino)-2-methyl-3-(2-chloro-4-methoxyphenyl)-6,7-dihydro-5H-cyclopenta[d]pyrazolo[1,5-a]pyrimidine,
(195) 8-(N-cyclopropylmethyl-N-(4-cyanophenyl)methylamino)-2-methyl-3-(2-chloro-4-methoxyphenyl)-6,7-dihydro-5H-cyclopenta[d]pyrazolo[1,5-a]pyrimidine,
(196) 8-(N-butyl-N-cyclopropylmethylamino)-2-methyl-3-(2-chloro-4-methoxyphenyl)-6,7-dihydro-5H-cyclopenta[d]pyrazolo[1,5-a]pyrimidine,
(197) 8-(3-pentylamino)-2-methyl-3-(2-chloro-4-ethoxycarbonylphenyl)-6,7-dihydro-5H-cyclopenta[d]pyrazolo[1,5-a]pyrimidine,
(198) 8-(N-propyl-N-(2-fluorophenyl)methylamino)-2-methyl-3-(2-chloro-4-methoxyphenyl)-6,7-dihydro-5H-cyclopenta[d]pyrazolo[1,5-a]pyrimidine,
(199) 8-(N-propyl-N-(5-methylthiophen-2-yl)methylamino)-2-methyl-3-(2-chloro-4-methoxyphenyl)-6,7-dihydro-5H-cyclopenta[d]pyrazolo[1,5-a]pyrimidine,
(200) 8-(N-propyl-N-(thiophen-3-yl)methylamino)-2-methyl-3-(2-chloro-4-methoxyphenyl)-6,7-dihydro-5H-cyclopenta[d]pyrazolo[1,5-a]pyrimidine,
(201) 8-(N-ethyl-N-propylamino)-2-methyl-3-(2-chloro-4-methoxyphenyl)-6,7-dihydro-5H-cyclopenta[d]pyrazolo[1,5-a]pyrimidine,
(202) 8-(3-pentylamino)-2-methyl-3-(2-chloro-4-carbamoylphenyl)-6,7-dihydro-5H-cyclopenta[d]pyrazolo[1,5-a]pyrimidine,
(203) 8-(3-pentylamino)-2-methyl-3-(2-chloro-4-(N-methylcarbamoyl)phenyl)-6,7-dihydro-5H-cyclopenta[d]pyrazolo[1,5-a]pyrimidine,
(204) 8-(3-pentylamino)-2-methyl-3-(2-chloro-4-(N,N-dimethylcarbamoyl)phenyl))-6,7-dihydro-5H-cyclopenta[d]pyrazolo[1,5-a]pyrimidine,
(205) 8-(N-ethyl-N-(4-fluorophenyl)methylamino)-2-methyl-3-(2-chloro-4-methoxyphenyl)-6,7-dihydro-5H-cyclopenta[d]pyrazolo[1,5-a]pyrimidine,
(206) 8-(3-pentylamino)-2-methyl-3-(2-chloro-4,6-dimethoxyphenyl)-6,7-dihydro-5H-cyclopenta[d]pyrazolo[1,5-a]pyrimidine,
(207) 8-(3-pentylamino)-2-methyl-3-(2-chloro-4-aminophenyl)-6,7-dihydro-5H-cyclopenta[d]pyrazolo[1,5-a]pyrimidine,
(208) 8-(3-pentylamino)-2-methyl-3-(2-chloro-4-methylaminophenyl)-6,7-dihydro-5H-cyclopenta[d]pyrazolo[1,5-a]pyrimidine,
(209) 8-(3-pentylamino)-2-methyl-3-(2-formyl-4-methoxyphenyl)-6,7-dihydro-5H-cyclopenta[d]pyrazolo[1,5-a]pyrimidine,
(210) 8-(3-pentylamino)-2-methyl-3-(2-cyano-4-methoxyphenyl)-6,7-dihydro-5H-cyclopenta[d]pyrazolo[1,5-a]pyrimidine,
(211) 8-(3-pentylamino)-2-methyl-3-(2-ethyl-4-methoxyphenyl)-6,7-dihydro-5H-cyclopenta[d]pyrazolo[1,5-a]pyrimidine,
(212) 8-(4-heptylamino)-3-(2-chloro-4-methoxyphenyl)-6,7-dihydro-5H-cyclopenta[d]pyrazolo[1,5-a]pyrimidine,
(213) 8-(N, N-dipropylamino)-3-(2-chloro-4-methoxyphenyl)-6,7-dihydro-5H-cyclopenta[d]pyrazolo[1,5-a]pyrimidine,
(214) 8-(3-pentylamino)-2-methyl-3-(2-methoxycarbonyl-4-methoxyphenyl)-6,7-dihydro-5H-cyclopenta[d]pyrazolo[1,5-a]pyrimidine,
(215) 8-(N-cyclopropyl-N-(2-fluorophenyl)methylamino)-2-methyl-3-(2-chloro-4-methoxyphenyl)-6,7-dihydro-5H-cyclopenta[d]pyrazolo[1,5-a]pyrimidine,
(216) 8-(N-cyclopropylmethyl-N-(2-fluorophenyl)methylamino)-2-methyl-3-(2-chloro-4-methoxyphenyl)-6,7-dihydro-5H-cyclopenta[d]pyrazolo[1,5-a]pyrimidine,
(217) 8-(N-cyclopropylmethyl-N-propylamino)-3-(2-chloro-4-methoxyphenyl)-6,7-dihydro-5H-cyclopenta[d]pyrazolo[1,5-a]pyrimidine,
(218) 8N-propyl-N-(4-methylphenyl)methylamino)-3-(2-chloro-4-methoxyphenyl)-6,7-dihydro-5H-cyclopenta[d]pyrazolo[1,5-a]pyrimidine,
(219) 8-N-benzyl -N-cyclopropylmethylamino)-3-(2-chloro-4-methoxyphenyl)-6,7-dihydro-5H-cyclopenta[d]pyrazolo[1,5-a]pyrimidine,
(220) Sclopropyhncthyl-N-(4-methylphenyl)methylamino)-3-(2-chloro-4-methoxyphenyl)-6,7-dihydro-5H-cyclopenta[d]pyrazolo[1,5-a]pyrimidine,
(221) 8-(N-propyl-N-(4-methylphenyl)methylamino)-3-(2-chloro-4-methoxyphenyl)-6,7-dihydro-5H-cyclopenta[d]pyrazolo[1,5-a]pyrimidine,
(222) 8-dicyclopropylmethylamino-3-(2-chloro-4-methoxyphenyl)-6,7-dihydro-5H-cyclopenta[d]pyrazolo[1,5-a]pyrimidine,
(223) 84N-cyclopropyl-N-(4-methylphenyl)methylamino)-3-(2-chloro-4-methoxyphenyl)-6,7-dihydro-5H-cyclopenta[d]pyrazolo[1,5-a]pyrimidine,
(224) 8-(N-cyclopropylmethyl-N-(4-tritluoromethylphenyl)methylamino)-3-(2-chloro-4-methoxyphenyl)-6,7-dihydro-5H-cyclopenta[d]pyrazolo[1,5-a]pyrimidine, (225) 8-(3-pentylamino)-3-(2-chloro-4-methoxyphenyl)-6,7-dihydro-5H-cyclopenta[d]pyrazolo[1,5-a]pyrimidine,
(226) 8-(N-cyclopropylmethyl-N-(4-fluorophenyl)methylamino)-3-(2-chloro-4-methoxyphenyl)-6,7-dihydro-5H-cyclopenta[d]pyrazolo[1,5-a]pyrimidine,
(227) 8-(3-pentylamino)-2-methyl-3-(2-(1-methyl-i -hydroxyethyl)-4-methoxyphenyl)-6,7-dihydro-5H-cyclopenta[d]pyrazolo[1,5-a]pyrimidine,
(228) 8-(N-propyl-N-(4-trifluoromethyloxyphenyl)methylamino)-2-methyl-3-(2-chloro-4-methoxyphenyl)-6,7-dihydro-5H-cyclopenta[d]pyrazolo[1,5-a]pyrimidine,
(229) 8-(3-hexylamino)-2-methyl-3-(2-chloro-4-methoxyphenyl)-6,7-dihydro-5H-cyclopenta[d]pyrazolo[1,5-a]pyrimidine,
(230) 8-(3-pentylamino)-2-methyl-3-(2-methoxy-4-methylpyridin-5-yl)-6,7-dihydro-5H-cyclopenta[d]pyrazolo[1,5-a]pyrimidine,
(231) 8-(N-butyl-N-cyclopropylmethylamino)-3-(2-chloro-4-methoxyphenyl)-6,7-dihydro-5H-cyclopenta[d]pyrazolo[1,5-a]pyrimidine,
(232) 8-(N-propyl-N-(4-methylphenyl)methylamino)-2-methyl-3-(2-chloro-4-methoxyphenyl)-6,7-dihydro-5H-cyclopenta[d]pyrazolo[1,5-a]pyrimidine,
(233) 8-(N-propyl-N-(4-cyanophenyl)methylamino)-2-methyl-3-(2-chloro-4-methoxyphenyl)-6,7-dihydro-5H-cyclopenta[d]pyrazolo[1,5-a]pyrimidine,
(234) 8-(N-cyclopropylmethyl-N-methylamino)-2-methyl-3-(2-chloro-4-methoxyphenyl)-6,7-dihydro-5H-cyclopenta[d]pyrazolo[1,5-a]pyrimidine,
(235) 8-(N-ethyl-N-n-butylamino)-2-hydroxymethyl-3-(2-methyl-4-hydroxyphenyl)-6,7-dihydro-5H-cyclopenta[d]pyrazolo[1,5-a]pyrimidine,
(236) 8-(N-ethyl-N-n-butylamino)-2-hydroxymethyl-3-(2-methyl-4-methoxyphenyl)-6,7-dihydro-5H-cyclopenta[d]pyrazolo[1,5-a]pyrimidine,
(237) 8-(N-propyl-N-(2-methoxyiminoethyl)amino)-2-methyl-3-(2-methyl-4-methoxyphenyl)-6,7-dihydro-5H-cyclopenta[d]pyrazolo[1,5-a]pyrimidine,
(238) 8-(N-ethyl-N-n-butylamino)-2-hydroxyiminomethyl-3-(2-methyl-4-methoxyphenyl)-6,7-dihydro-5H-cyclopenta[d]pyrazolo[1,5-a]pyrimidine,
(239) 8-[(2S)-1-hydroxyiminobutan-2-yl]amino-2-methyl-3-(2-methyl-4-methoxyphenyl)-6,7-dihydro-5H-cyclopenta[d]pyrazolo[1,5-a]pyrimidine,
(240) 8-[(1S)-1-cyanopropylamino]-2-methyl-3-(2-methyl-4-methoxyphenyl)-6,7-dihydro-5H-cyclopenta[d]pyrazolo[1,5-a]pyrimidine,
(241) 8-(N-ethyl-N-n-butylamino)-2-cyano-3-(2-methyl-4-methoxyphenyl)-6,7-dihydro-5H-cyclopenta[d]pyrazolo[1,5-a]pyrimidine,
(242) 1-cyano-2-methyl-8-(3-pentylamino)-3-(2-chloro-4-methoxyphenyl)-6,7-dihydro-5H-cyclopenta[d]pyrazolo[1,2-a]pyrimidine,
(243) 1-cyano-2-methyl-8-dipropylamino-3-(2-chloro-4-methoxyphenyl)-6,7-dihydro-5H-cyclopenta[d]pyrazolo[1,2-a]pyrimidine,
(244) 8-(4-heptylamino)-3-(2,6-dimethyl-4-methoxyphenyl)-6,7-dihydro-5H-cyclopenta[d]pyrazolo[1,5-a]pyrimidine,
(245) 8-dipropylamino-3-(2,6-dimethyl-4-methoxyphenyl)-6,7-dihydro-5H-cyclopenta[d]pyrazolo[1,5-a]pyrimidine,
(246) 8-(N-cyclopropylmethyl-N-propylaznino)-3-(2,6-dimethyl-4-methoxyphenyl)-6,7-dihydro-5H-cyclopenta[d]pyrazolo[1,5-a]pyrhnidine,
(247) 8-(N-bcnzyl-N-cyclopropylmethylamino)-3-(2,6-dimethyl-4-methoxyphenyl)-6,7-dihydro-5H-cyclopenta[d]pyrazolo[1,5-a]pyrimidine,
(248) 8-(N-cyclopropylmethyl-N-(4-methylphenylmethyl)aznino)-3-(2,6-dimethyl-4-methoxyphenyl)-6,7-dihydro-5H-cyclopenta[]pyrazolo[1,5-a]pyrimidine,
(249) 8-(N-propyl-N-(4-fluorophenylmethyl)aznino)-3-(2,6-dimethyl-4-methoxyphenyl)-6,7-dihydro-5H-cyclopenta[d]pyrazolo[1,5-a]pyrimidine,
(250) 8-dicyclopropylmethylaznino-3-(2,6-dimethyl-4-methoxyphenyl)-6,7-dihydro-5H-cyclopenta[d]pyrazolo[1,5-a]pyrimidine,
(251) 8-N-butyl-N-cyclopropylmethylamino)-3-(2,6-dimethyl-4-methoxyphenyl)-6,7-dihydro-5H-cyclopenta[d]pyrazolo[1,5-a]pyrimidine, and
(252) 8(N-cyclopropylmethyl-N-(4-fluorophenyl)methylamino)-3-(2,6-dimethyl-4-methoxyphenyl)-6,7-ihydro-5H-cyclopenta[d]pyrazolo[1,5-a]pyrimidine, a pharmaceutically acceptable salt thereof or a hydrate thereof.

11. The compound according to claim 1, which is selected from (1) 8-hydroxy-2-methyl-3-(2-methyl-4-methoxyphenyl)-6,7-dihydro-5H-cyclopenta[d]pyrazolo[1,5-a]pyrimidine,
(2) 2-methyl-3-(2-methyl-4-methoxyphenyl)-8-[(2S, 4R)-4-methoxy-2-methoxymethylpyrolidin-1-yl]-6,7-dihydro-5H-cyclopenta[d]pyrazolo[1,5-a]pyrimidine,
(3) 8-(1,2,5,6-tetrahydropyridyl)-2-methyl-3-(2-methyl-4-methoxyphenyl)-6,7-dihydro-5H-cyclopenta[d]pyrazolo[1,5-a]pyrimidine,
(4) 8-(1,2,3,4-tetrahydroisoquinolin-2-yl)-2-methyl-3-(2-methyl-4-methoxyphenyl)-6,7-dihydro-5H-cyclopenta[d]pyrazolo[1,5-a]pyrimidine,
(5) 8-((3S)-3-mehoxymethyl-1,2,3,4-tetrahydroisoquinolin-2-yl)-2-methyl-3-(2-methyl-4-methoxyphenyl)-6,7-dihydro-5H-cyclopenta[d]pyrazolo[1,5-a]pyrimidine,
(6) 8-(4-phenylpiperazin-1-yl)-2-methyl-3-(2-methyl-4-methoxyphenyl)-6,7-dihydro-5H-cyclopenta[d]pyrazolo[1,5-a]pyrimidine,
(7) 8-(4-(2-chlorophenyl)piperazin-1-yl)-2-methyl-3-(2-methyl-4-methoxyphenyl)-6,7-dihydro-5H-cyclopenta[d]pyrazolo[1,5-a]pyrimidine,
(8) 8-(3-ethoxycarbonyl-1,2,5,6-tetrahydropyridyl)-2-methyl-3-(2-methyl-4-methoxyphenyl)-6,7-dihydro-5H-cyclopenta[d]pyrazolo[1,5-a]pyrimidine,
(9) 8-(3-(3-methyl-i, 2,4-oxadiazol-5-yl)-l, 2,5, 6-tetrahydropyridyl)-2-methyl-3-(2-methyl-4-methoxyphenyl)-6,7-dihydro-5H-cyclopenta[d]pyrazolo[1,5-a]pyrimidine,
(10) 8-(4-(4-chlorophenyl)-1,2,5,6-tetrahydropyridyl)-2-methyl-3-(2-methyl-4-methoxyphenyl)-6,7-dihydro-5H-cyclopenta[d]pyrazolo[1,5-a]pyrimidine,
(11) 8-(3-pentyloxy)-2-methyl-3-(2-methyl-4-methoxyphenyl)-6,7-dihydro-5H-cyclopenta[d]pyrazolo[1,5-a]pyrimidine,
(12) 8-(3-pentyloxy)-2-methyl-3-(2-chloro-4-methoxyphenyl)-6,7-dihydro-5H-cyclopenta[d]pyrazolo[1,5-a]pyrimidine,
(13) 8-(4-heptyloxy)-2-methyl-3-(2-chloro-5-methoxyphenyl)-6,7-dihydro-5H-cyclopenta[d]pyrazolo[1,5-a]pyrimidine,
(14) 8-i propyloxy-2-methyl-3-(2-chloro-5-methoxyphenyl)-6,7-dihydro-5H-cyclopenta[d]pyrazolo[1,5-a]pyrimidine,

(15) 8-(1, 6-heptadian-4-yl)oxy-2-methyl-3-(2-chloro-4-methoxyphenyl)-6,7-dihydro-5H-cyclopenta[d]pyrazolo[1,5-a]pyrimidine,
(16) 8-(3-pentylthio)-2-methyl-3-(2-chloro-5-methoxyphenyl)-6,7-dihydro-5H-cyclopenta[d]pyrazolo[1,5-a]pyrimidine,
(17) 8-(4-methylphenyl)-2-methyl-3-(2-methyl-4-methoxyphenyl)-6,7-dlhydro-5H-cyclopenta[d]pyrazolo[1,5-a]pyrimidine,
(18) 8-(2,4-dichlorophenyl)-2-methyl-3-(2-methyl-4-methoxyphenyl)-6,7-dihydro-5H-cyclopenta[d]pyrazolo[1,5-a]pyrimidine,
(19) 8-(3-trifluoromethylphenyl)-2-methyl-3-(2-methyl-4-methoxyphenyl)-6,7-dihydro-5H-cyclopenta[d]pyrazolo[1,5-a]pyrimidine,
(20) 8-(4-methoxyphenyl)-2-methyl-3-(2-methyl-4-methoxyphenyl)-6,7-dihydro-5H-cyclopenta[d]pyrazolo[1,5-a]pyrimidine,
(21) 8-(3, 5-dichlorophenyl)-2-methyl-3-(2-methyl-4-methoxyphenyl)-6,7-dihydro-5H-cyclopenta[d]pyrazolo[1,5-a]pyrimidine,
(22) 8-(2-methylphenyl)-2-methyl-3-(2-methyl-4-methoxyphenyl)-6,7-dihydro-5H-cyclopenta[d]pyrazolo[1,5-a]pyrimidine,
(23) 8-bis(ethoxycarbonyl)methyl-2-methyl-3-(2-methyl-4-methoxyphenyl)-6,7-dihydro-5H-cyclopenta[d]pyrazolo[1,5-a]pyrimidine,
(24) 8-(1-dimethylamino-1,3-dioxo-2-butyl)-2-methyl-3-(2-methyl-4-methoxyphenyl)-6,7-dihydro-5H-cyclopenta[d]pyrazolo[1,5-a]pyrimidine,
(25) 8-(2,4-dioxo-3-pentyl)-2-methyl-3-(2-methyl-4-methoxyphenyl)-6,7-dihydro-5H-cyclopenta[d]pyrazolo[1,5-a]pyrimidine,
(26) 8-bis(ethoxycarbonyl)methyl-2-methyl-3-(2-chloro-4-methoxyphenyl)-6,7-dihydro-5H-cyclopenta[d]pyrazolo[1,5-a]pyrimidine,
(27) 8-(1,3-hydroxy-2-propyl)-2-methyl-3-(2-methyl-4-methoxyphenyl)-6,7-dihydro-5H-cyclopenta[d]pyrazolo[1,5-a]pyrimidine,
(28) 8-(1,3-dimethoxy-2-propyl)-2-methyl-3-(2-methyl-4-methoxyphenyl)-6,7-dihydro-5H-cyclopenta[d]pyrazolo[1,5-a]pyrimidine,
(29) 8-(N, N-dimethylcarbamoylmethyl)-2-methyl-3-(2-methyl-4-methoxyphenyl)-6,7-dihydro-5H-cyclopenta[d]pyrazolo[1,5-a]pyrimidine and
(30) 1-cyano-2-methyl-8-hydroxy-3-(2-chloro-4-methoxyphenyl)-6,7-dihydro-5H-cyclopenta[d]pyrazolo[1,2-a]pyrimidine,
a pharmaceutically acceptable salt thereof or a hydrate thereof.

12. A pharmaceutical composition which comprises the compound of formula (I) described in claim 1, a pharmaceutically acceptable salt thereof or a hydrate thereof and a pharmaceutically acceptable carrier.

* * * * *